US010411200B2

(12) United States Patent
Ma et al.

(10) Patent No.: US 10,411,200 B2
(45) Date of Patent: *Sep. 10, 2019

(54) ELECTROLUMINESCENT (2-PHENYLPYRIDINE)IRIDIUM COMPLEXES AND DEVICES

(71) Applicant: Universal Display Corporation, Ewing, NJ (US)

(72) Inventors: Bin Ma, Plainsboro, NJ (US); Walter Yeager, Yardley, PA (US); Edward Barron, Hamilton, NJ (US); Alan Deangelis, Pennington, NJ (US); Chuanjun Xia, Lawrenceville, NJ (US); Vadim Adamovich, Yardley, PA (US); Scott Beers, Flemington, NJ (US); Harvey Wendt, Medford Lakes, NJ (US); Suman Layek, Lawrenceville, NJ (US)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 193 days.

This patent is subject to a terminal disclaimer.

(21) Appl. No.: 14/796,213

(22) Filed: Jul. 10, 2015

(65) Prior Publication Data

US 2016/0049599 A1    Feb. 18, 2016

Related U.S. Application Data

(63) Continuation-in-part of application No. 14/453,777, filed on Aug. 7, 2014, now abandoned.

(51) Int. Cl.
| C07F 15/00 | (2006.01) |
| C09K 11/06 | (2006.01) |
| H01L 51/00 | (2006.01) |
| H01L 51/50 | (2006.01) |
| H01L 51/52 | (2006.01) |
| H05B 33/14 | (2006.01) |

(52) U.S. Cl.
CPC ...... H01L 51/0085 (2013.01); C07F 15/0033 (2013.01); C09K 11/06 (2013.01);
(Continued)

(58) Field of Classification Search
CPC combination set(s) only.
See application file for complete search history.

(56) References Cited

U.S. PATENT DOCUMENTS 4,769,292 A   9/1988 Tang et al.
5,061,569 A   10/1991 VanSlyke et al.
(Continued)

FOREIGN PATENT DOCUMENTS

EP   0650955   5/1995
EP   1725079   11/2006
(Continued)

OTHER PUBLICATIONS

U.S. Appl. No. 14/951,764, filed Nov. 2015, Hwang et al.*
(Continued)

Primary Examiner — Amanda L Aguirre
(74) Attorney, Agent, or Firm — Duane Morris LLP

(57) ABSTRACT

A compound having the formula $Ir(L_A)_n(L_B)_{3-n}$ is disclosed wherein $L_A$ is an aza-DBF ligand and $L_B$ is an alkyl-substituted phenylpyridine ligand, wherein the compound has a structure according to Formula I:

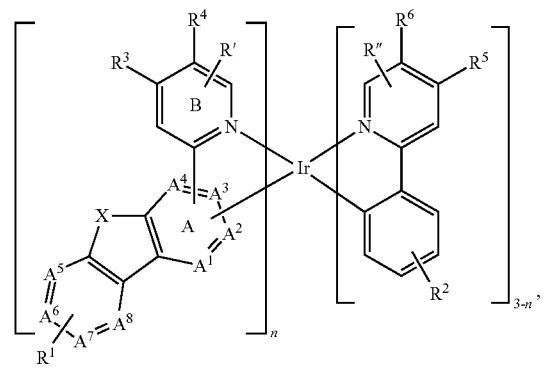

Formula I wherein $A^1$, $A^2$, $A^3$, $A^4$, $A^5$, $A^6$, $A^7$, and $A^8$ comprise carbon or nitrogen; wherein at least one of $A^1$, $A^2$, $A^3$, $A^4$, $A^5$, $A^6$, $A^7$, and $A^8$ is nitrogen; wherein ring B is bonded to ring A through a C—C bond; wherein the iridium is bonded to ring A through a Ir—C bond; wherein X is O, S, or Se; wherein $R^1$ and $R^2$ each independently represent mono-, di-, tri-, tetra-substitution, or no substitution; wherein R' and R" each independently represent mono-, di-substitution, or no substitution; wherein any adjacent substitutions in R', R", $R^1$, $R^2$, $R^3$, $R^4$, $R^5$, and $R^6$ are optionally linked together to form a ring; wherein $R^1$, $R^2$, R', and R" are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; wherein $R^3$, $R^4$, $R^5$, and $R^6$ are each independently selected from the group consisting of hydrogen, deuterium, alkyl, cycloalkyl, and combinations thereof; wherein n is an integer from 1 to 3; and wherein total number of carbons in at least one of the pairs $R^3$ and $R^4$, and $R^5$ and $R^6$ is at least four.

16 Claims, 3 Drawing Sheets

(52) U.S. Cl.
CPC ...... *H01L 51/5016* (2013.01); *H01L 51/5024* (2013.01); *H05B 33/14* (2013.01); *C09K 2211/1029* (2013.01); *C09K 2211/1048* (2013.01); *H01L 51/5206* (2013.01); *H01L 51/5221* (2013.01)

(56) References Cited

U.S. PATENT DOCUMENTS

| | | | |
|---|---|---|---|
| 5,247,190 | A | 9/1993 | Friend et al. |
| 5,703,436 | A | 12/1997 | Forrest et al. |
| 5,707,745 | A | 1/1998 | Forrest et al. |
| 5,834,893 | A | 11/1998 | Bulovic et al. |
| 5,844,363 | A | 12/1998 | Gu et al. |
| 6,013,982 | A | 1/2000 | Thompson et al. |
| 6,087,196 | A | 7/2000 | Sturm et al. |
| 6,091,195 | A | 7/2000 | Forrest et al. |
| 6,097,147 | A | 8/2000 | Baldo et al. |
| 6,294,398 | B1 | 9/2001 | Kim et al. |
| 6,303,238 | B1 | 10/2001 | Thompson et al. |
| 6,337,102 | B1 | 1/2002 | Forrest et al. |
| 6,468,819 | B1 | 10/2002 | Kim et al. |
| 6,528,187 | B1 | 3/2003 | Okada |
| 6,687,266 | B1 | 2/2004 | Ma et al. |
| 6,835,469 | B2 | 12/2004 | Kwong et al. |
| 6,921,915 | B2 | 7/2005 | Takiguchi et al. |
| 7,087,321 | B2 | 8/2006 | Kwong et al. |
| 7,090,928 | B2 | 8/2006 | Thompson et al. |
| 7,154,114 | B2 | 12/2006 | Brooks et al. |
| 7,250,226 | B2 | 7/2007 | Tokito et al. |
| 7,279,704 | B2 | 10/2007 | Walters et al. |
| 7,332,232 | B2 | 2/2008 | Ma et al. |
| 7,338,722 | B2 | 3/2008 | Thompson et al. |
| 7,393,599 | B2 | 7/2008 | Thompson et al. |
| 7,396,598 | B2 | 7/2008 | Takeuchi et al. |
| 7,431,968 | B1 | 10/2008 | Shtein et al. |
| 7,445,855 | B2 | 11/2008 | Mackenzie et al. |
| 7,534,505 | B2 | 5/2009 | Lin et al. |
| 8,946,697 | B1* | 2/2015 | Ma ................. C07F 15/0033 257/40 |
| 9,634,264 | B2* | 4/2017 | Beers ................. H01L 51/0085 |
| 9,685,617 | B2* | 6/2017 | Beers ................. H01L 51/0085 |
| 9,748,500 | B2* | 8/2017 | Ma ................. H01L 51/0085 |
| 9,929,353 | B2* | 3/2018 | Kottas ................. H01L 51/0072 |
| 2002/0034656 | A1 | 3/2002 | Thompson et al. |
| 2002/0134984 | A1 | 9/2002 | Igarashi |
| 2002/0158242 | A1 | 10/2002 | Son et al. |
| 2003/0138657 | A1 | 7/2003 | Li et al. |
| 2003/0151042 | A1 | 8/2003 | Marks et al. |
| 2003/0152802 | A1 | 8/2003 | Tsuboyama et al. |
| 2003/0175553 | A1 | 9/2003 | Thompson et al. |
| 2003/0230980 | A1 | 12/2003 | Forrest et al. |
| 2004/0036077 | A1 | 2/2004 | Ise |
| 2004/0137267 | A1 | 7/2004 | Igarashi et al. |
| 2004/0137268 | A1 | 7/2004 | Igarashi et al. |
| 2004/0174116 | A1 | 9/2004 | Lu et al. |
| 2005/0025993 | A1 | 2/2005 | Thompson et al. |
| 2005/0112407 | A1 | 5/2005 | Ogasawara et al. |
| 2005/0238919 | A1 | 10/2005 | Ogasawara |
| 2005/0244673 | A1 | 11/2005 | Satoh et al. |
| 2005/0260441 | A1 | 11/2005 | Thompson et al. |
| 2005/0260449 | A1 | 11/2005 | Walters et al. |
| 2006/0008670 | A1 | 1/2006 | Lin et al. |
| 2006/0202194 | A1 | 9/2006 | Jeong et al. |
| 2006/0240279 | A1 | 10/2006 | Adamovich et al. |
| 2006/0251923 | A1 | 11/2006 | Lin et al. |
| 2006/0263635 | A1 | 11/2006 | Ise |
| 2006/0280965 | A1 | 12/2006 | Kwong et al. |
| 2007/0190359 | A1 | 8/2007 | Knowles et al. |
| 2007/0278938 | A1 | 12/2007 | Yabunouchi et al. |
| 2008/0015355 | A1 | 1/2008 | Schafer et al. |
| 2008/0018221 | A1 | 1/2008 | Egen et al. |
| 2008/0106190 | A1 | 5/2008 | Yabunouchi et al. |
| 2008/0124572 | A1 | 5/2008 | Mizuki et al. |
| 2008/0220265 | A1 | 9/2008 | Xia et al. |
| 2008/0297033 | A1 | 12/2008 | Knowles et al. |
| 2009/0008605 | A1 | 1/2009 | Kawamura et al. |
| 2009/0009065 | A1 | 1/2009 | Nishimura et al. |
| 2009/0017330 | A1 | 1/2009 | Iwakuma et al. |
| 2009/0030202 | A1 | 1/2009 | Iwakuma et al. |
| 2009/0039776 | A1 | 2/2009 | Yamada et al. |
| 2009/0045730 | A1 | 2/2009 | Nishimura et al. |
| 2009/0045731 | A1 | 2/2009 | Nishimura et al. |
| 2009/0101870 | A1 | 4/2009 | Pakash et al. |
| 2009/0108737 | A1 | 4/2009 | Kwong et al. |
| 2009/0115316 | A1 | 5/2009 | Zheng et al. |
| 2009/0165846 | A1 | 7/2009 | Johannes et al. |
| 2009/0167162 | A1 | 7/2009 | Lin et al. |
| 2009/0179554 | A1 | 7/2009 | Kuma et al. |
| 2014/0131663 | A1* | 5/2014 | Beers ................. H01L 51/0085 257/40 |
| 2014/0131676 | A1 | 5/2014 | Beers et al. |
| 2015/0287933 | A1* | 10/2015 | Kottas ................. C07D 487/06 257/40 |

FOREIGN PATENT DOCUMENTS

| | | |
|---|---|---|
| EP | 2034538 | 3/2009 |
| EP | 2730583 | 5/2014 |
| JP | 200511610 | 1/2005 |
| JP | 2007123392 | 5/2007 |
| JP | 2007254297 | 10/2007 |
| JP | 2008074939 | 4/2008 |
| WO | 2001039234 | 5/2001 |
| WO | 2002002714 | 1/2002 |
| WO | 200215645 | 2/2002 |
| WO | 2003040257 | 5/2003 |
| WO | 2003060956 | 7/2003 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008044723 | 4/2008 |
| WO | 2008056746 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009050290 | 4/2009 |
| WO | 2009021126 | 5/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |
| WO | 2014/115528 | 7/2014 |

OTHER PUBLICATIONS

U.S. Appl. No. 13/673,338, filed Nov. 2012, Beers et al.*
U.S. Appl. No. 13/928,456, filed Jun. 2013, Beers et al.*
U.S. Appl. No. 14/636,310, filed Mar. 2015, Kottas et al.*
U.S. Appl. No. 14/597,857, filed Jan. 2015, Ma et al.*

(56) References Cited

OTHER PUBLICATIONS

Adachi, Chihaya et al., "Organic Electroluminescent Device Having a Hole Conductor as an Emitting Layer," Appl. Phys. Lett., 55(15): 1489-1491 (1989).
Adachi, Chihaya et al., "Nearly 100% Internal Phosphorescence Efficiency in an Organic Light Emitting Device," J. Appl. Phys., 90(10): 5048-5051 (2001).
Adachi, Chihaya et al., "High-Efficiency Red Electrophosphorescence Devices," Appl. Phys. Lett., 78(11)1622-1624 (2001).
Baldo et al., Highly Efficient Phosphorescent Emission from Organic Electroluminescent Devices, Nature, vol. 395, 151-154, (1998).
Baldo et al., Very high-efficiency green organic light-emitting devices based on electrophosphorescence, Appl. Phys. Lett., vol. 75, No. 3, 4-6 (1999).
Gao, Zhiqiang et al., "Bright-Blue Electroluminescence From a Silyl-Substituted ter-(phenylene-vinylene) derivative," Appl. Phys. Lett., 74(6): 865-867 (1999).
Guo, Tzung-Fang et al., "Highly Efficient Electrophosphorescent Polymer Light-Emitting Devices," Organic Electronics, 115-20 (2000).
Hamada, Yuji et al., "High Luminance in Organic Electroluminescent Devices with Bis(10-hydroxybenzo[h]quinolinato) beryllium as an Emitter," Chem. Lett., 905-906 (1993).
Holmes, R.J. et al., "Blue Organic Electrophosphorescence Using Exothermic Host-Guest Energy Transfer," Appl. Phys. Lett., 82(15):2422-2424 (2003).
Hu, Nan-Xing et al., "Novel High Tg Hole-Transport Molecules Based on Indolo[3,2-b]carbazoles for Organic Light-Emitting Devices," Synthetic Metals, 111-112:421-424 (2000).
Huang, Jinsong et al., "Highly Efficient Red-Emission Polymer Phosphorescent Light-Emitting Diodes Based on Two Novel Tris(1-phenylisoquinolinato-C2,N)iridium(III) Derivates," Adv. Mater., 19:739-743 (2007).
Huang, Wei-Sheng et al., "Highly Phosphorescent Bis-Cyclometalated Iridium Complexes Containing Benzoimidazole-Based Ligands," Chem. Mater., 16(12):2480-2488 (2004).
Hung, L.S. et al., "Anode Modification in Organic Light-Emitting Diodes by Low-Frequency Plasma Polymerization of CHF3," Appl. Phys. Lett., 78(5):673-675 (2001).
Ikai, Masamichi and Tokito, Shizuo, "Highly Efficient Phosphorescence From Organic Light-Emitting Devices with an Exciton-Block Layer," Appl. Phys. Lett., 79(2):156-158 (2001).
Ikeda, Hisao et al., "P-185 Low-Drive-Voltage OLEDs with a Buffer Layer Having Molybdenum Oxide," SID Symposium Digest, 37:923-926 (2006).
Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).
Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).
Kido, Junji et al., 1,2,4-Triazole Derivative as an Electron Transport Layer in Organic Electroluminescent Devices, Jpn. J. Appl. Phys., 32:L917-L920 (1993).
Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino)triphenylamine (m-MTDATA), as Hole-Transport Materials," Adv. Mater., 6(9):677-679 (1994).
Kwong, Raymond C. et al., "High Operational Stability of Electrophosphorescent Devices," Appl. Phys. Lett., 81(1) 162-164 (2002).
Lamansky, Sergey et al., "Synthesis and Characterization of Phosphorescent Cyclometalated Iridium Complexes," Inorg. Chem., 40(7):1704-1711 (2001).
Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).

Lo, Shih-Chun et al., "Blue Phosphorescence from Iridium(III) Complexes at Room Temperature," Chem. Mater., 18(21)5119-5129 (2006).
Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).
Mi, Bao-Xiu et al., "Thermally Stable Hole-Transporting Material for Organic Light-Emitting Diode an Isoindole Derivative," Chem. Mater., 15(16):3148-3151 (2003).
Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).
Niu, Yu-Hua et al., "Highly Efficient Electrophosphorescent Devices with Saturated Red Emission from a Neutral Osmium Complex," Chem. Mater., 17(13):3532-3536 (2005).
Noda, Tetsuya and Shirota,Yasuhiko, "5,5"-Bis(dimesitylboryl)-2,2'-bithiophene and 5,5"-Bis (dimesitylboryl)-2,2'5',2"-terthiophene as a Novel Family of Electron-Transporting Amorphous Molecular Materials," J. Am. Chem. Soc., 120 (37):9714-9715 (1998).
Okumoto, Kenji et al., "Green Fluorescent Organic Light-Emitting Device with External Quantum Efficiency of Nearly 10%," Appl. Phys. Lett., 89:063504-1-063504-3 (2006).
Palilis, Leonidas C., "High Efficiency Molecular Organic Light-Emitting Diodes Based on Silole Derivatives and Their Exciplexes," Organic Electronics, 4:113-121 (2003).
Paulose, Betty Marie Jennifer S. et al., "First Examples of Alkenyl Pyridines as Organic Ligands for Phosphorescent Iridium Complexes," Adv. Mater., 16(22):2003-2007 (2004).
Ranjan, Sudhir et al., "Realizing Green Phosphorescent Light-Emitting Materials from Rhenium(I) Pyrazolato Diimine Complexes," Inorg. Chem., 42(4):1248-1255 (2003).
Sakamoto, Youichi et al., "Synthesis, Characterization, and Electron-Transport Property of Perfluorinated Phenylene Dendrimers," J. Am. Chem. Soc., 122(8):1832-1833 (2000).
Salbeck, J. et al., "Low Molecular Organic Glasses for Blue Electroluminescence," Synthetic Metals, 91209-215 (1997).
Shirota, Yasuhiko et al., "Starburst Molecules Based on p-Electron Systems as Materials for Organic Electroluminescent Devices," Journal of Luminescence, 72-74:985-991 (1997).
Sotoyama, Wataru et al., "Efficient Organic Light-Emitting Diodes with Phosphorescent Platinum Complexes Containing N^C^N-Coordinating Tridentate Ligand," Appl. Phys. Lett., 86:153505-1-153505-3 (2005).
Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).
T. Östergård et al., "Langmuir-Blodgett Light-Emitting Diodes of Poly(3-Hexylthiophene) Electro-Optical Characteristics Related to Structure," Synthetic Metals, 87:171-177 (1997).
Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).
Tang, C.W. and VanSlyke, S.A., "Organic Electroluminescent Diodes," Appl. Phys. Lett., 51(12):913-915 (1987).
Tung, Yung-Liang et al., "Organic Light-Emitting Diodes Based on Charge-Neutral Ru II PHosphorescent Emitters," Adv. Mater., 17(8)1059-1064 (2005).
Van Slyke, S. A. et al., "Organic Electroluminescent Devices with Improved Stability," Appl. Phys. Lett., 69(15):2160-2162 (1996).
Wang, Y. et al., "Highly Efficient Electroluminescent Materials Based on Fluorinated Organometallic Iridium Compounds," Appl. Phys. Lett., 79(4):449-451 (2001).
Wong, Keith Man-Chung et al., A Novel Class of Phosphorescent Gold(III) Alkynyl-Based Organic Light-Emitting Devices with Tunable Colour, Chem. Commun., 2906-2908 (2005).
Wong, Wai-Yeung, "Multifunctional Iridium Complexes Based on Carbazole Modules as Highly Efficient Electrophosphors," Angew. Chem. Int. Ed., 45:7800-7803 (2006).
Aonuma et al., "Material design of hole transport materials capable of thick-film formation in organic light emitting diodes", Applied Physics Letters, 90:183503 (2007).

(56) References Cited

OTHER PUBLICATIONS

EPO Communication pursuant to Article 94(3) EPC dated Jun. 6, 2017 for corresponding European Patent Application No. 15179944.2.

* cited by examiner

Formula I

ELECTROLUMINESCENT (2-PHENYLPYRIDINE)IRIDIUM COMPLEXES AND DEVICES

CROSS-REFERENCE TO RELATED APPLICATIONS

This application is a continuation-in-part of U.S. patent application Ser. No. 14/453,777, filed on Aug. 7, 2014, the entire contents of which is incorporated herein by reference.

PARTIES TO A JOINT RESEARCH AGREEMENT

The claimed invention was made by, on behalf of, and/or in connection with one or more of the following parties to a joint university corporation research agreement: Regents of the University of Michigan, Princeton University, University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to organic light emitting devices. More specifically, the present disclosure pertains to luminescent iridium complexes comprising alkyl-substituted phenylpyridine ligand and aza-dibenzofuran (aza-DBF) ligand that are useful as green phosphorescent emitters in phosphorescent light emitting devices (PHOLEDs).

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted $Ir(ppy)_3$, which has the following structure:

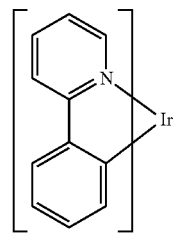

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

According to an embodiment of the present disclosure, a compound having the formula $Ir(L_A)_n(L_B)_{3-n}$ is disclosed wherein $L_A$ is an aza-DBF ligand and $L_B$ is an alkyl-substituted phenylpyridine ligand, wherein the compound has a structure according to Formula I:

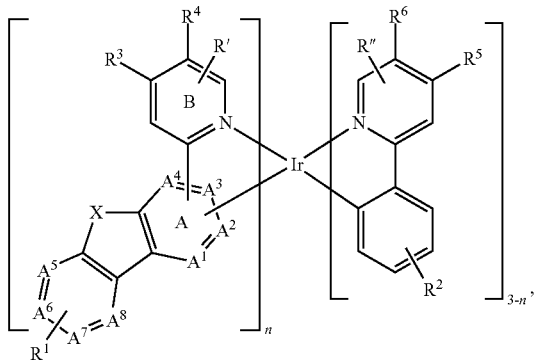

Formula I wherein $A^1$, $A^2$, $A^3$, $A^4$, $A^5$, $A^6$, $A^7$, and $A^8$ comprise carbon or nitrogen;
wherein at least one of $A^1$, $A^2$, $A^3$, $A^4$, $A^5$, $A^6$, $A^7$, and $A^8$ is nitrogen;
wherein ring B is bonded to ring A through a C—C bond;
wherein the iridium is bonded to ring A through a Ir—C bond;
wherein X is O, S, or Se;
wherein $R^1$ and $R^2$ each independently represent mono-, di-, tri-, tetra-substitution, or no substitution;
wherein R' and R" each independently represent mono-, di-substitution, or no substitution;
wherein any adjacent substitutions in R', R", $R^1$, $R^2$, $R^3$, $R^4$, $R^5$, and $R^6$ are optionally linked together to form a ring;
wherein $R^1$, $R^2$, R', and R" are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
wherein $R^3$, $R^4$, $R^5$, and $R^6$ are each independently selected from the group consisting of hydrogen, deuterium, alkyl, cycloalkyl, and combinations thereof;
wherein n is an integer from 1 to 3; and
wherein total number of carbons in at least one of the pairs $R^3$ and $R^4$, and $R^5$ and $R^6$ is at least four.

According to another embodiment, a first device comprising a first organic light emitting device is also disclosed. The first organic light emitting device comprises: an anode; a cathode; and an organic layer, disposed between the anode and the cathode. The organic layer comprises a compound having a structure according to Formula I.

According to yet another embodiment, a formulation comprising a compound that having a structure according to Formula I is also disclosed.

The luminescent iridium complexes disclosed herein can be used in OLEDs as emitters in phosphorescent OLEDs. The compound exhibits lower sublimation temperature more saturated color CIE which is desired.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
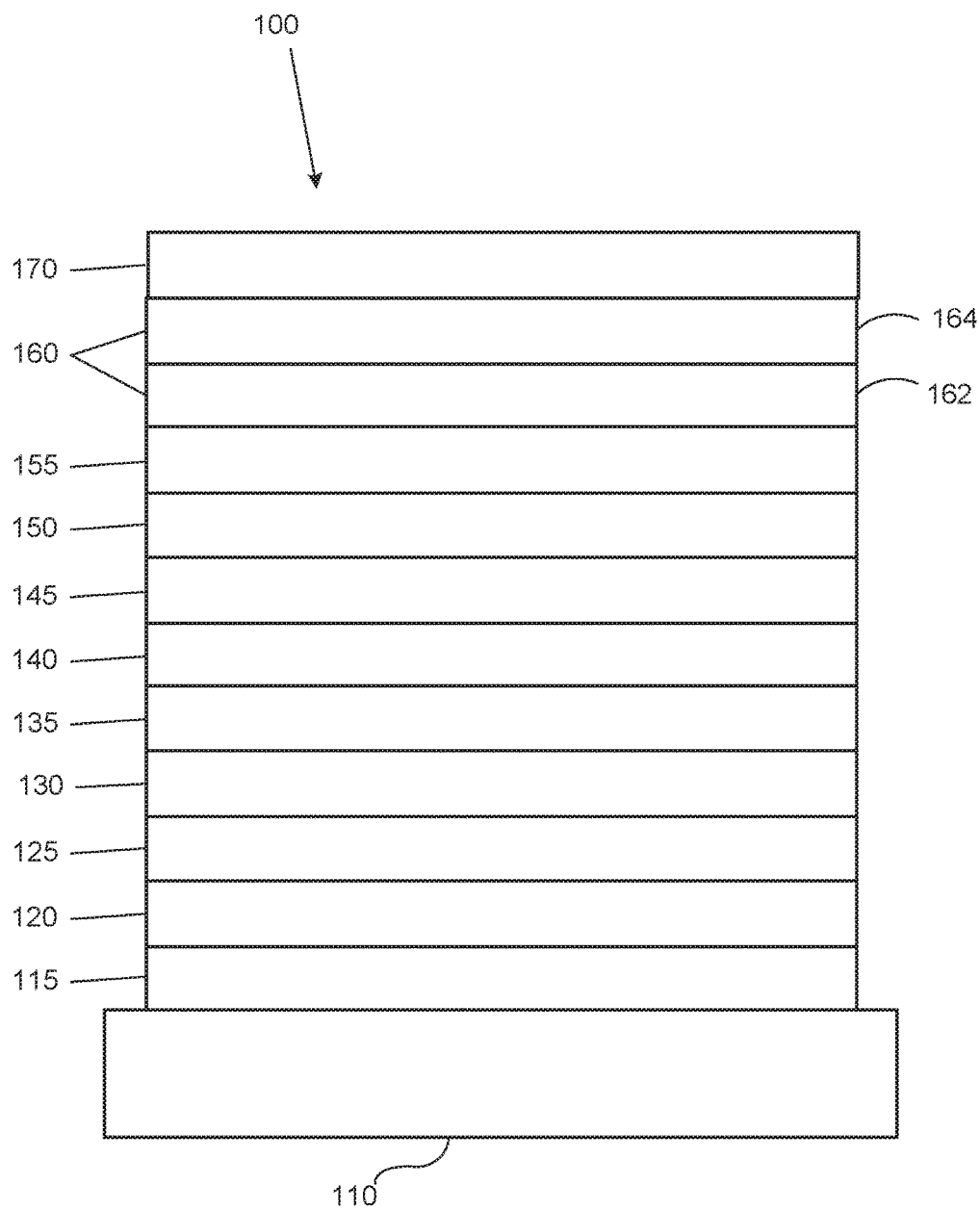
FIG. 1 shows an organic light emitting device that can incorporate the inventive host material disclosed herein.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
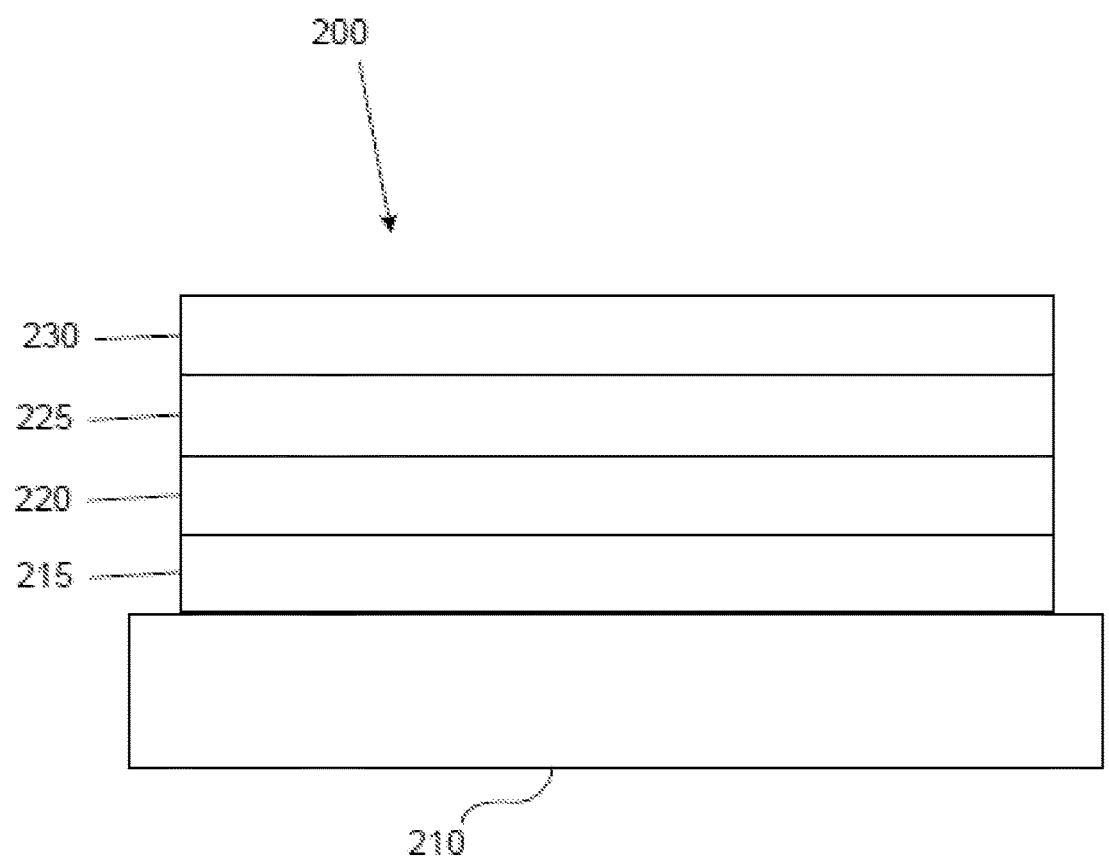
FIG. 2 shows an inverted organic light emitting device that can incorporate the inventive host material disclosed herein.
Figure 3:
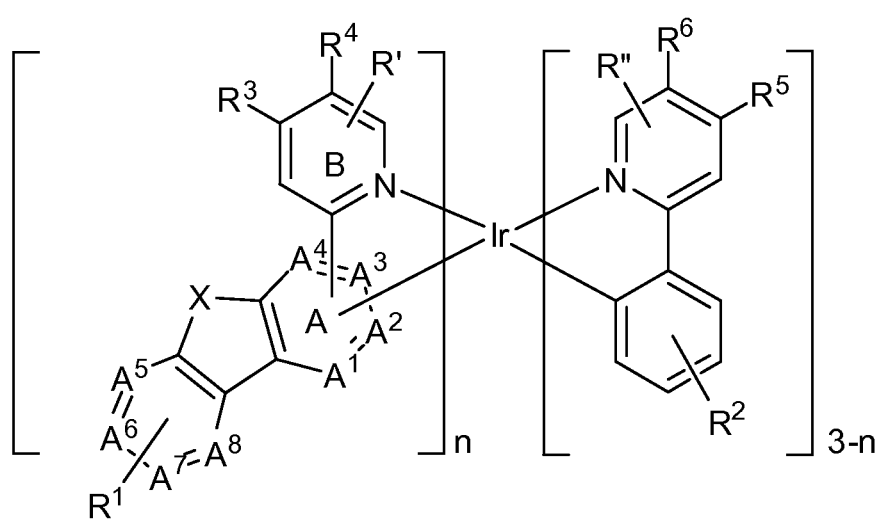
FIG. 3 shows Formula 1 as disclosed herein.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al., which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention may be incorporated into a wide variety of consumer products, including flat panel displays, computer monitors, medical monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, 3-D displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.), but could be used outside this temperature range, for example, from −40 degree C. to +80 degree C.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The term "halo" or "halogen" as used herein includes fluorine, chlorine, bromine, and iodine.

The term "alkyl" as used herein contemplates both straight and branched chain alkyl radicals. Preferred alkyl groups are those containing from one to fifteen carbon atoms and includes methyl, ethyl, propyl, isopropyl, butyl, isobutyl, tert-butyl, and the like. Additionally, the alkyl group may be optionally substituted.

The term "cycloalkyl" as used herein contemplates cyclic alkyl radicals. Preferred cycloalkyl groups are those containing 3 to 7 carbon atoms and includes cyclopropyl, cyclopentyl, cyclohexyl, and the like. Additionally, the cycloalkyl group may be optionally substituted.

The term "alkenyl" as used herein contemplates both straight and branched chain alkene radicals. Preferred alkenyl groups are those containing two to fifteen carbon atoms. Additionally, the alkenyl group may be optionally substituted.

The term "alkynyl" as used herein contemplates both straight and branched chain alkyne radicals. Preferred alkynyl groups are those containing two to fifteen carbon atoms. Additionally, the alkynyl group may be optionally substituted.

The terms "aralkyl" or "arylalkyl" as used herein are used interchangeably and contemplate an alkyl group that has as a substituent an aromatic group. Additionally, the aralkyl group may be optionally substituted.

The term "heterocyclic group" as used herein contemplates aromatic and non-aromatic cyclic radicals. Heteroaromatic cyclic radicals also refer to heteroaryl. Preferred hetero-non-aromatic cyclic groups are those containing 3 or 7 ring atoms which includes at least one hetero atom, and includes cyclic amines such as morpholino, piperdino, pyrrolidino, and the like, and cyclic ethers, such as tetrahydrofuran, tetrahydropyran, and the like. Additionally, the heterocyclic group may be optionally substituted.

The term "aryl" or "aromatic group" as used herein contemplates single-ring groups and polycyclic ring systems. The polycyclic rings may have two or more rings in which two carbons are common to two adjoining rings (the rings are "fused") wherein at least one of the rings is aromatic, e.g., the other rings can be cycloalkyls, cycloalkenyls, aryl, heterocycles, and/or heteroaryls. Additionally, the aryl group may be optionally substituted.

The term "heteroaryl" as used herein contemplates single-ring hetero-aromatic groups that may include from one to three heteroatoms, for example, pyrrole, furan, thiophene, imidazole, oxazole, thiazole, triazole, pyrazole, pyridine, pyrazine and pyrimidine, and the like. The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. Additionally, the heteroaryl group may be optionally substituted.

The alkyl, cycloalkyl, alkenyl, alkynyl, aralkyl, heterocyclic group, aryl, and heteroaryl may be optionally substituted with one or more substituents selected from the group consisting of hydrogen, deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof.

As used herein, "substituted" indicates that a substituent other than H is bonded to the relevant position, such as carbon. Thus, for example, where $R^1$ is mono-substituted, then one $R^1$ must be other than H. Similarly, where $R^1$ is di-substituted, then two of $R^1$ must be other than H. Similarly, where $R^1$ is unsubstituted, $R^1$ is hydrogen for all available positions.

The "aza" designation in the fragments described herein, i.e. aza-dibenzofuran, aza-dibenzothiophene, etc. means that one or more of the C—H groups in the respective fragment can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

As used herein, the phrase "electron acceptor" or "acceptor" means a fragment that can accept electron density from an aromatic system, and the phrase "electron donor" or "donor" means a fragment that donates electron density into an aromatic system.

In this disclosure, luminescent iridium complexes comprising alkyl-substituted phenylpyridine ligand and aza-dibenzofuran (aza-DBF) ligand that are useful as green phosphorescent emitters in PHOLEDs are disclosed. Thermal stability of iridium complexes is an important factor in the usability of such complexes in manufacturing of PHOLED devices. Molecular modification of iridium complexes can effectively change solid state packing of the complexes and therefore has impact on their thermal stability and sublimation temperature. The inventors have discovered that di-substituted alkyl groups (at least four carbon atoms in total) on heteroleptic iridium complex containing ppy and aza-DBF ligands unexpectedly lowered sublimation temperature and improved color CIE to a significant degree.

According to an embodiment, a compound having the formula $Ir(L_A)_n(L_B)_{3-n}$ is disclosed wherein $L_A$ is an aza-dibenzofuran ligand and $L_B$ is an alkyl-substituted phenylpyridine ligand, wherein the compound has a structure according to Formula I:

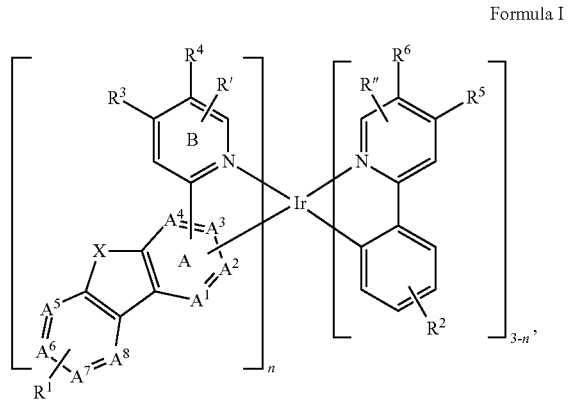

Formula I wherein $A^1$, $A^2$, $A^3$, $A^4$, $A^5$, $A^6$, $A^7$, and $A^8$ comprise carbon or nitrogen;
wherein at least one of $A^1$, $A^2$, $A^3$, $A^4$, $A^5$, $A^6$, $A^7$, and $A^8$ is nitrogen;
wherein ring B is bonded to ring A through a C—C bond;
wherein the iridium is bonded to ring A through a Ir—C bond;
wherein X is O, S, or Se;
wherein $R^1$ and $R^2$ each independently represent mono-, di-, tri-, tetra-substitution, or no substitution;
wherein R' and R" each independently represent mono-, di-substitution, or no substitution;
wherein any adjacent substitutions in R', R", $R^1$, $R^2$, $R^3$, $R^4$, $R^5$, and $R^6$ are optionally linked together to form a ring;
wherein $R^1$, $R^2$, R', and R" are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
wherein $R^3$, $R^4$, $R^5$, and $R^6$ are each independently selected from the group consisting of hydrogen, deuterium, alkyl, cycloalkyl, and combinations thereof;
wherein n is an integer from 1 to 3; and
wherein total number of carbons in at least one of the pairs $R^3$ and $R^4$, and $R^5$ and $R^6$ is at least four.

In one embodiment of the compound having a structure according to Formula I, n is 1.

In one embodiment, the compound according to Formula I has a structure according to Formula II:

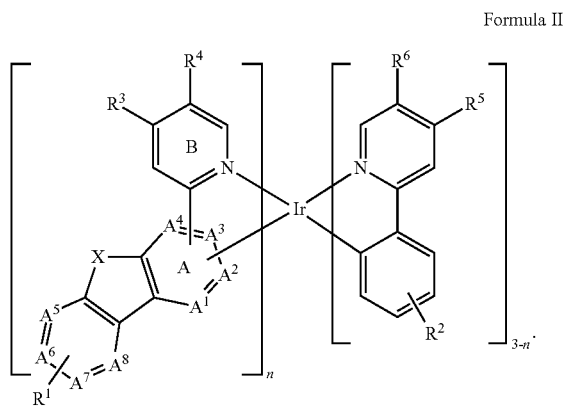

Formula II

In one embodiment, the compound according to Formula I has a structure according to Formula III:

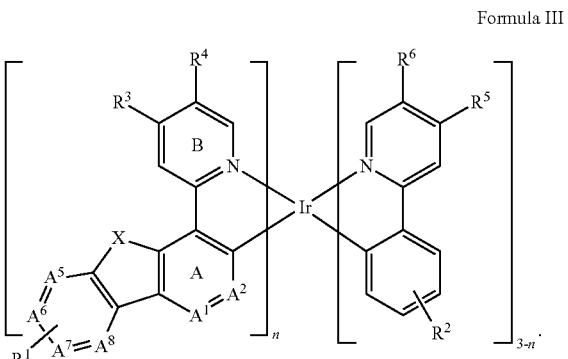

Formula III

In one embodiment, the compound according to Formula I has a structure according to Formula IV:

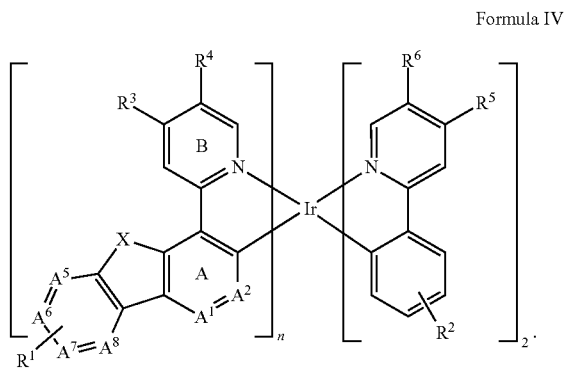

Formula IV

In another embodiment of the compound having a structure according to Formula I, only one of $A^1$ to $A^8$ is nitrogen and the remainder of $A^1$ to $A^8$ are carbon. In another embodiment, one of $A^5$ to $A^8$ is nitrogen and the remainder of $A^1$ to $A^8$ are carbon.

According to an embodiment, X is O in Formula I through Formula IV.

According to an embodiment, $R^1$ and $R^2$ in Formula I through Formula IV are each independently selected from the group consisting of hydrogen, deuterium, alkyl, cycloalkyl, and combinations thereof.

According to another aspect, in the compound having a structure according to Formula I, at least one of the following conditions (1) and (2) is true:

(1) $R^3$ and $R^4$ are each independently selected from the group consisting of alkyl, cycloalkyl, partially or fully deuterated variants thereof, and combinations thereof; and total number carbons in $R^3$ and $R^4$ combined is at least four; and (2) $R^5$ and $R^6$ are each independently selected from the group consisting of alkyl, cycloalkyl, partially or fully deuterated variants thereof, and combinations thereof; and total number of carbons in $R^5$ and $R^6$ combined is at least four.

According to another aspect, in the compound having a structure according to Formula I, at least one of the following conditions (3) and (4) is true:

(3) $R^3$ and $R^4$ are each independently selected from the group consisting of alkyl, cycloalkyl, partially or fully deuterated variants thereof, and combinations thereof; at least one of $R^3$ and $R^4$ contain at least one deuterium; and total number of carbons in $R^3$ and $R^4$ combined is at least four; and (4) $R^5$ and $R^6$ are each independently selected from the group consisting of alkyl, cycloalkyl, partially or fully deuterated variants thereof, and combinations thereof; at least one of $R^3$ and $R^4$ contain at least one deuterium; and total number of carbons in $R^5$ and $R^6$ combined is at least four.

According to another aspect, $R^3$, $R^4$, $R^5$, and $R^6$ in Formula I through Formula IV are each independently selected from the group consisting of hydrogen, deuterium, methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, cyclopentyl, cyclohexyl, and combinations thereof.

In another aspect of the present disclosure, the compound according to Formula I has a structure according to Formula V:

Formula V

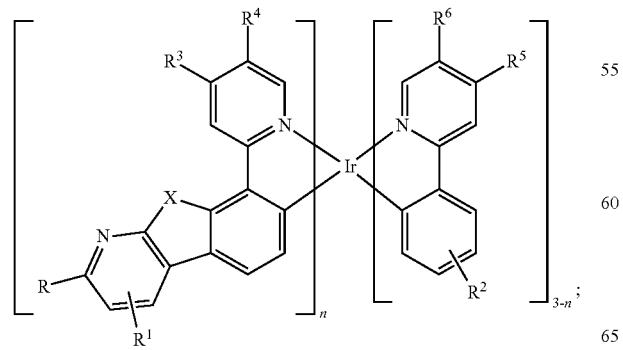

wherein R is selected from the group consisting of alkyl, cycloalkyl, its partially or fully deuterated variants thereof, and combinations thereof.

In one embodiment of the compound according to Formula V, R is selected from the group consisting of methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, cyclopentyl, cyclohexyl, partially or fully deuterated variants thereof, and combinations thereof. In one embodiment of the compound according to Formula V, X is O.

In one embodiment of the compound disclosed herein, the ligand $L_A$ in formula $Ir(L_A)_n(L_B)_{3-n}$ is selected from the group consisting of:

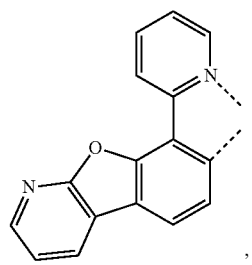

$L_{A1}$

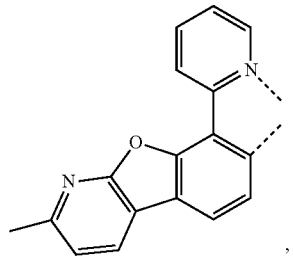

$L_{A2}$

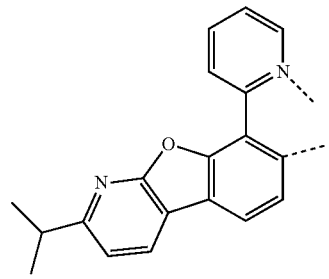

$L_{A3}$

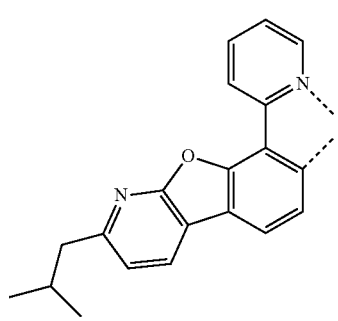

$L_{A4}$

-continued

L<sub>A5</sub>, L<sub>A6</sub>, L<sub>A7</sub>, L<sub>A8</sub>, L<sub>A9</sub>, L<sub>A10</sub>, L<sub>A11</sub>, L<sub>A12</sub>, L<sub>A13</sub>, L<sub>A14</sub>

-continued
L<sub>A15</sub>
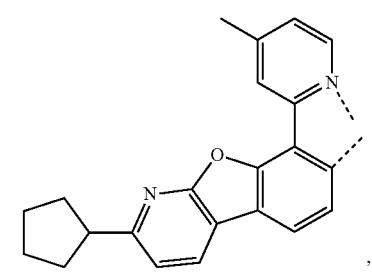
L<sub>A16</sub>
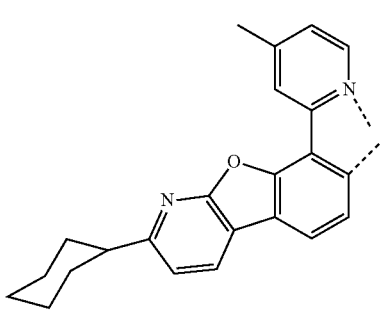
L<sub>A17</sub>
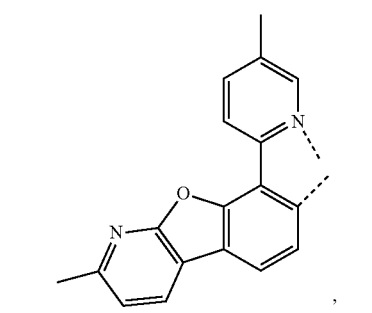
L<sub>A18</sub>
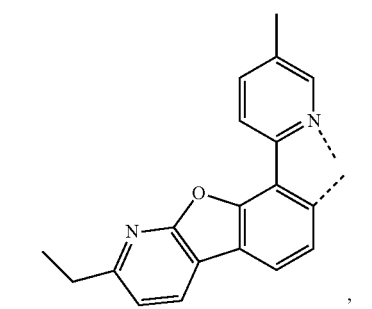
L<sub>A19</sub>
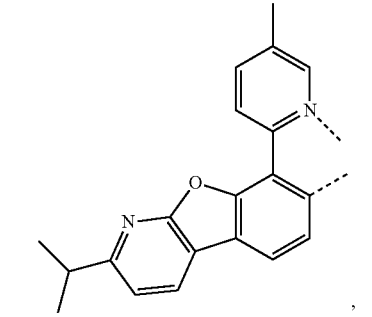
L<sub>A20</sub>
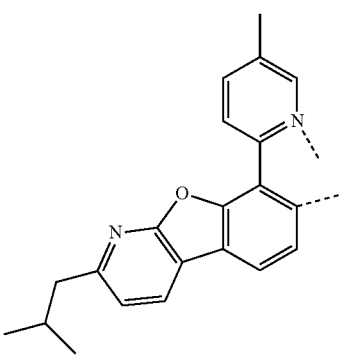
L<sub>A21</sub>
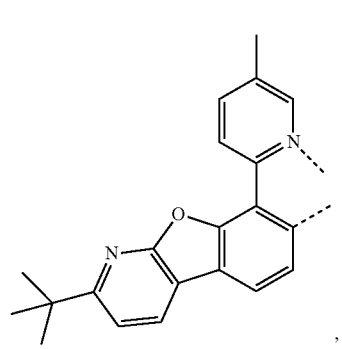
L<sub>A22</sub>
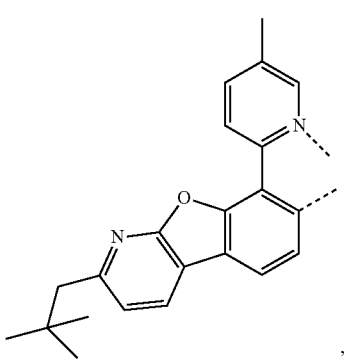
L<sub>A23</sub>
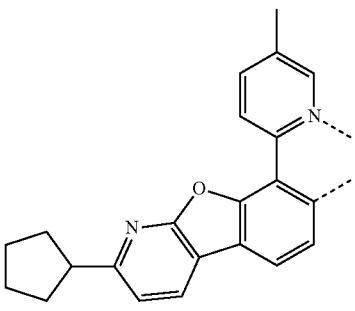

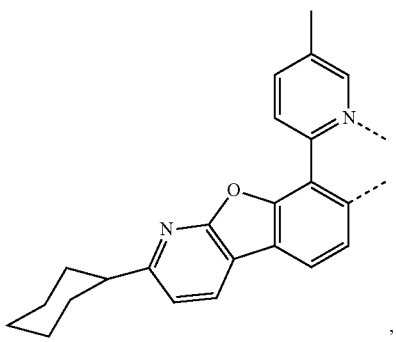 L<sub>A24</sub>,
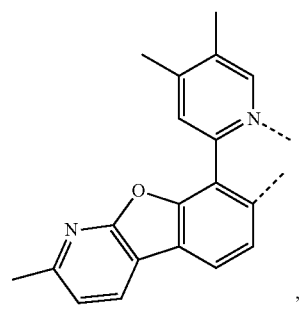 L<sub>A25</sub>,
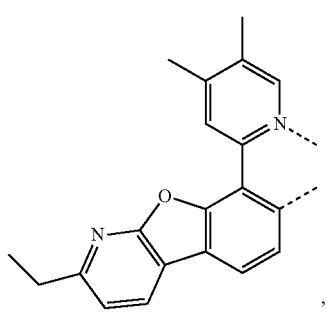 L<sub>A26</sub>,
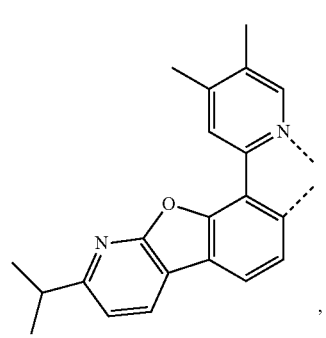 L<sub>A27</sub>,
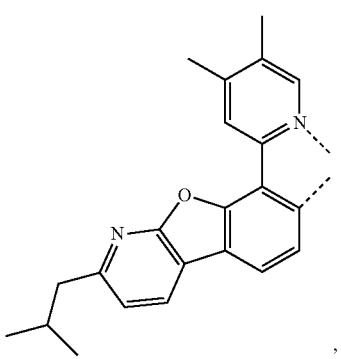 L<sub>A28</sub>,
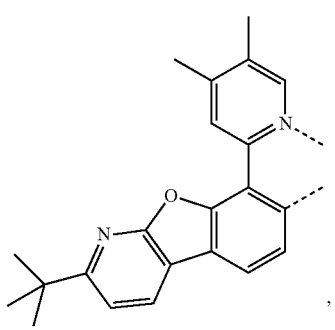 L<sub>A29</sub>,
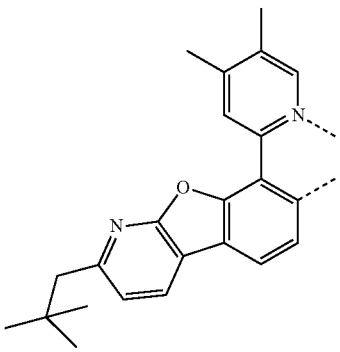 L<sub>A30</sub>,
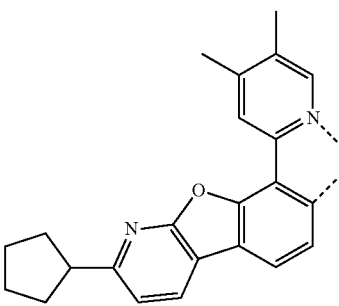 L<sub>A31</sub>,
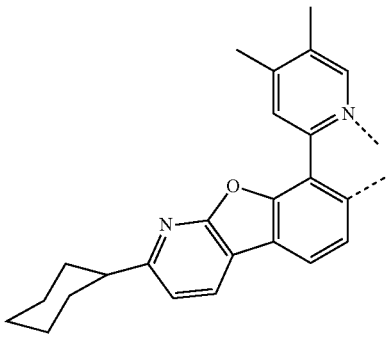 L<sub>A32</sub>,
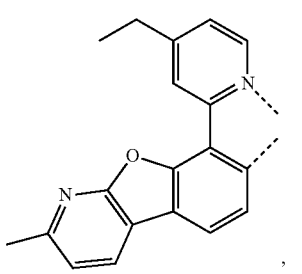 L<sub>A33</sub>,

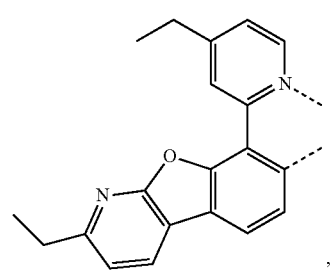
L_{A34}
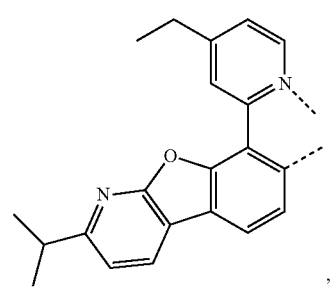
L_{A35}
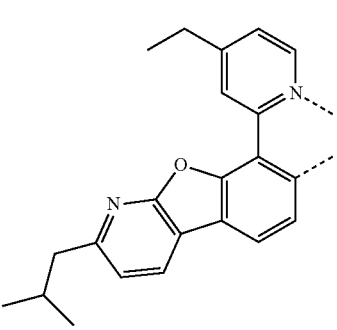
L_{A36}
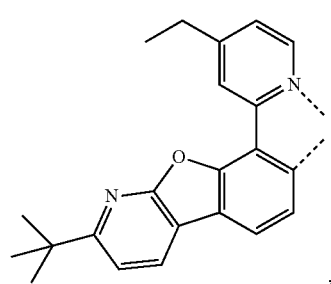
L_{A37}
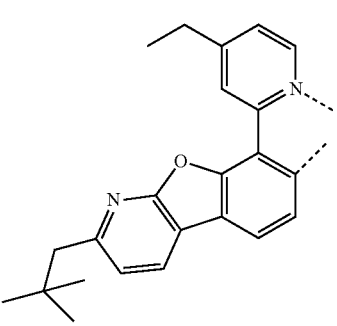
L_{A38}
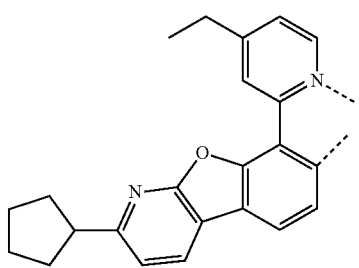
L_{A39}
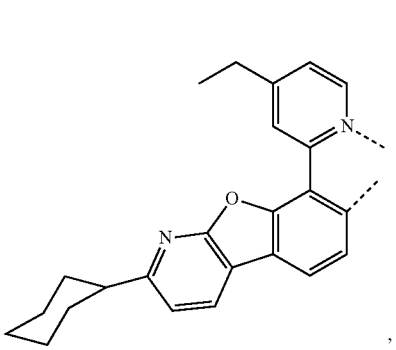
L_{A40}
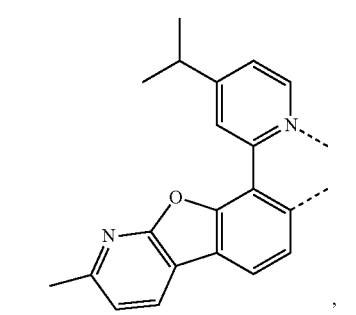
L_{A41}
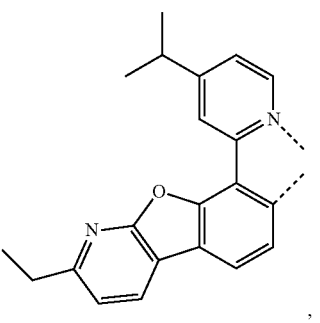
L_{A42}
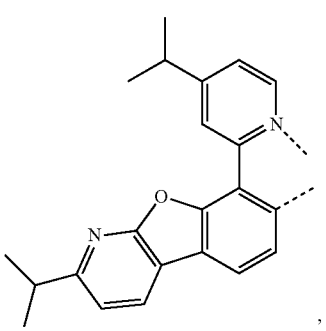
L_{A43}

L<sub>A44</sub>
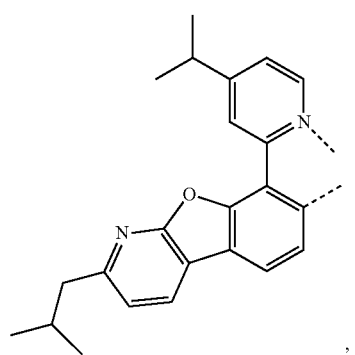
L<sub>A48</sub>
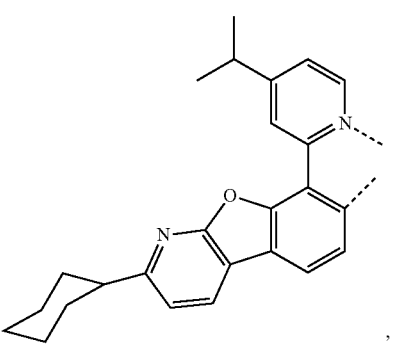
L<sub>A45</sub>
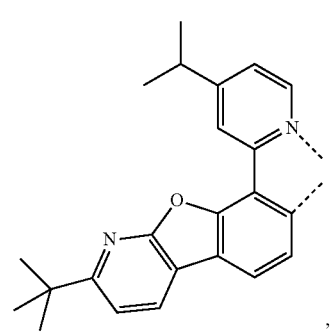
L<sub>A49</sub>
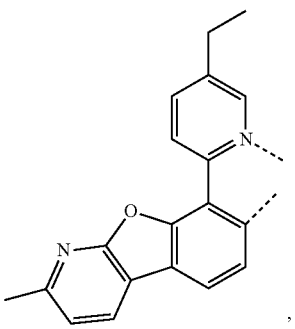
L<sub>A46</sub>
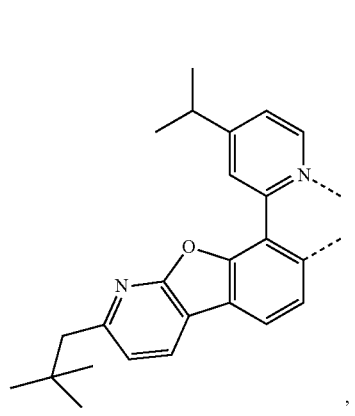
L<sub>A50</sub>
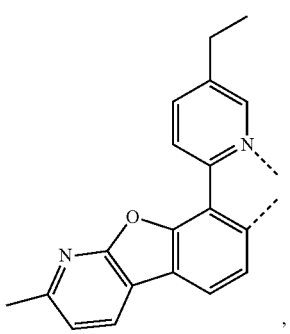
L<sub>A47</sub>
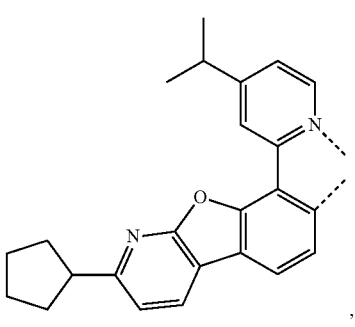
L<sub>A51</sub>
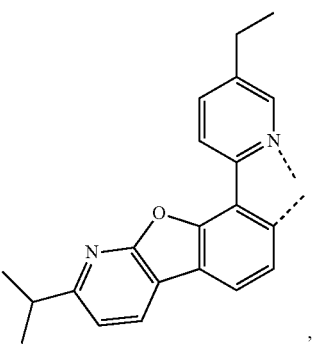

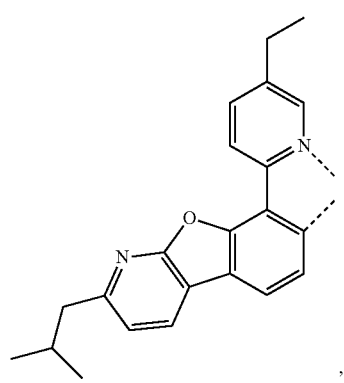 L_{A52}
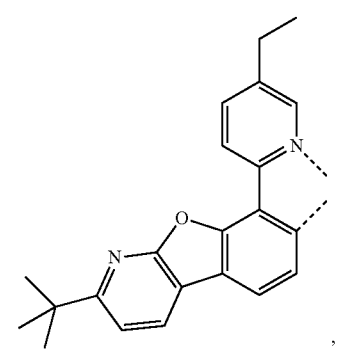 L_{A53}
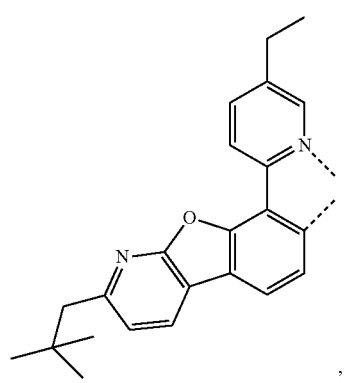 L_{A54}
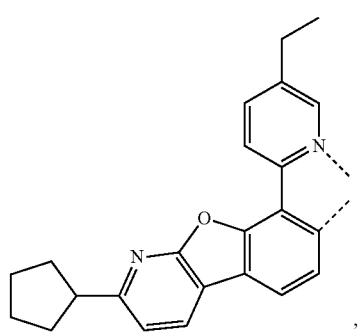 L_{A55}
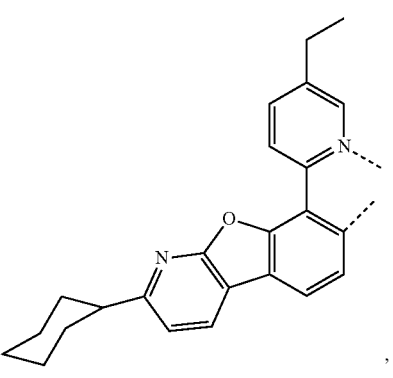 L_{A56}
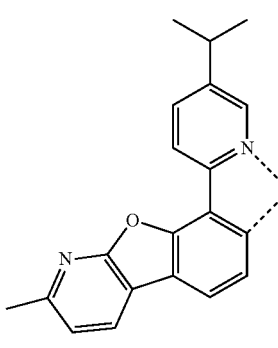 L_{A57}
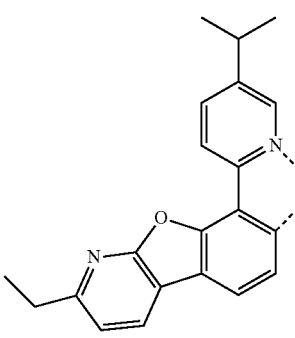 L_{A58}
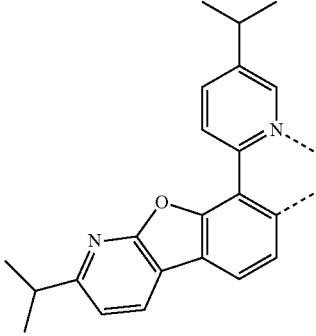 L_{A59}

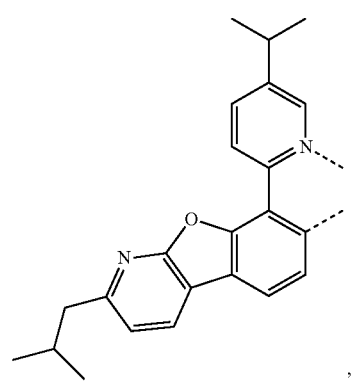 L_{A60}
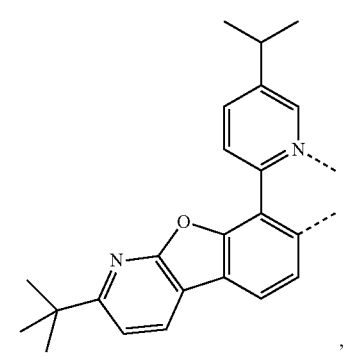 L_{A61}
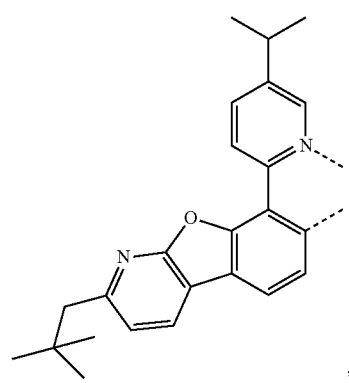 L_{A62}
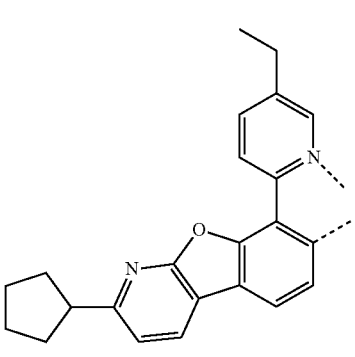 L_{A63}
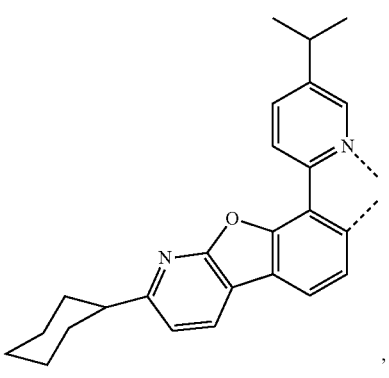 L_{A64}
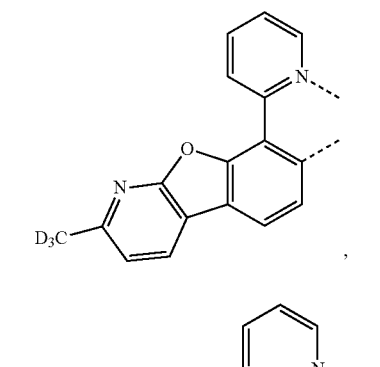 L_{A65}
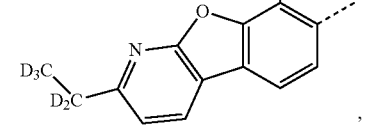 L_{A66}
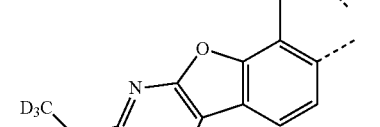 L_{A67}
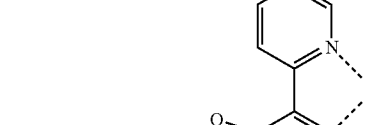 L_{A68}

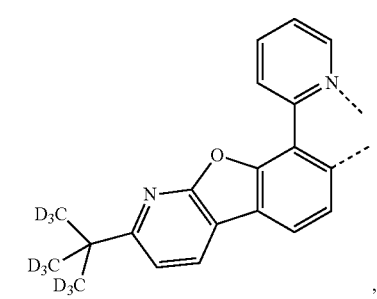 L<sub>A69</sub>
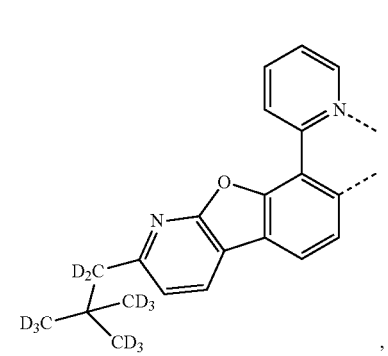 L<sub>A70</sub>
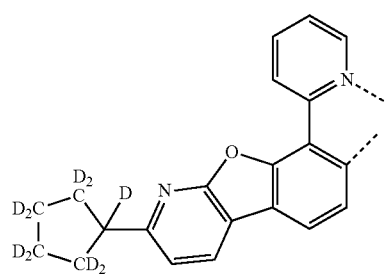 L<sub>A71</sub>
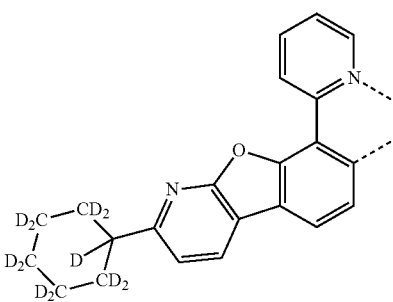 L<sub>A72</sub>
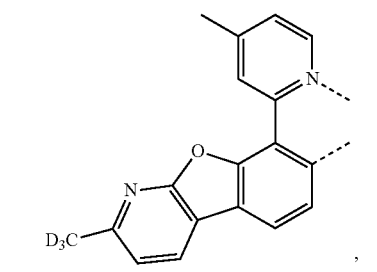 L<sub>A73</sub>
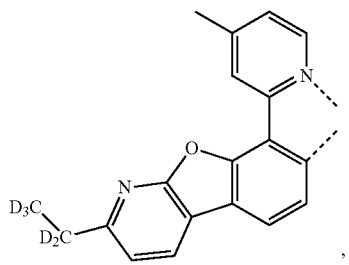 L<sub>A74</sub>
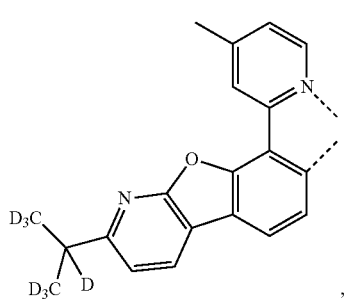 L<sub>A75</sub>
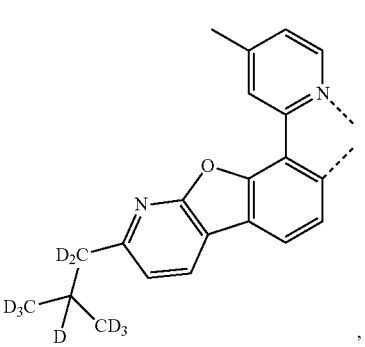 L<sub>A76</sub>
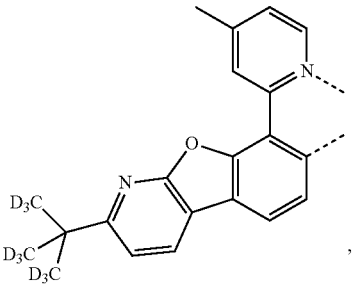 L<sub>A77</sub>
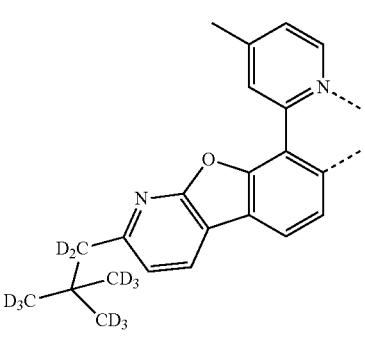 L<sub>A78</sub>

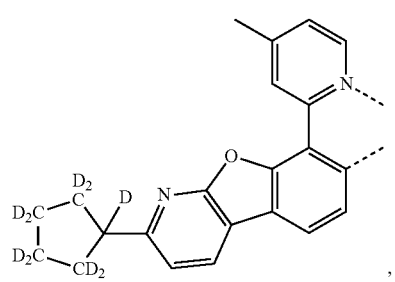 L_{A79}
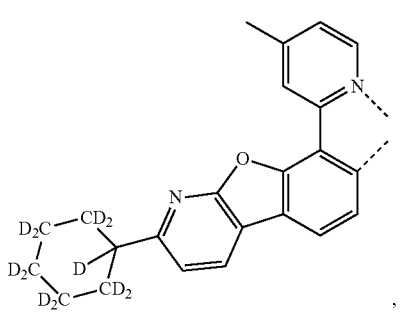 L_{A80}
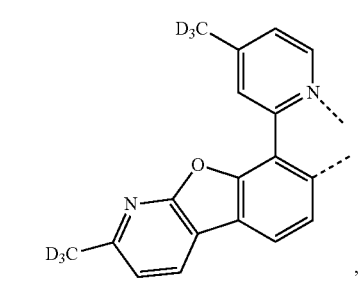 L_{A81}
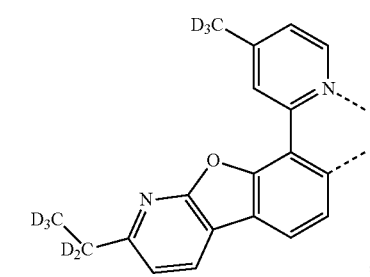 L_{A82}
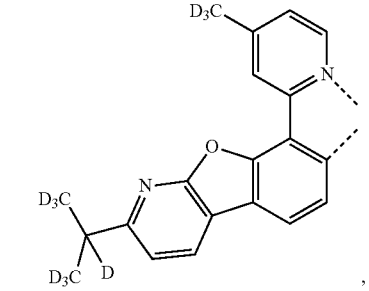 L_{A83}
 L_{A84}
 L_{A85}
 L_{A86}
 L_{A87}
 L_{A88}

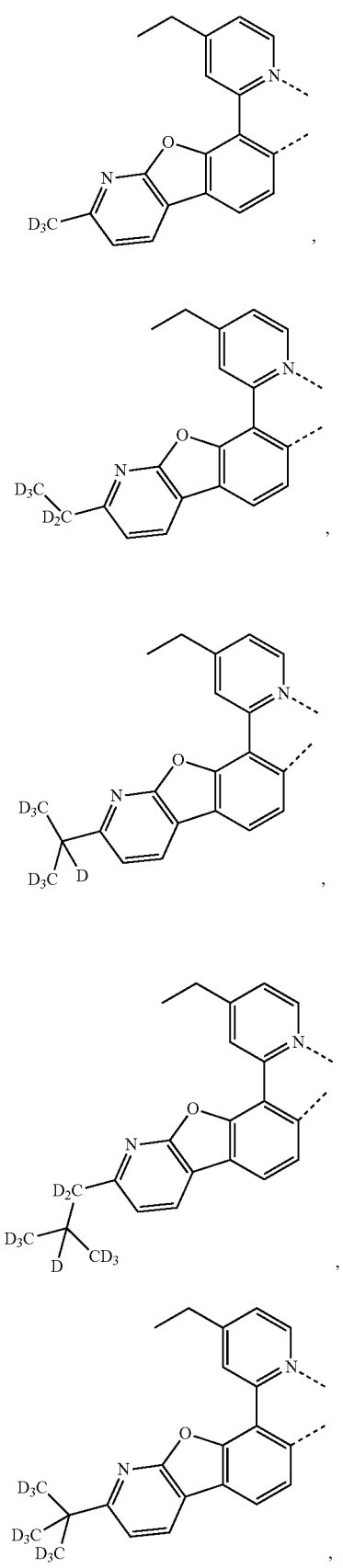
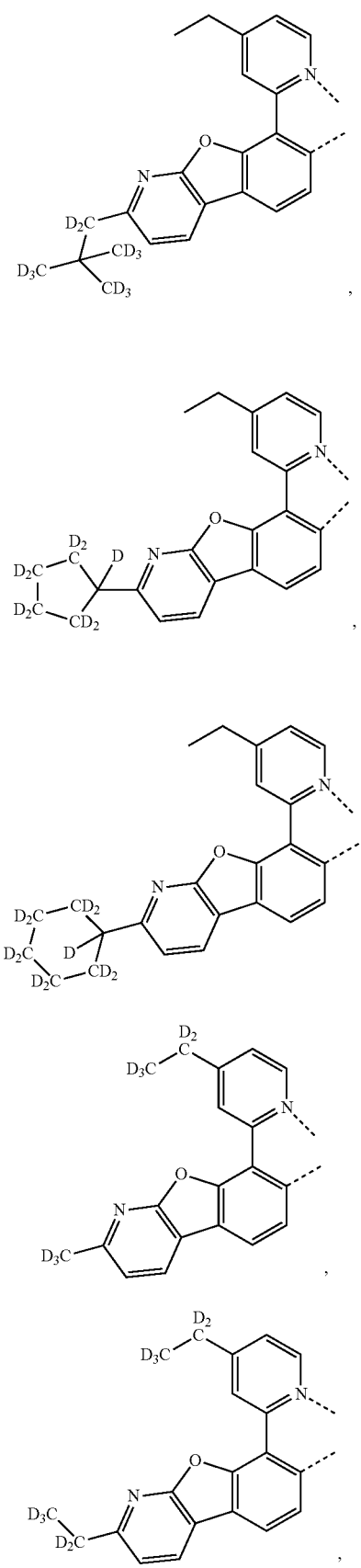

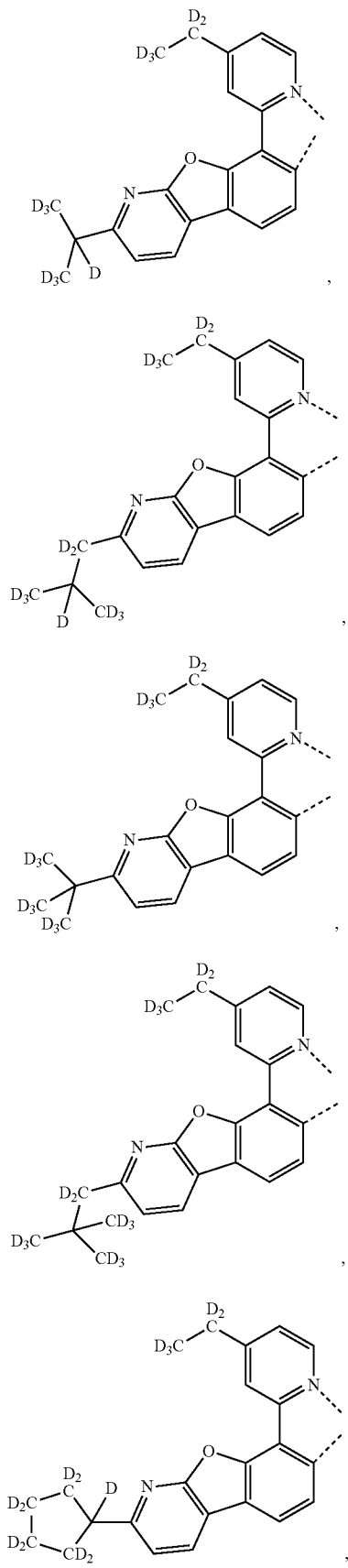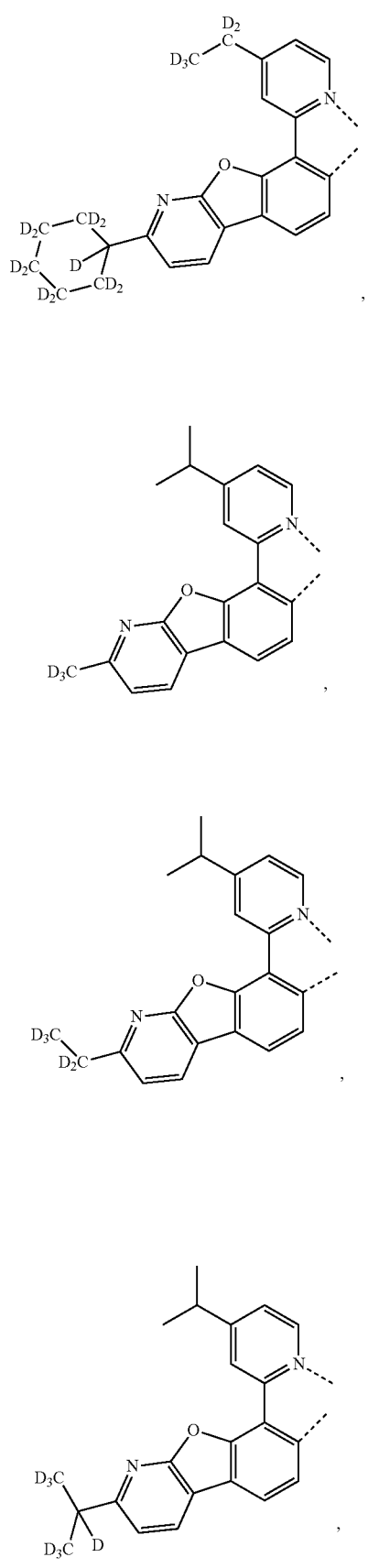

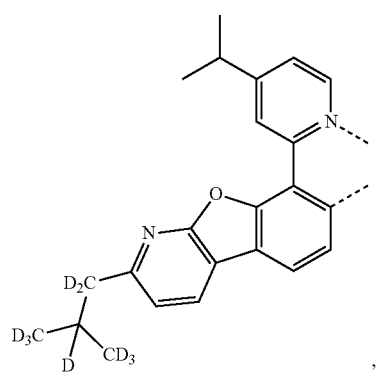
L_{A108}
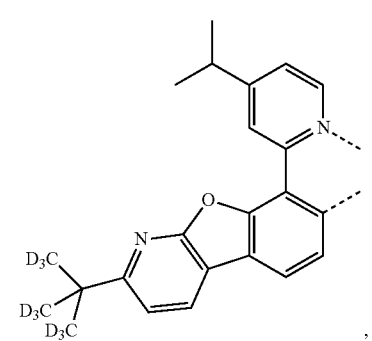
L_{A109}
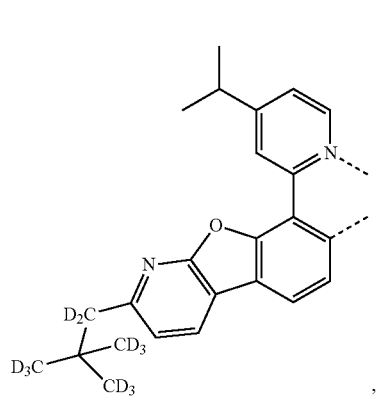
L_{A110}
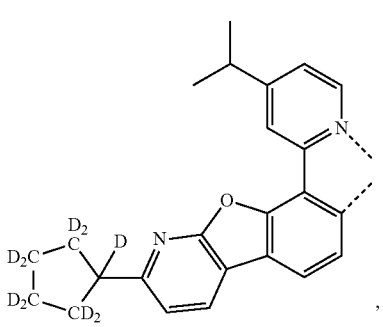
L_{A111}
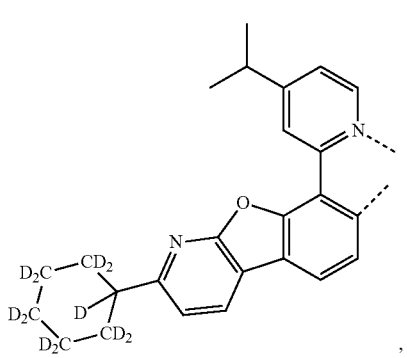
L_{A112}
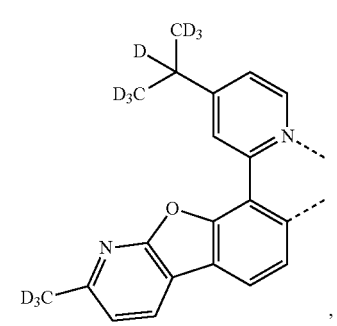
L_{A113}
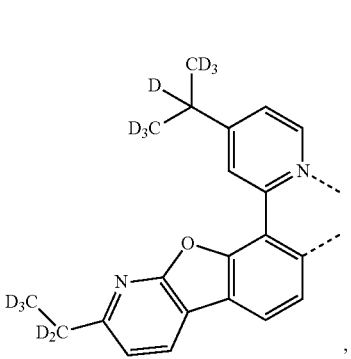
L_{A114}
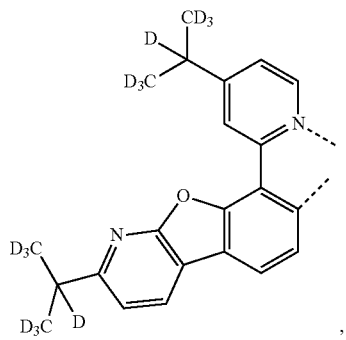
L_{A115}

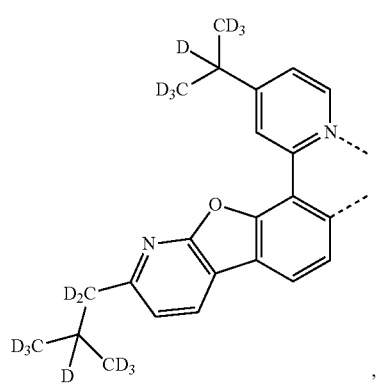 L_{A116}
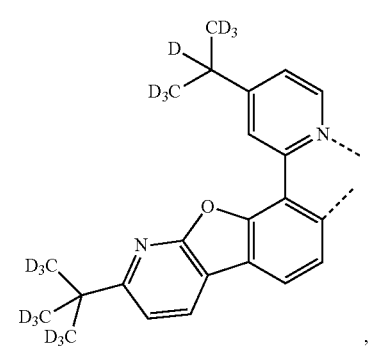 L_{A117}
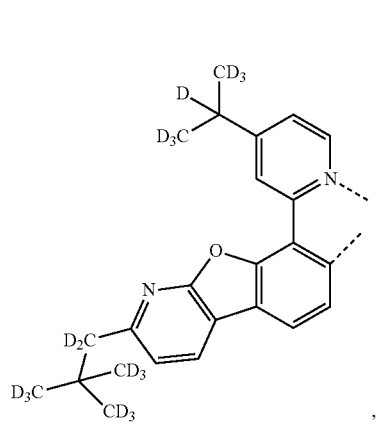 L_{A118}
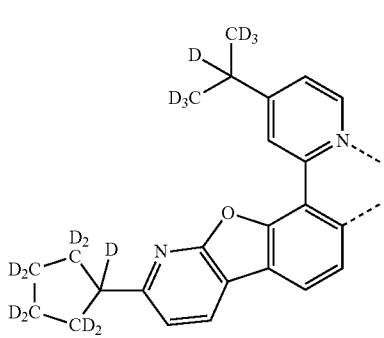 L_{A119}
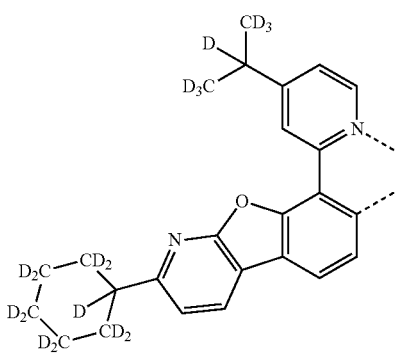 L_{A120}
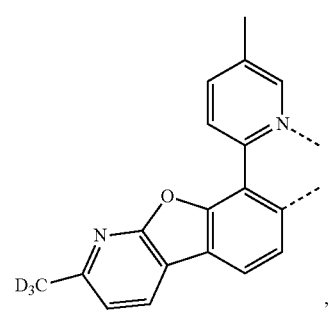 L_{A121}
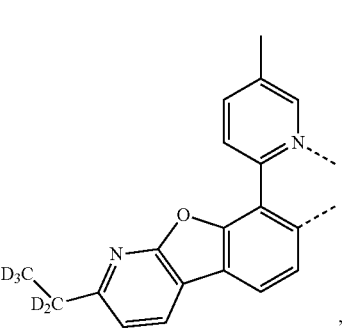 L_{A122}
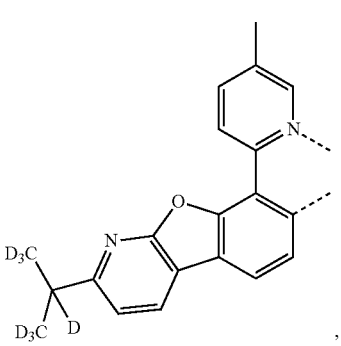 L_{A123}

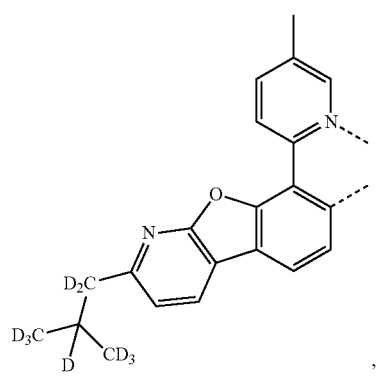
L<sub>A124</sub>
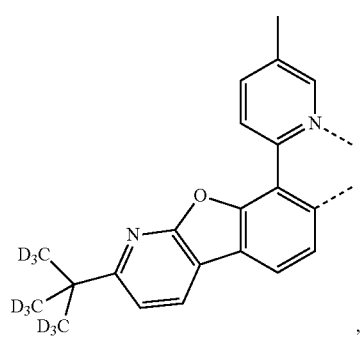
L<sub>A125</sub>
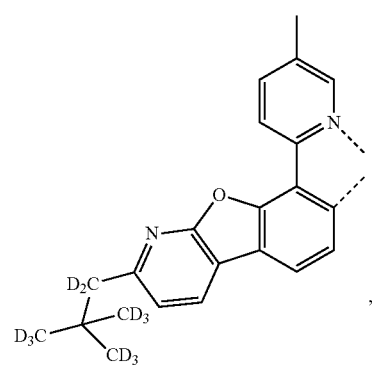
L<sub>A126</sub>
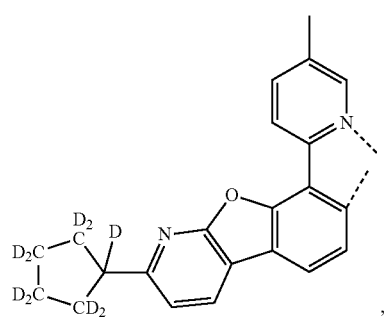
L<sub>A127</sub>
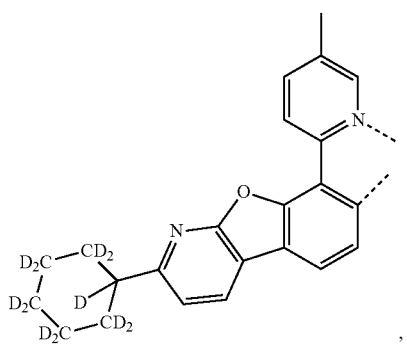
L<sub>A128</sub>
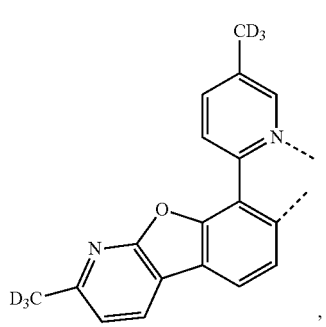
L<sub>A129</sub>
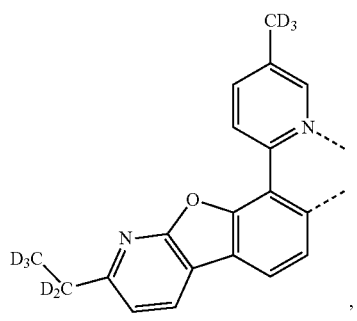
L<sub>A130</sub>
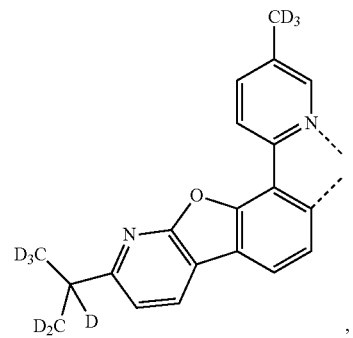
L<sub>A131</sub>

L_{A132}
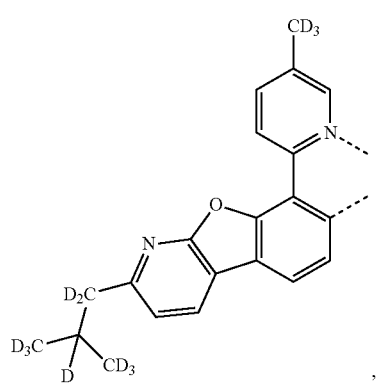
L_{A133}
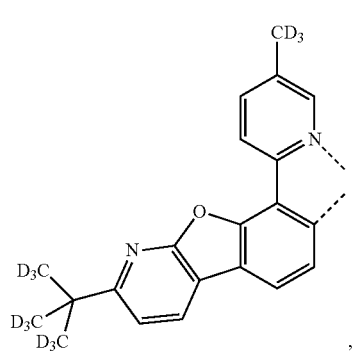
L_{A134}
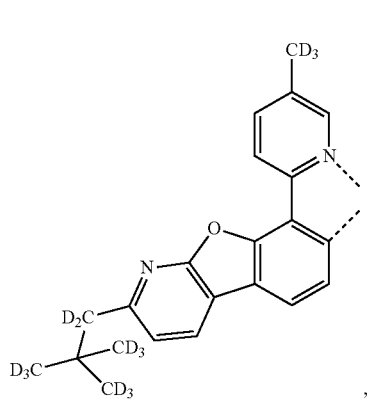
L_{A135}
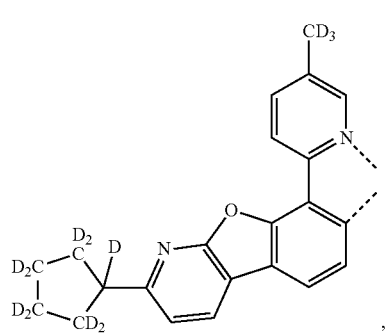
L_{A136}
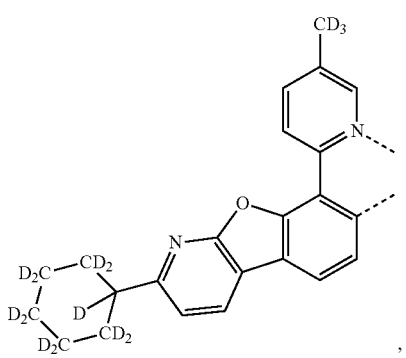
L_{A137}
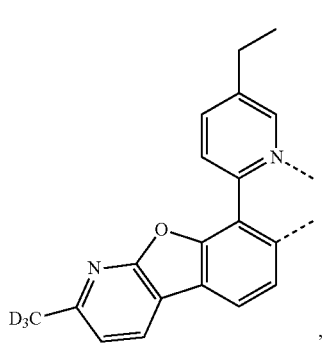
L_{A138}
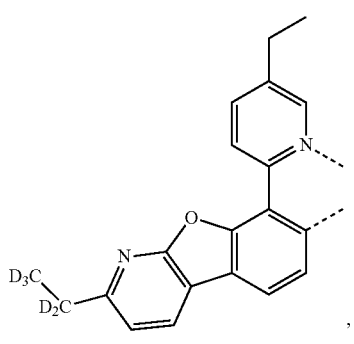
L_{A139}
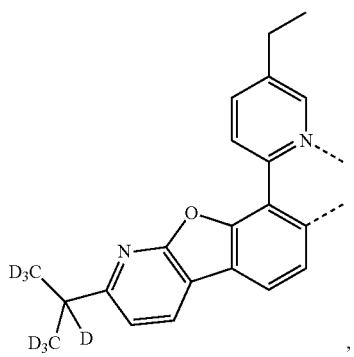

-continued
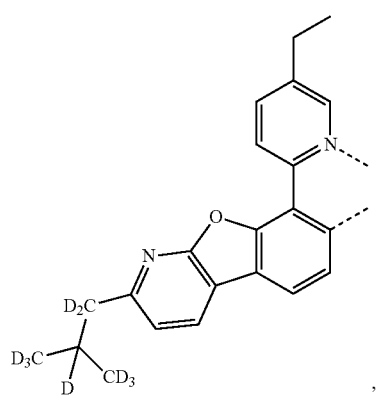 L_A140
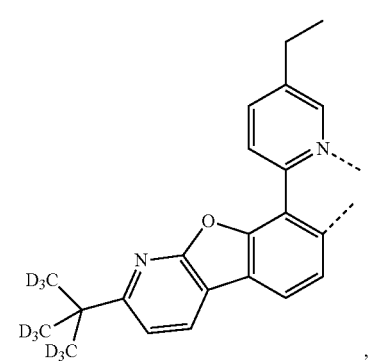 L_A141
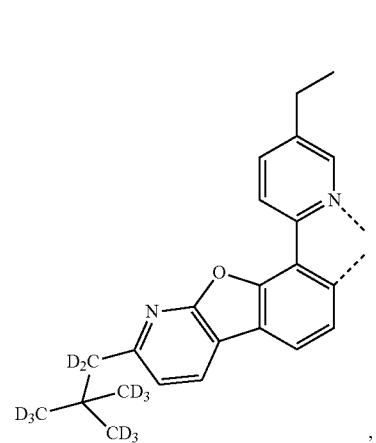 L_A142
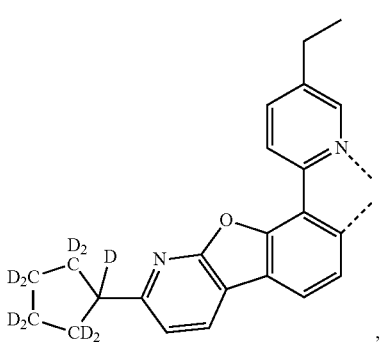 L_A143
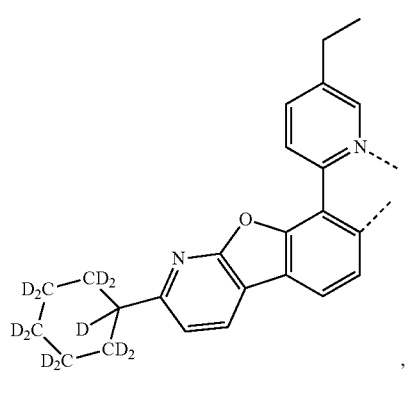 L_A144
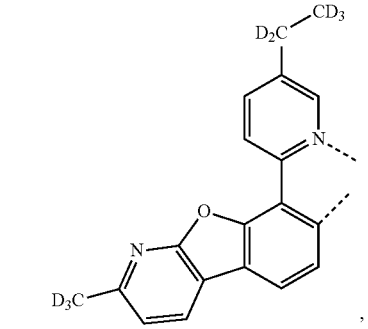 L_A145
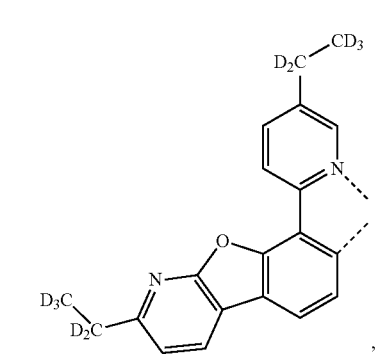 L_A146
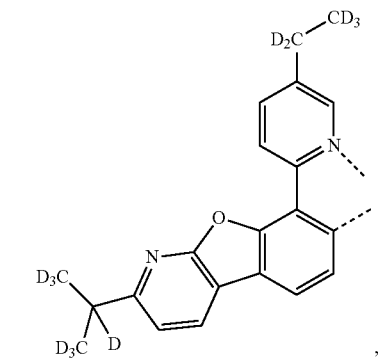 L_A147

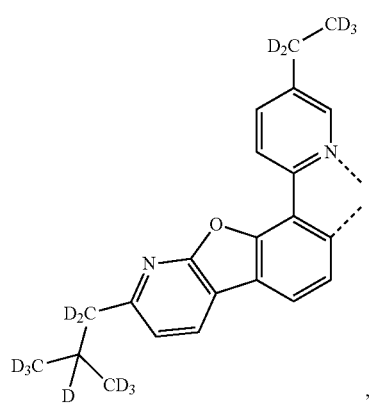 L_A148
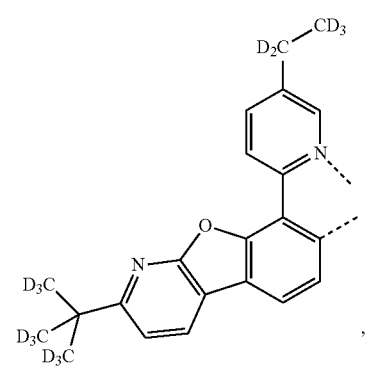 L_A149
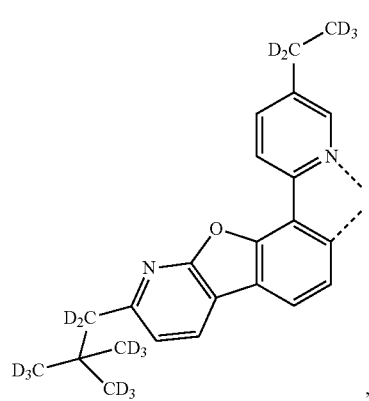 L_A150
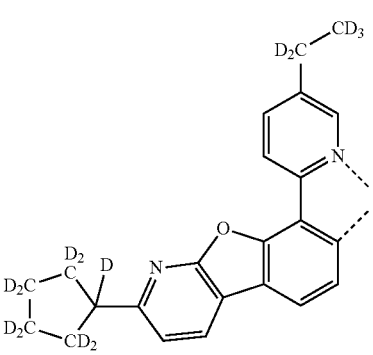 L_A151
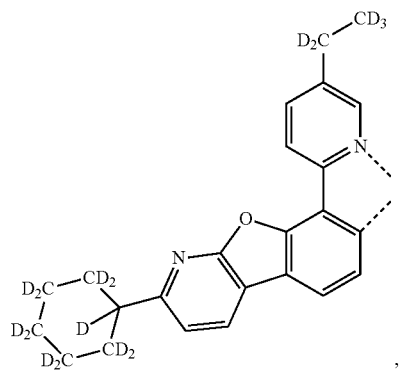 L_A152
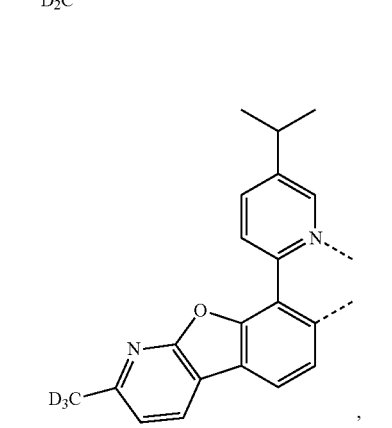 L_A153
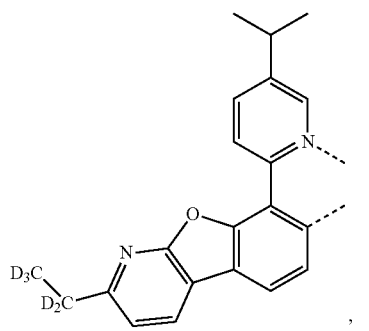 L_A154
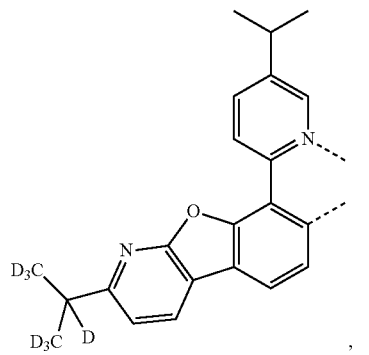 L_A155

-continued

L<sub>A156</sub>, L<sub>A157</sub>, L<sub>A158</sub>, L<sub>A159</sub>, L<sub>A160</sub>, L<sub>A161</sub>, L<sub>A162</sub>, L<sub>A163</sub>

-continued
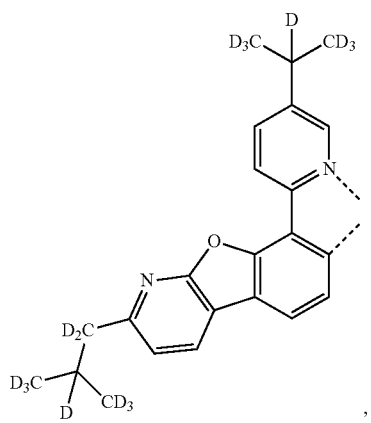
L_{A164}
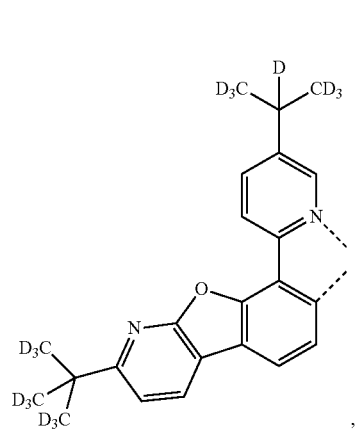
L_{A165}
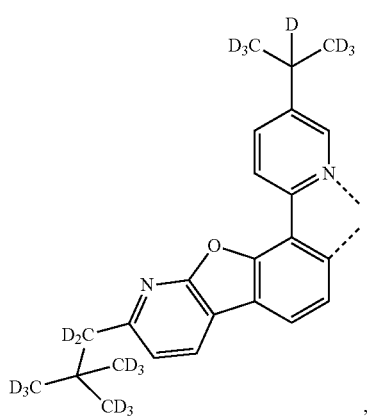
L_{A166}
L_{A167}
-continued
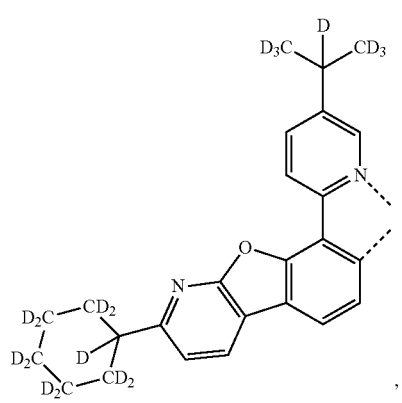
L_{A168}
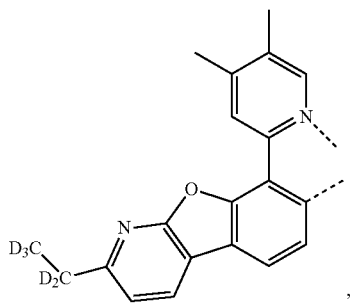
L_{A169}
L_{A170}
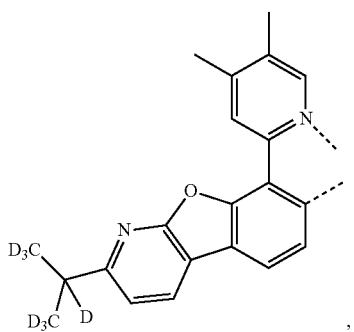
L_{A171}
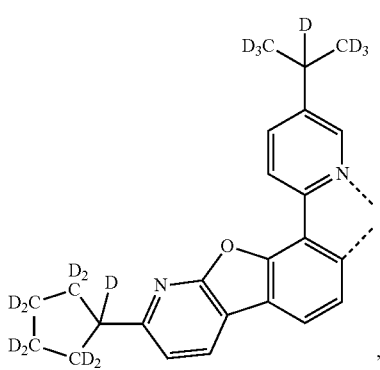

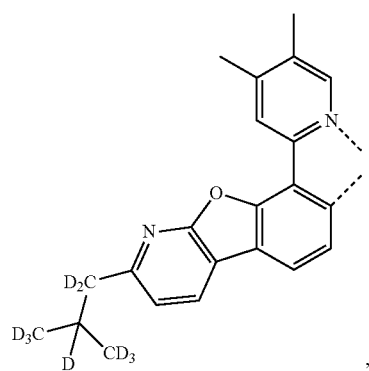
L<sub>A172</sub>,
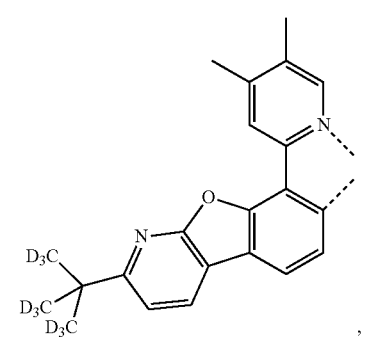
L<sub>A173</sub>,
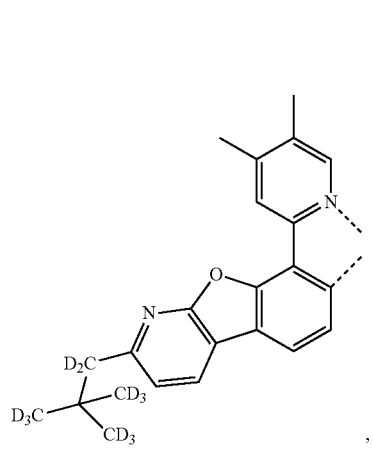
L<sub>A174</sub>,
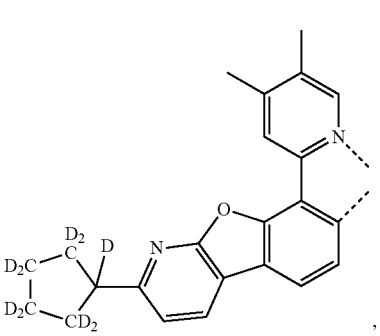
L<sub>A175</sub>,
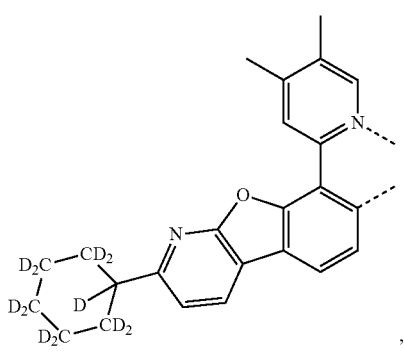
L<sub>A176</sub>,
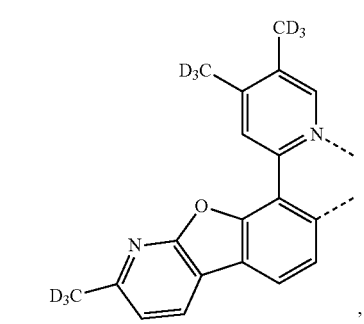
L<sub>A177</sub>,
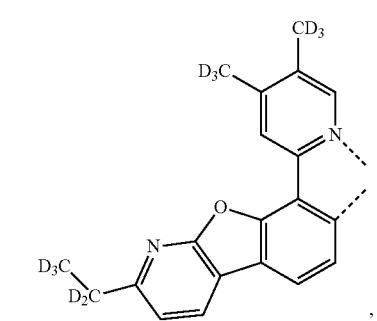
L<sub>A178</sub>,
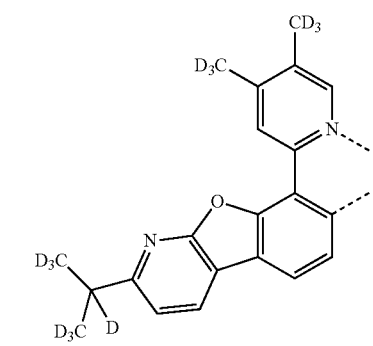
L<sub>A179</sub>,

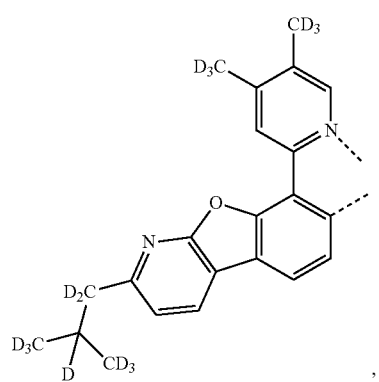 L_{A180}
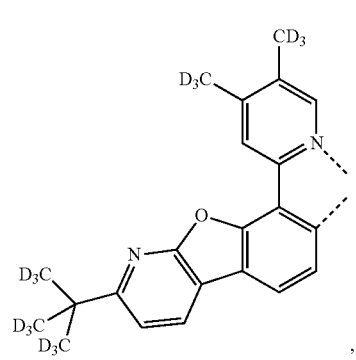 L_{A181}
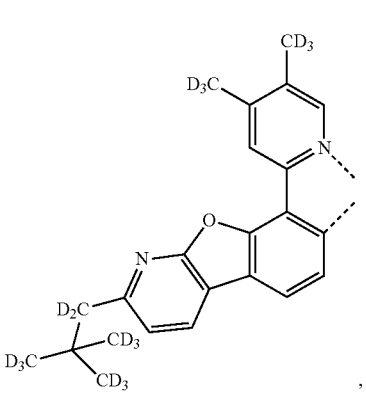 L_{A182}
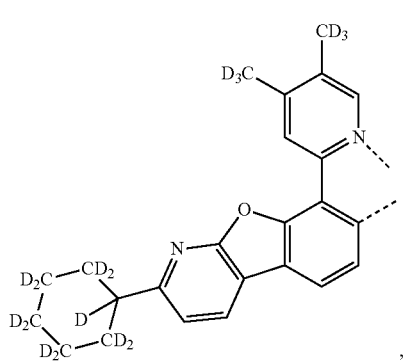 L_{A184}
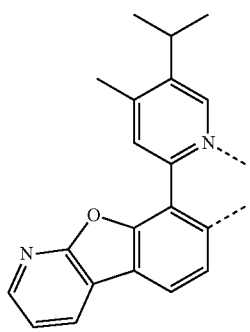 L_{A185}
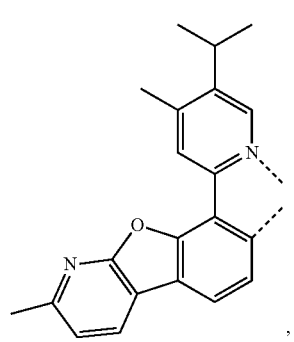 L_{A186}
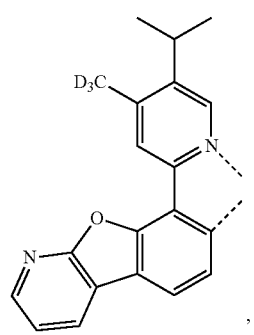 L_{A187}
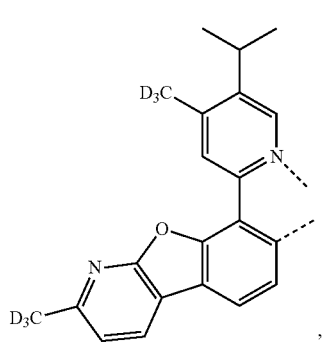 L_{A188}

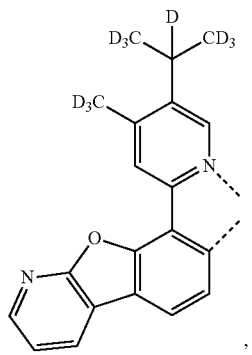 L_{A189}
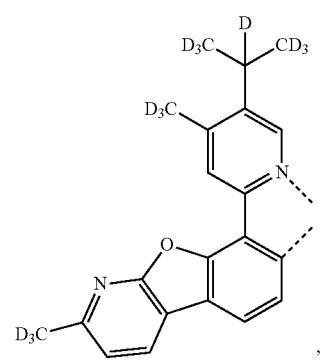 L_{A190}
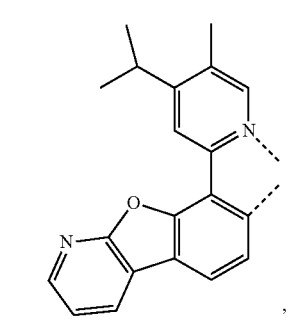 L_{A191}
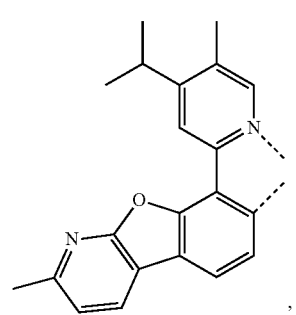 L_{A192}
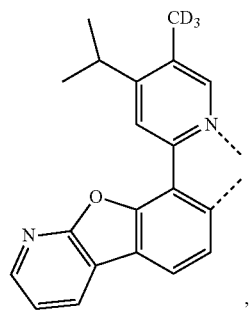 L_{A193}
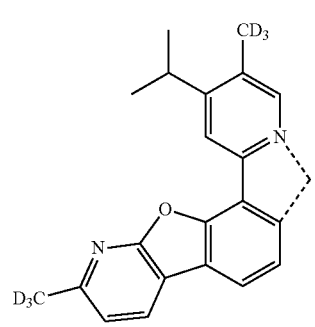 L_{A194}
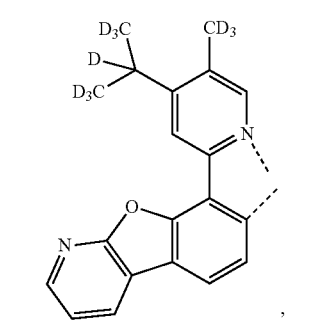 L_{A195}
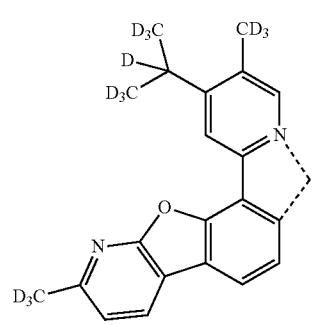 L_{A196}
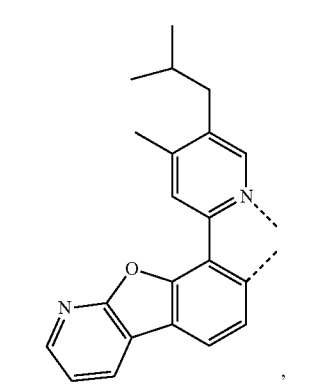 L_{A197}

L_{A198}
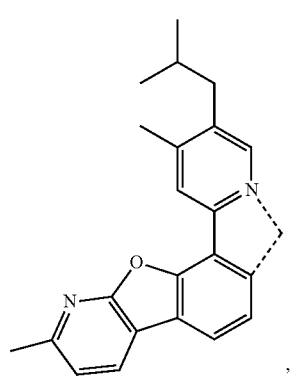
L_{A199}
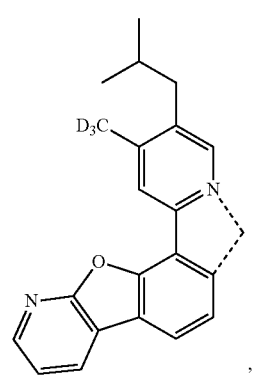
L_{A200}
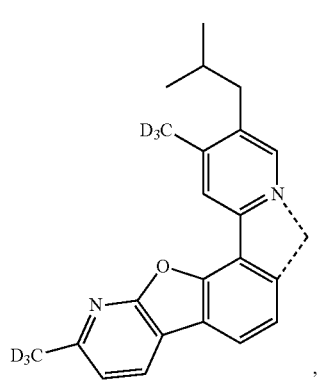
L_{A201}
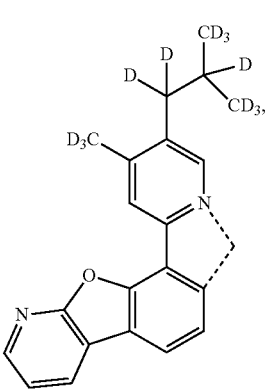
L_{A202}
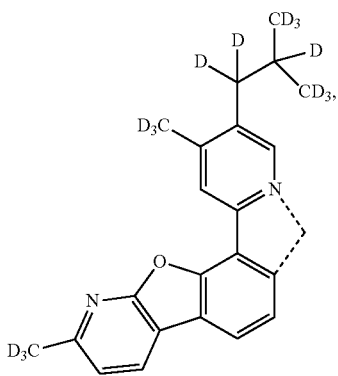
L_{A203}
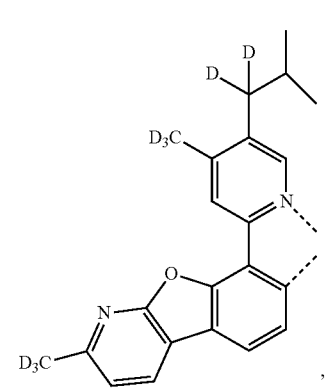
L_{A204}
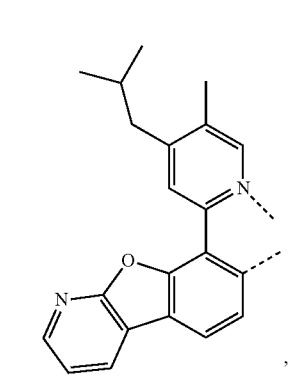
L_{A205}
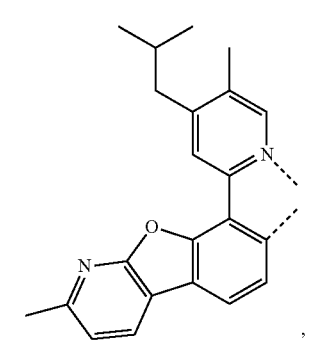

L_A206 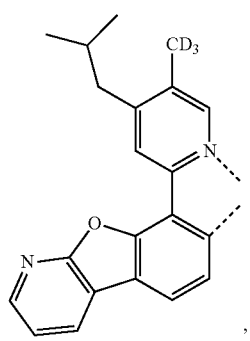
L_A207 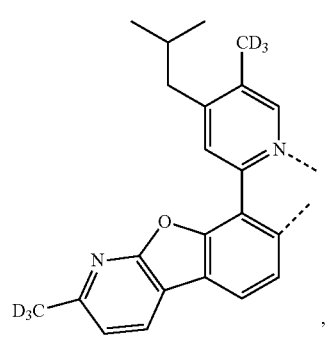
L_A208 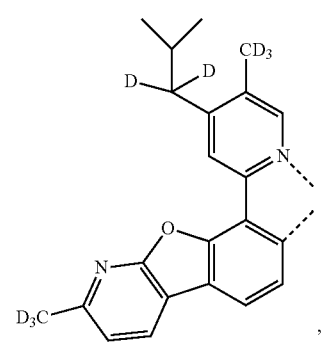
L_A209 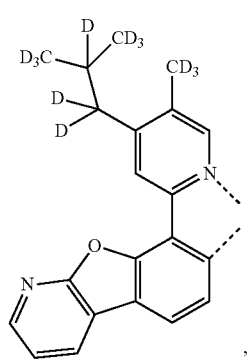
L_A210 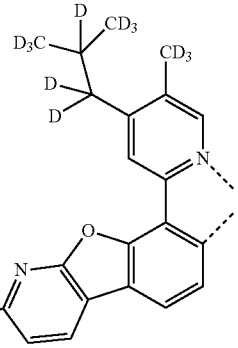
L_A211 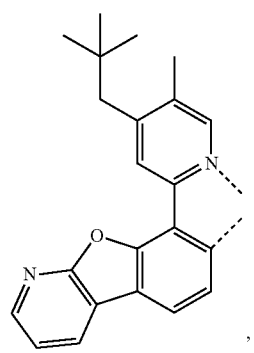
L_A212 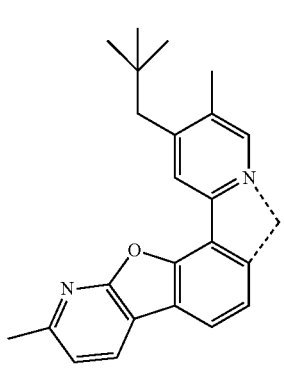
L_A213 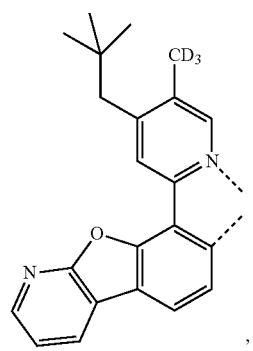

L<sub>A214</sub>
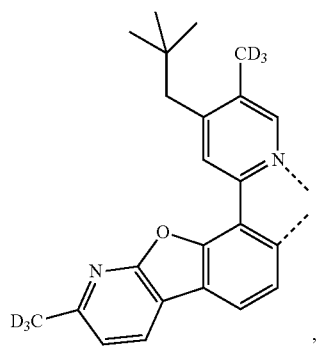
L<sub>A215</sub>
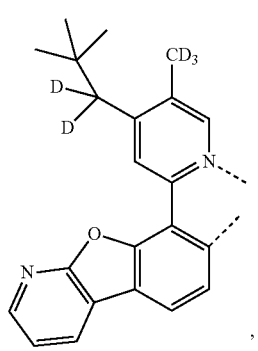
L<sub>A216</sub>
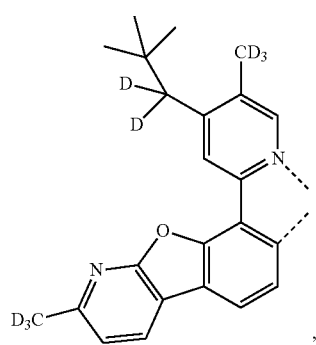
L<sub>A217</sub>
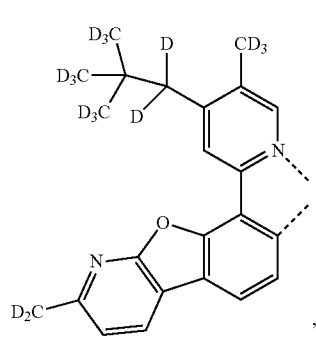
L<sub>A218</sub>
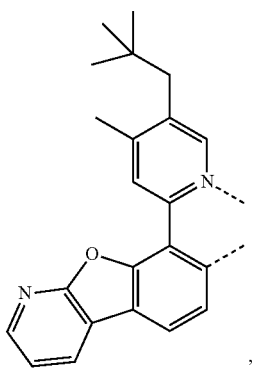
L<sub>A219</sub>
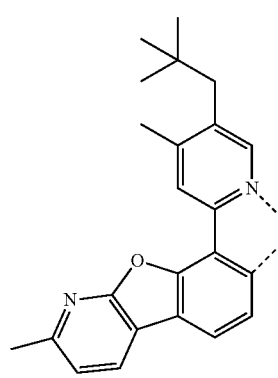
L<sub>A220</sub>
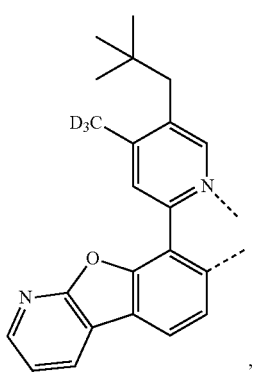
L<sub>A221</sub>
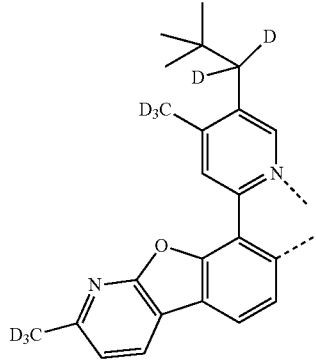

L<sub>A222</sub> 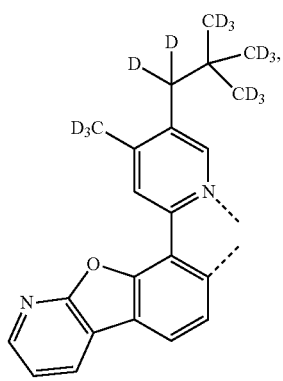
L<sub>A223</sub> 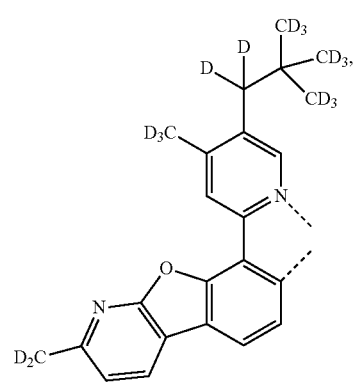
L<sub>A224</sub> 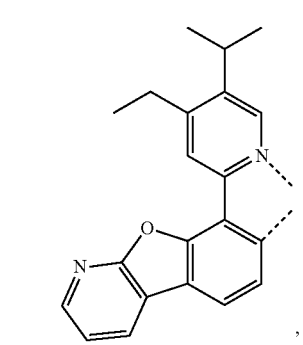
L<sub>A225</sub> 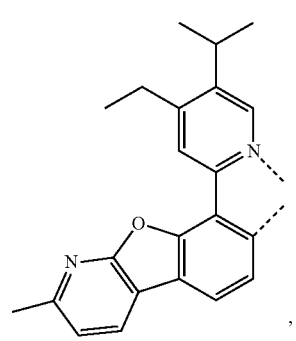
L<sub>A226</sub> 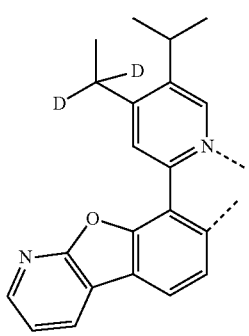
L<sub>A227</sub> 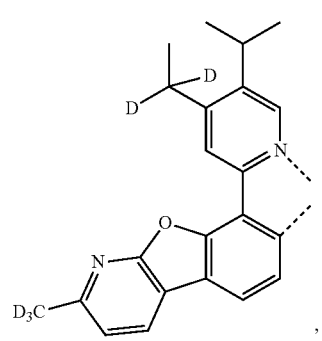
L<sub>A228</sub> 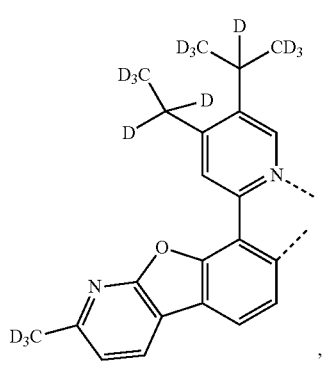
L<sub>A229</sub> 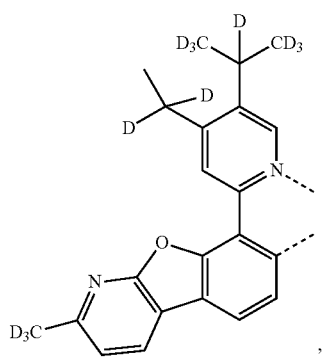

L<sub>A230</sub>
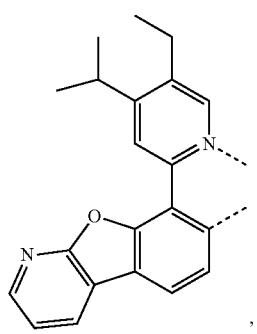
L<sub>A231</sub>
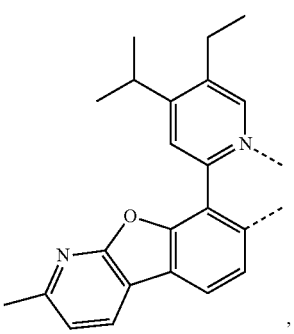
L<sub>A232</sub>
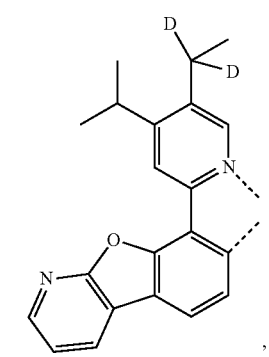
L<sub>A233</sub>
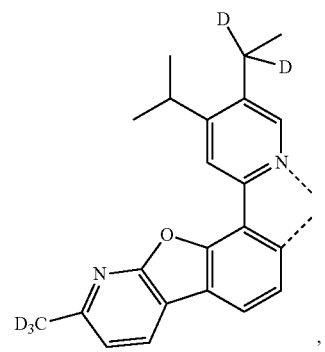
L<sub>A234</sub>
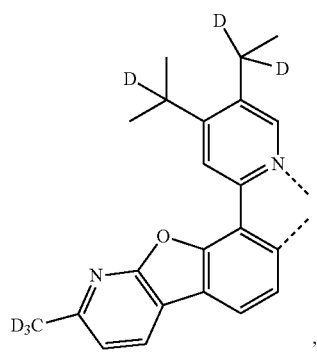
L<sub>A235</sub>
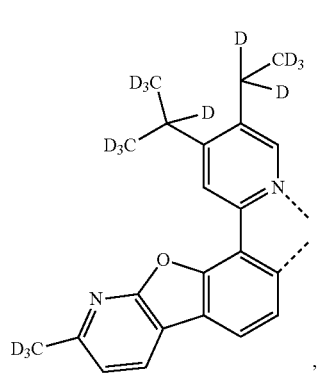
L<sub>A236</sub>
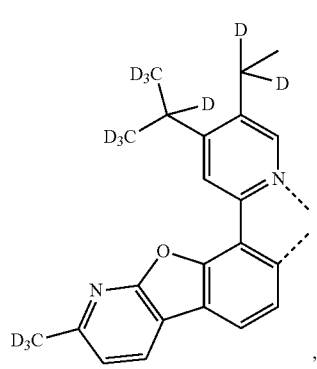
L<sub>A237</sub>
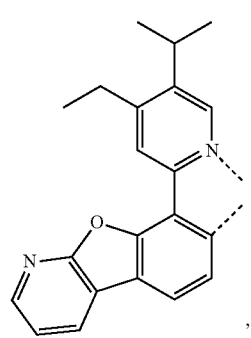

L<sub>A238</sub>
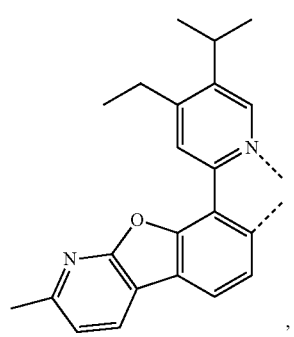
L<sub>A239</sub>
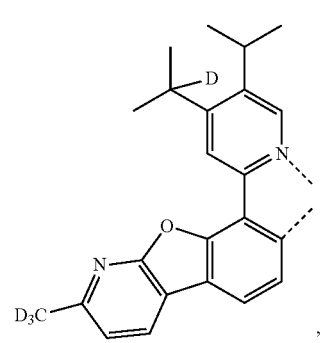
L<sub>A240</sub>
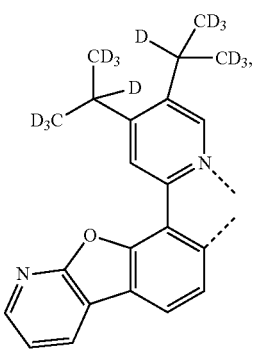
L<sub>A241</sub>
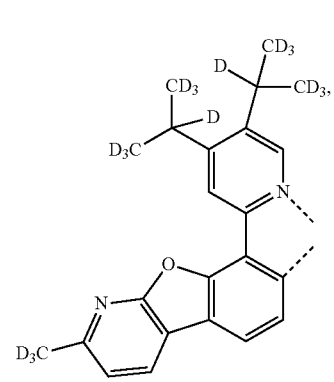
L<sub>A242</sub>
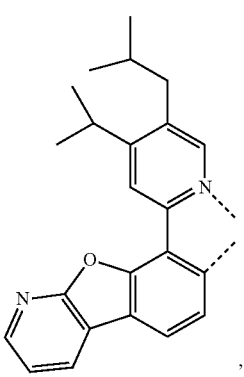
L<sub>A243</sub>
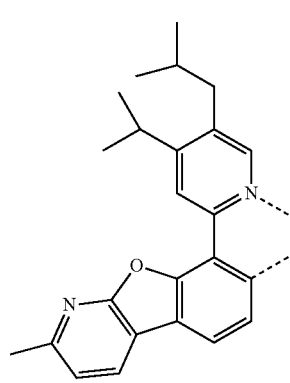
L<sub>A244</sub>
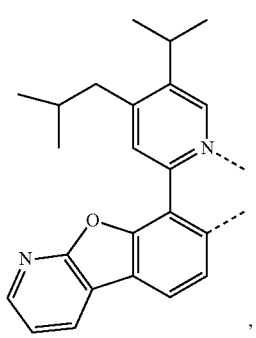
L<sub>A245</sub>
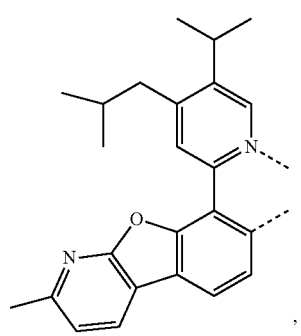

L<sub>A246</sub> 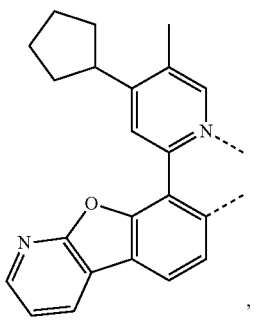
L<sub>A247</sub> 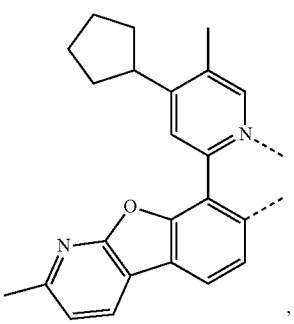
L<sub>A248</sub> 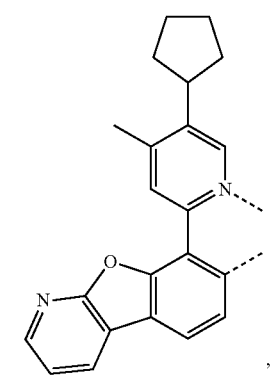
L<sub>A249</sub> 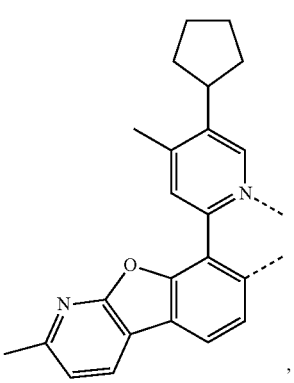
L<sub>A250</sub> 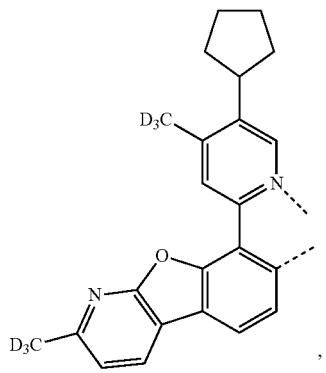
L<sub>A251</sub> 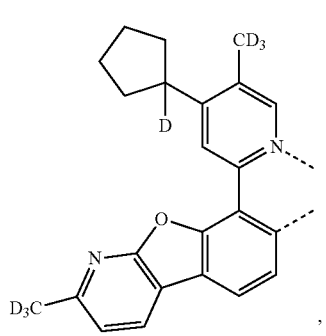
L<sub>A252</sub> 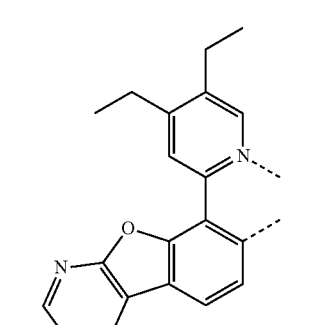
L<sub>A253</sub> 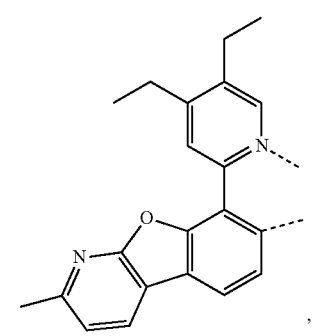

L<sub>A254</sub>
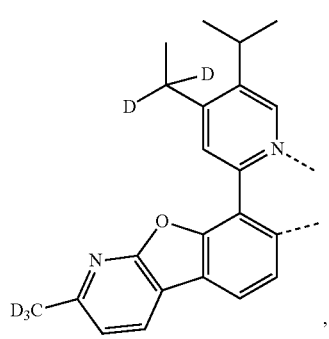
L<sub>A255</sub>
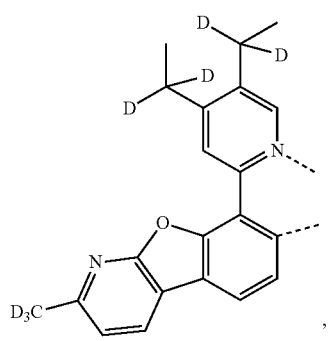
L<sub>A256</sub>
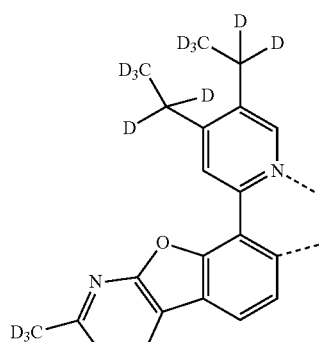
L<sub>A257</sub>
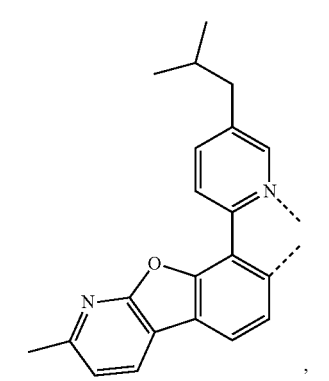
L<sub>A258</sub>
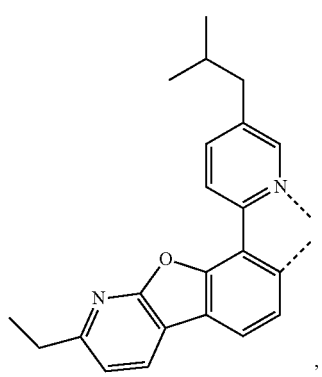
L<sub>A259</sub>
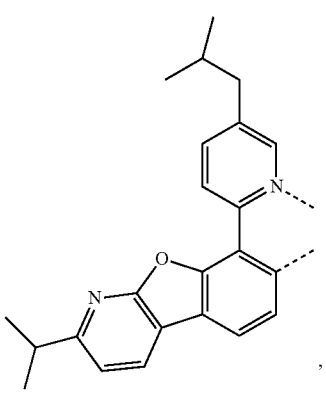
L<sub>A260</sub>
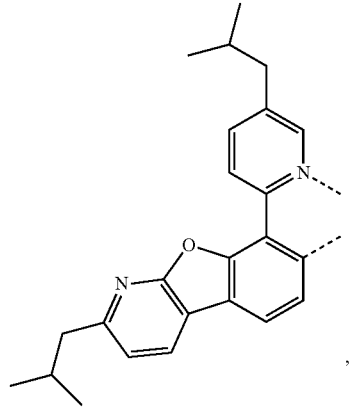
L<sub>A261</sub>
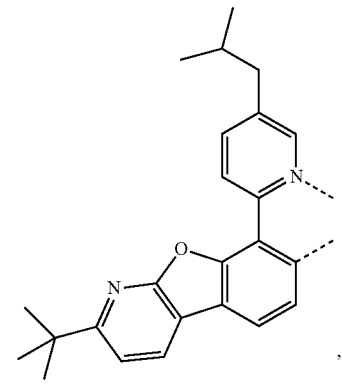

L<sub>A262</sub>
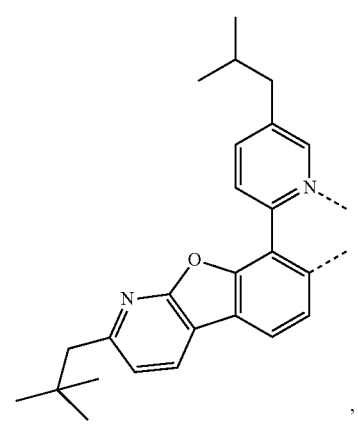
L<sub>A263</sub>
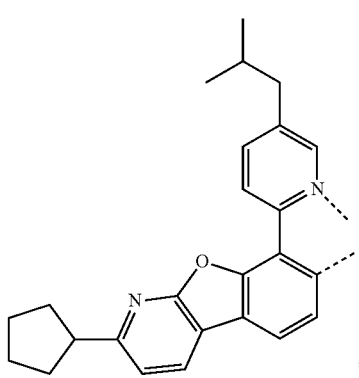
L<sub>A264</sub>
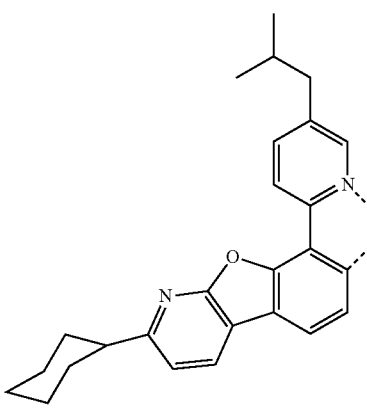
L<sub>A265</sub>
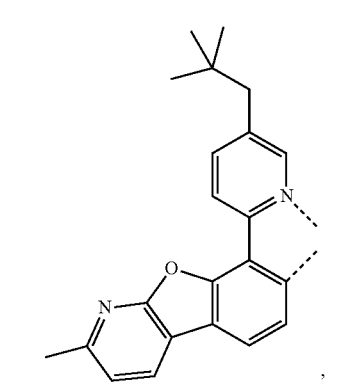
L<sub>A266</sub>
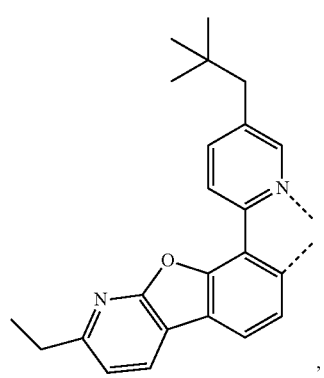
L<sub>A267</sub>
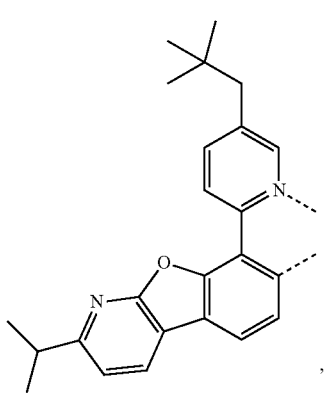
L<sub>A268</sub>
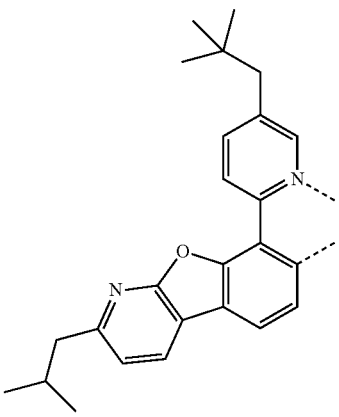
L<sub>A269</sub>
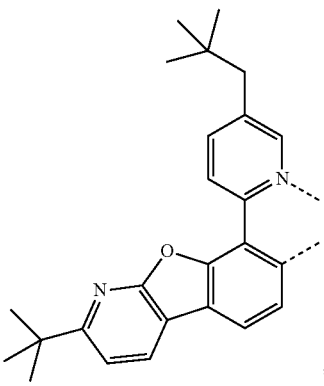

L_{A270}
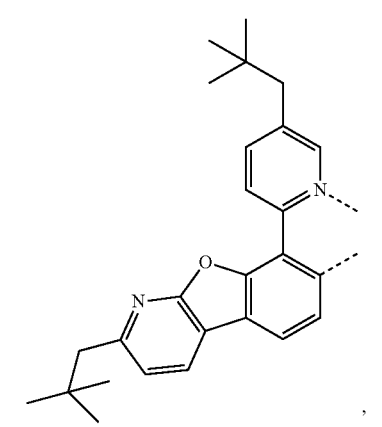
L_{A271}
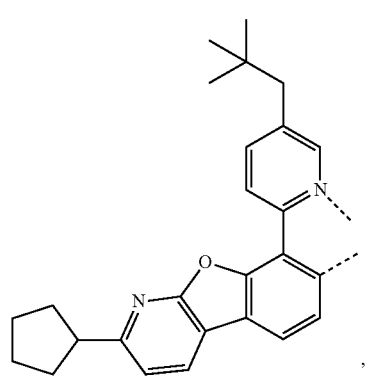
L_{A273}
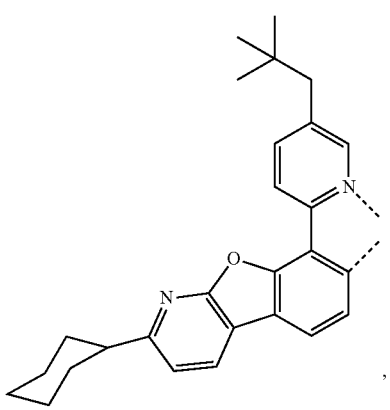
L_{A274}
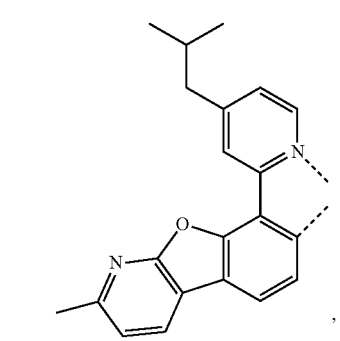
L_{A275}
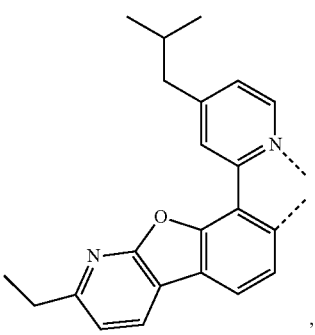
L_{A276}
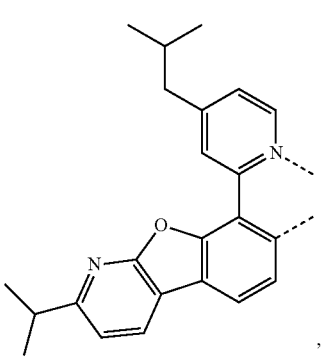
L_{A277}
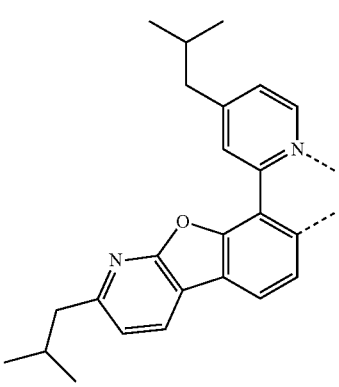
L_{A278}
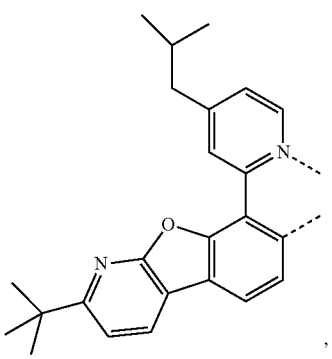

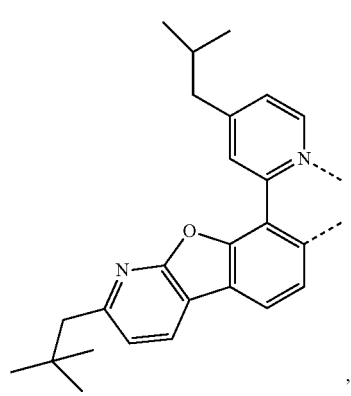 L_A279
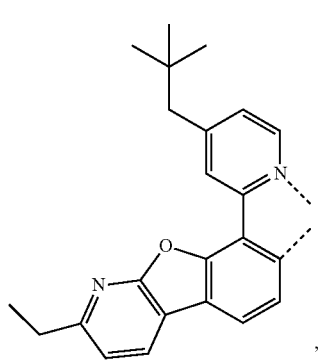 L_A283
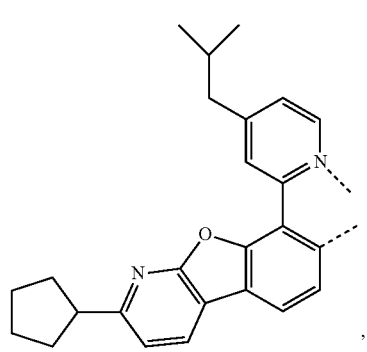 L_A280
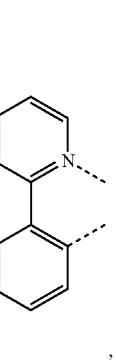 L_A284
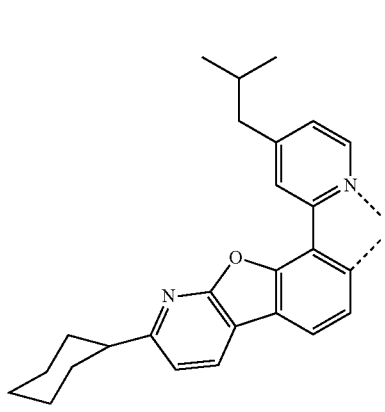 L_A281
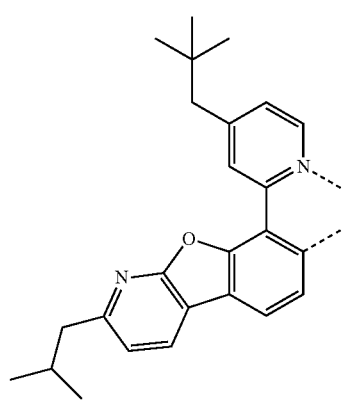 L_A285
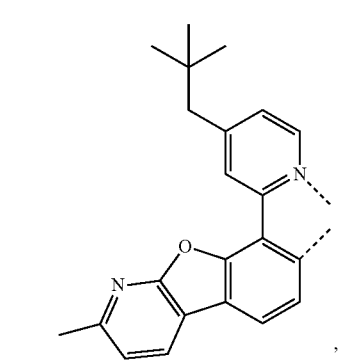 L_A282
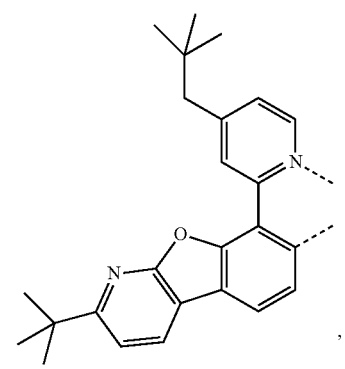 L_A286

-continued
L$_{A287}$
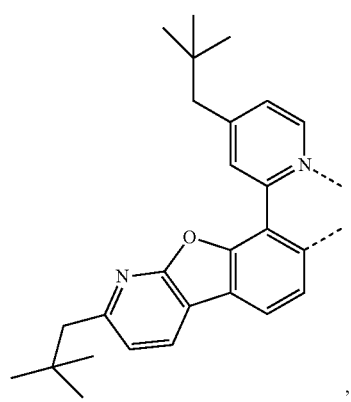
L$_{A288}$
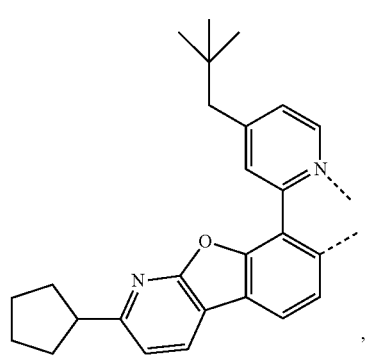
L$_{A289}$
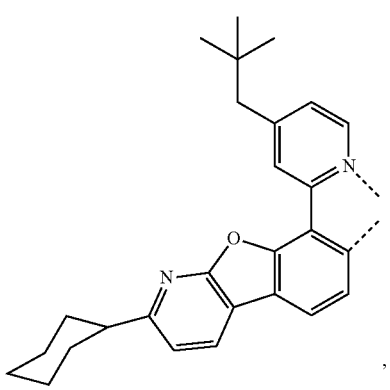
L$_{A290}$
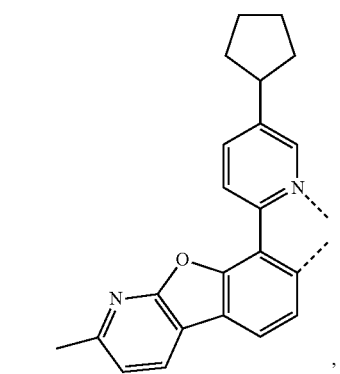
-continued
L$_{A291}$
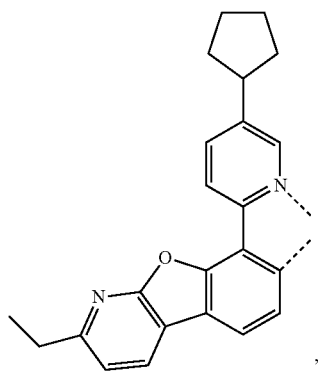
L$_{A292}$
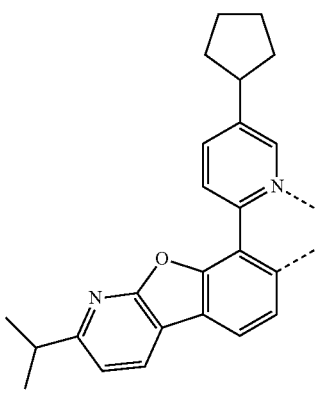
L$_{A293}$
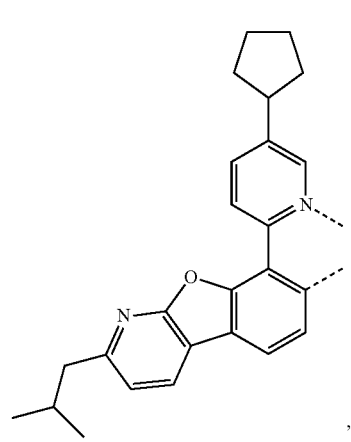
L$_{A294}$
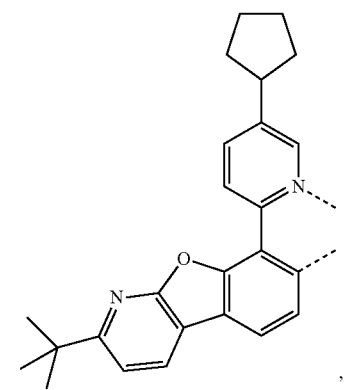

L<sub>A295</sub>
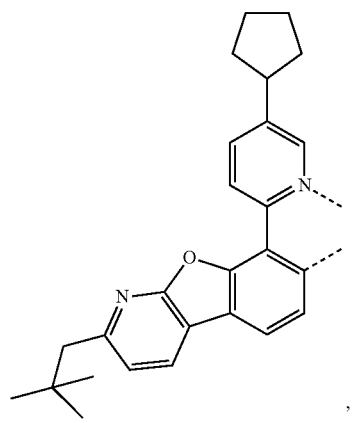
L<sub>A296</sub>
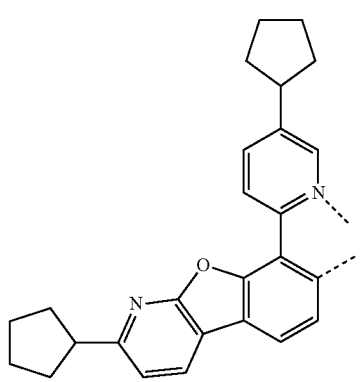
L<sub>A297</sub>
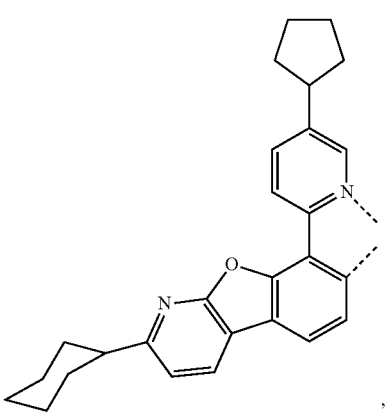
L<sub>A298</sub>
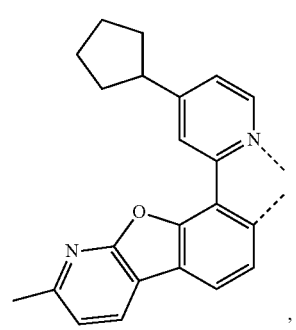
L<sub>A299</sub>
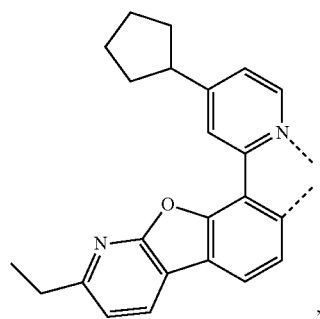
L<sub>A300</sub>
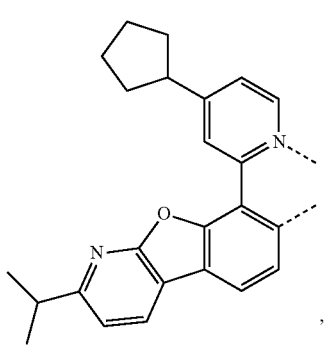
L<sub>A301</sub>
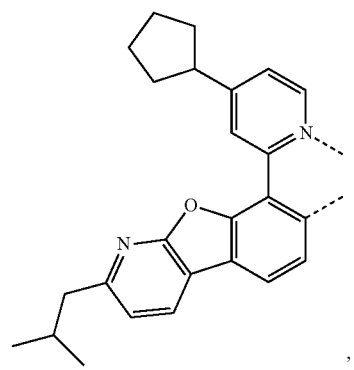
L<sub>A302</sub>
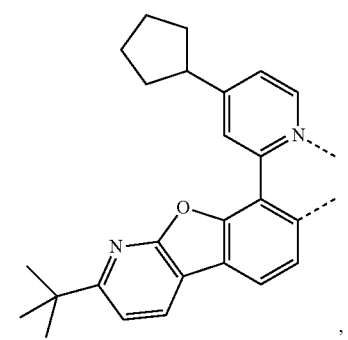

L_{A303}
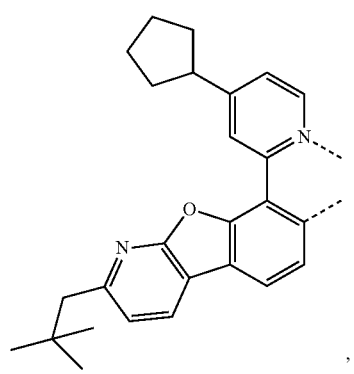
L_{A304}
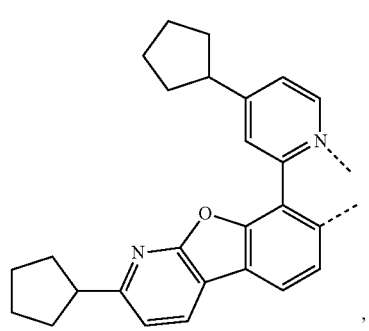
L_{A305}
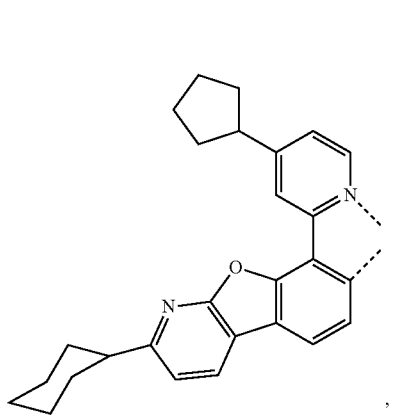
L_{A306}
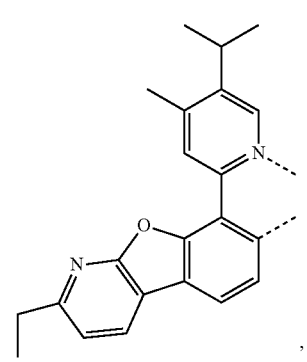
L_{A307}
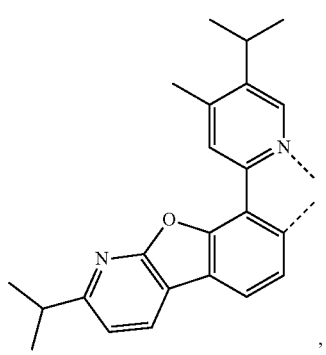
L_{A308}
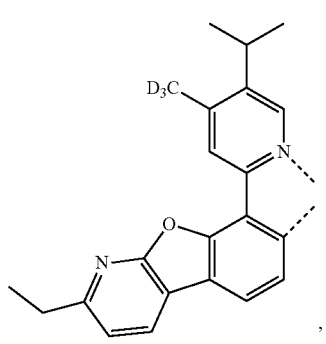
L_{A309}
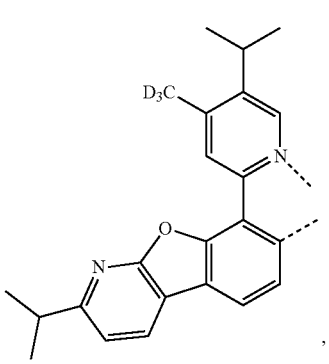
L_{A310}
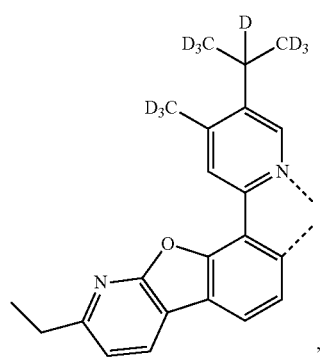

L<sub>A311</sub>
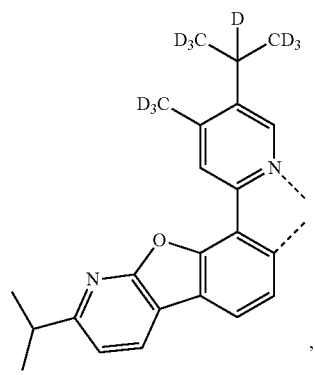
L<sub>A312</sub>
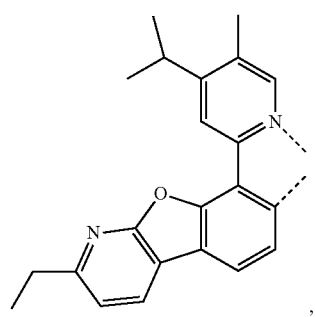
L<sub>A313</sub>
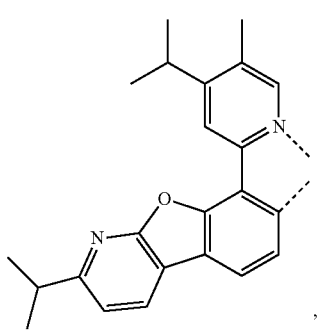
L<sub>A314</sub>
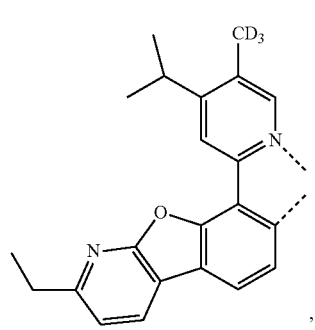
L<sub>A315</sub>
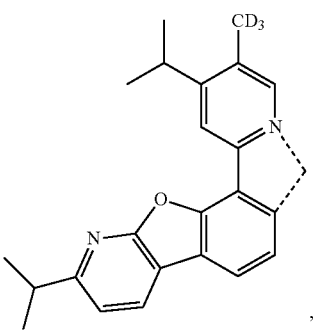
L<sub>A316</sub>
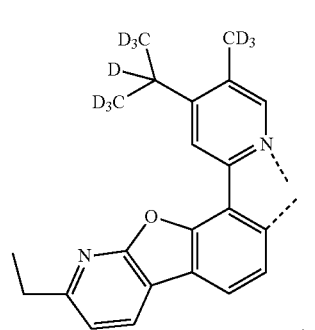
L<sub>A317</sub>
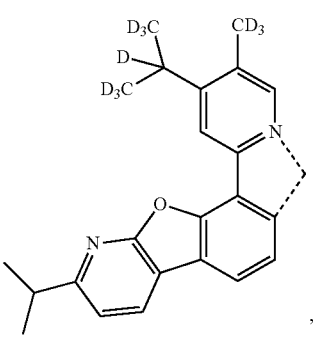
L<sub>A318</sub>
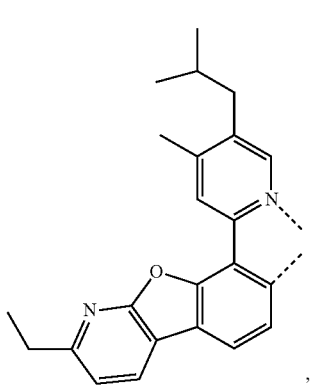

L_{A319}
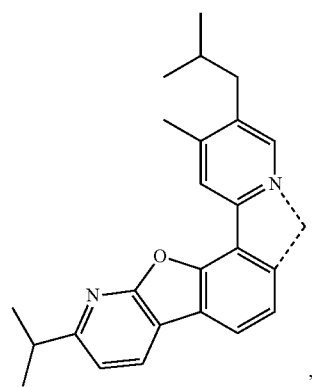
L_{A320}
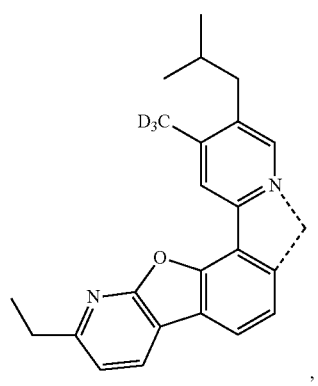
L_{A321}
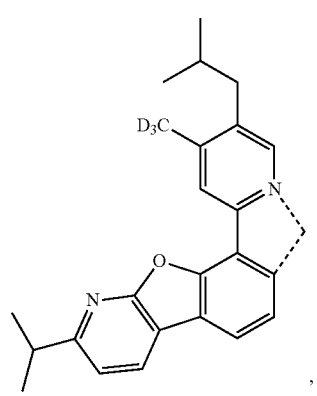
L_{A322}
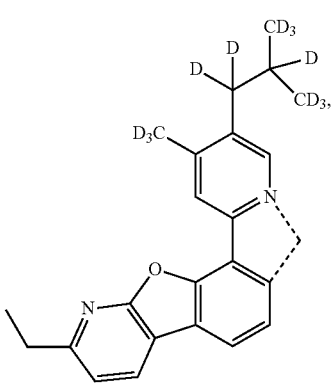
L_{A323}
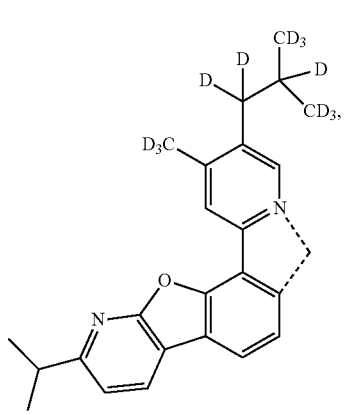
L_{A324}
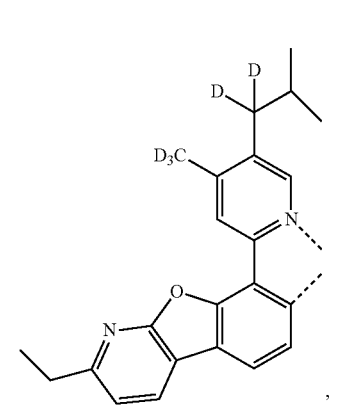
L_{A325}
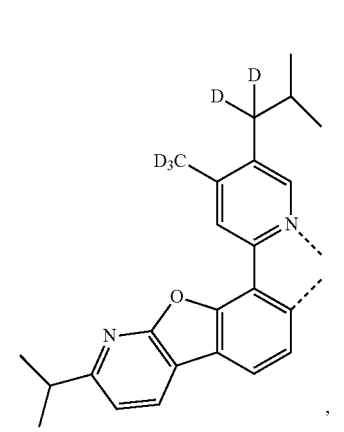
L_{A326}
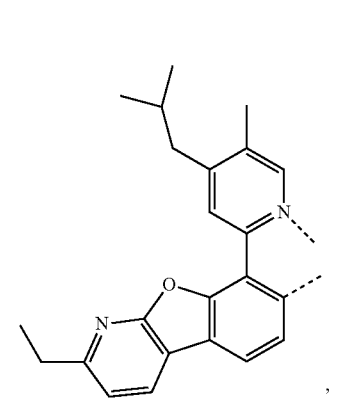

L<sub>A327</sub>
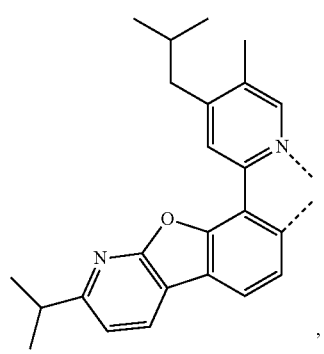
L<sub>A328</sub>
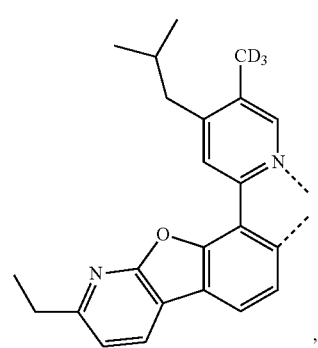
L<sub>A329</sub>
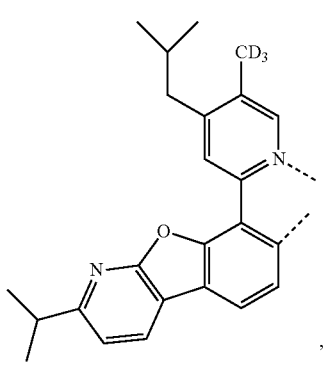
L<sub>A330</sub>
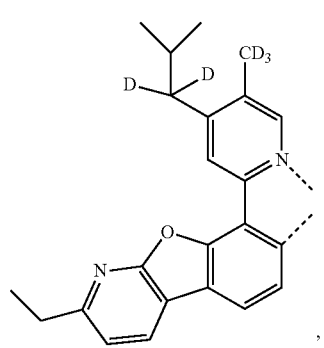
L<sub>A331</sub>
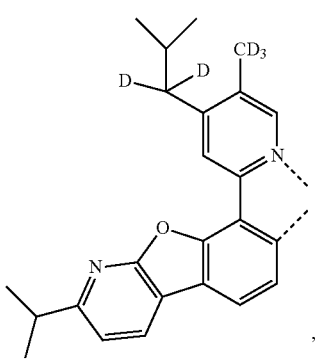
L<sub>A332</sub>
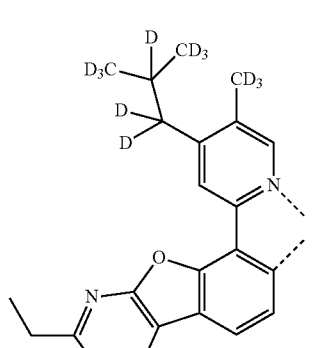
L<sub>A333</sub>
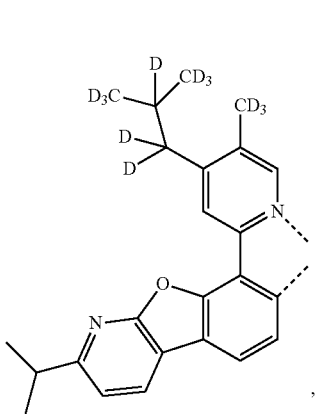
L<sub>A334</sub>
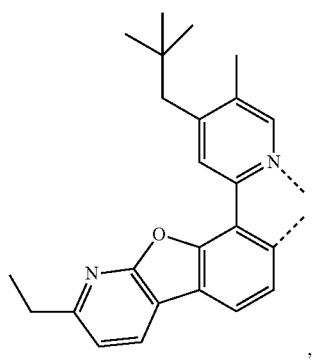

L_{A335}
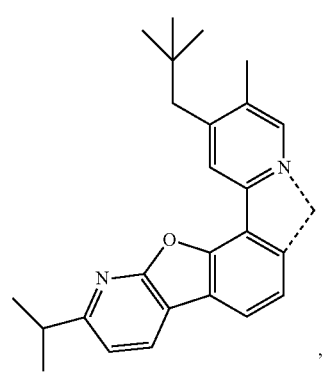
L_{A336}
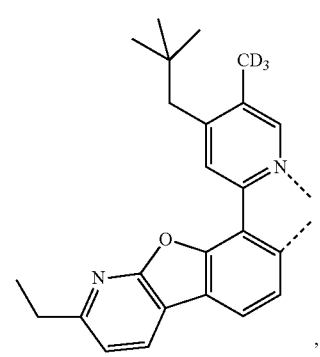
L_{A337}
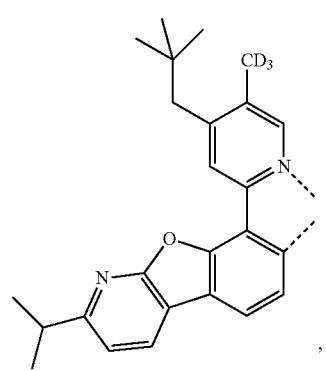
L_{A338}
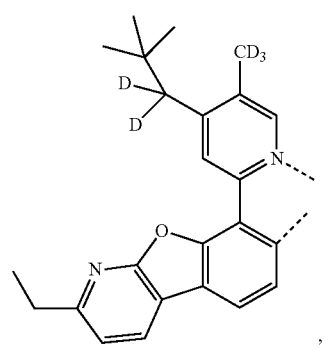
L_{A339}
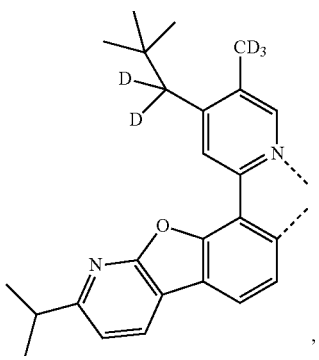
L_{A340}
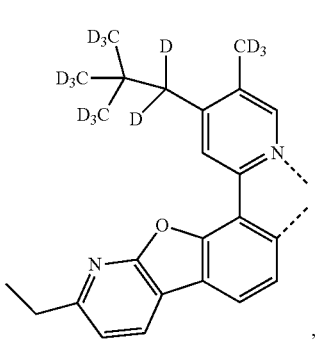
L_{A341}
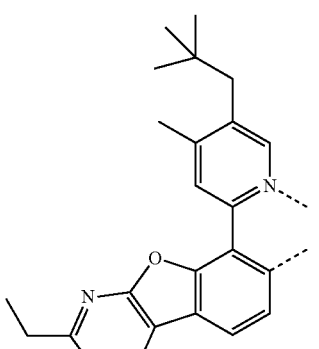
L_{A342}
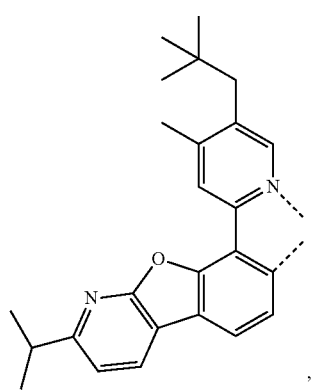

L<sub>A343</sub>
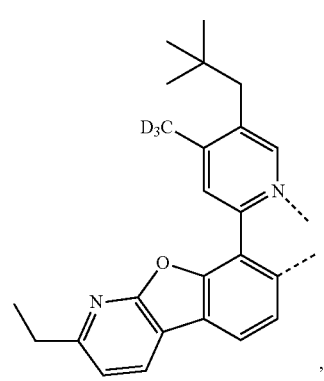
L<sub>A344</sub>
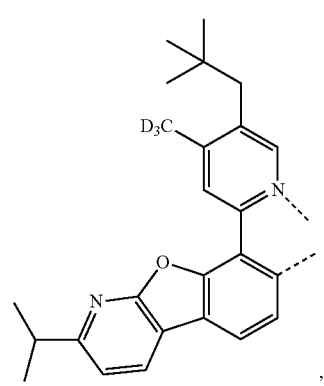
L<sub>A345</sub>
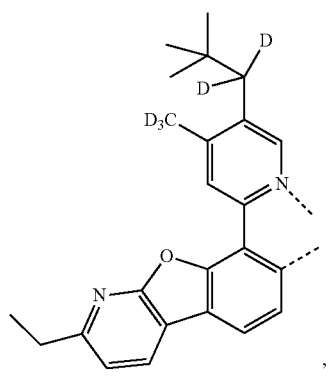
L<sub>A346</sub>
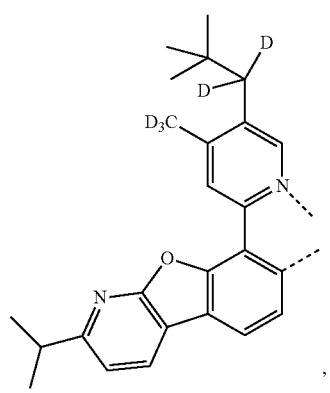
L<sub>A347</sub>
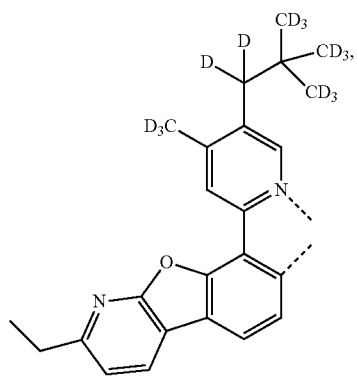
L<sub>A348</sub>
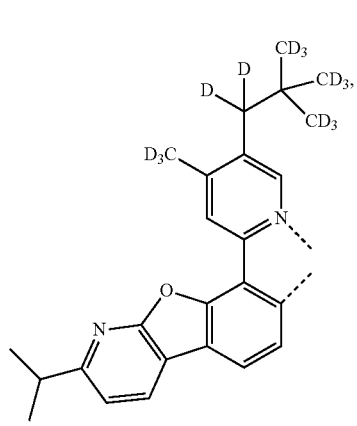
L<sub>A349</sub>
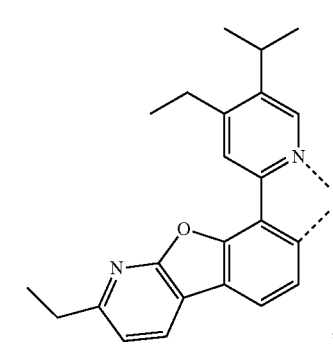
L<sub>A350</sub>
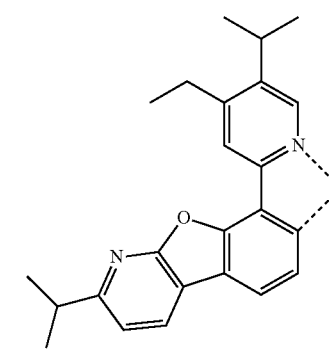

L_{A351}
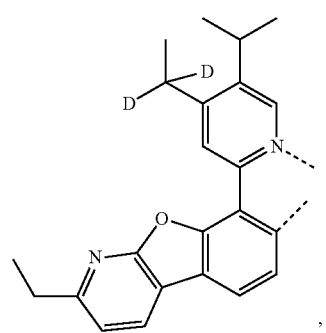
L_{A352}
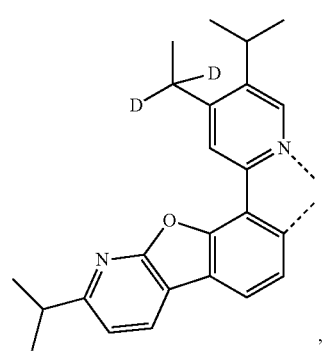
L_{A353}
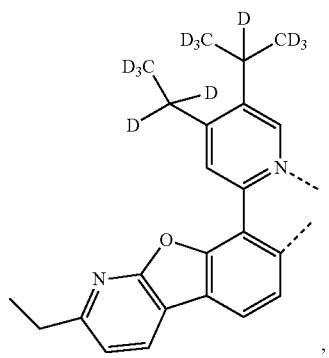
L_{A354}
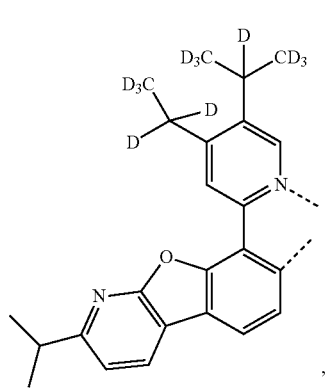
L_{A355}
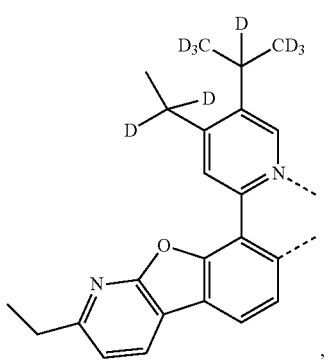
L_{A356}
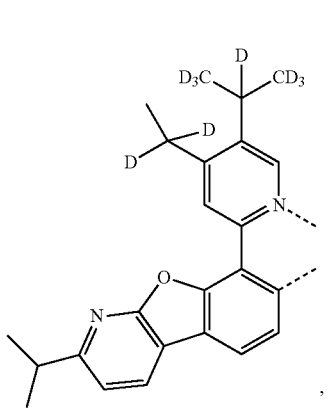
L_{A357}
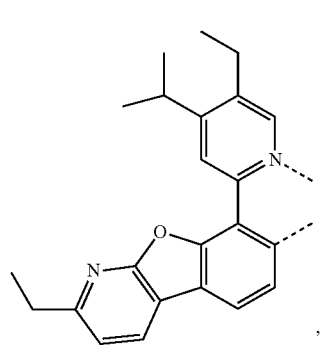
L_{A358}
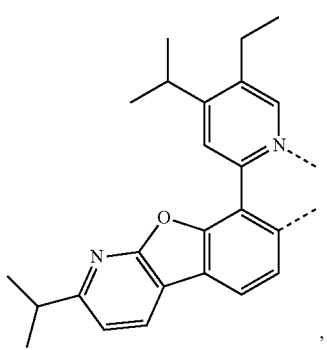

L<sub>A359</sub> 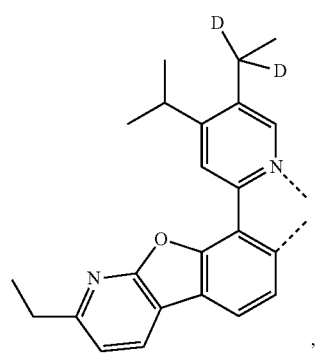
L<sub>A360</sub> 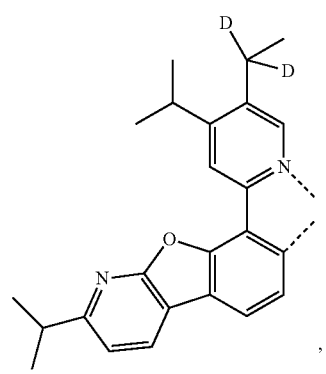
L<sub>A361</sub> 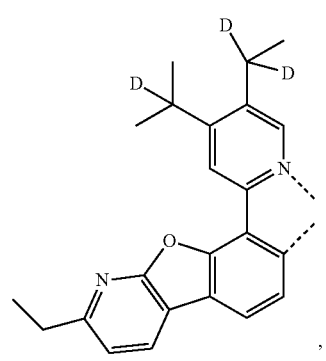
L<sub>A362</sub> 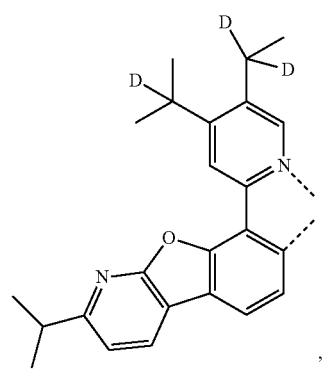
L<sub>A363</sub> 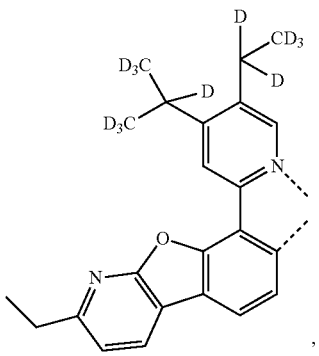
L<sub>A364</sub> 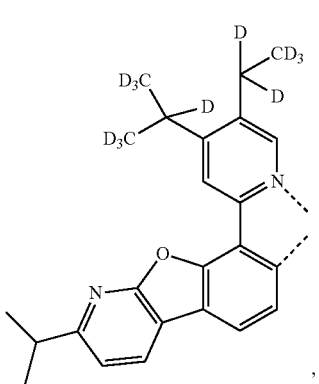
L<sub>A365</sub> 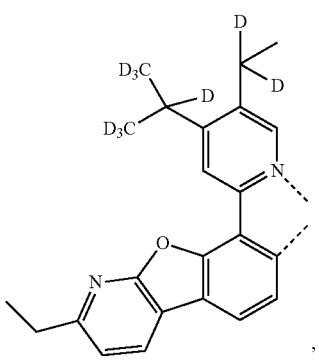
L<sub>A366</sub> 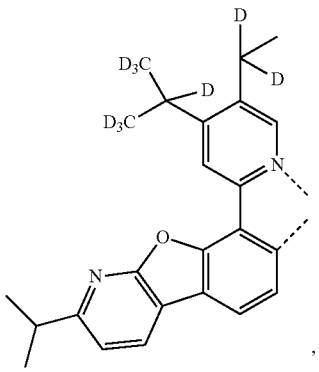

L_{A367}
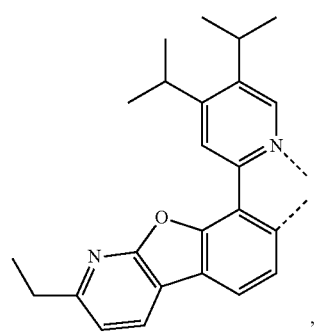
L_{A368}
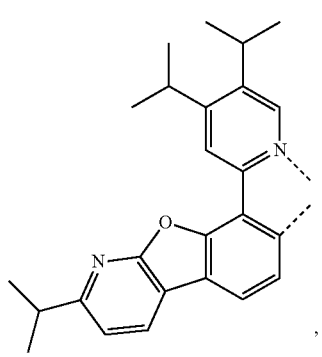
L_{A369}
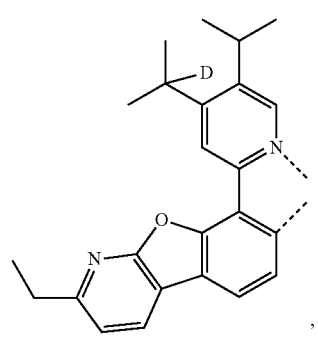
L_{A370}
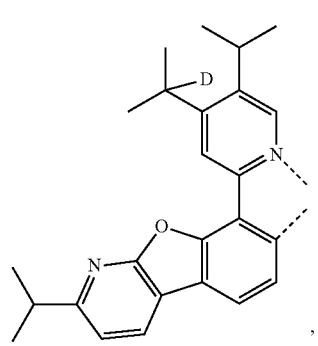
L_{A371}
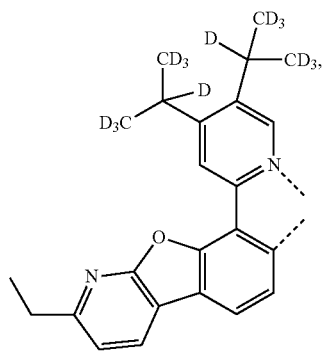
L_{A372}
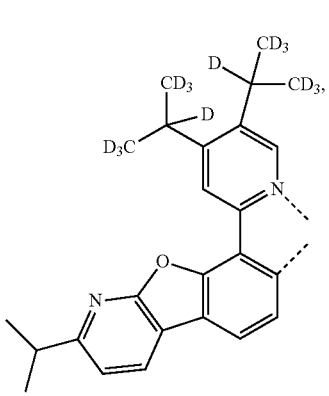
L_{A373}
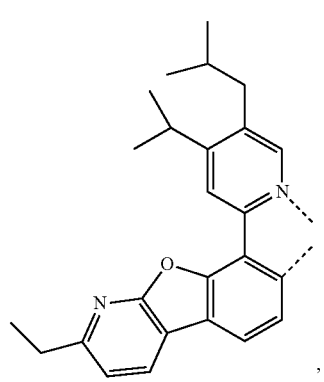
L_{A374}
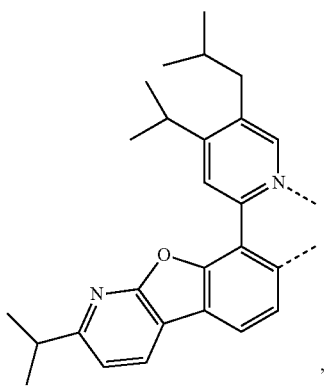

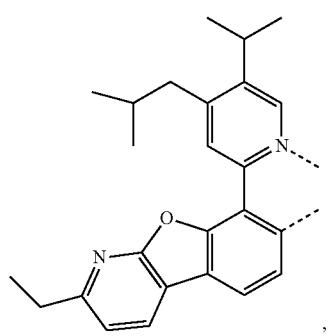 L_{A375}
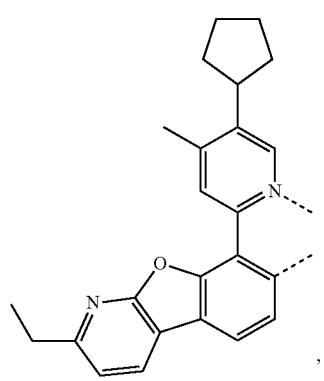 L_{A379}
L_{A376}
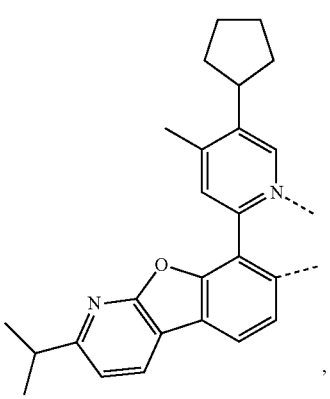 L_{A380}
L_{A377}
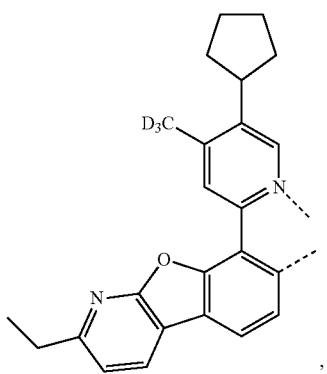 L_{A381}
L_{A378}
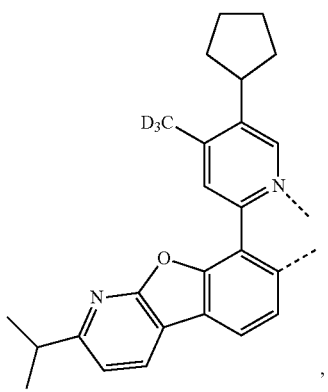 L_{A382}

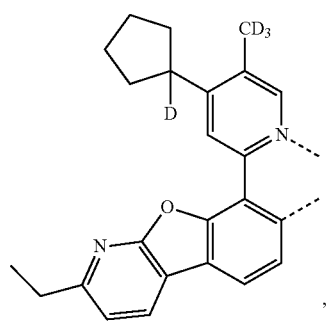
$L_{A383}$
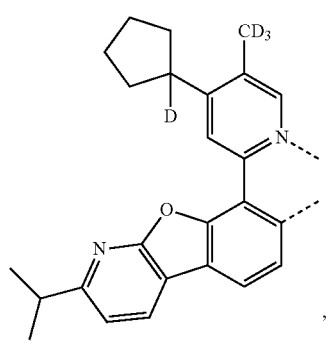
$L_{A384}$
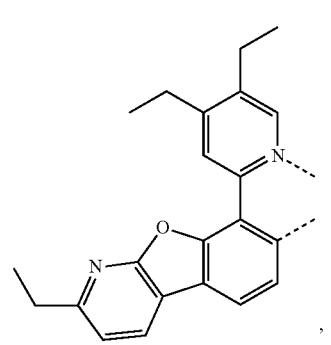
$L_{A385}$
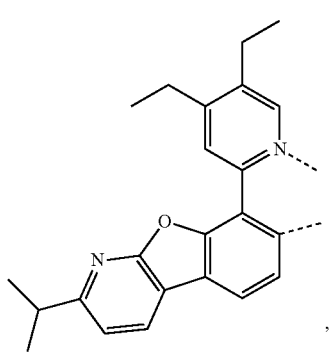
$L_{A386}$
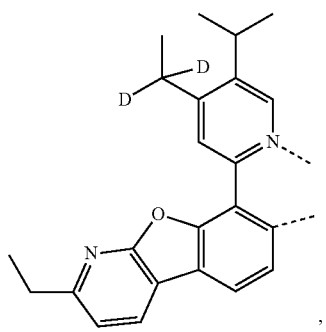
$L_{A387}$
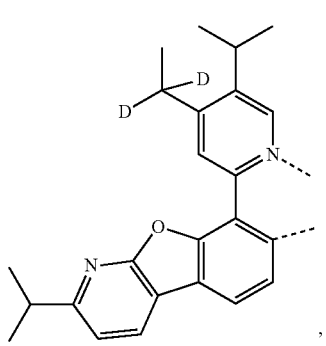
$L_{A388}$
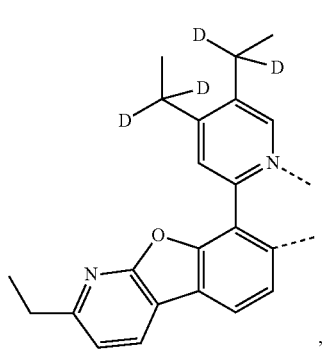
$L_{A389}$
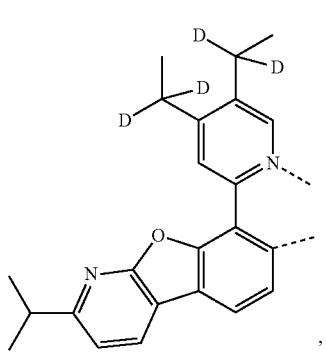
$L_{A390}$ L_{A391} 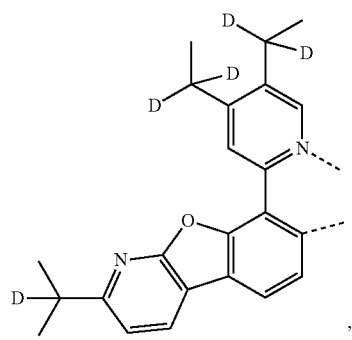
L_{A392} 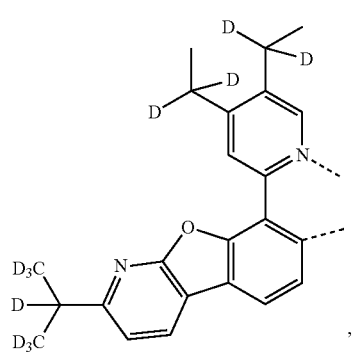
L_{A393} 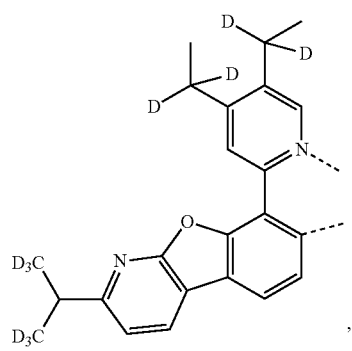
L_{A394} 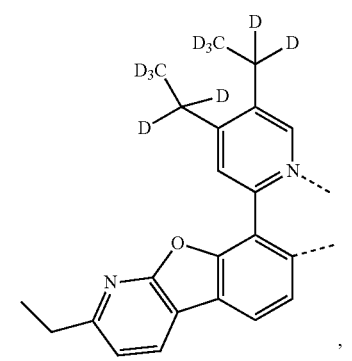
L_{A395} 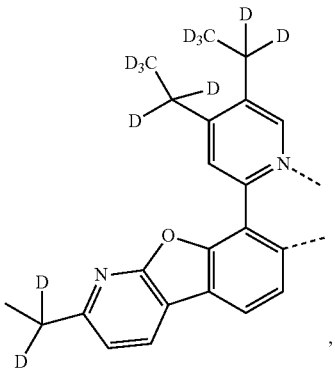
L_{A396} 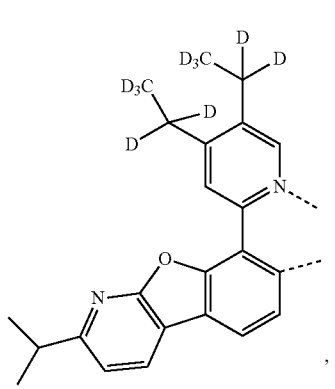
L_{A397} 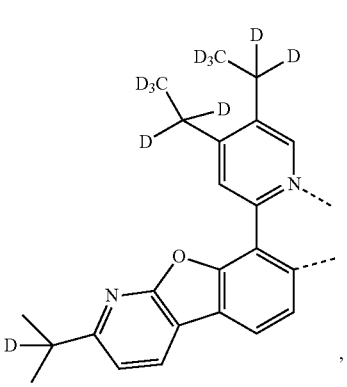
L_{A398} 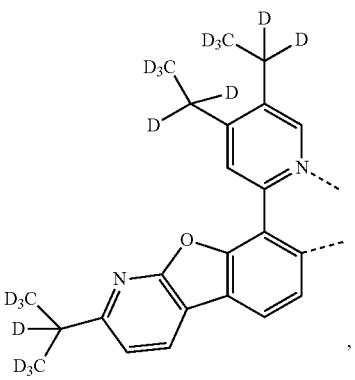

| L<sub>A399</sub> | L<sub>A403</sub> |
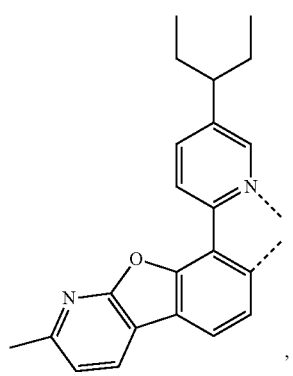
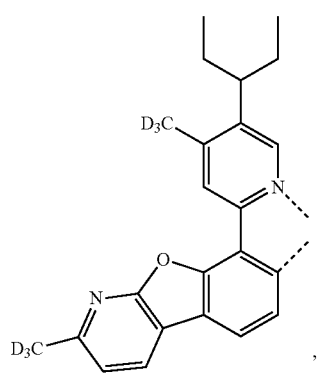
L<sub>A400</sub>
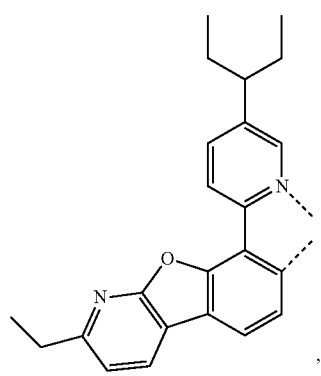
L<sub>A404</sub>
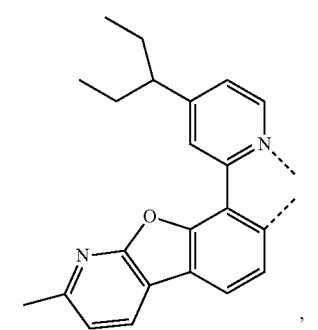
L<sub>A401</sub>
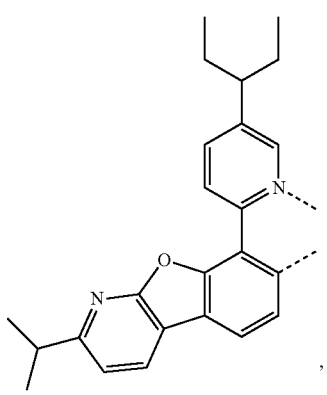
L<sub>A405</sub>
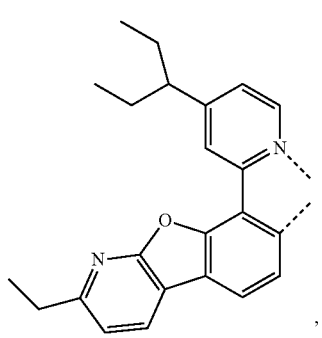
L<sub>A402</sub>
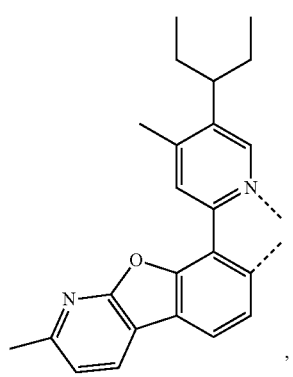
L<sub>A406</sub>
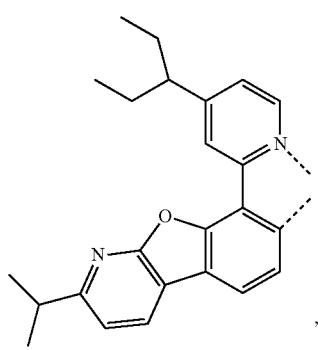

L_{A407}
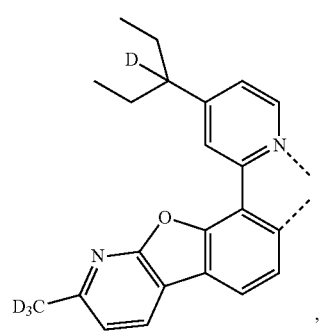
L_{A408}
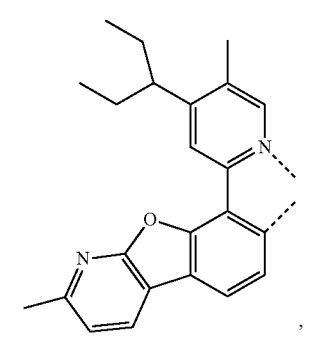
L_{A409}
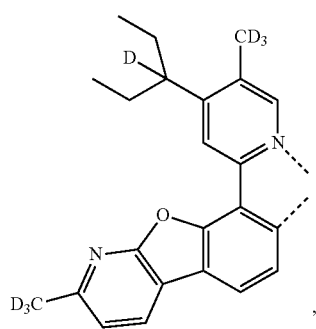
L_{A410}
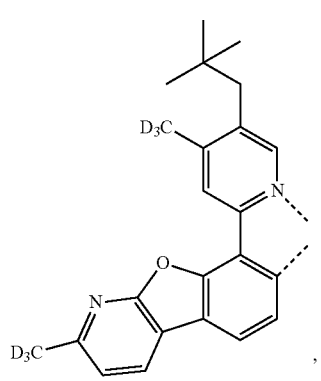
L_{A411}
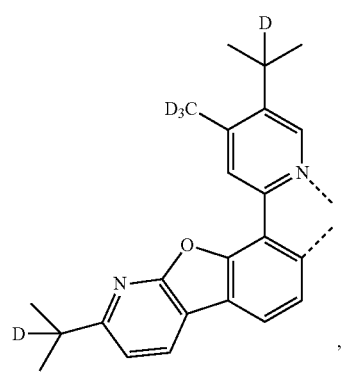
L_{A412}
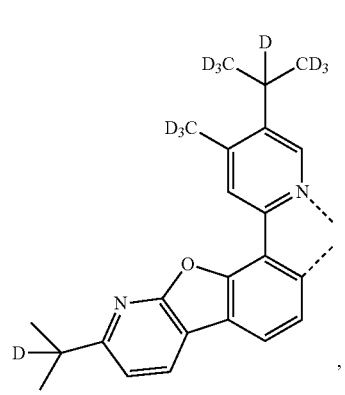
L_{A413}
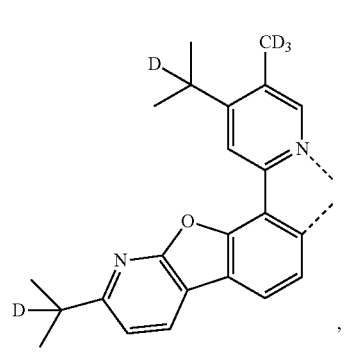
L_{A414}
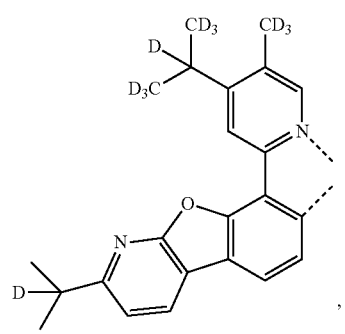

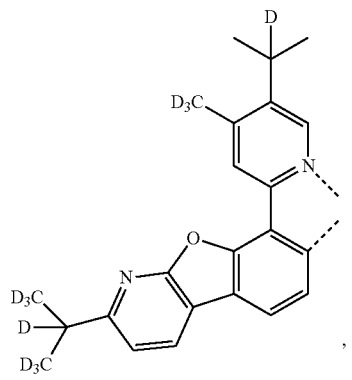
L_A415
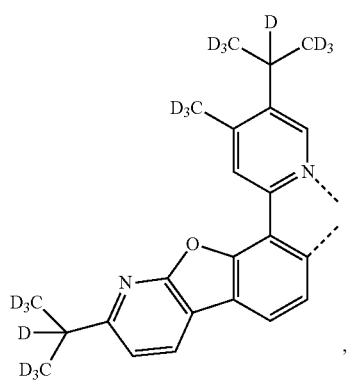
L_A416
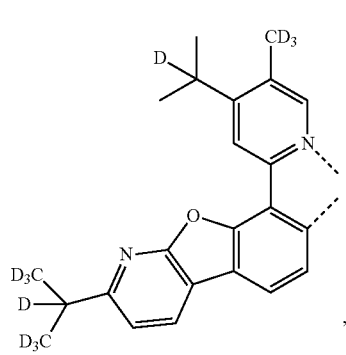
L_A417
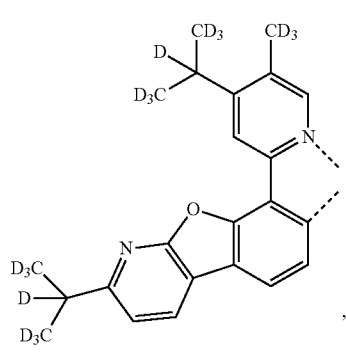
L_A418
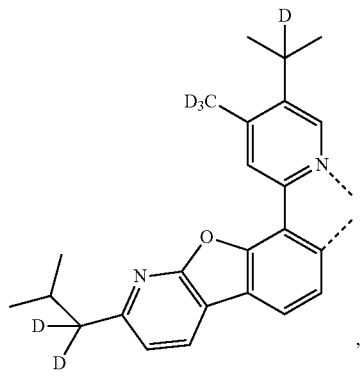
L_A419
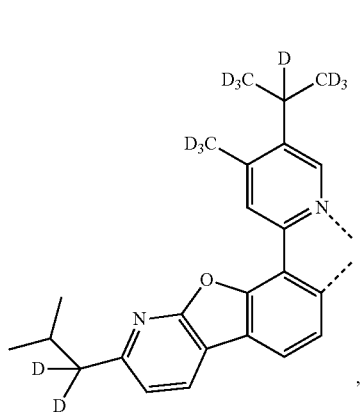
L_A420
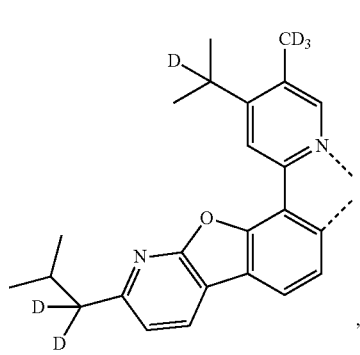
L_A421
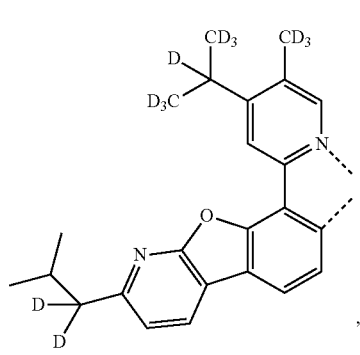
L_A422

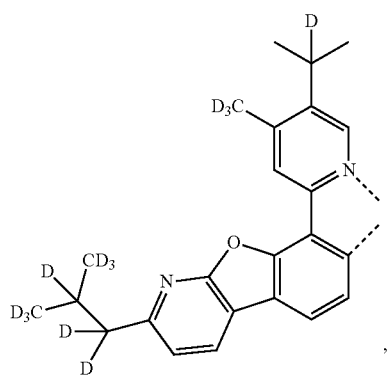
L<sub>A423</sub>
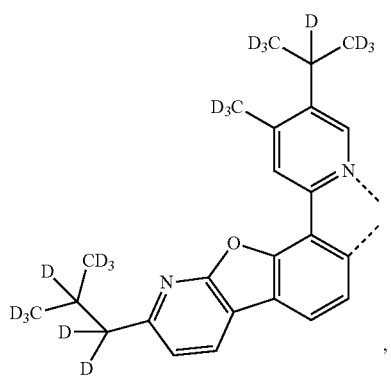
L<sub>A424</sub>
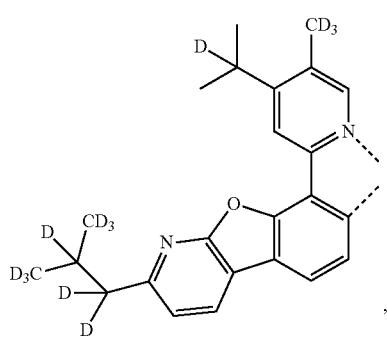
L<sub>A425</sub>
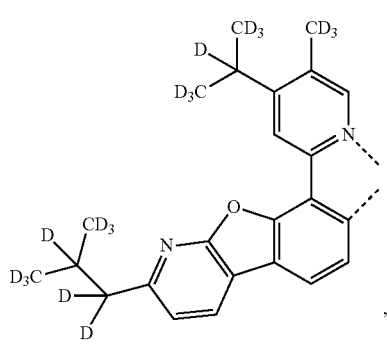
L<sub>A426</sub>
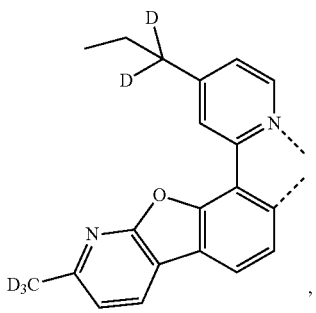
LA427
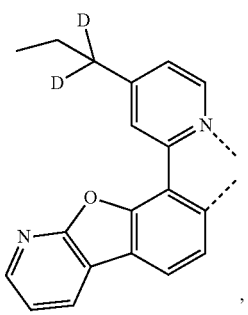
LA428
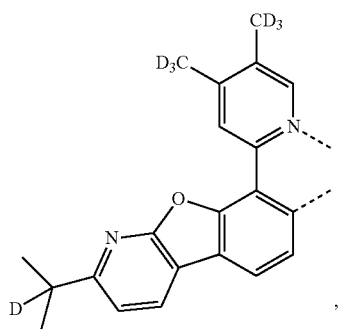
L<sub>A429</sub>
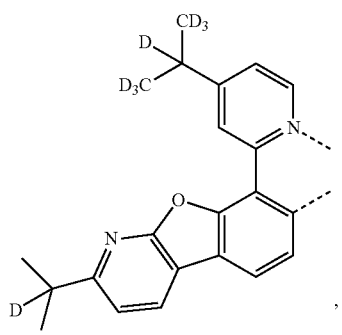
L<sub>A430</sub>
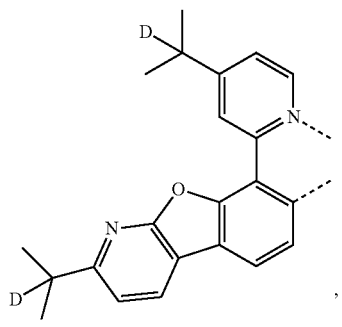
L<sub>A431</sub>

L<sub>A432</sub>
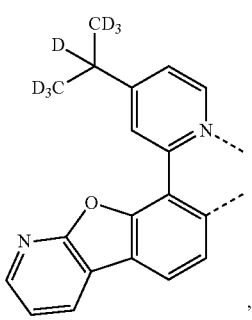
L<sub>A433</sub>
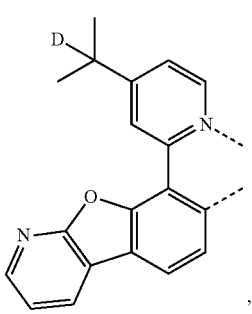
L<sub>A434</sub>

L<sub>A435</sub>

L<sub>A436</sub>

L<sub>A437</sub>
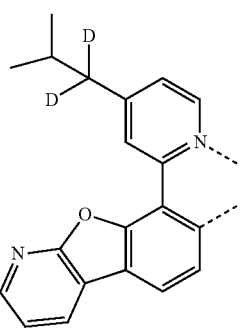
L<sub>A438</sub>
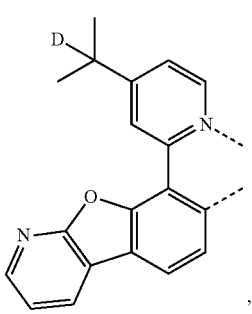
L<sub>A439</sub>
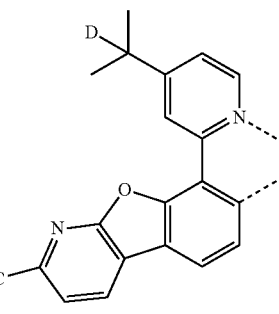
, and
L<sub>A440</sub>
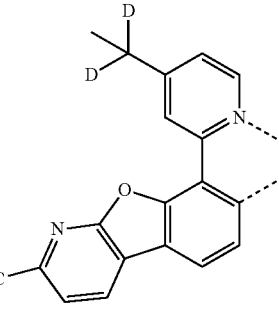
In another embodiment of the compound disclosed herein, the ligand L<sub>B</sub> in formula Ir(L<sub>A</sub>)<sub>n</sub>(L<sub>B</sub>)<sub>3-n</sub> is selected from the group consisting of:

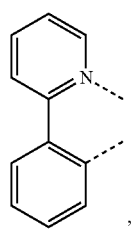 L<sub>B1</sub>
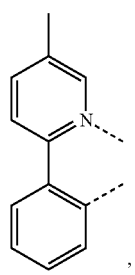 L<sub>B2</sub>
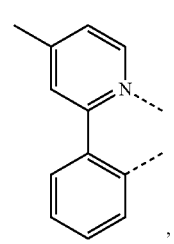 L<sub>B3</sub>
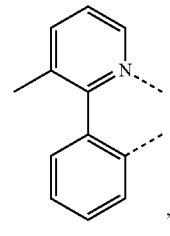 L<sub>B4</sub>
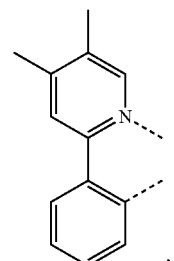 L<sub>B5</sub>
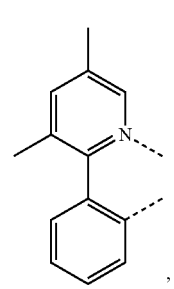 L<sub>B6</sub>
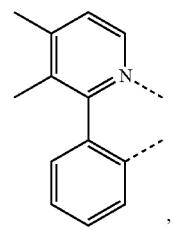 L<sub>B7</sub>
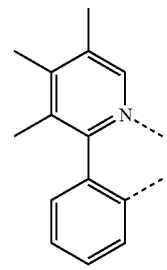 L<sub>B8</sub>
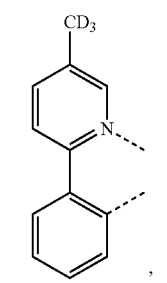 L<sub>B9</sub>
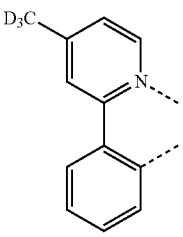 L<sub>B10</sub>
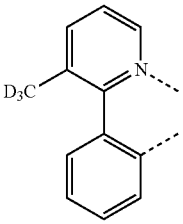 L<sub>B11</sub>
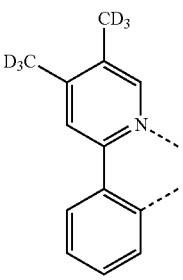 L<sub>B12</sub>

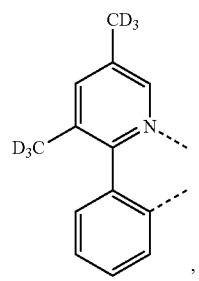 L_{B13},
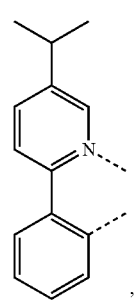 L_{B18},
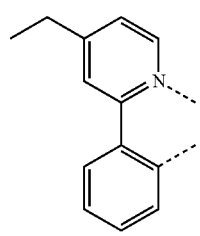 L_{B14},
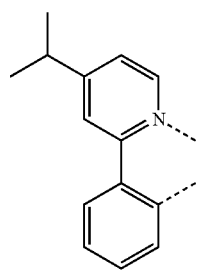 L_{B19},
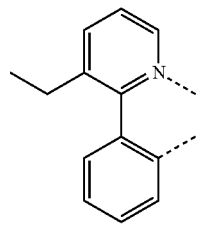 L_{B15},
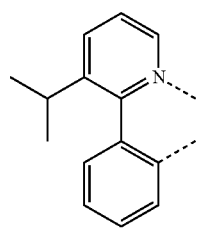 L_{B20},
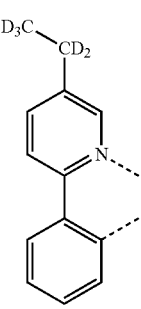 L_{B16},
L_{B21},
L_{B17},
L_{B22},
L_{B23}, L$_{B24}$ 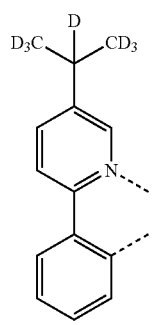
L$_{B25}$
L$_{B26}$
L$_{B27}$
L$_{B28}$
L$_{B30}$
L$_{B31}$ 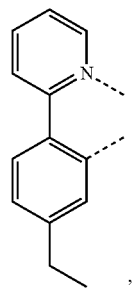
L$_{B32}$ 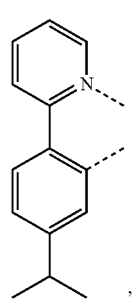
L$_{B33}$ 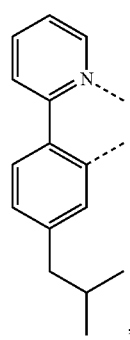
L$_{B34}$ 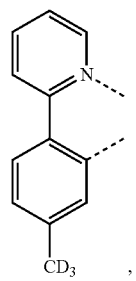
L$_{B35}$ 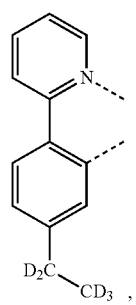

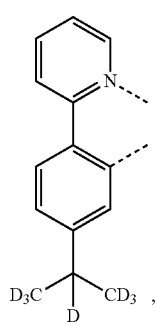, L<sub>B36</sub>
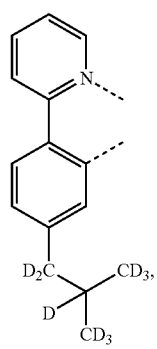, L<sub>B37</sub>
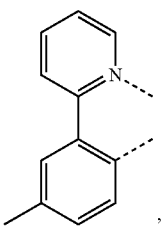, L<sub>B38</sub>
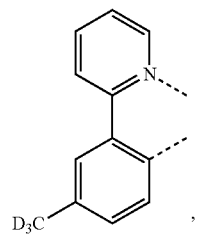, L<sub>B39</sub>
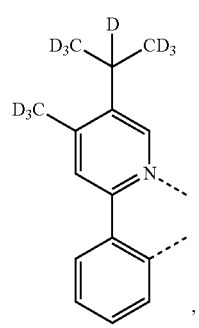, L<sub>B40</sub>
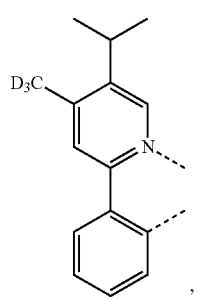, L<sub>B41</sub>
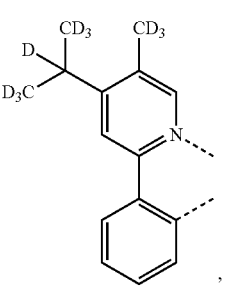, L<sub>B42</sub>
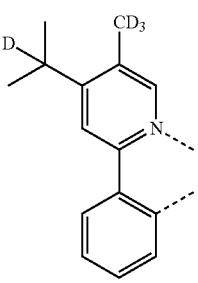, L<sub>B43</sub>
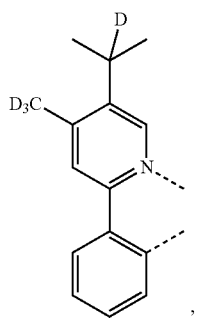, L<sub>B44</sub>
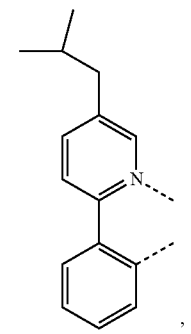, L<sub>B45</sub>

125
-continued
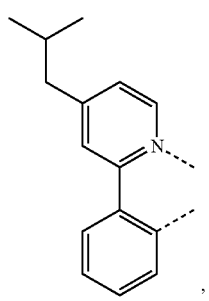 L_{B46}
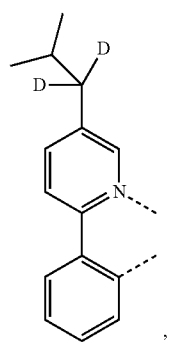 L_{B47}
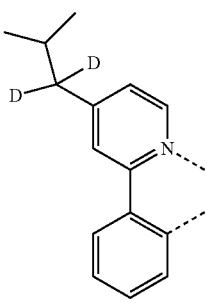 L_{B48}
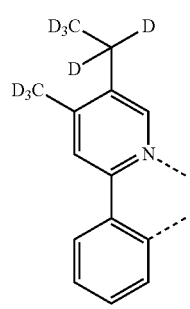 L_{B49}
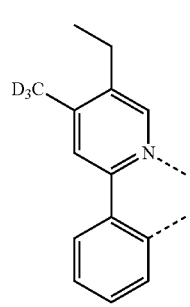 L_{B50}
126
-continued
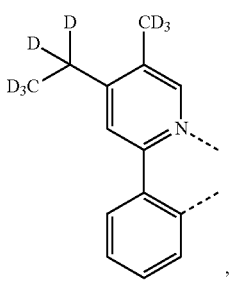 L_{B51}
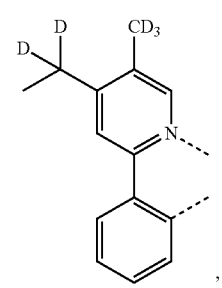 L_{B52}
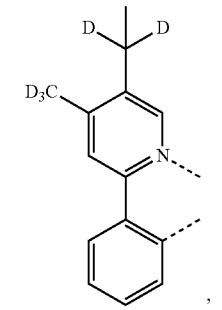 L_{B53}
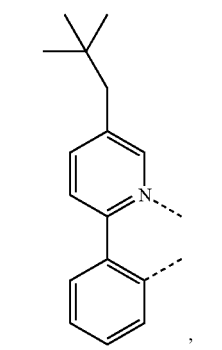 L_{B54}
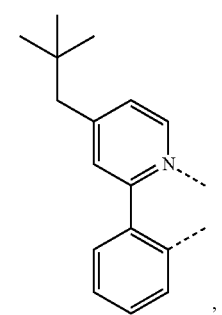 L_{B55}

127
-continued
L<sub>B57</sub>
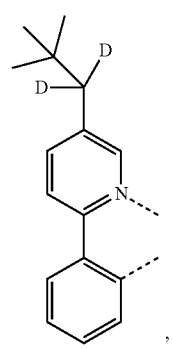
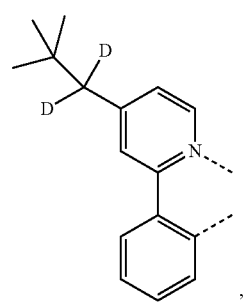
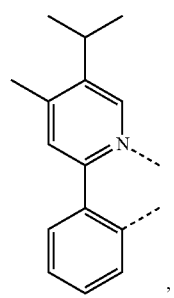
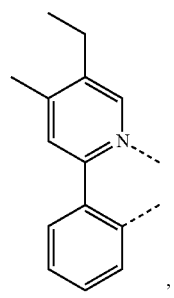
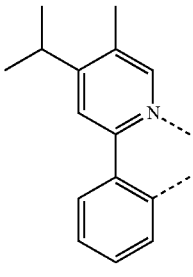
128
-continued
L<sub>B56</sub>
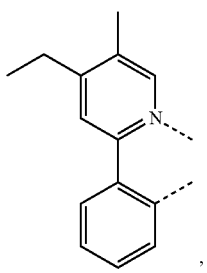
L<sub>B57</sub>
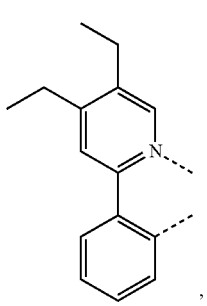
L<sub>B58</sub>
L<sub>B59</sub>
L<sub>B60</sub>
L<sub>B61</sub>
L<sub>B62</sub>
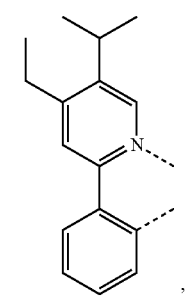
L<sub>B63</sub>
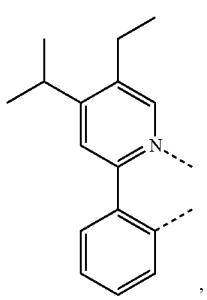
L<sub>B64</sub>
L<sub>B65</sub>
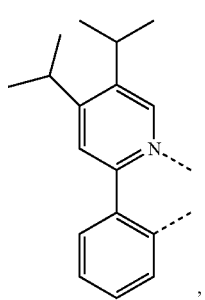

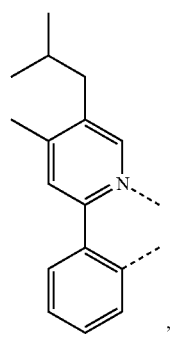 $L_{B66}$
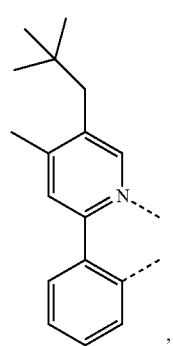 $L_{B67}$
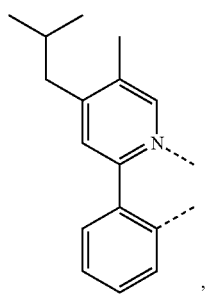 $L_{B68}$
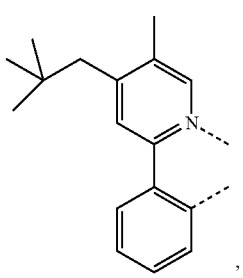 $L_{B69}$
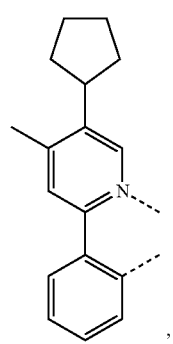 $L_{B70}$
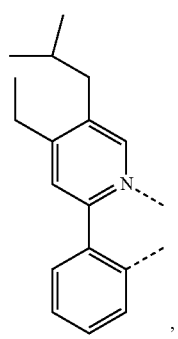 $L_{B71}$
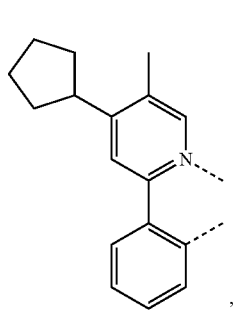 $L_{B72}$
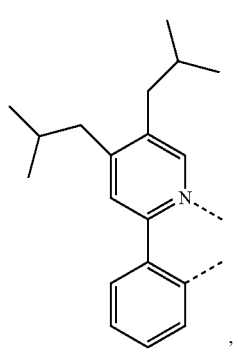 $L_{B73}$
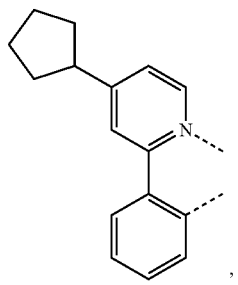 $L_{B74}$
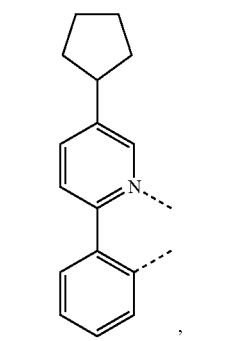 $L_{B75}$ 131
-continued
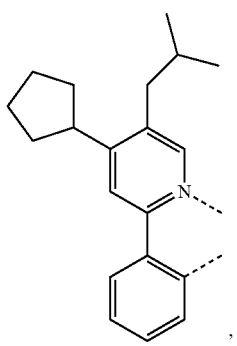
L_{B76}
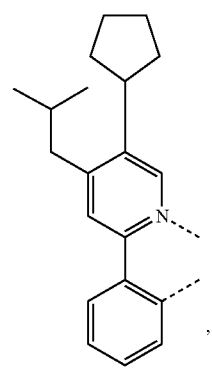
L_{B77}
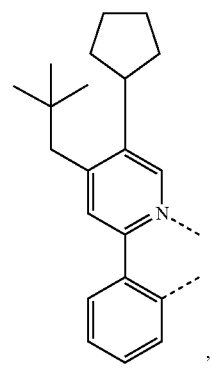
L_{B78}
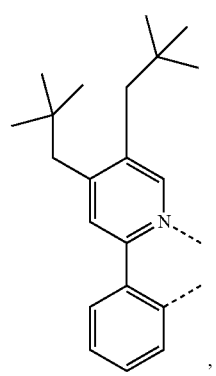
L_{B79}
132
-continued
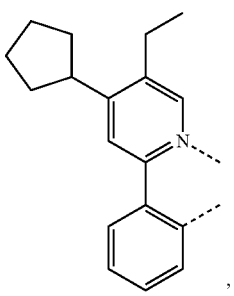
L_{B80}
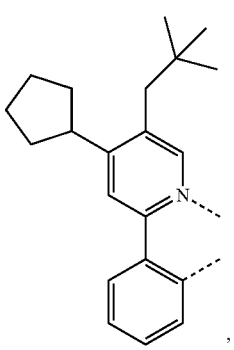
L_{B81}
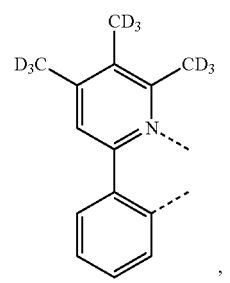
L_{B82}
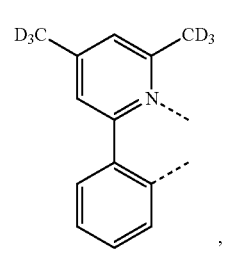
L_{B83}
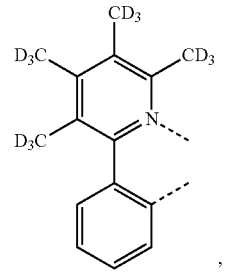
L_{B84}

-continued

L_B85, L_B86, L_B87, L_B88, L_B89, L_B90, L_B91, L_B92, L_B93, L_B94

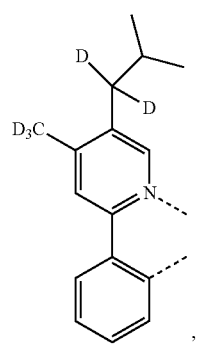 L$_{B95}$
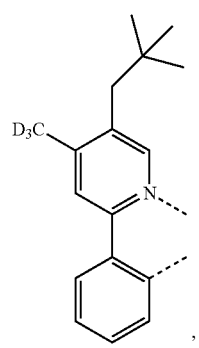 L$_{B96}$
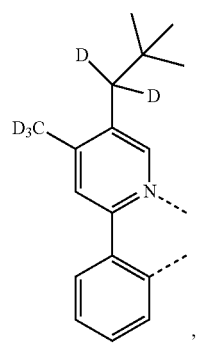 L$_{B97}$
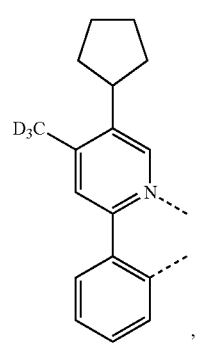 L$_{B98}$
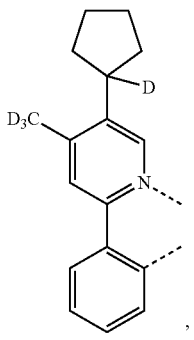 L$_{B99}$
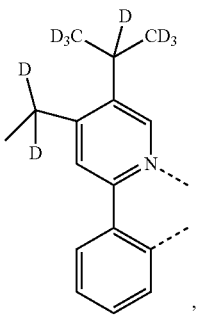 L$_{B100}$
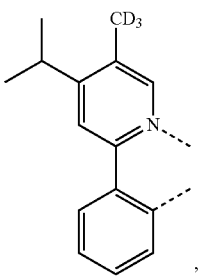 L$_{B101}$
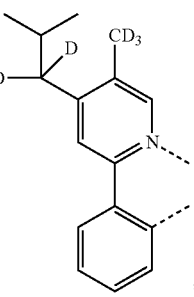 L$_{B102}$
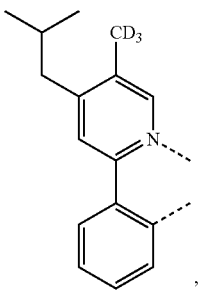 L$_{B103}$

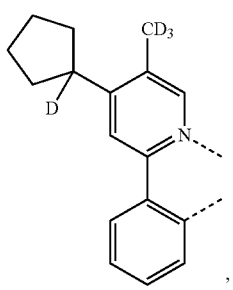 L_{B104}
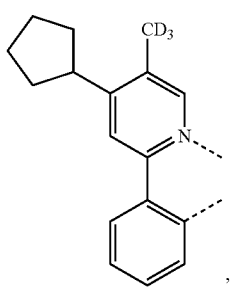 L_{B105}
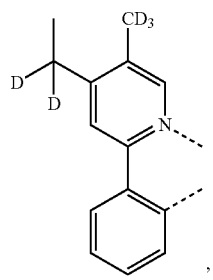 L_{B106}
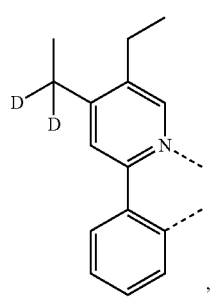 L_{B107}
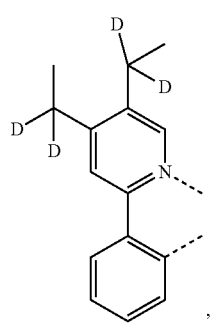 L_{B108}
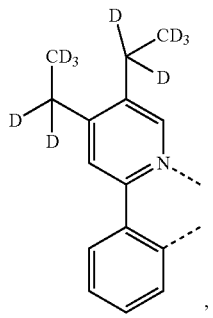 L_{B109}
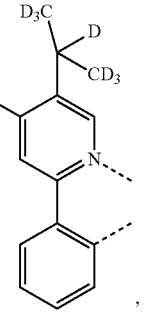 L_{B110}
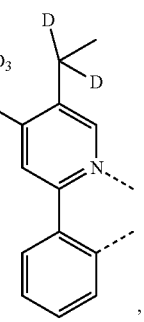 L_{B111}
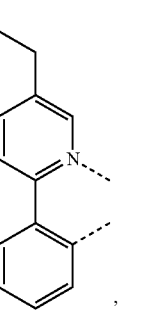 L_{B112}
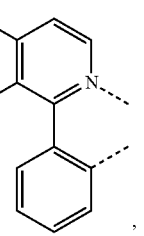 L_{B113}

L_{B114}
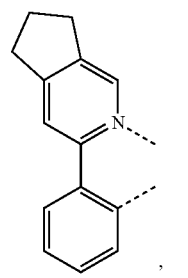
L_{B115}
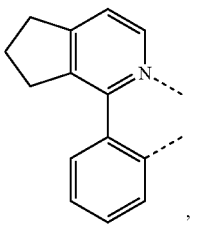
L_{B116}
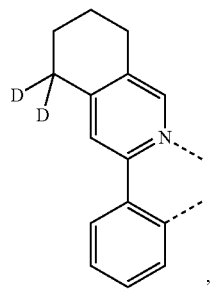
L_{B117}
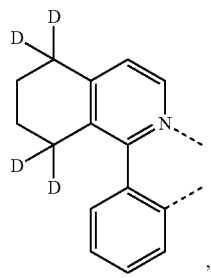
L_{B118}
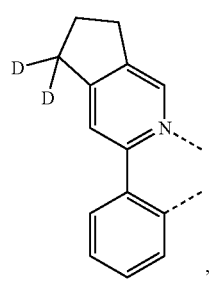
L_{B119}
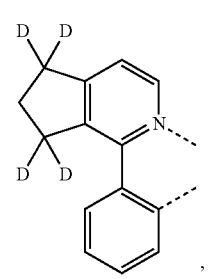
L_{B120}
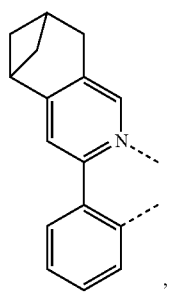
L_{B121}
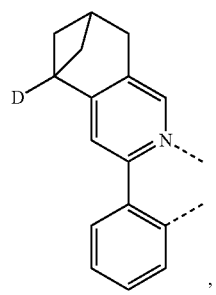
L_{B122}
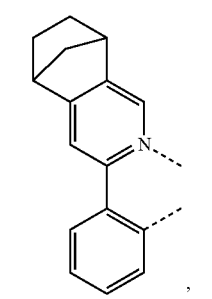
L_{B123}
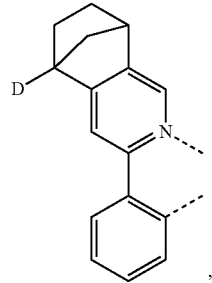
L_{B124}
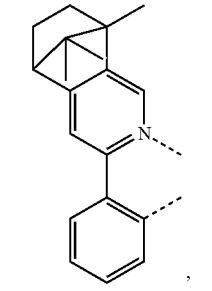

L_{B125}
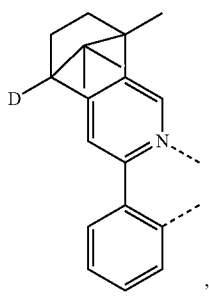
L_{B126}
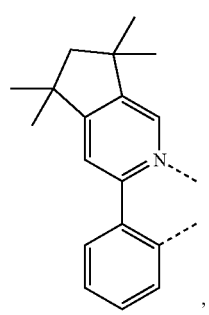
L_{B127}
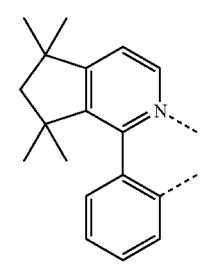
L_{B128}
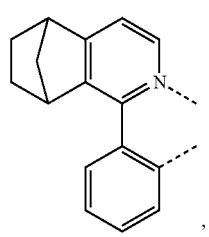
L_{B129}
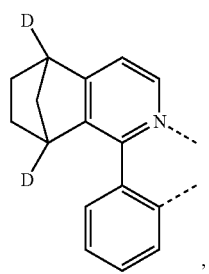
L_{B130}
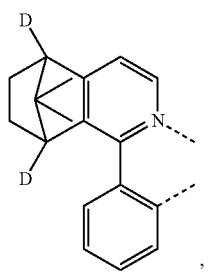
L_{B132}
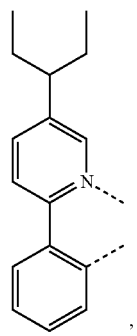
L_{B132}
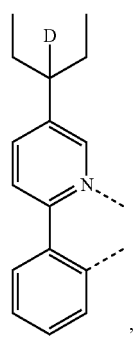
L_{B133}
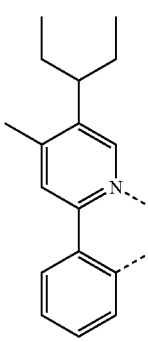
L_{B134}
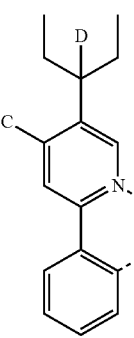

L_B135 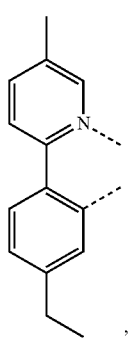
L_B136 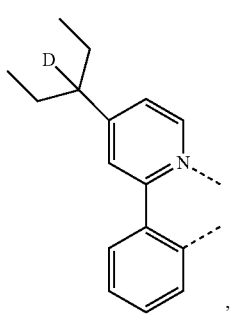
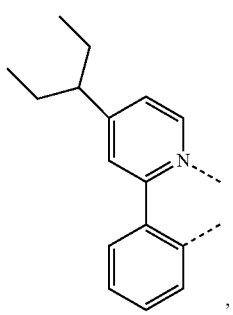
L_B137 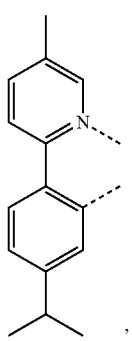
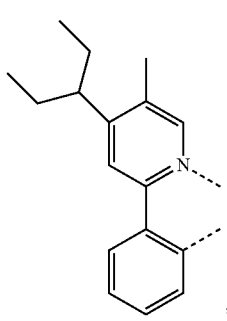
L_B138 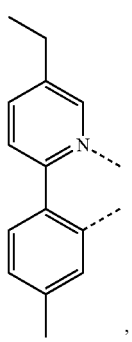
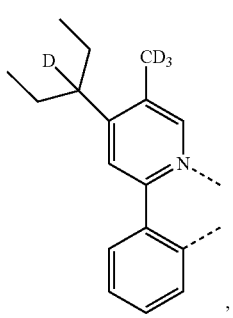
L_B139 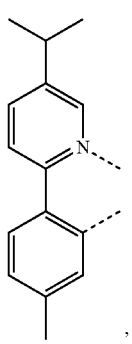
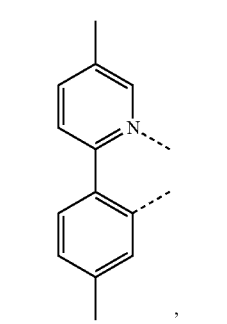

L_{B144}
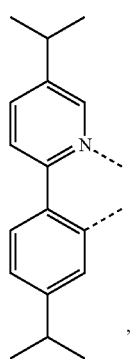
L_{B145}
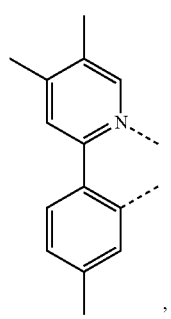
L_{B146}
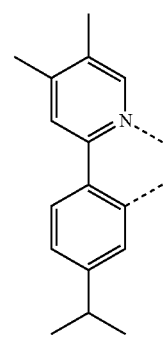
L_{B147}
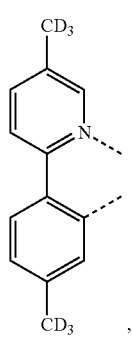
L_{B148}
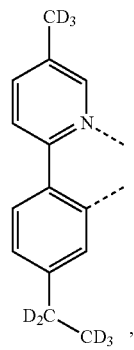
L_{B149}
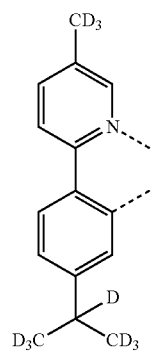
L_{B150}
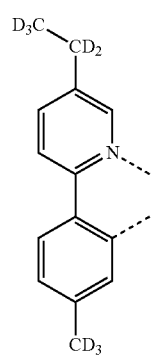
L_{B151}
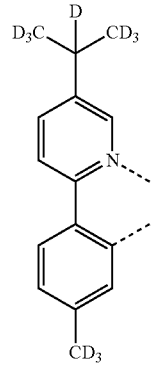

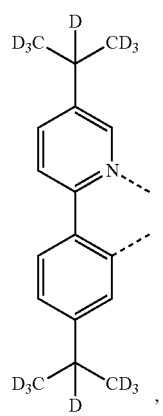
L_{B152}
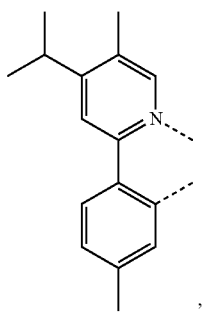
L_{B156}
L_{B153}
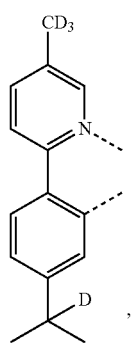
L_{B157}
L_{B154}
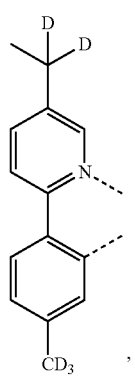
L_{B158}
L_{B155}
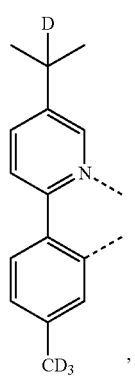
L_{B159}

L<sub>B160</sub>

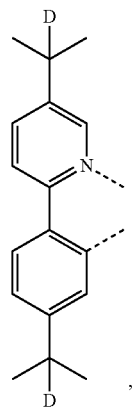

L<sub>B161</sub>

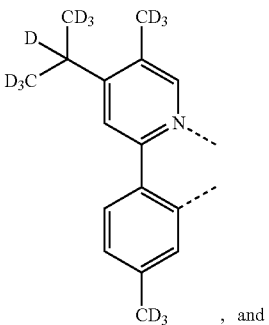, and

L<sub>B162</sub>

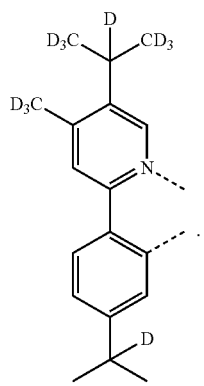

In another embodiment of the compound disclosed herein, the compound is selected from the group consisting of Compound A-1 through Compound A-72,280, wherein each of Compound A-x, where x=440j+k−440, k is an integer from 1 to 440, and j is an integer from 1 to 162, has the formula Ir(L$_{Ak}$) (L$_{Bj}$)$_2$.

In another embodiment of the compound disclosed herein, the compound is selected from the group consisting of:

Compound 1

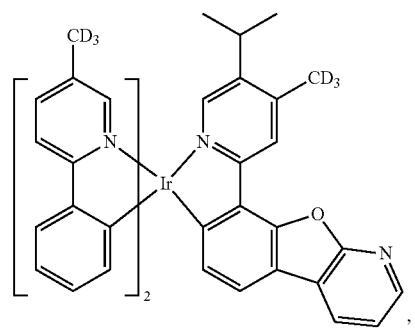

Compound 2

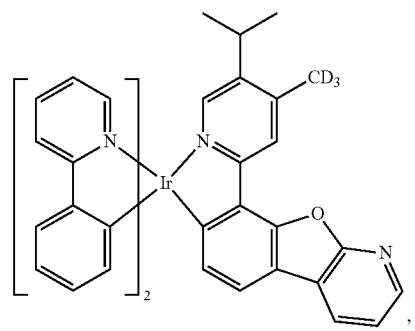

Compound 3

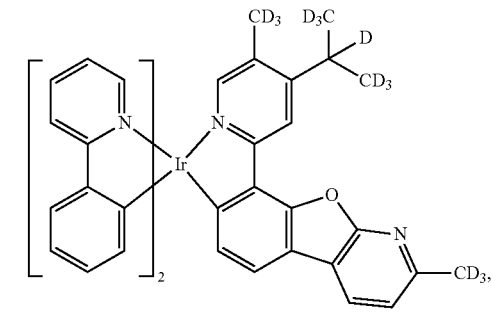

Compound 4

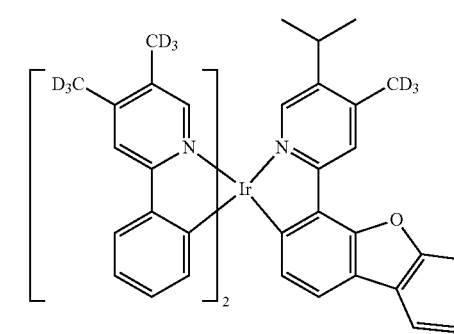

Compound 5
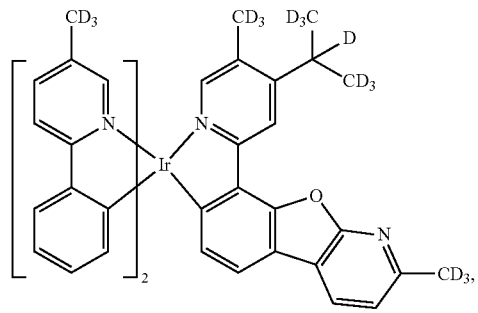
Compound 6
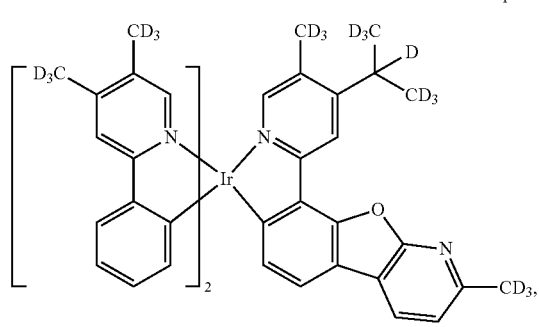
Compound 7
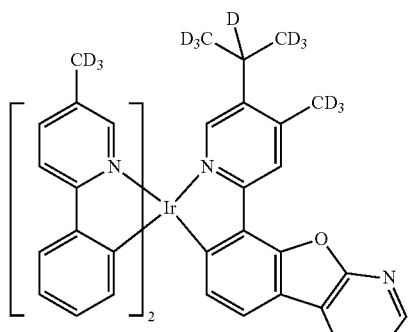
Compound 8
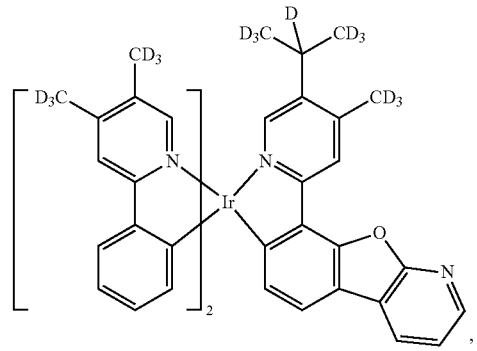
Compound 9
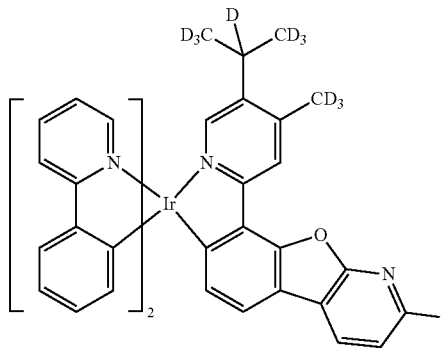
Compound 10
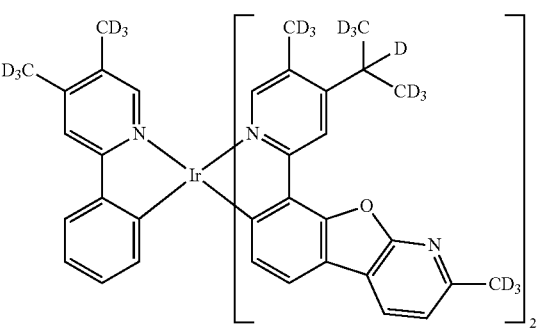
Compound 11
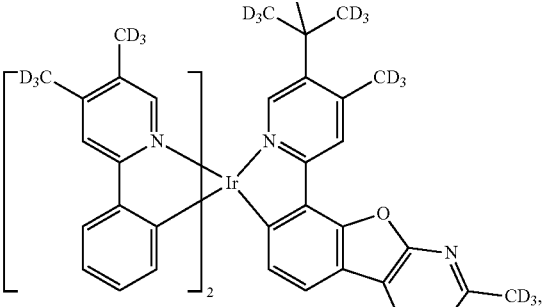
Compound 12
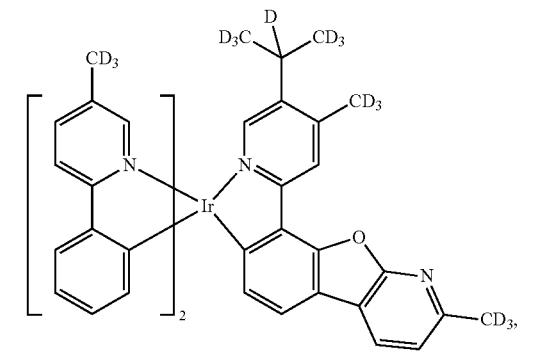

Compound 13
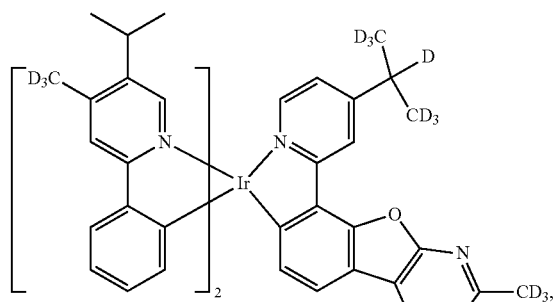
Compound 17
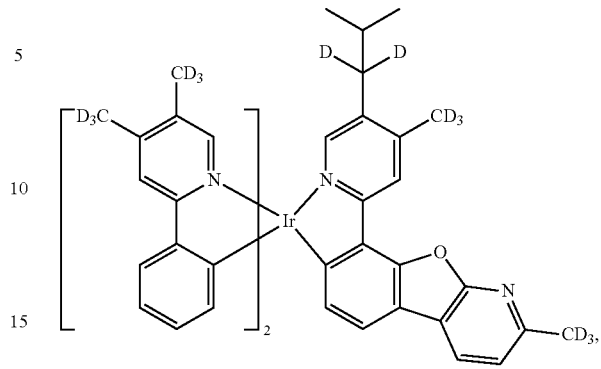
Compound 14
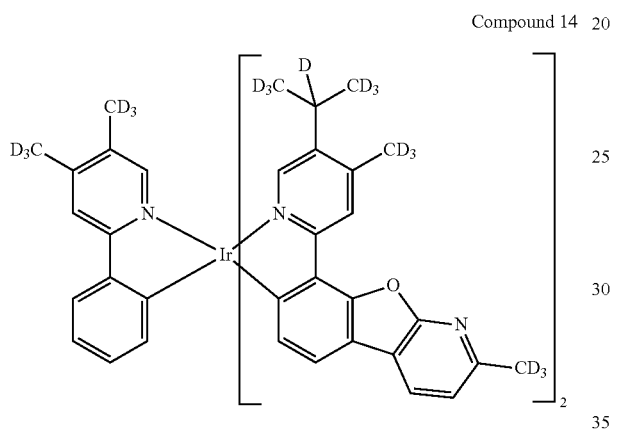
Compound 18
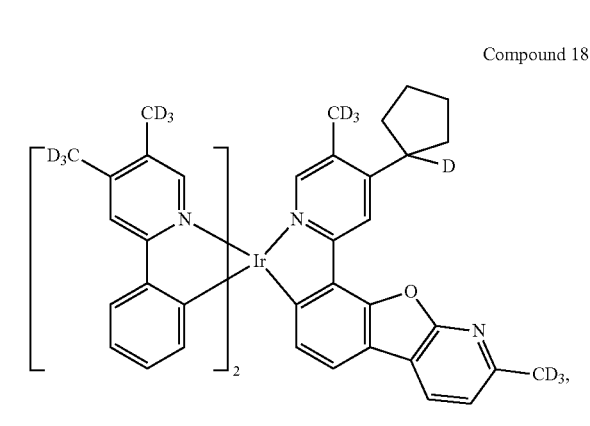
Compound 15
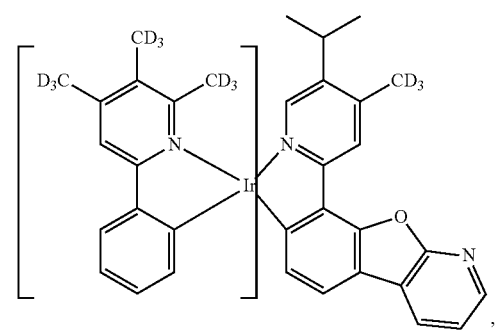
Compound 19
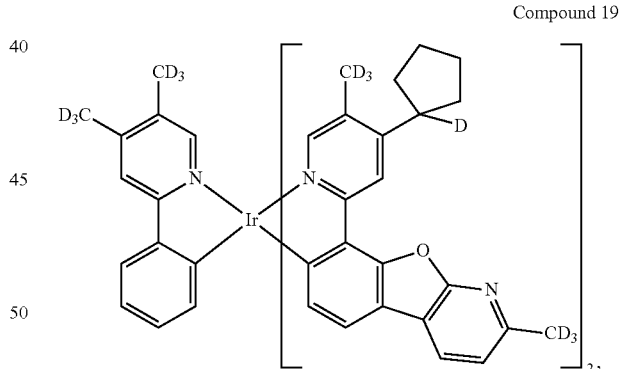
Compound 16
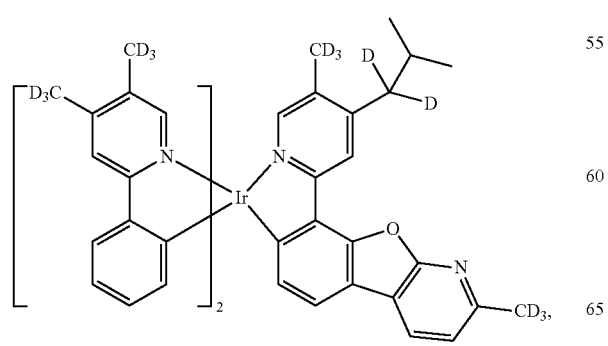
Compound 20
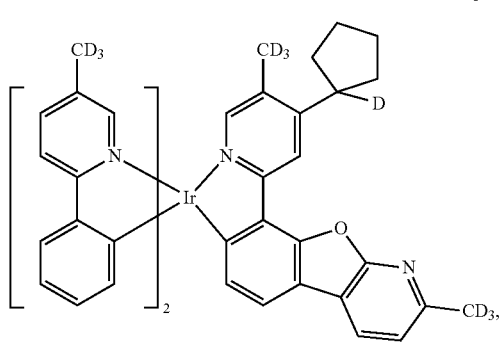

Compound 21
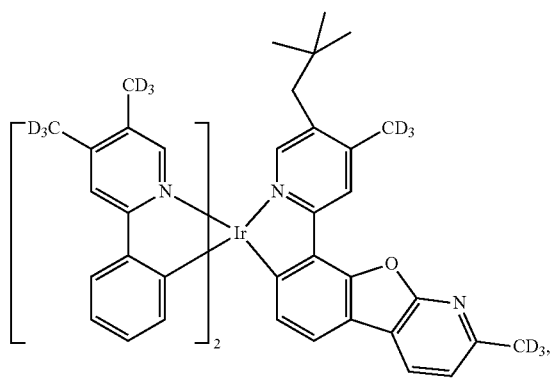
Compound 25
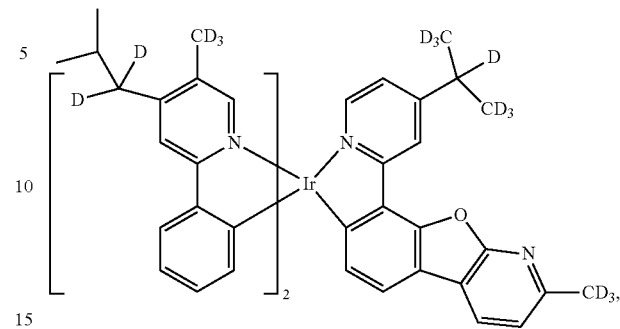
Compound 22
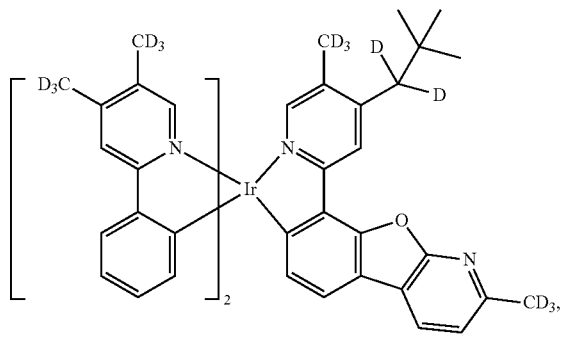
Compound 26
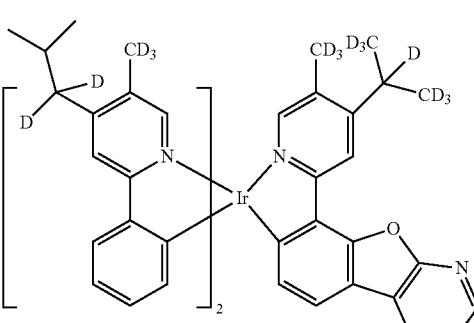
Compound 23
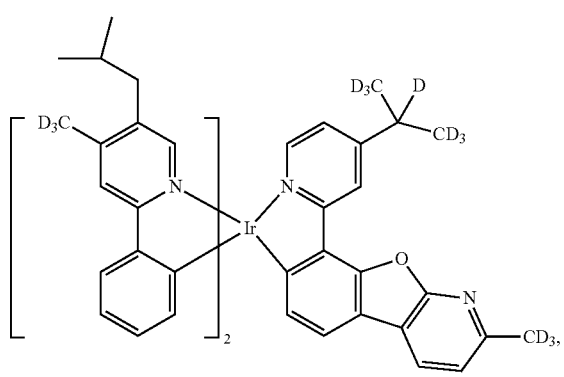
Compound 27
Compound 24
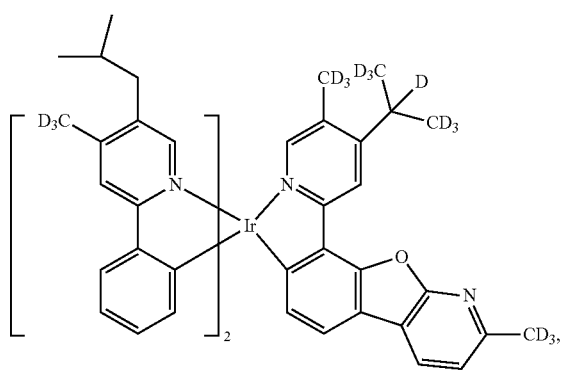
Compound 28
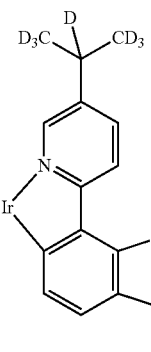

Compound 29
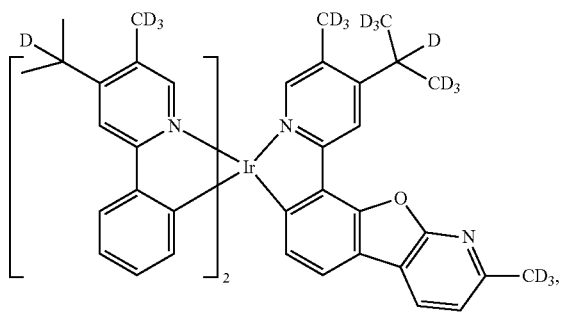
Compound 33
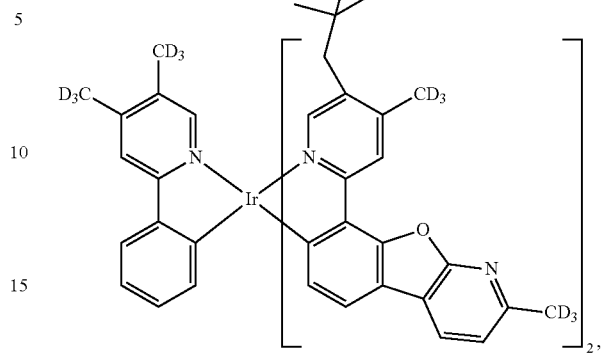
Compound 30
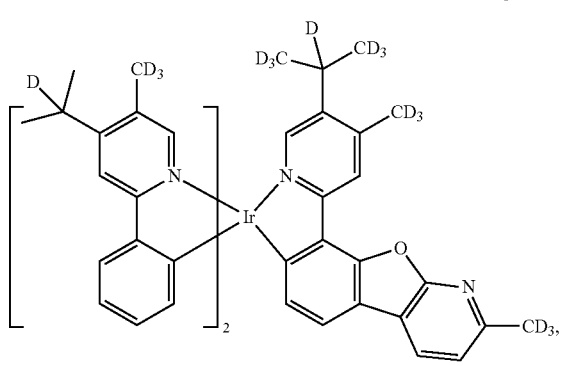
Compound 34
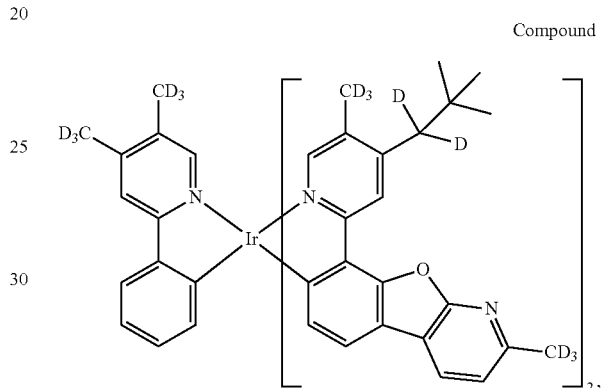
Compound 31
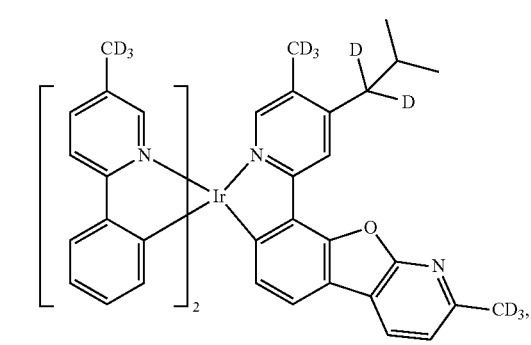
Compound 35
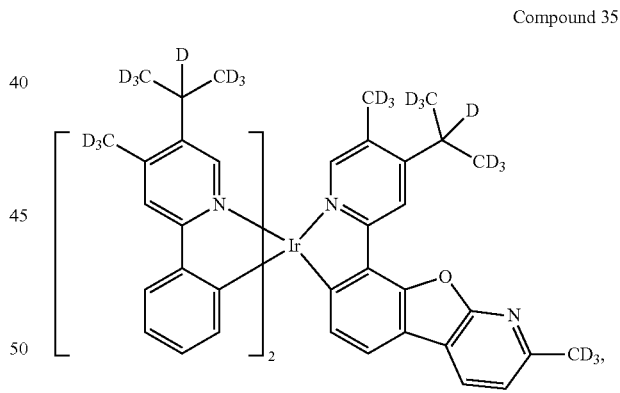
Compound 32
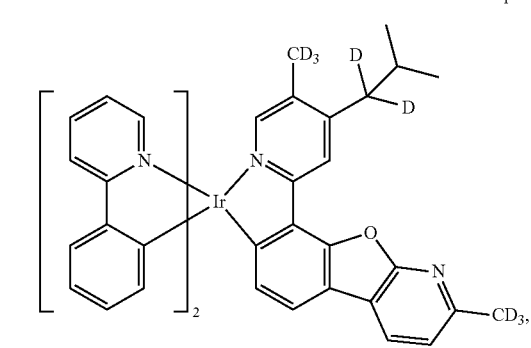
Compound 36
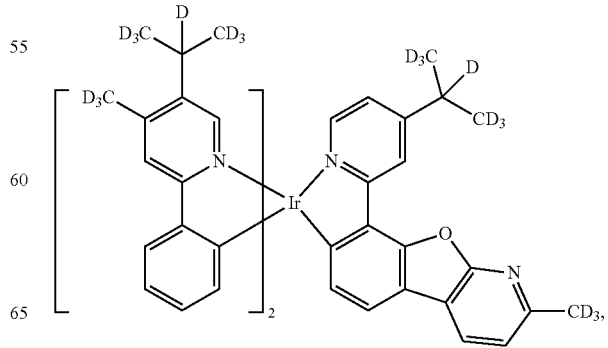

Compound 37
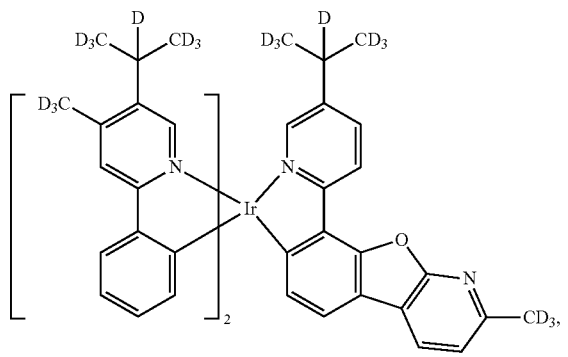
Compound 41
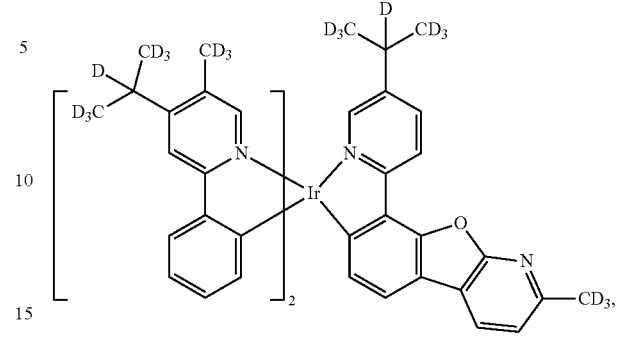
Compound 38
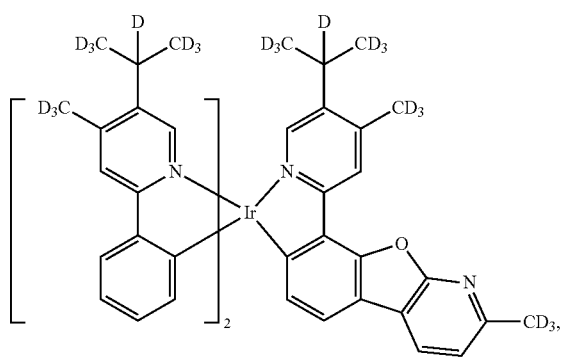
Compound 42
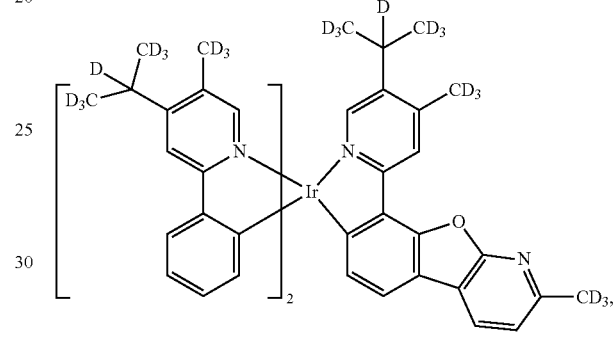
Compound 39
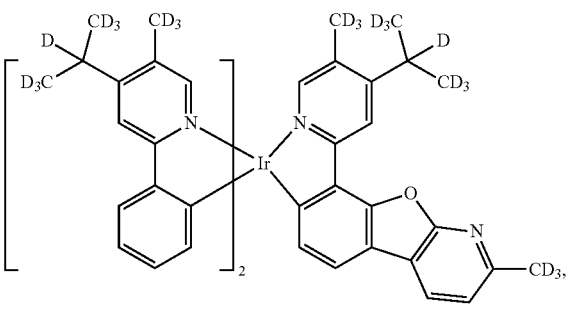
Compound 43
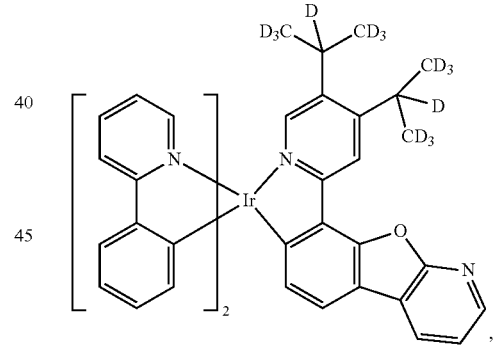
Compound 40
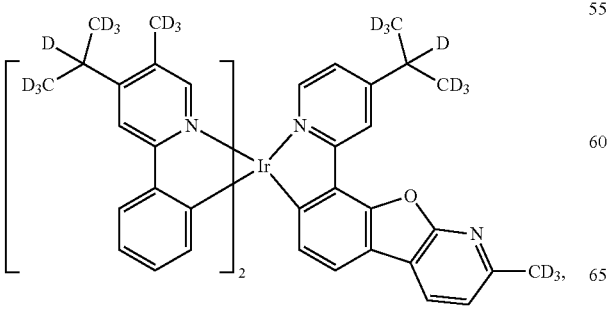
Compound 44
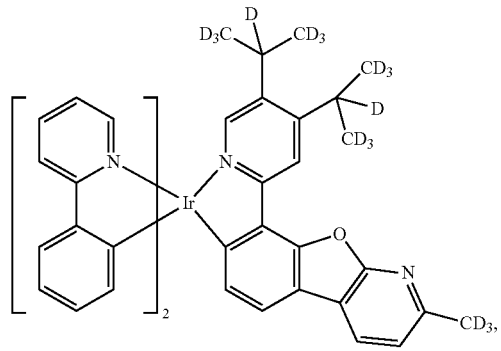

Compound 45
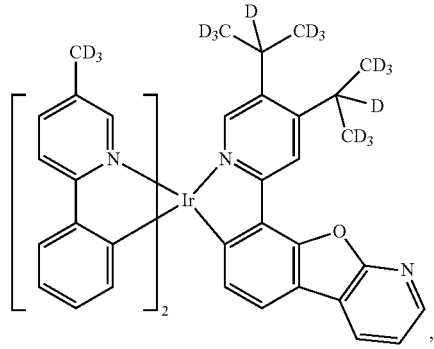
Compound 46
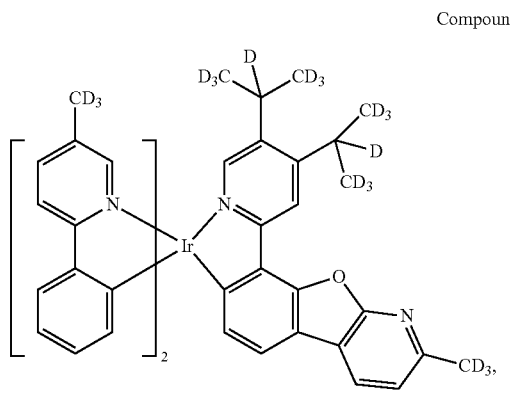
Compound 47
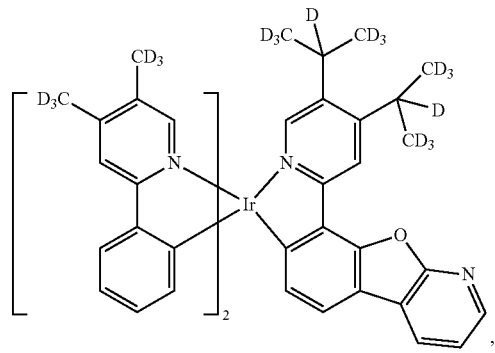
Compound 48
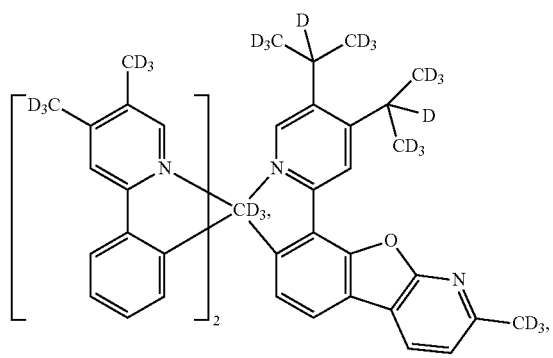
Compound 49
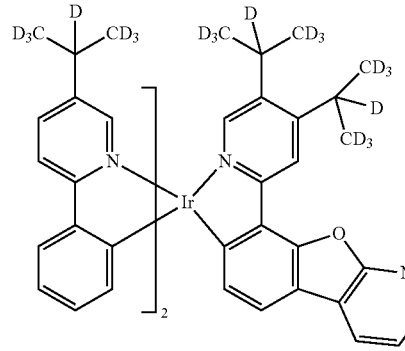
Compound 50
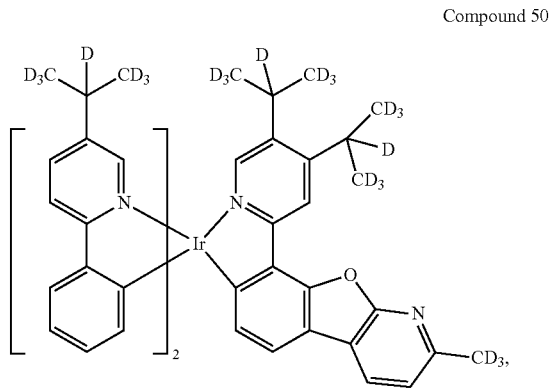
Compound 50
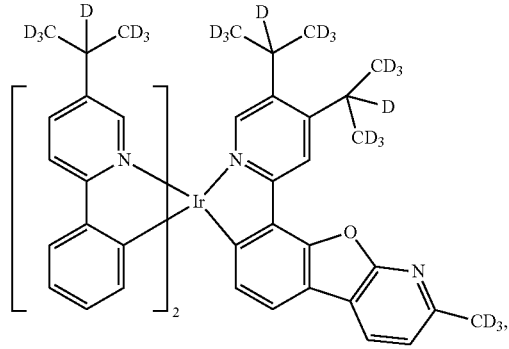
Compound 51
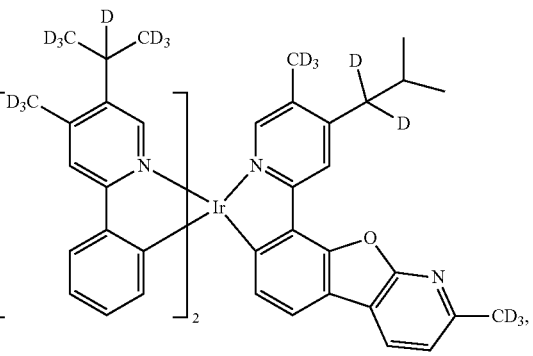

-continued
Compound 52
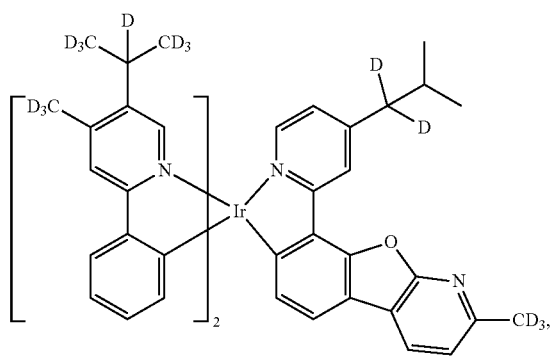
Compound 53
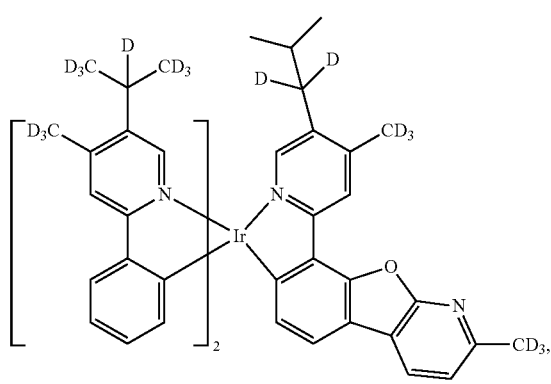
Compound 54
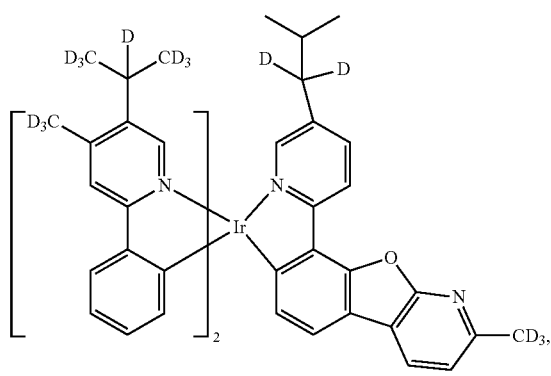
Compound 55
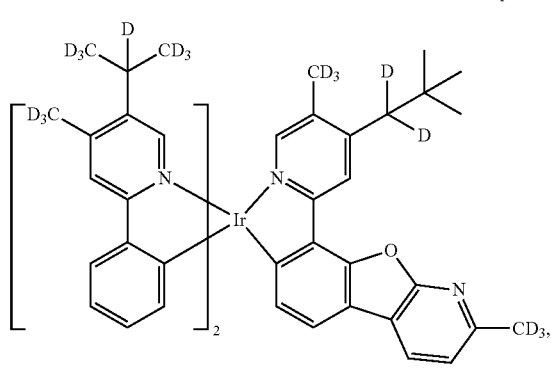
-continued
Compound 56
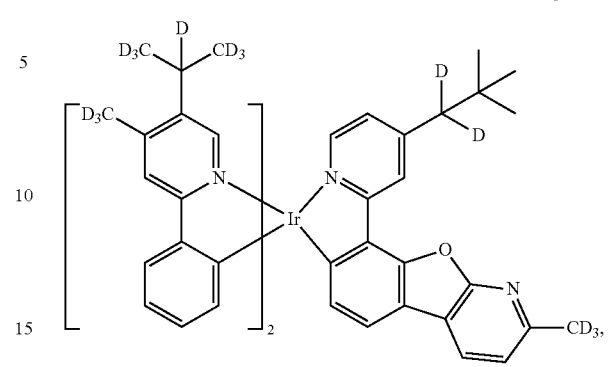
Compound 57
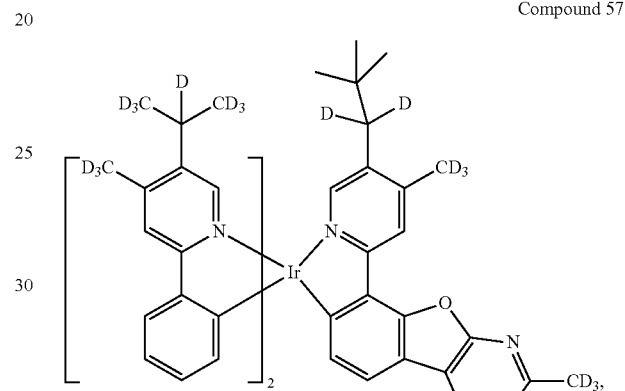
Compound 58
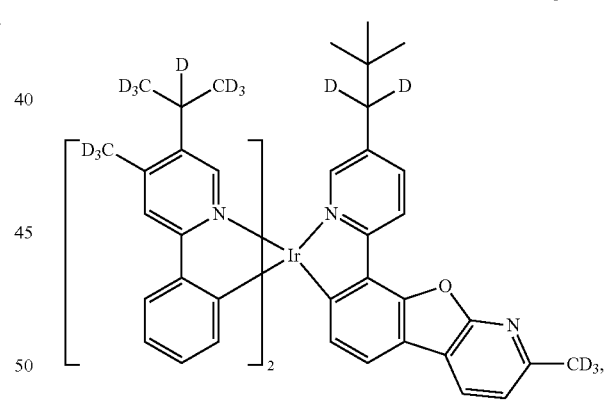
Compound 59
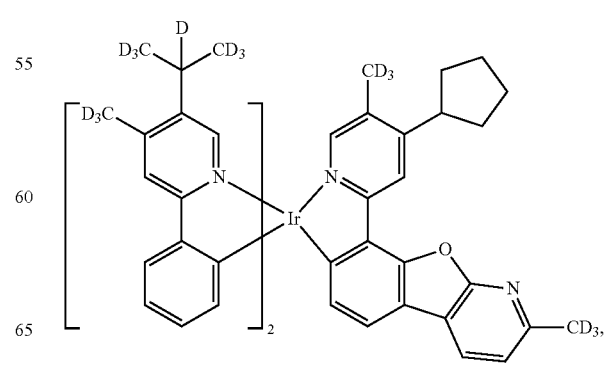

Compound 60
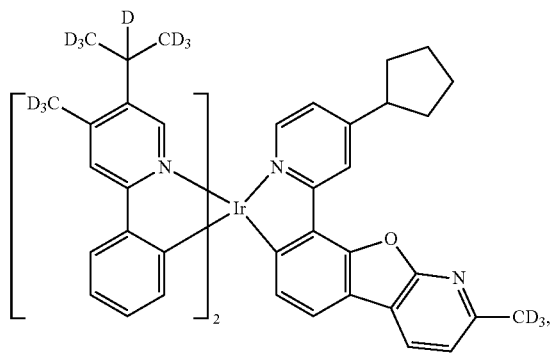
Compound 64
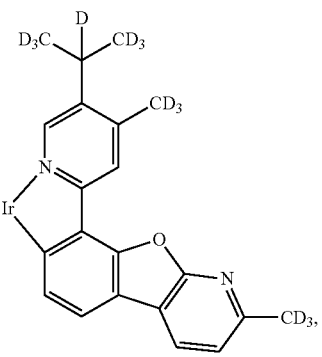
Compound 61
Compound 65
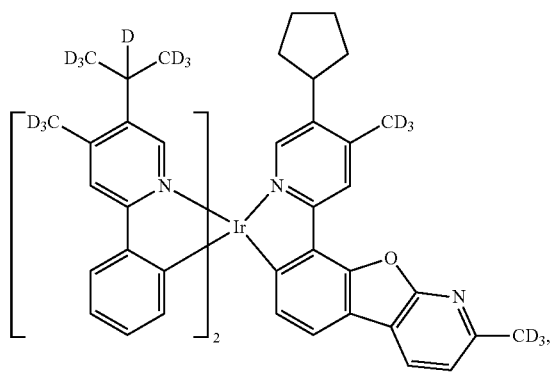 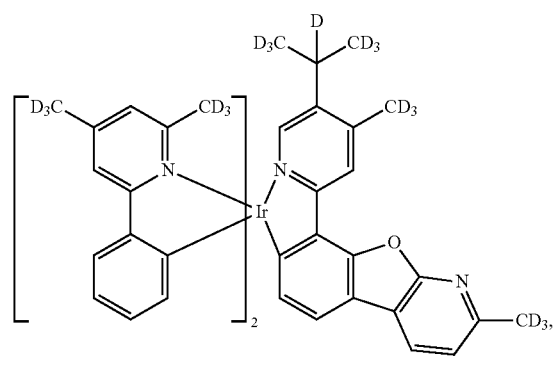
Compound 62
Compound 66
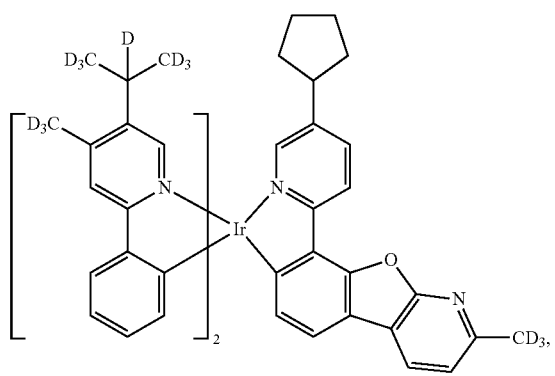 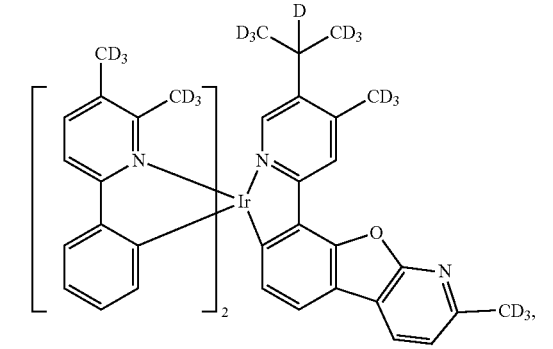
Compound 63
Compound 67
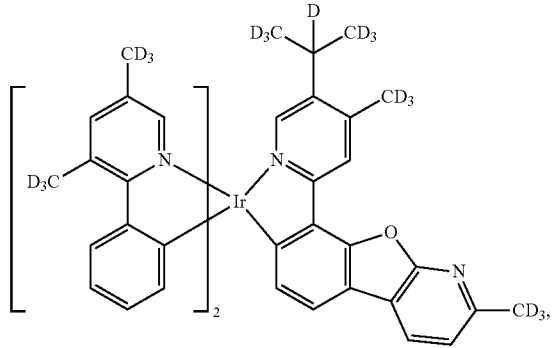 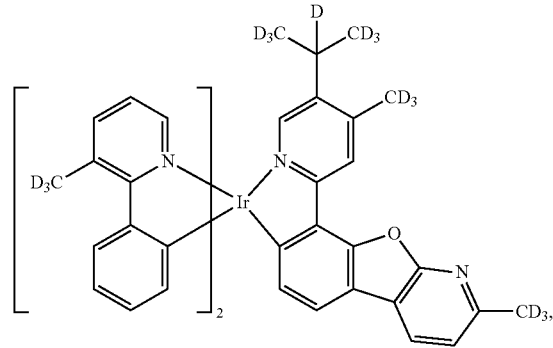

Compound 68
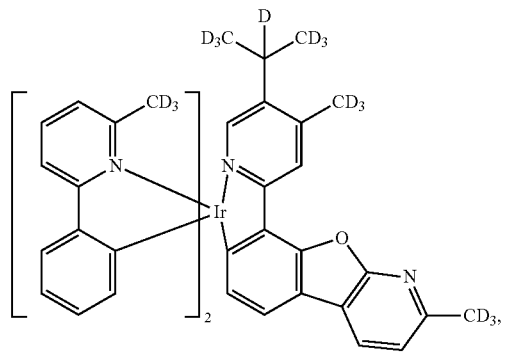
Compound 69
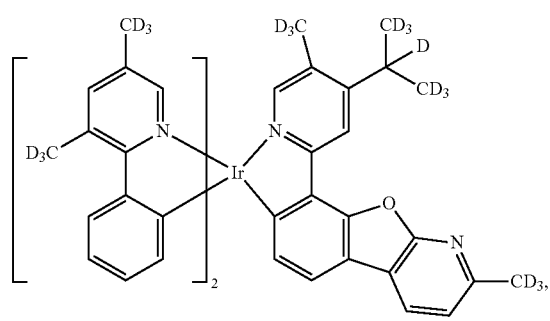
Compound 70
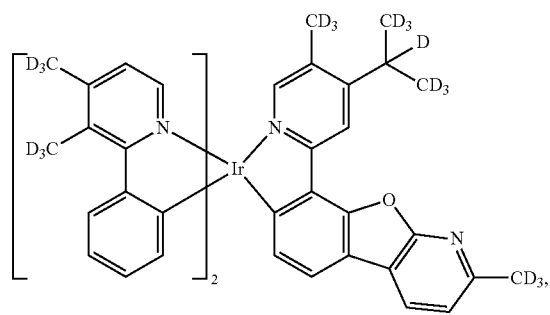
Compound 71
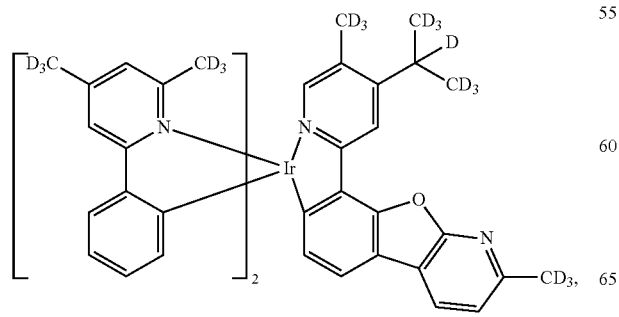
Compound 72
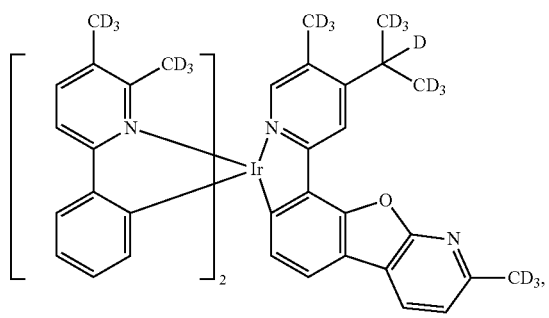
Compound 73
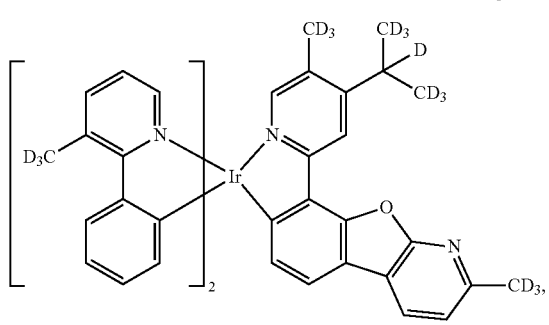
Compound 74
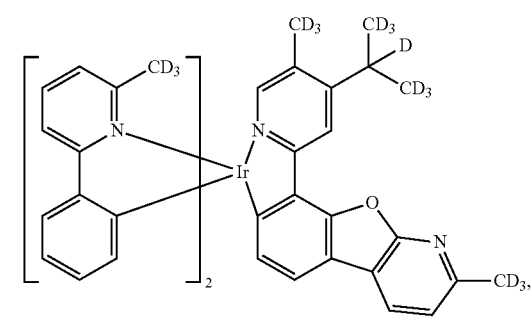
Compound 75
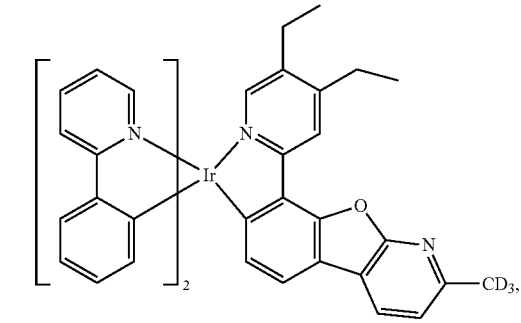

Compound 76
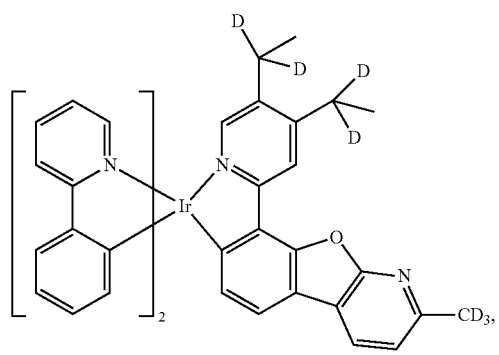
Compound 77
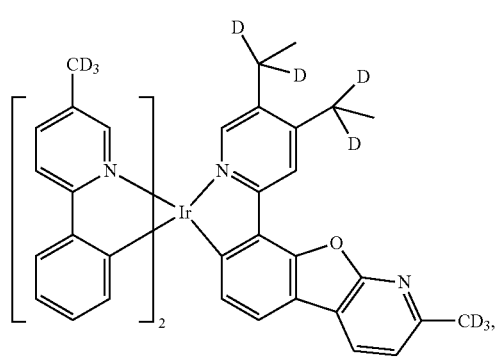
Compound 78
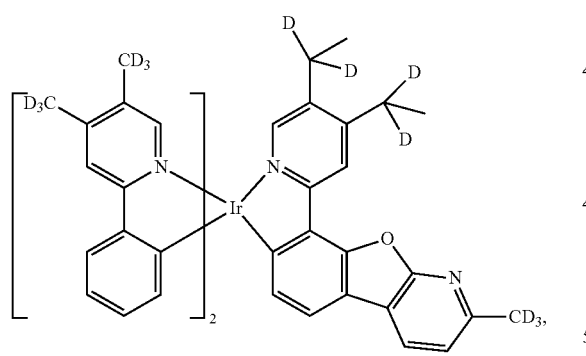
Compound 79
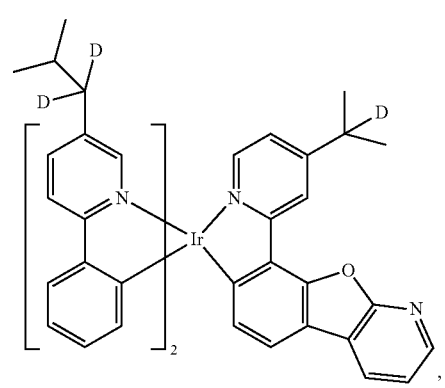
Compound 80
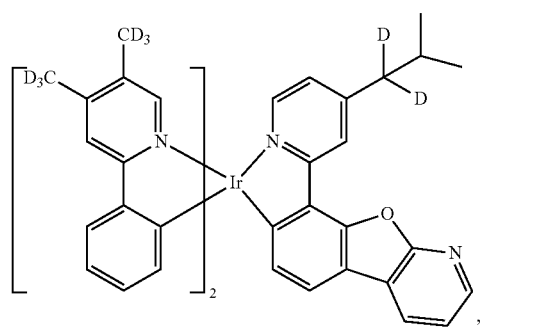
Compound 81
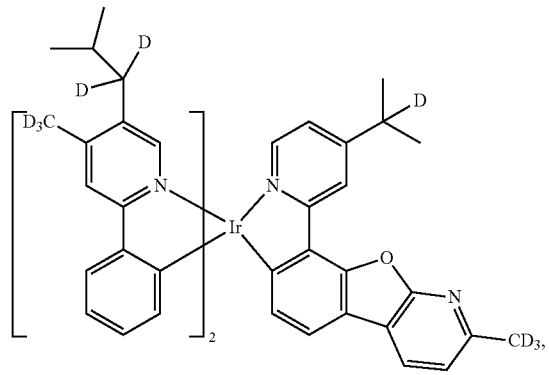
Compound 82
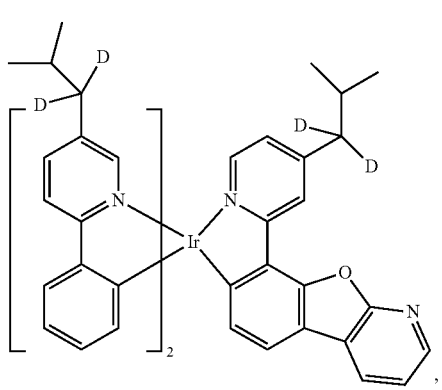
Compound 83
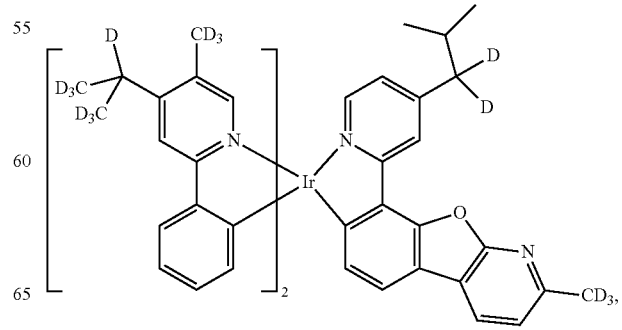

Compound 84
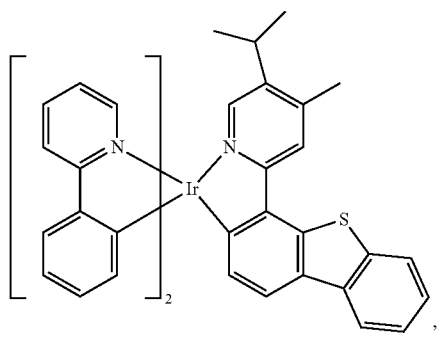
Compound 85
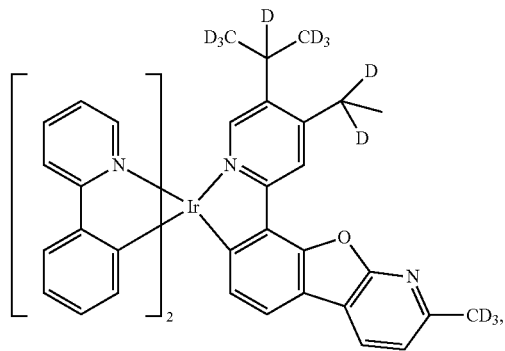
Compound 86
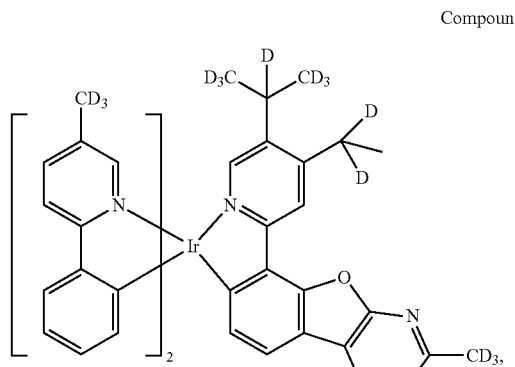
Compound 87
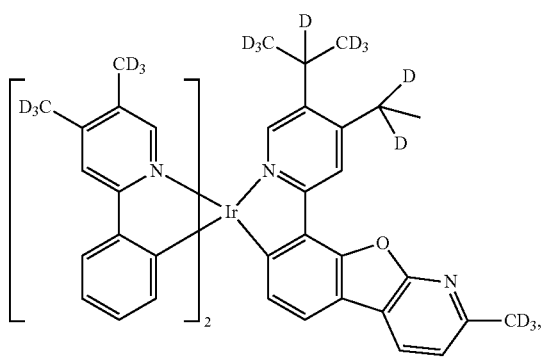
Compound 88
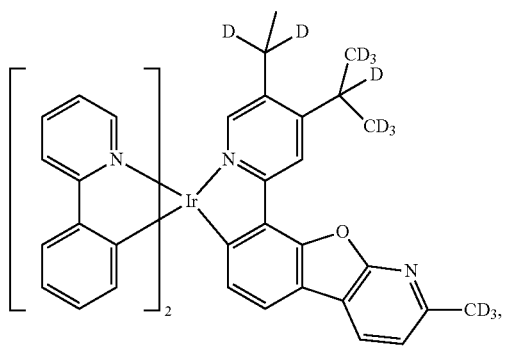
Compound 89
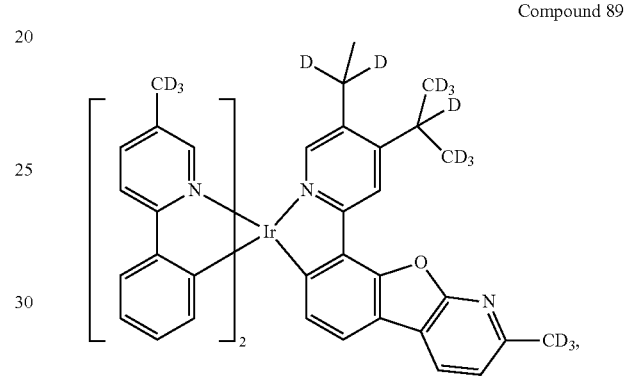
Compound 90
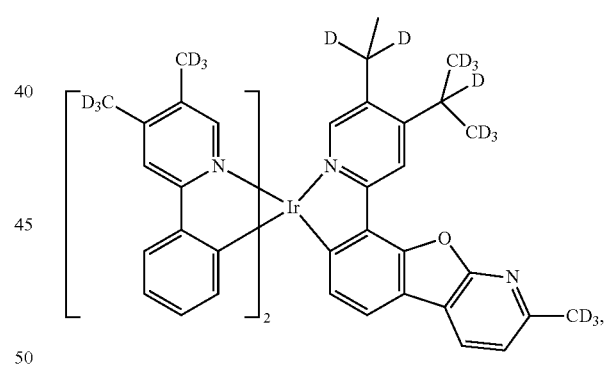
Compound 91
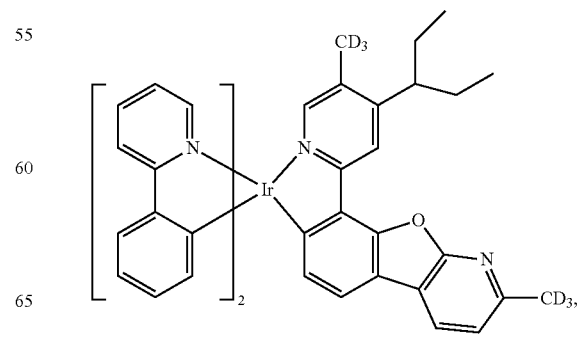

Compound 92
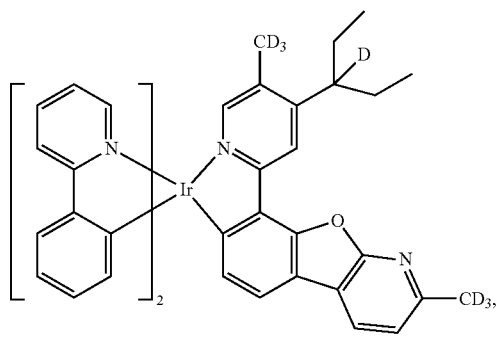
Compound 93
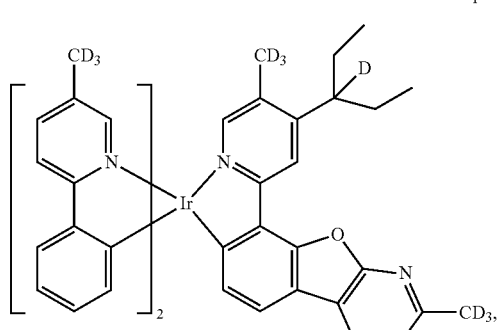
Compound 94
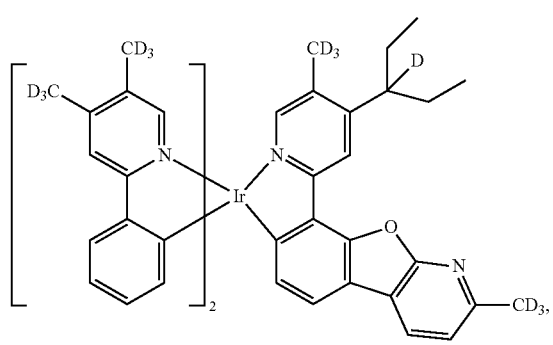
Compound 95
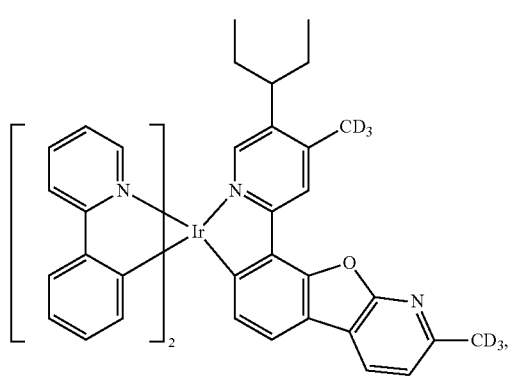
Compound 96
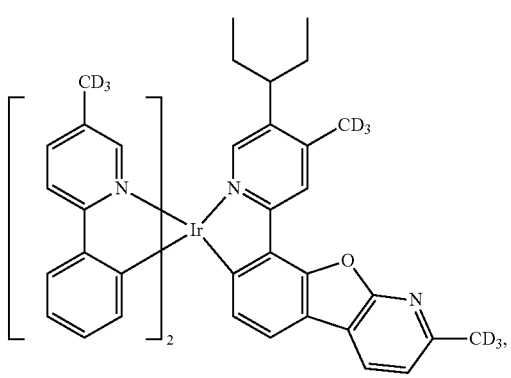
Compound 97
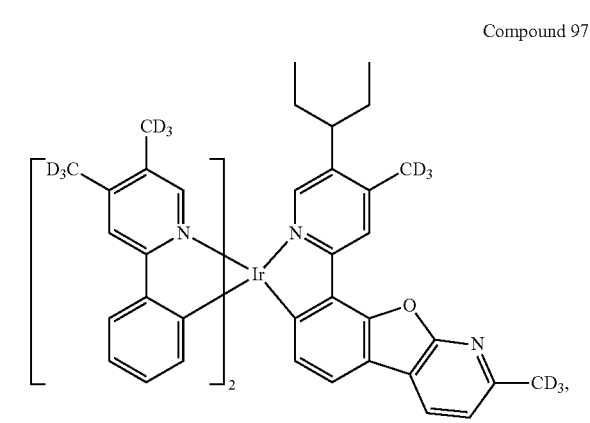
Compound 98
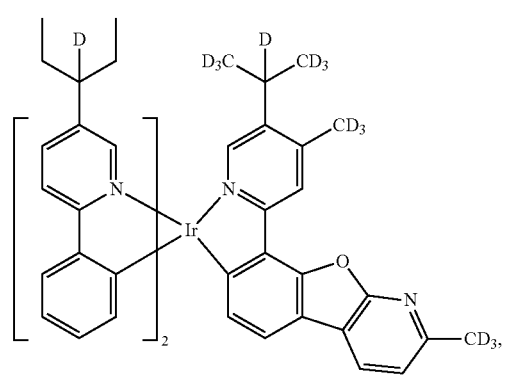
Compound 99
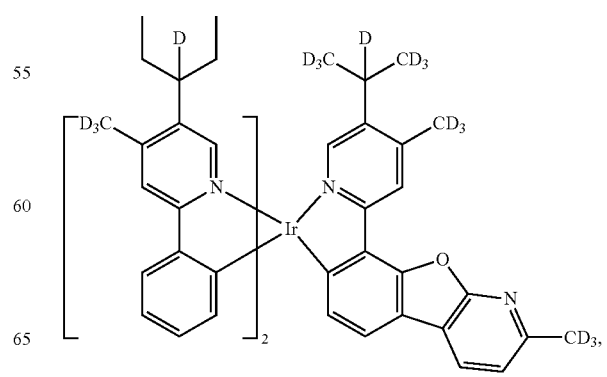

Compound 100
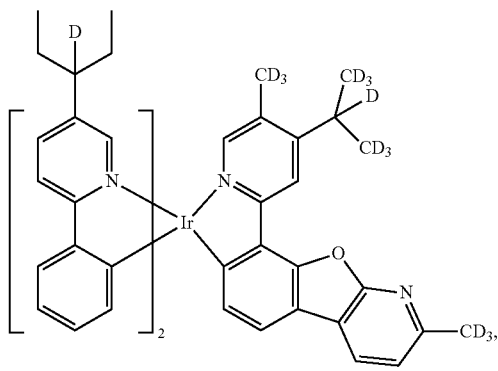
Compound 104
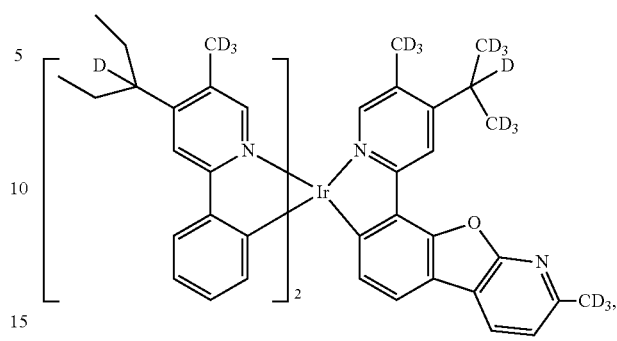
Compound 101
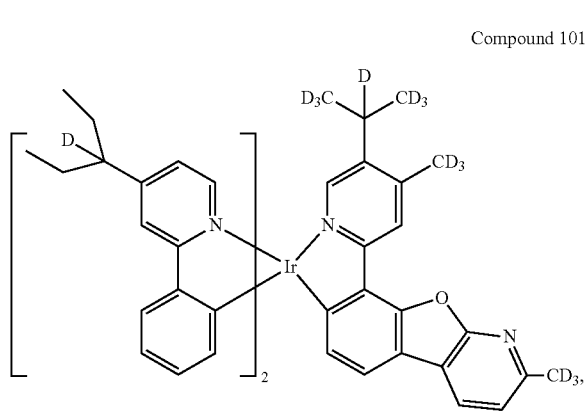
Compound 105
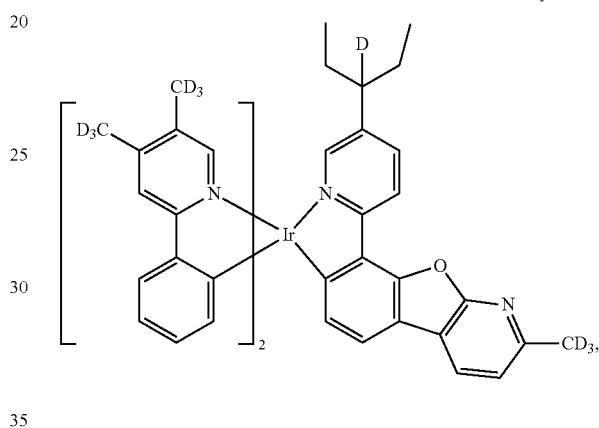
Compound 102
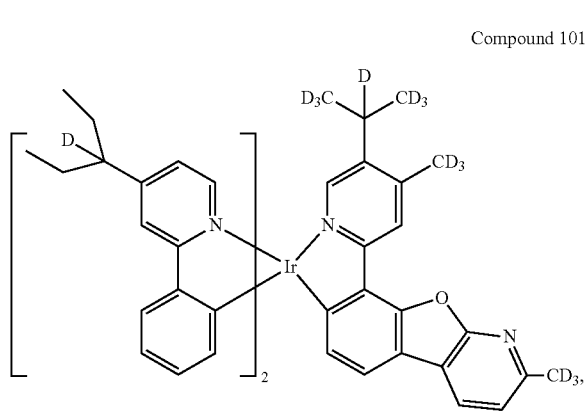
Compound 106
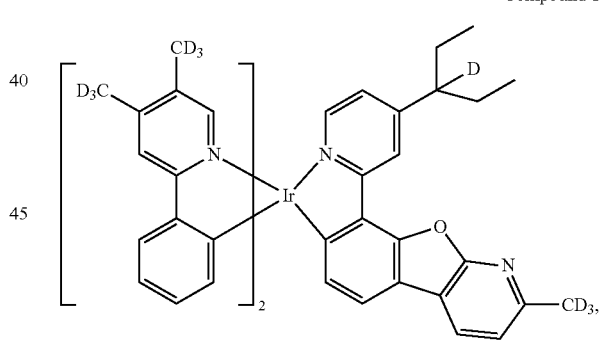
Compound 103
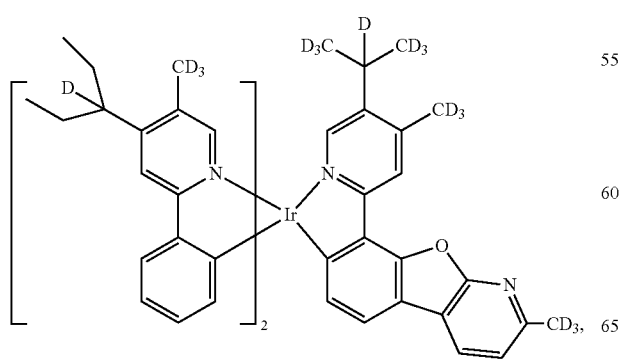
Compound 107
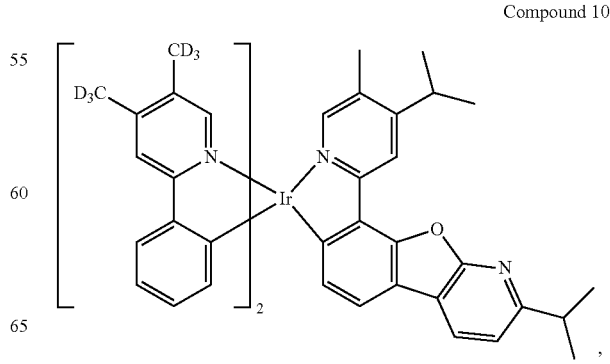

Compound 108
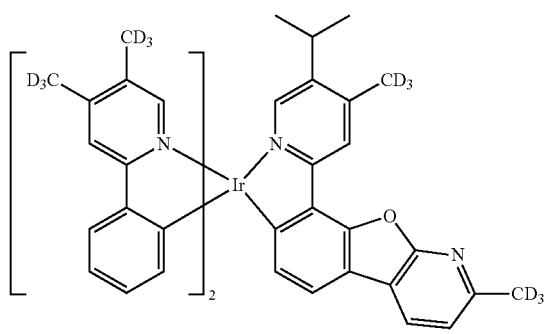
Compound 112
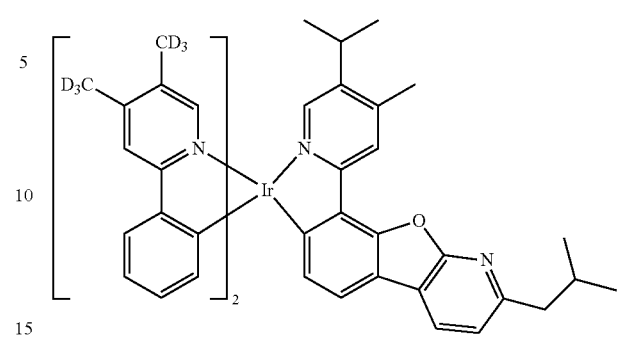
Compound 109
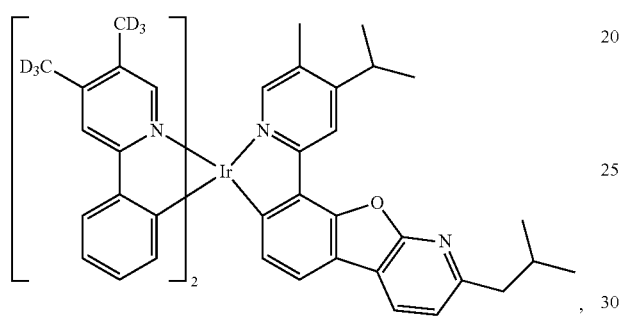
Compound 113
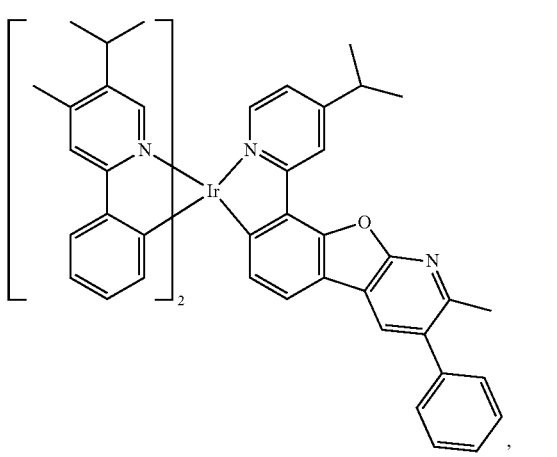
Compound 110
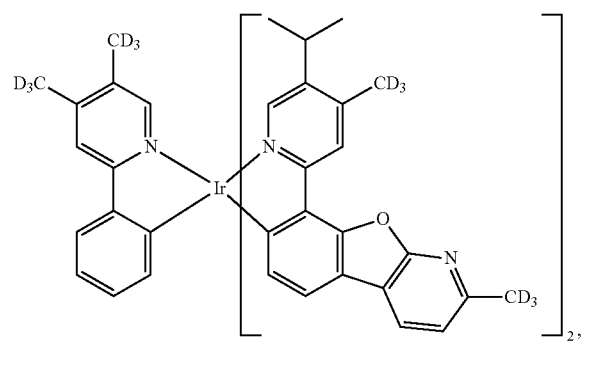
Compound 114
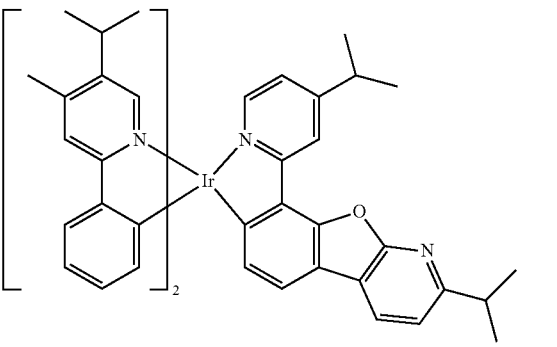
Compound 111
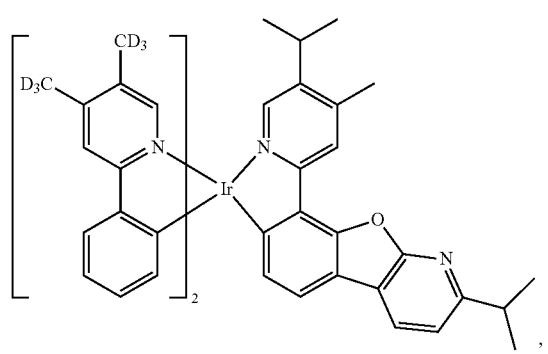
Compound 115

Compound 116

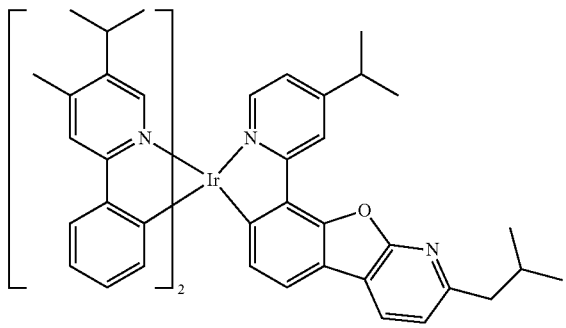

Compound 117

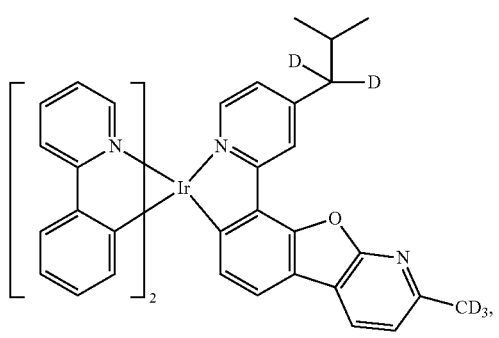

Compound 118

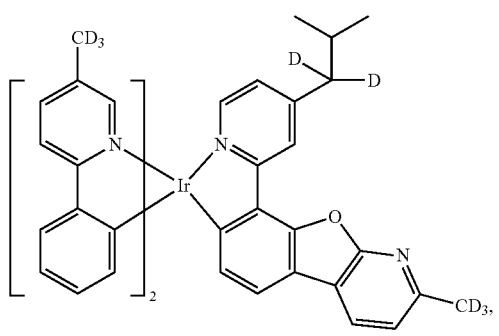

Compound 119

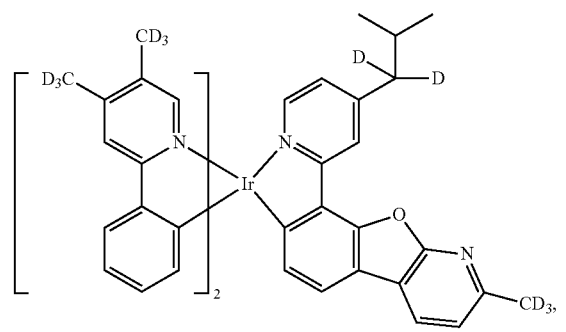

Compound 120

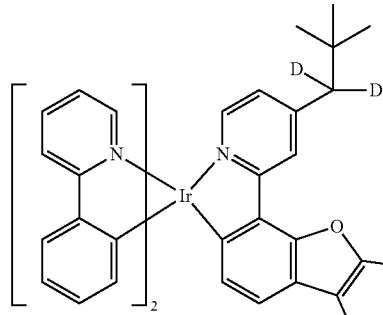

Compound 121

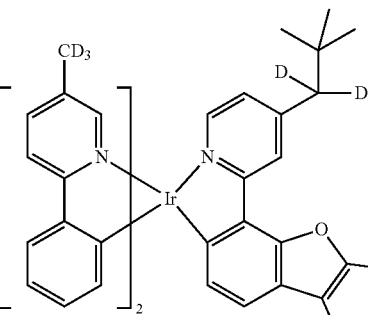

Compound 122

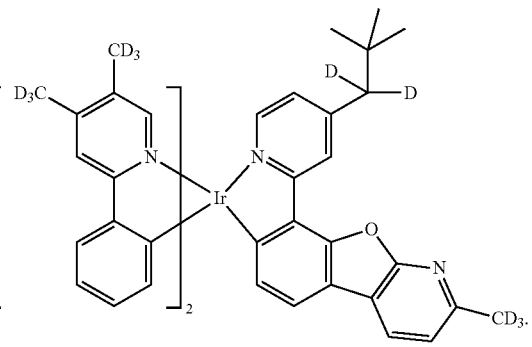

According to another aspect of the present disclosure, a first device comprising a first organic light emitting device is also disclosed. The first organic light emitting device comprises: an anode; a cathode; and an organic layer, disposed between the anode and the cathode. The organic layer comprises a compound having a structure according to Formula I, wherein A1, A2, A3, A4, A5, A6, A7, and A8 comprise carbon or nitrogen;

wherein at least one of A1, A2, A3, A4, A5, A6, A7, and A8 is nitrogen;

wherein ring B is bonded to ring A through a C—C bond;

wherein the iridium is bonded to ring A through a Ir—C bond;

wherein X is O, S, or Se;

wherein R1 and R2 each independently represent mono-, di-, tri-, tetra-substitution, or no substitution;

wherein R' and R" each independently represent mono-, di-substitution, or no substitution;

wherein any adjacent substitutions in R', R", R1, R2, R3, R4, R5, and R6 are optionally linked together to form a ring;

wherein R1, R2, R', and R" are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
wherein R3, R4, R5, and R6 are each independently selected from the group consisting of hydrogen, deuterium, alkyl, cycloalkyl, and combinations thereof;
wherein n is an integer from 1 to 3; and
wherein total number of carbons in at least one of the pairs R3 and R4, and R5 and R6 is at least four.

In one embodiment, the first device can be a consumer product. The first device can be an organic light-emitting device. The first device can be a lighting panel.

In one embodiment, the organic layer in the first device is an emissive layer and the compound is an emissive dopant.

In another embodiment, the organic layer in the first device is an emissive layer and the compound is a non-emissive dopant.

In another embodiment, the organic layer in the first device can further comprise a host material. The host material comprises a triphenylene containing benzo-fused thiophene or benzo-fused furan; wherein any substituent in the host is an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv C-C_nH_{2n+1}$, $Ar_1$, $Ar_1$-$Ar_2$, $C_nH_{2n}$-$Ar_1$, or no substitution;
wherein n is from 1 to 10; and
wherein $Ar_1$ and $Ar_2$ are independently selected from the group consisting of benzene, biphenyl, naphthalene, triphenylene, carbazole, and heteroaromatic analogs thereof.

In one embodiment, the host material comprises at least one chemical group selected from the group consisting of triphenylene, carbazole, dibenzothiophene, dibenzofuran, dibenzoselenophene, azatriphenylene, azacarbazole, aza-dibenzothiophene, aza-dibenzofuran, and aza-dibenzoselenophene. In another embodiment, the host material is selected from the group consisting of:

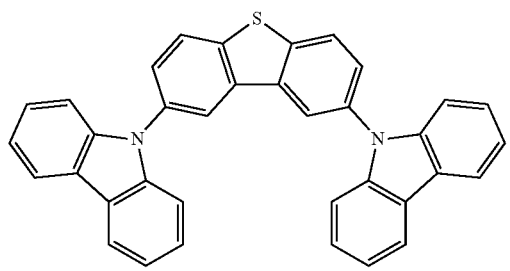

,

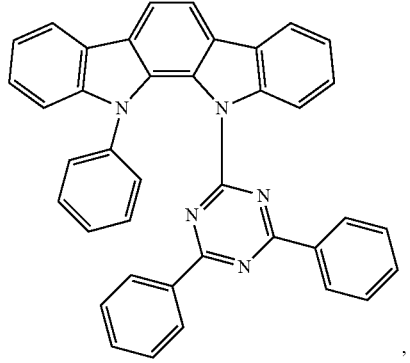

,

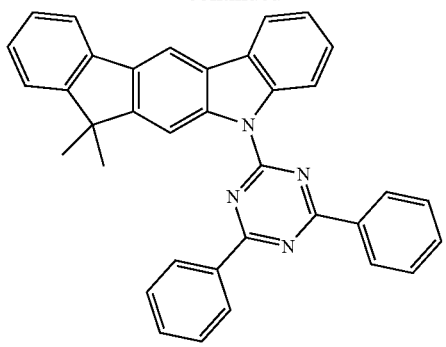

,

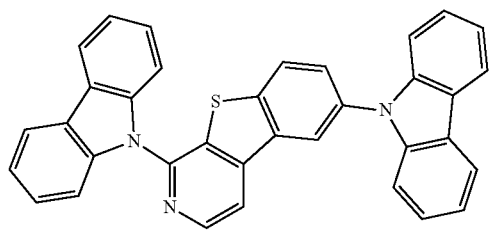

,

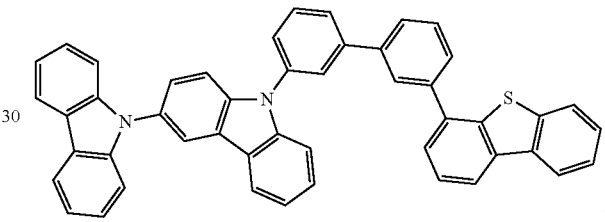

,

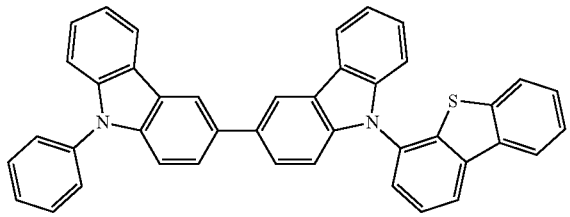

,

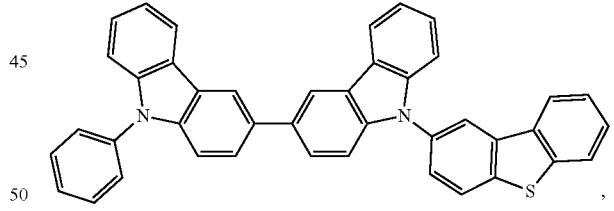

,

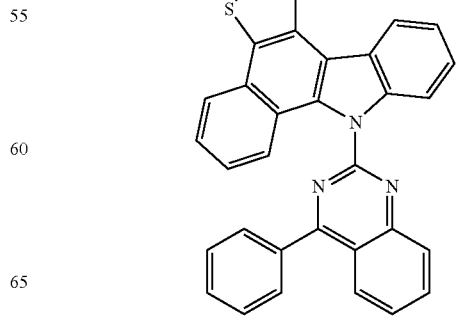

,

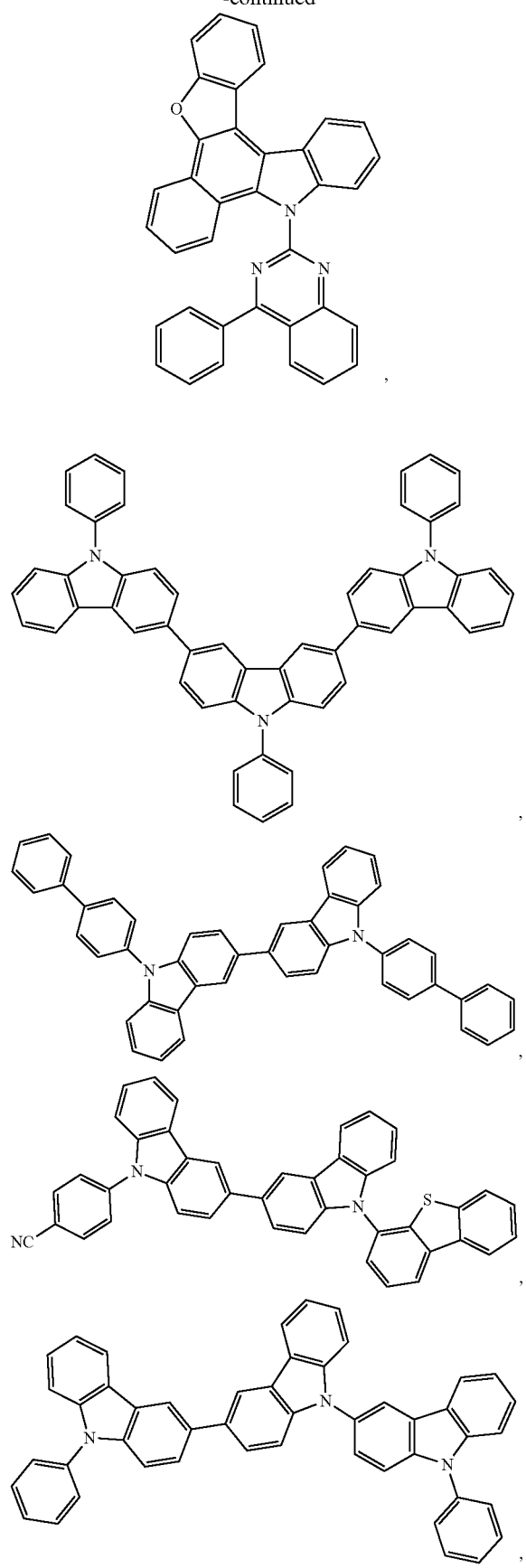

-continued

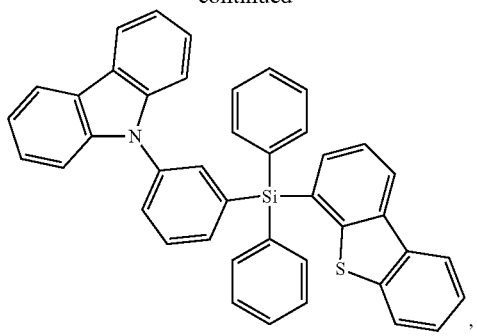

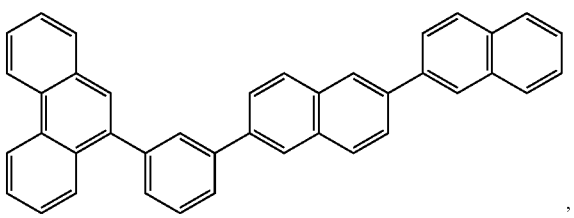

and combinations thereof.

In another embodiment of the first device, the host material comprises a metal complex.

According to another aspect of the present disclosure, a formulation comprising the compound having a structure according to Formula I is also disclosed, wherein Formula I being as defined above. The formulation can include one or more components selected from the group consisting of a solvent, a host, a hole injection material, hole transport material, and an electron transport layer material, disclosed herein.

Materials Synthesis

All reactions were carried out under nitrogen protections unless specified otherwise. All solvents for reactions are anhydrous and used as received from commercial sources. Precursors and ligands can be produced by methods known to those skilled in the art, and have been described in detail in U.S. patent application Ser. No. 13/928,456, which is incorporated herein by reference in its entirety.

Synthesis of Compound 2

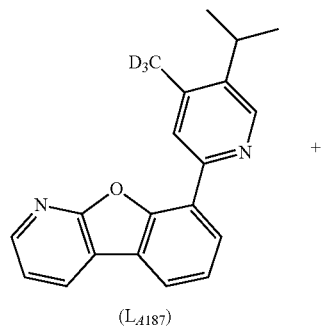

(L$_{A187}$)

-continued

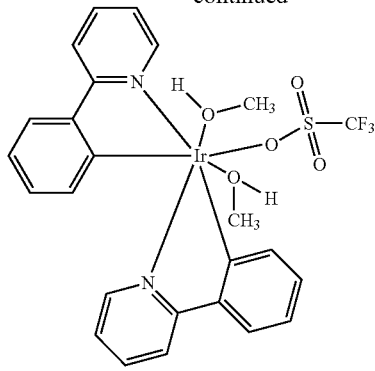

(i)

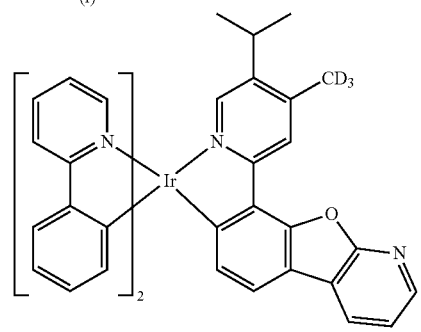

Compound 2

A mixture of 8-(4-d3-methyl-5-isopropyl)pyridine-2-yl (L$_{A187}$) (1.925 g, 6.30 mmol), an iridium precursor (i) (2.5 g, 3.50 mmol), 2-ethoxyethanol 40.0 mL, and dimethylformamide (DMF) 40 mL was heated in a 130° C. oil bath for 20 hours under N$_2$. The reaction mixture was concentrated to remove solvents and filtered through a small plug of silica gel and then further purified by column chromatography on silica gel using ethyl acetate and dichloromethane solvent mixture as elute to give 0.93 g of the desired product, Compound 2, (33% yield).

Synthesis of Compound 6

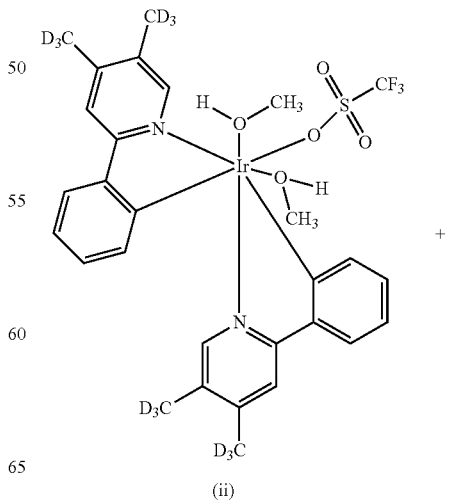

(ii)

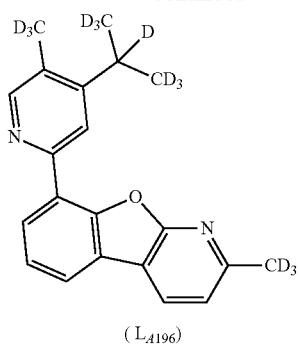

(L$_{A196}$)

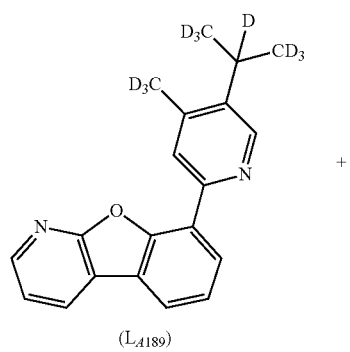

Compound 6

A mixture of aza-dibenzofuran ligand (L$_{A196}$) (1.5 g, 4.55 mmol) and an iridium precursor (ii) (1.98 g, 2.53 mmol), 2-ethoxyethanol 40 mL and DMF 40 mL was heated in a 130° C. oil bath for 17 hours under N$_2$. The reaction mixture was concentrated to remove solvents and filtered through a small silica gel plug and further purified by column chromatography using dichloromethane to give 0.65 g of the desired product, Compound 6, (29% yield).

Synthesis of Compound 8

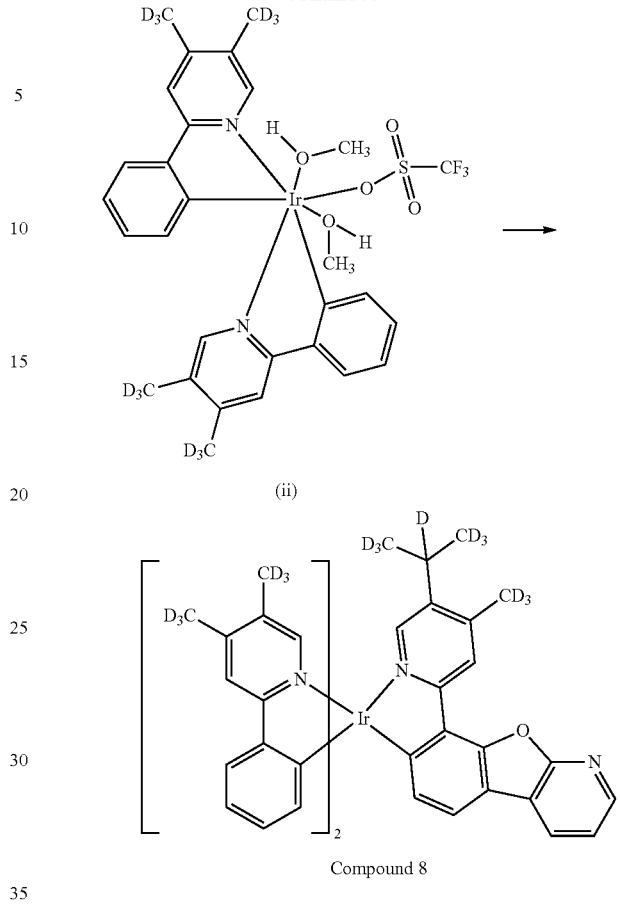

The aza-dibenzofuran ligand (L$_{A189}$) (1.1 g, 3.52 mmol), an iridium precursor (ii) (1.72 g, 2.20 mmol), 2-ethoxyethanol (30 mL) and DMF (30 mL) were charged in a flask and heated in a 130° C. oil bath for 15 hours under N$_2$. The reaction solvent was evaporated and the solid was dissolved to filter through a small silica gel plug and further purified by column chromatography using ethyl acetate in dichloromethane to give 0.34 g of Compound 8 (18% yield).

Synthesis of Compound 12

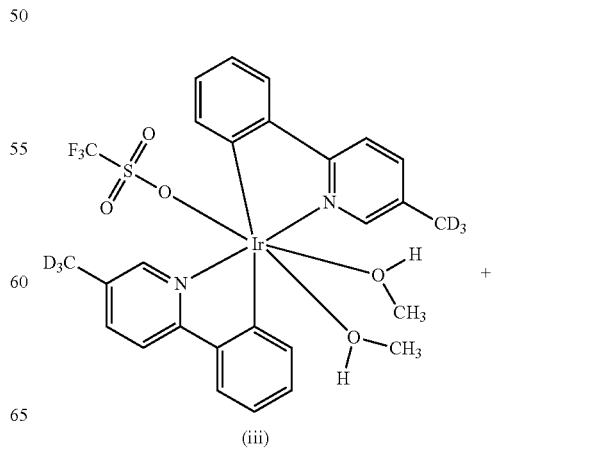

-continued

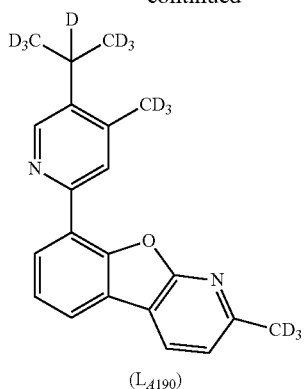

(L$_{A190}$)

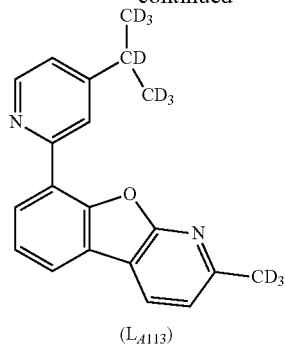

(L$_{A113}$)

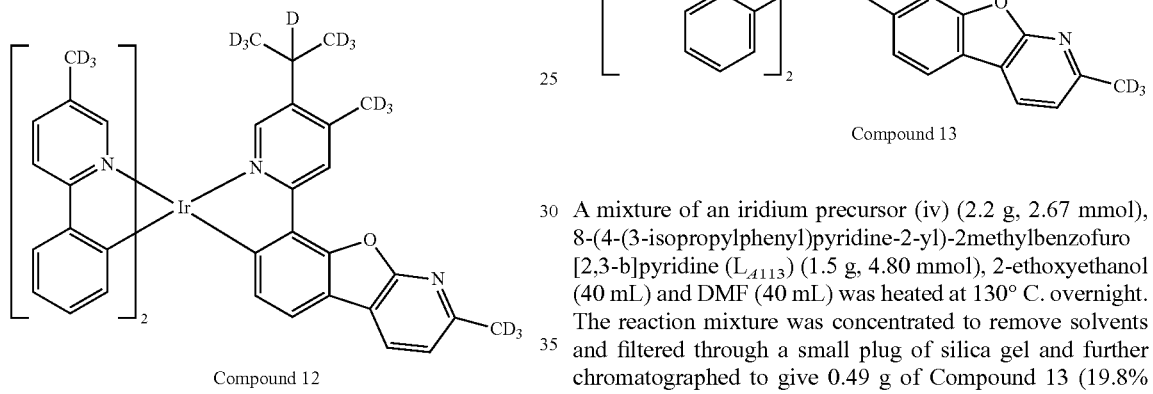

Compound 13

A mixture of an iridium precursor (iv) (2.2 g, 2.67 mmol), 8-(4-(3-isopropylphenyl)pyridin-2-yl)-2methylbenzofuro[2,3-b]pyridine (L$_{A113}$) (1.5 g, 4.80 mmol), 2-ethoxyethanol (40 mL) and DMF (40 mL) was heated at 130° C. overnight. The reaction mixture was concentrated to remove solvents and filtered through a small plug of silica gel and further chromatographed to give 0.49 g of Compound 13 (19.8% yield).

Synthesis of Compound 9

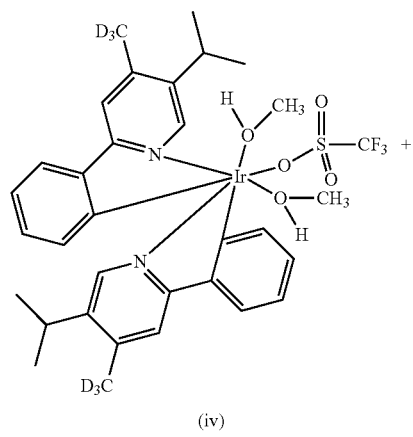

Compound 12

A mixture of an iridium precursor (iii) (2.34 g, 3.02 mmol), 8-(5-isopropyl-4-methylpyridin-2-yl)-2-methylbenzofuro[2,3-b]pyridine-d$_{13}$ (L$_{A190}$) (1.7 g, 5.44 mmol), 2-ethoxyethanol (60 mL) and DMF (60 mL) was heated at 130° C. overnight. The reaction mixture was concentrated to remove solvents and filtered through a small plug of silica gel and further chromatographed to give 0.77 g of Compound 12 (35% yield).

Synthesis of Compound 13

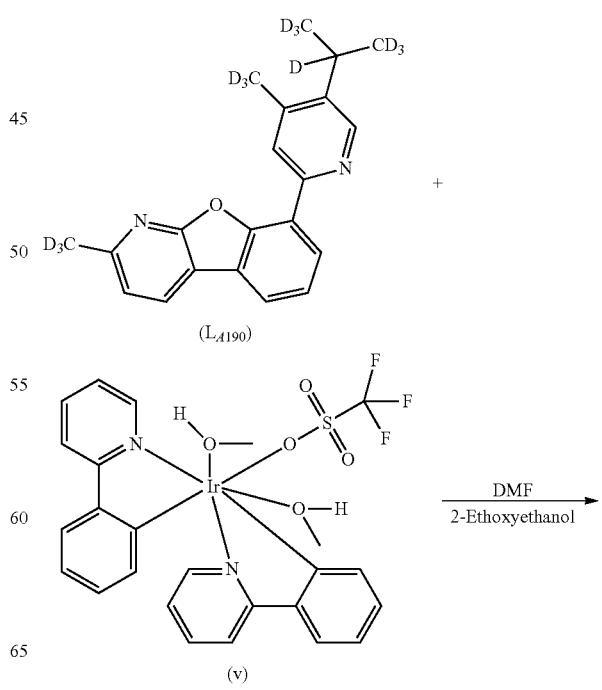

(L$_{A190}$)

+

(iv)

(v)

$\xrightarrow{\text{DMF}}_{\text{2-Ethoxyethanol}}$

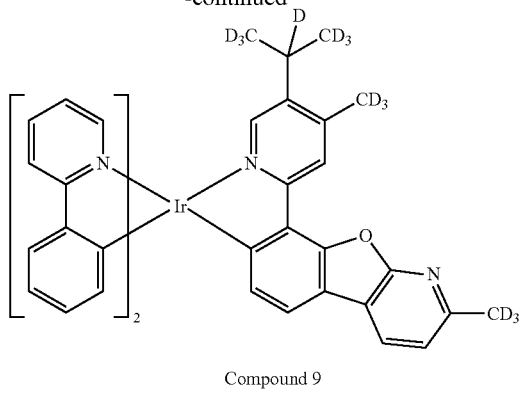

Compound 9

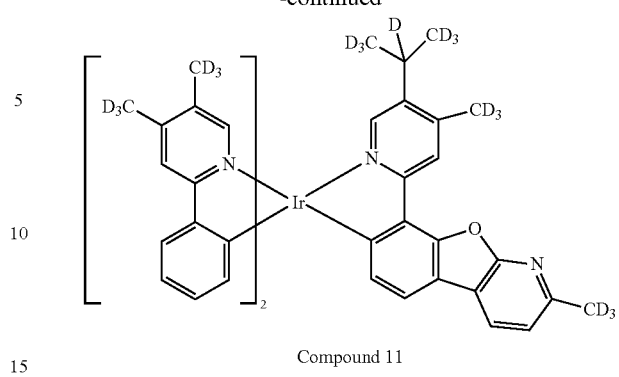

Compound 11

The aza-dibenzofuran ligand (L$_{A190}$) (1.5 g, 4.55 mmol) and an iridium precursor (v) (1.9 g, 2.66 mmol) were charged into the reaction flask with 30 mL of DMF and 30 mL of 2-ethoxyethanol. This mixture was stirred and heated in an oil bath set at 130° C. for 19 hours. The reaction mixture was cooled to room temperature then was concentrated under vacuum. The crude residue was dried under vacuum. This crude residue was dissolved in 200 mL of DCM then was passed through a silica gel plug. The DCM filtrate was concentrated under vacuum. This crude residue was passed through a silica gel column using 60-75% DCM/heptanes. Clean product fractions were combined and concentrated under vacuum yielding (1.0 g, 45.5%) of the desired iridium complex, Compound 9. The desired mass was confirmed by LC/MS analysis.

Synthesis of Compound 11

The aza-dibenzofuran ligand (L$_{A190}$) (1.5 g, 4.55 mmol) and an iridium precursor (vi) (1.98 g, 2.53 mmol) were charged into the reaction flask with 40 mL of DMF and 40 mL of 2-ethoxyethanol. This mixture was stirred and heated in an oil bath set at 130° C. for 18 hours. The reaction mixture was cooled to room temperature then was concentrated under vacuum. The crude residue was dried under vacuum. This crude residue was dissolved in 200 mL of DCM then was passed through a silica gel plug. The DCM filtrate was concentrated under vacuum. This crude residue was passed through a silica gel column using 60-75% DCM/heptanes. Clean product fractions were combined and concentrated under vacuum yielding (0.45 g, 19.8%) of the desired iridium complex, Compound 11. The mass was confirmed by LC/MS.

Synthesis of Compound 14

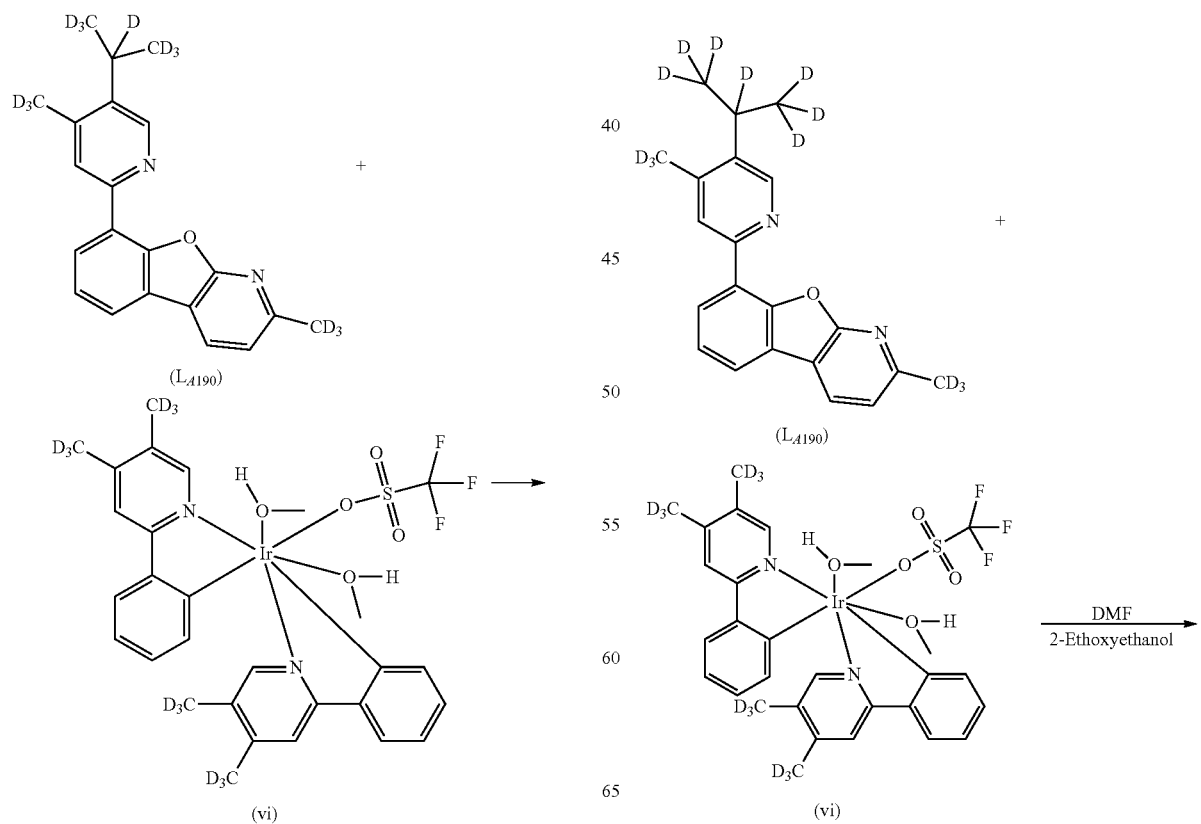

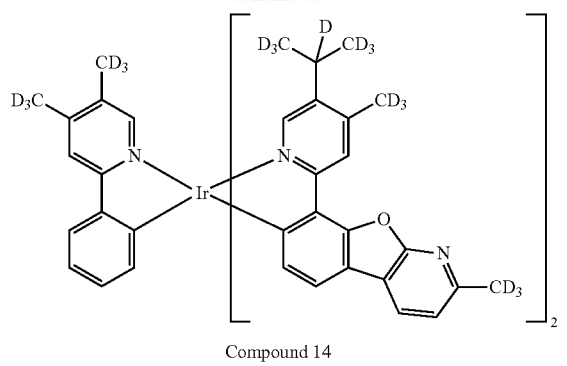

Compound 14

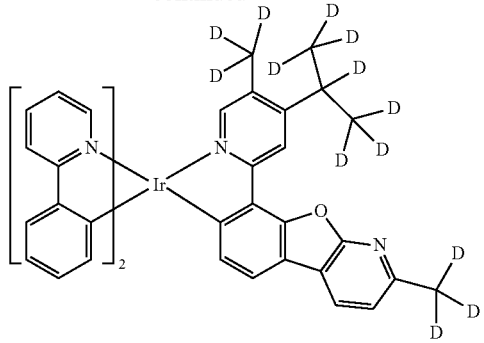

Compound 3

The aza-dibenzofuran ligand ($L_{A190}$) (1.5 g, 4.55 mmol) and the iridium precursor (vi) (1.98 g, 2.53 mmol) were charged into the reaction flask with 40 mL of DMF and 40 mL of 2-ethoxyethanol. This mixture was stirred and heated in an oil bath set at 130° C. for 18 hours. The reaction mixture was cooled to room temperature then was concentrated under vacuum. The crude residue was dried under vacuum. This crude residue was dissolved in 200 mL of DCM then was passed through a silica gel plug. The DCM filtrate was concentrated under vacuum. This crude residue was passed through a silica gel column using 60-75% DCM/heptanes. Clean product fractions were combined and concentrated under vacuum yielding (0.77 g, 29.3%) of the desired iridium complex, Compound 14. The desired mass was confirmed by LC/MS analysis.

Synthesis of Compound 3

The aza-dibenzofuran ligand ($L_{A196}$) (1.5 g, 4.55 mmol) and the iridium precursor (v) (1.9 g, 2.66 mmol) were charged into the reaction mixture with 30 mL of DMF and 30 mL of 2-ethoxyethanol. The reaction mixture was degassed with nitrogen then was stirred and heated in an oil bath set at 130° C. for 17 hours. Heating was then discontinued. The solvent were removed under vacuum. The crude residue was dissolved in DCM then was passed through a silica gel plug. The plug was eluted with 2 L of DCM. The DCM filtrate was evaporated under vacuum. This crude residue was passed through a silica gel column using 90% DCM/heptanes. The clean column fractions were combined and concentrated under vacuum yielding the desired iridium complex, Compound 3 (0.95 g, 1.146 mmol, 43.0% yield) as a yellow solid. The desired mass was confirmed by LC/MS analysis.

Synthesis of Compound 18

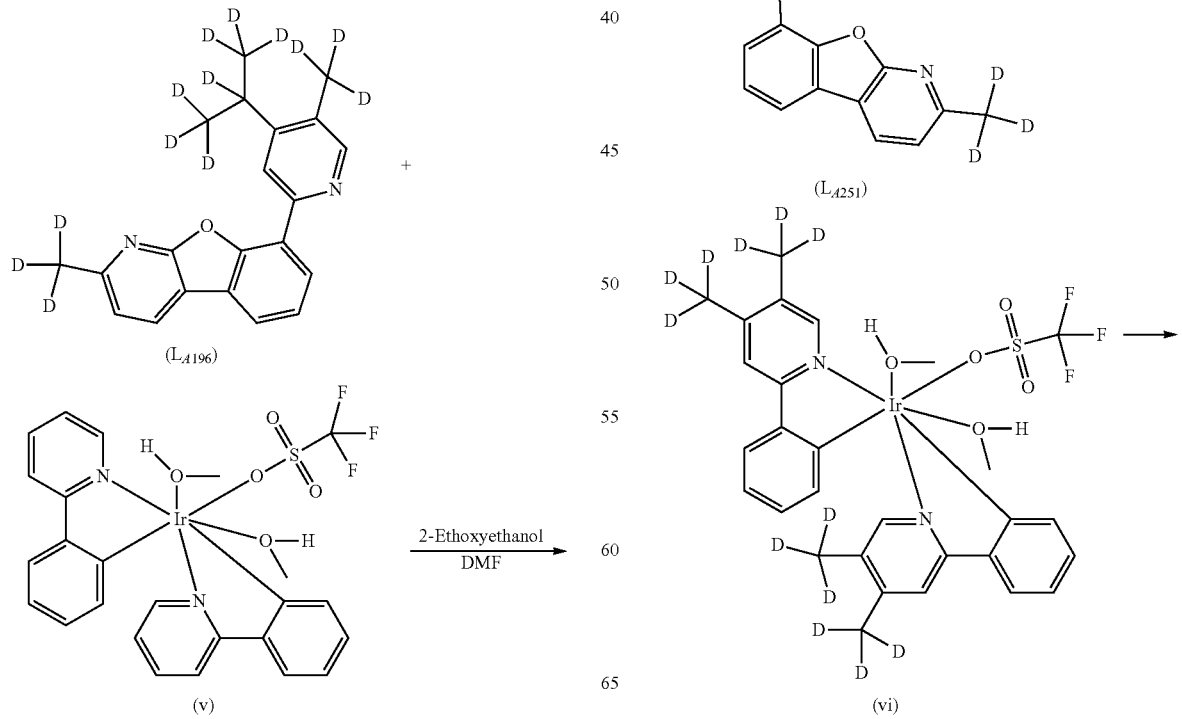

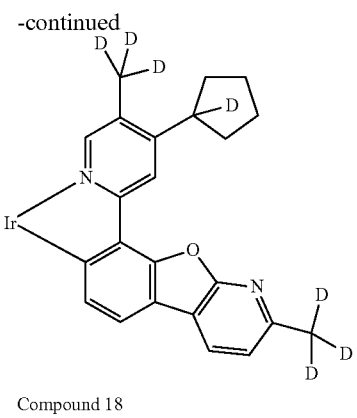

Compound 18

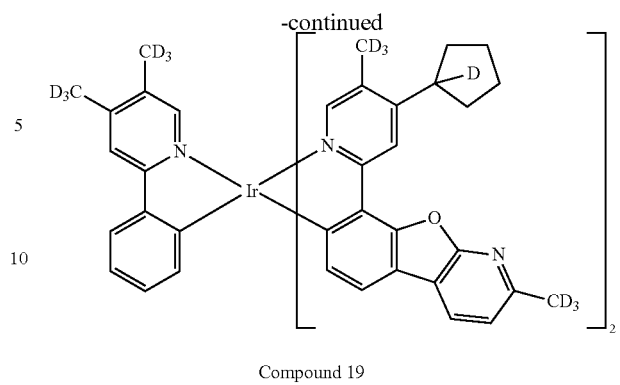

Compound 19

The aza-dibenzofuran ligand (L$_{A251}$) (1.406 g, 4.02 mmol) and iridium precursor (vi) (1.85 g, 2.366 mmol) were charged into the reaction mixture with 35 mL of DMF and 35 mL of 2-ethoxyethanol. This mixture was degassed with nitrogen then was stirred and heated in an oil bath set at 130° C. for 18 hours. The reaction mixture was concentrated and dried under vacuum. This crude product was dissolved in 300 mL of DCM then was passed through a plug of silica gel. The DCM filtrate was concentrated under vacuum. The crude residue was passed through a silica gel column eluting the column with 60-90% DCM/heptanes. The desired iridium complex, Compound 18 (0.6 g, 0.65 mmol, 27.6% yield) was isolated as a yellow solid. The desired mass was confirmed by LC/MS analysis.

Synthesis of Compound 19

The aza-dibenzofuran ligand (L$_{A251}$) (1.406 g, 4.02 mmol) and the iridium precursor (vi) (1.85 g, 2.366 mmol) were charged into the reaction mixture with 35 mL of DMF and 35 mL of 2-ethoxyethanol. This mixture was degassed with nitrogen then was stirred and heated in an oil bath set at 130° C. for 18 hours. The reaction mixture was concentrated and dried under vacuum. This crude product was dissolved in 300 mL of DCM then was passed through a plug of silica gel. The DCM filtrate was concentrated under vacuum. The crude residue was passed through a silica gel column eluting the column with 60-90% DCM/heptanes. The desired iridium complex, Compound 19 (0.7 g, 0.65 mmol, 27.3% yield) was isolated as a yellow solid. The desired mass was confirmed by LC/MS analysis.

Synthesis of Compound 20

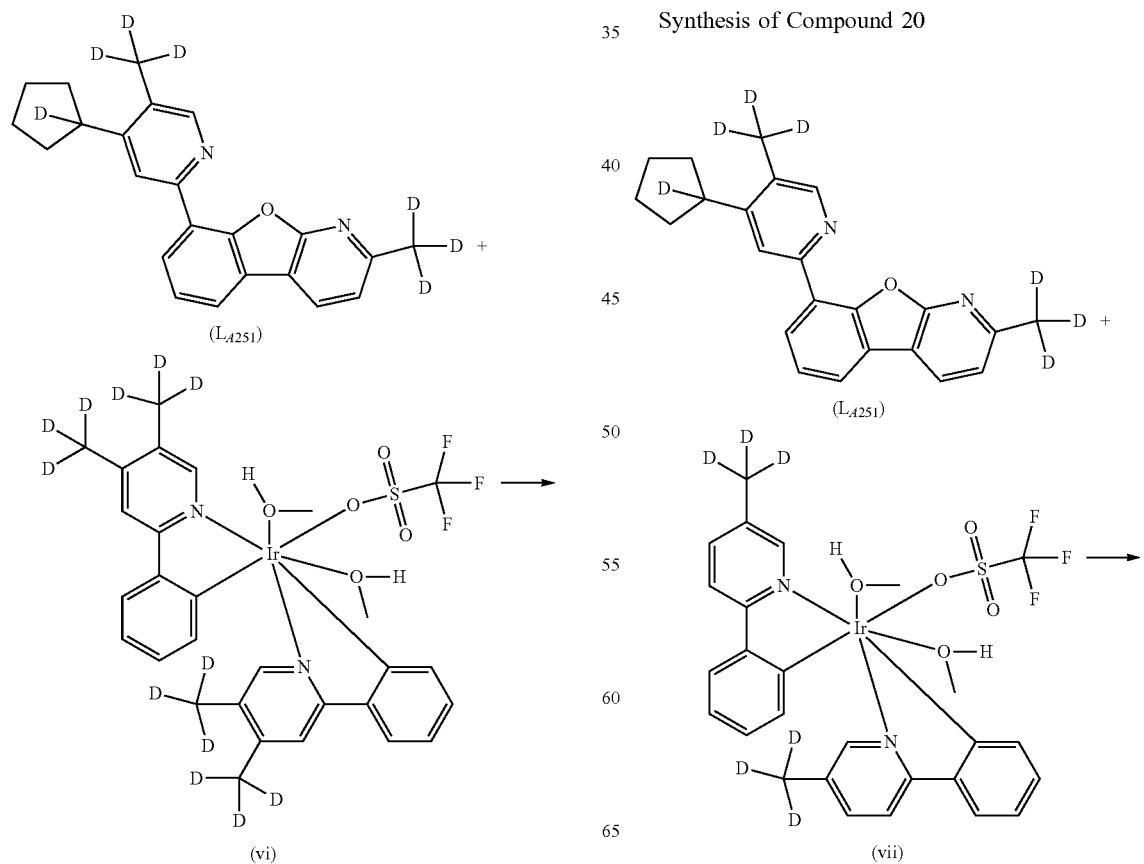

197

-continued

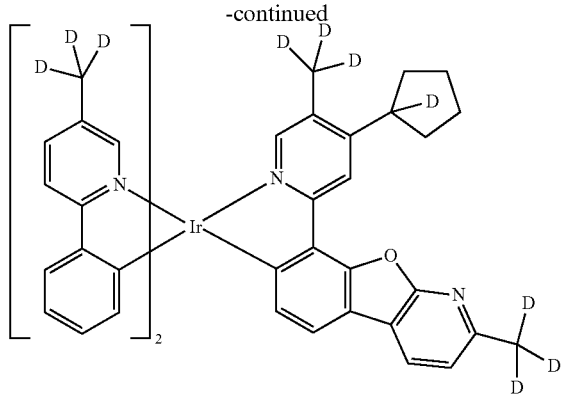

Compound 20

The aza-dibenzofuran ($L_{A251}$) (1.45 g, 4.15 mmol) and the iridium precursor (vii) (1.85 g, 2.474 mmol) were charged into the reaction flask with 35 mL of DMF and 35 mL of 2-ethoxyethanol. This mixture was degassed with nitrogen then was heated in an oil bath set at 130° C. for 24 hours. The reaction mixture was cooled to room temperature then was evaporated and dried under vacuum. The crude product was dissolved in 600 mL of hot DCM then was passed through a silica gel plug. The DCM filtrate was evaporated under vacuum then was passed through a silica gel column eluting the column with 60-75% DCM/heptanes. The clean column fractions were combined and concentrated under vacuum yielding the desired iridium complex, Compound 20 (0.7 g, 0.79 mmol, 32% yield). The desired mass was confirmed using LC/MS analysis.

Synthesis of Compound 21

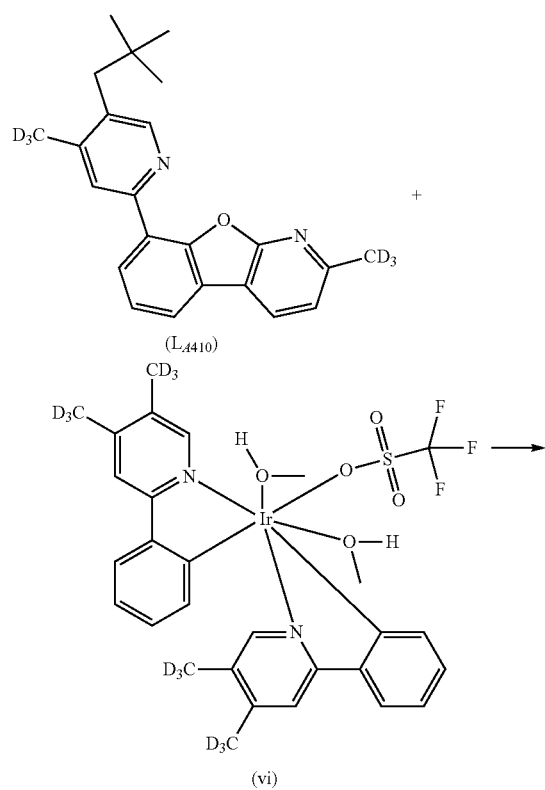

198

-continued

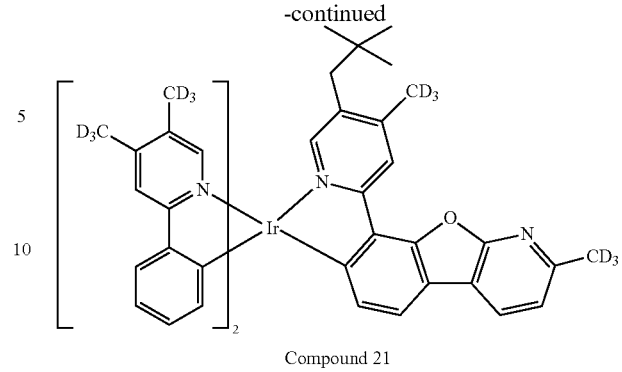

Compound 21

The aza-dibenzofuran ligand ($L_{A410}$) (1.45 g, 4.14 mmol) and the iridium precursor (vi) (1.9 g, 2.430 mmol) were charged into the reaction flask with 35 mL of DMF and 35 mL of 2-ethoxyethanol. This mixture was degassed with nitrogen then was heated in an oil bath set at 130° C. for 22 hours. The reaction mixture was cooled to room temperature then was concentrated and dried under vacuum. The crude product was passed through a silica gel plug. The plug was eluted with 2.5 L of DCM. The DCM filtrate was concentrated under vacuum and the crude residue was passed through a silica gel column eluting with 60-70% DCM/heptanes. The clean column fractions were combined and concentrated under vacuum yielding the desired Iridium complex, Compound 21 (0.72 g, 0.82 mmol, 33.6% yield) as a yellow solid. The mass of the desired product was confirmed by LC/MS analysis.

Synthesis of Compound 22

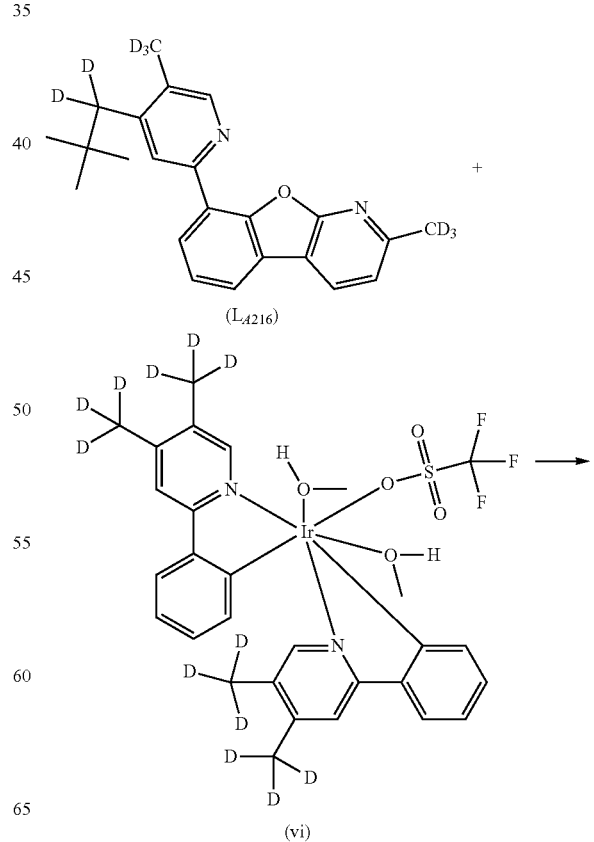

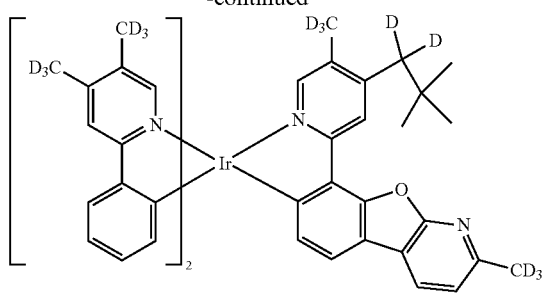

Compound 22

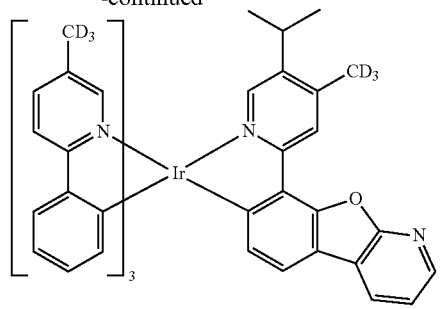

Compound 1

The aza-dibenzofuran ligand (L$_{A216}$) (1.43 g, 4.06 mmol) and the iridium precursor (vi) (1.9 g, 2.430 mmol) were charged into the reaction flask with 35 mL of DMF and 35 mL of 2-ethoxyethanol. This mixture was degassed with nitrogen then was heated in an oil bath set at 130° C. for 22 hours. The reaction mixture was cooled to room temperature then was concentrated and dried under vacuum. The crude product was passed through a silica gel plug. The plug was eluted with 2.5 L of DCM. The DCM filtrate was concentrated under vacuum and the crude residue was passed through a silica gel column eluting with 60-70% DCM/heptanes. The clean column fractions were combined and concentrated under vacuum yielding the desired iridium complex, Compound 22 (0.73 g, 0.79 mmol, 32.6% yield) as a yellow solid. The mass of the desired product was confirmed by LC/MS analysis.

Synthesis of Compound 1

A mixture of 8-(4-d3-methyl-5-isopropyl)pyridine-2-yl (L$_{A187}$) (1.985 g, 6.50 mmol), iridium precursor (viii) (2.7 g, 3.61 mmol), 2-ethoxyethanol 40 mL and DMF 40 mL was heated in an oil bath at 130° C. for 20 hours under N$_2$. The reaction mixture was purified by column chromatography on silica gel to give 1.45 g of the desired product Compound 2 (48% yield).

Synthesis of Compound 4

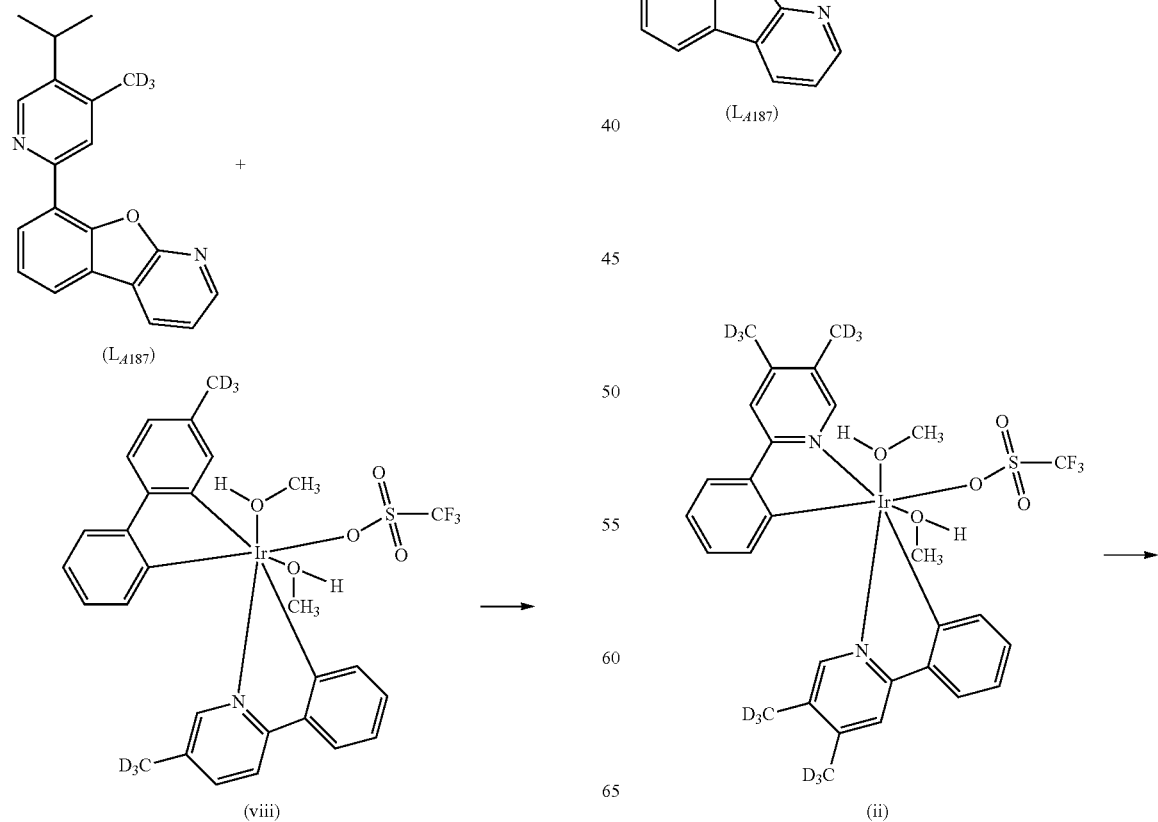

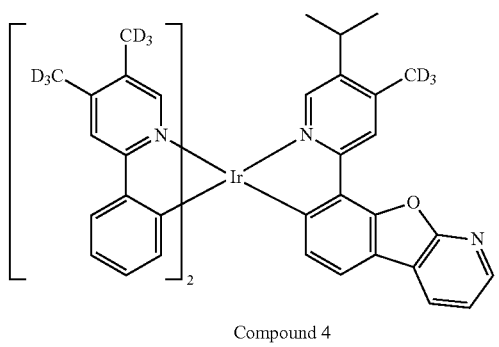

Compound 4

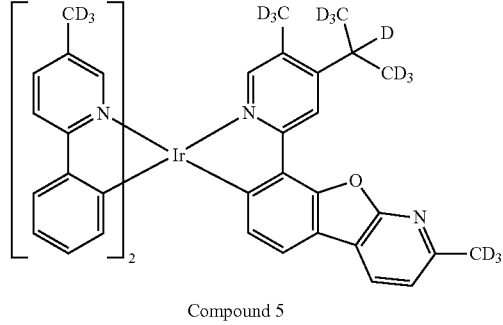

Compound 5

A mixture of 8-(4-d3-methyl-5-isopropyl)pyridine-2-yl (L$_{A187}$) (1.406 g, 4.6 mmol), iridium precursor (ii) (2.0 g, 2.56 mmol), 2-ethoxyethanol 30 mL and DMF 30 mL was heated in an oil bath at 130° C. for 20 hours under N$_2$. The reaction mixture was purified by column chromatography on silica gel to give 0.77 g of the desired product, Compound 4 (35% yield).

Synthesis of Compound 5

A mixture of aza-dibenzofuran ligand (L$_{A196}$) (1.5 g, 4.55 mmol) and iridium precursor (viii) (1.891 g, 2.53 mmol), 2-ethoxyethanol 40 mL and DMF 40 mL was heated in an oil bath at 130° C. for 17 hours under N$_2$. The reaction mixture was purified by silica gel column chromatography using ethyl acetate and dichloromethane solvent mixture to give 0.88 g of the desired product, Compound 5. (39% yield).

Synthesis of Compound 10

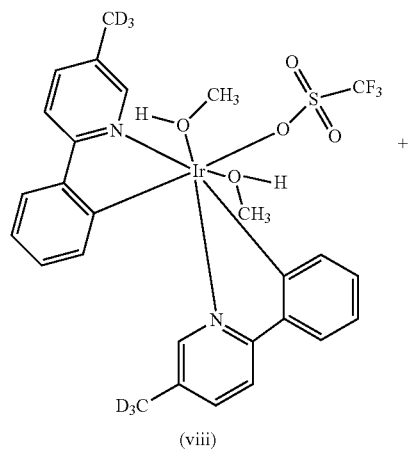

(viii)

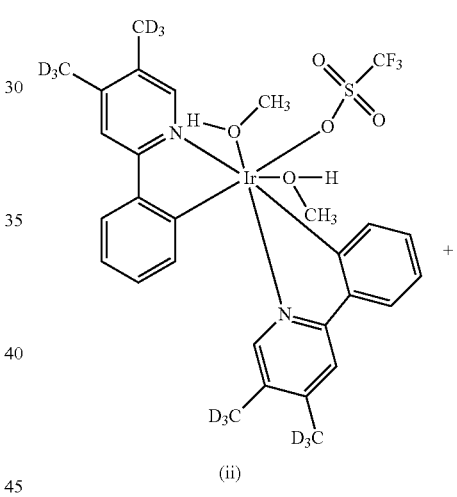

(ii)

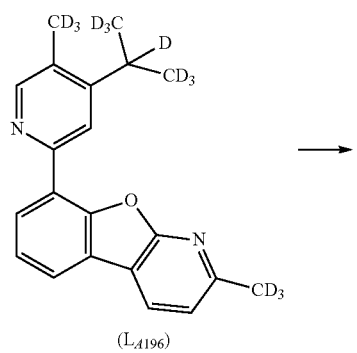

(L$_{A196}$)

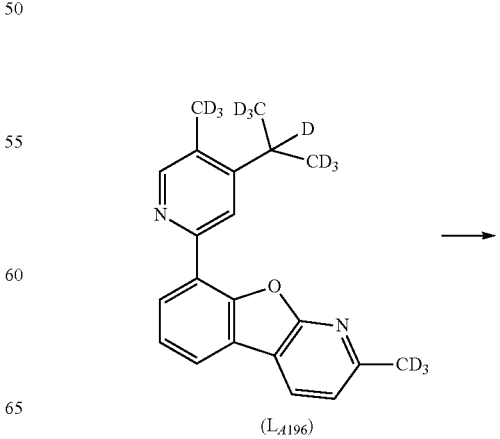

(L$_{A196}$)

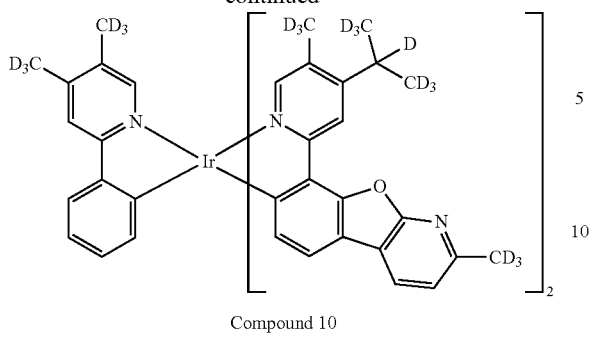

Compound 10

A mixture of aza-dibenzofuran ligand ($L_{A196}$) (1.5 g, 4.55 mmol) and iridium precursor (ii) (1.978 g, 2.53 mmol), 2-ethoxyethanol 40 mL and DMF 40 mL was heated in an oil bath at 130° C. for 17 hours under $N_2$. The reaction mixture was purified by silica gel column chromatography using ethyl acetate and dichloromethane solvent mixture to give 0.77 g (29% yield) of the desired product, Compound 10, which was confirmed by LC-MS.

Synthesis of Compound 7

Compound 7

The aza-dibenzofuran ligand ($L_{A189}$) (1.1 g, 3.52 mmol), iridium precursor (viii) (1.72 g, 2.20 mmol), 2-ethoxyethanol 40 mL and DMF 40 mL were charged in a flask and heated in an oil bath at 130° C. for 18 hours under $N_2$. The reaction solvent was evaporated and the solid was dissolved to filter through a small silica gel plug and further purified by column chromatography using ethyl acetate in dichloromethane to give 1.05 g the desired product, Compound 7 (52% yield).

Synthesis of Compound 15

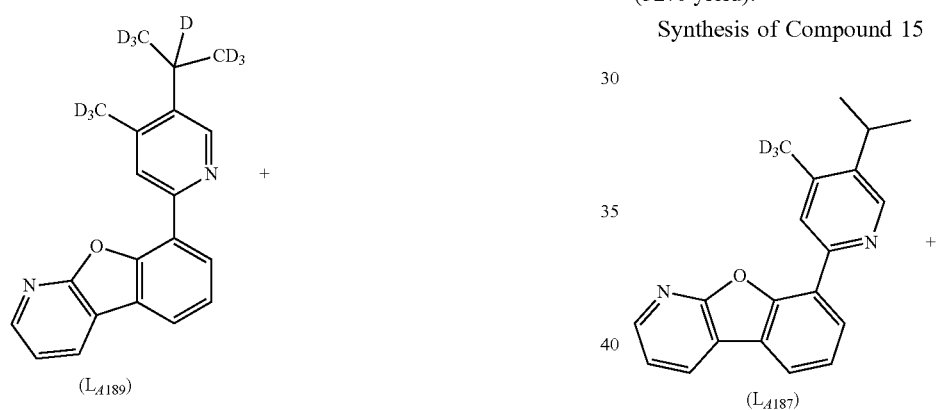

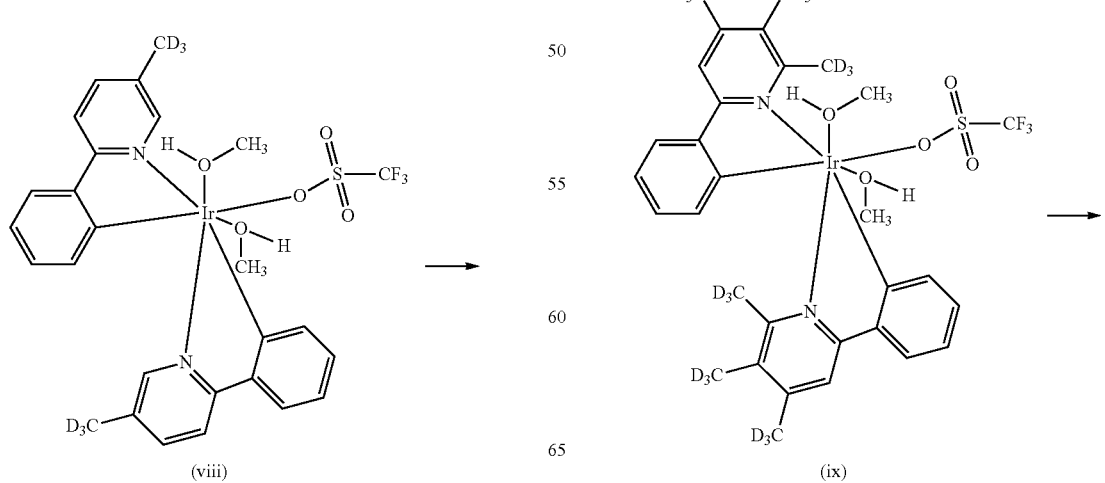

-continued

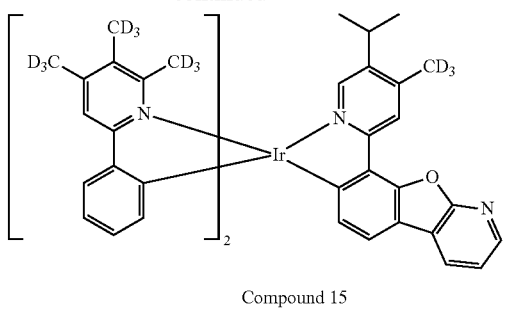

Compound 15

A mixture of 8-(4-d3-methyl-5-isopropyl)pyridine-2-yl ($L_{A187}$) (0.943 g, 3.01 mmol), iridium precursor (ix) (1.4 g, 1.72 mmol), 2-ethoxyethanol 30.0 mL and DMF 30 mL was heated in an oil bath at 130° C. for 72 hours under $N_2$. The reaction mixture was concentrated to remove solvents and filtered through a small plug of silica gel and then further purified by column chromatography on silica gel using ethyl acetate in dichloromethane to give 0.95 g of the desired product, Compound 15 (61% yield).

Synthesis of Compound 17

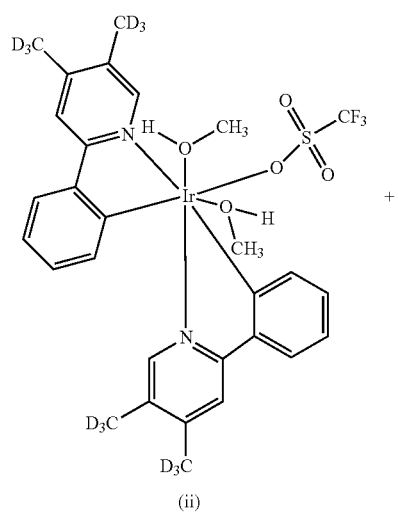

(ii)

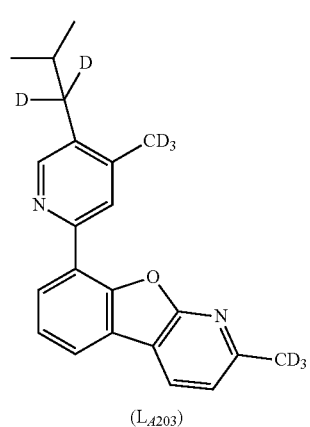

($L_{A203}$)

-continued

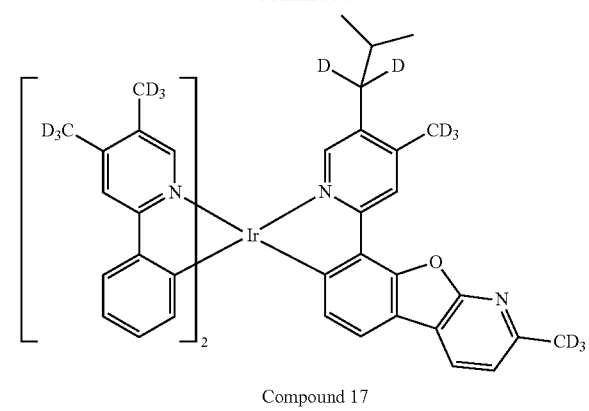

Compound 17

A mixture of an aza-dibenzofuran ligand ($L_{A203}$) (0.9 g, 2.66 mmol) and iridium precursor (ii) (1.29 g, 1.66 mmol), 2-ethoxyethanol 30 mL and DMF 30 mL was heated in an oil bath at 130° C. for 18 hours under $N_2$. The reaction mixture was purified by silica gel column chromatography using ethyl acetate and dichloromethane solvent mixture to give 0.5 g of the desired product, Compound 17. (33% yield).

Synthesis of Compound 16

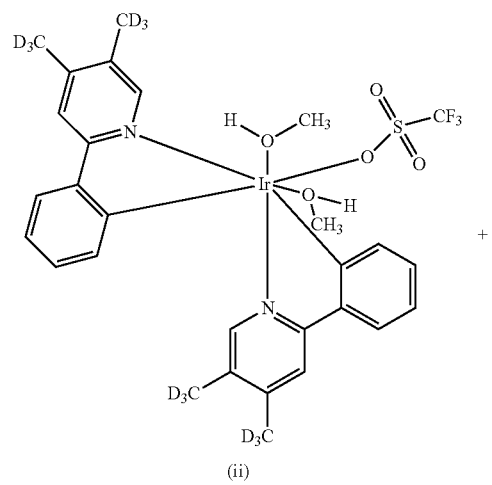

(ii)

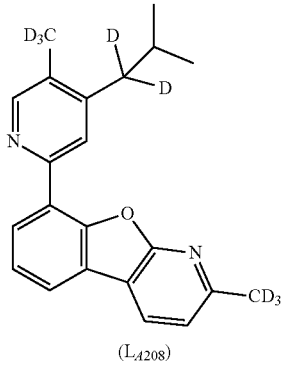

($L_{A208}$)

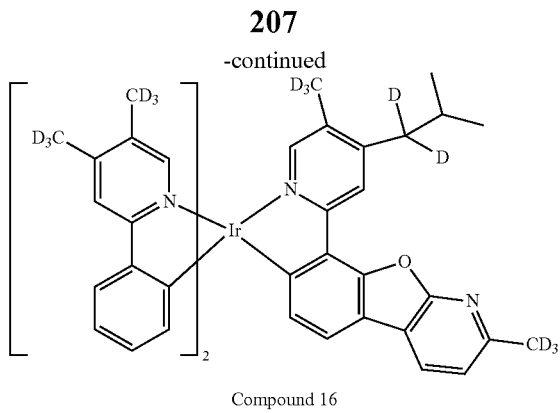

Compound 16

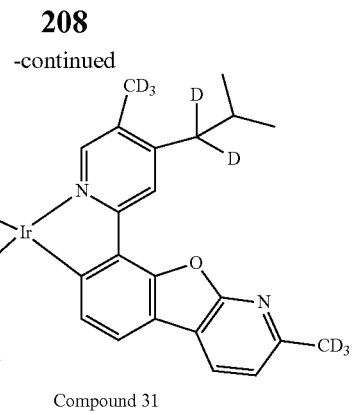

Compound 31

A mixture of aza-dibenzofuran ligand (L$_{A208}$) (0.85 g, 2.51 mmol) and iridium precursor (ii) (1.22 g, 1.56 mmol), 2-ethoxyethanol 30 mL and DMF 30 mL was heated in an oil bath at 130° C. for 20 hours under N$_2$. The reaction mixture was purified by silica gel column chromatography using ethyl acetate and dichloromethane solvent mixture to give 0.5 g of the desired product, Compound 16. (35% yield).

Synthesis of Compound 31

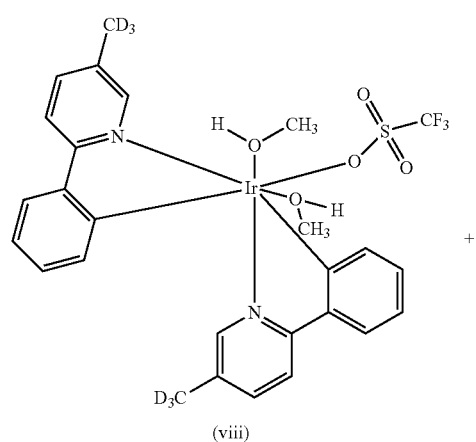

(viii)

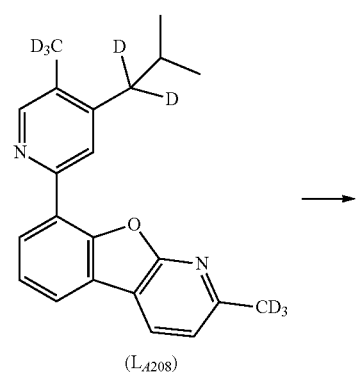

(L$_{A208}$)

A mixture of aza-dibenzofuran ligand (L$_{A208}$) (0.85 g, 2.51 mmol) and iridium precursor (viii) (1.12 g, 1.56 mmol), 2-ethoxyethanol 30 mL and DMF 30 mL was heated in an oil bath at 130° C. for 18 hours under N$_2$. The reaction mixture was purified by silica gel column chromatography using ethyl acetate and dichloromethane solvent mixture to give 0.55 g of the desired product, Compound 31. (40% yield).

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but not limit to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as MoO$_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

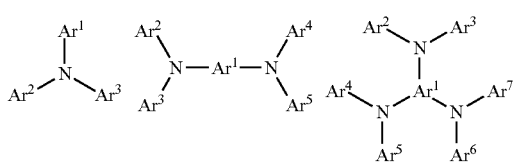

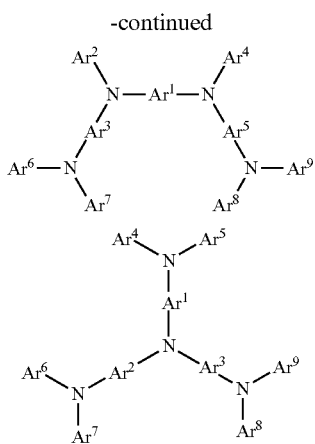

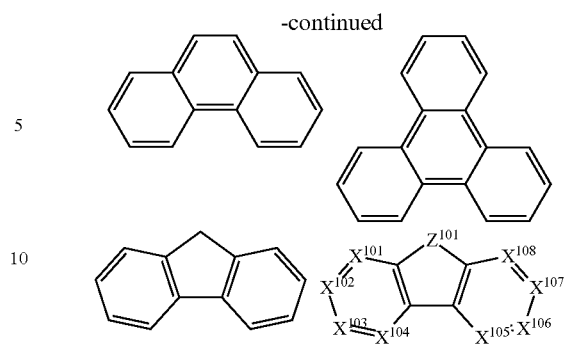

wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but not limit to the following general formula:

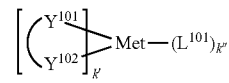

wherein Met is a metal, which can have an atomic weight greater than 40; ($Y^{101}$-$Y^{102}$) is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, ($Y^{101}$-$Y^{102}$) is a 2-phenylpyridine derivative. In another aspect, ($Y^{101}$-$Y^{102}$) is a carbene ligand. In another aspect, Met is selected from Ir, Pt, Os, and Zn. In a further aspect, the metal complex has a smallest oxidation potential in solution vs. $Fc^+/Fc$ couple less than about 0.6 V.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. While the Table below categorizes host materials as preferred for devices that emit various colors, any host material may be used with any dopant so long as the triplet criteria is satisfied.

Examples of metal complexes used as host are preferred to have the following general formula:

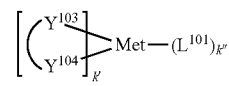

wherein Met is a metal; ($Y^{103}$-$Y^{104}$) is a bidentate ligand, $Y^{103}$ and $Y^{104}$ are independently selected from C, N, O, P, and S; $L^{101}$ is another ligand; k' is an integer value from 1 to the maximum number of ligands that may be attached to the metal; and k'+k" is the maximum number of ligands that may be attached to the metal.

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

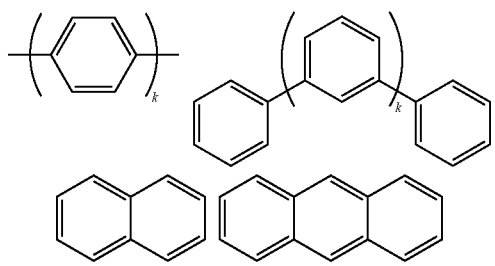

In one aspect, the metal complexes are:

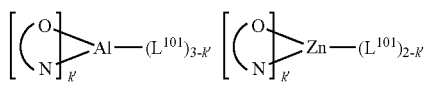

wherein (O—N) is a bidentate ligand, having metal coordinated to atoms O and N.

In another aspect, Met is selected from Ir and Pt. In a further aspect, ($Y^{103}$-$Y^{104}$) is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, host compound contains at least one of the following groups in the molecule:

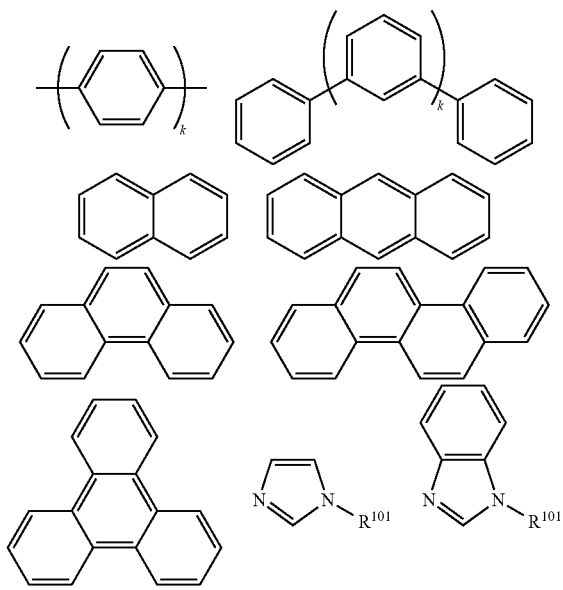

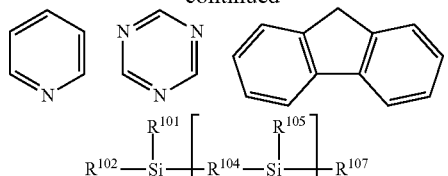

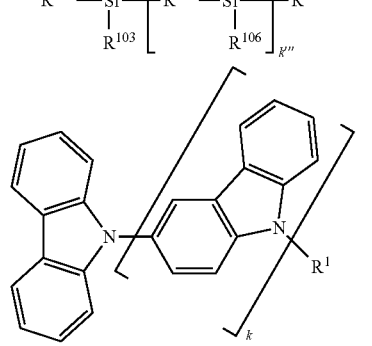

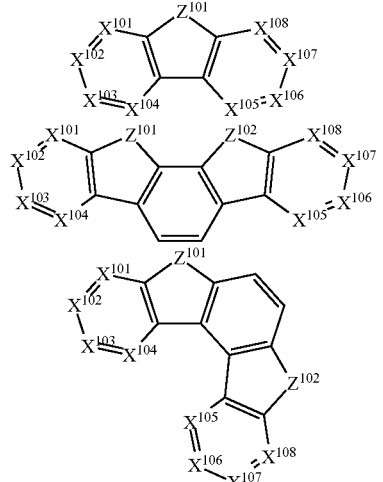

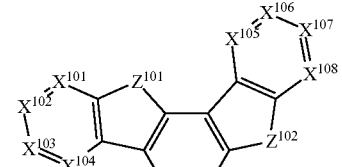

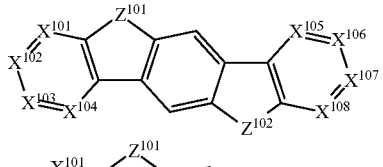

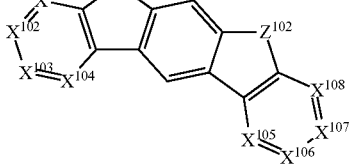

wherein $R^{101}$ to $R^{107}$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. k is an integer from 0 to 20 or 1 to 20; k' is an integer from 0 to 20. $X^{101}$ to $X^{108}$ is selected from C (including CH) or N. $Z^{101}$ and $Z^{102}$ is selected from $NR^{101}$, O, or S.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule or the same functional groups used as host described above.

In another aspect, compound used in HBL contains at least one of the following groups in the molecule:

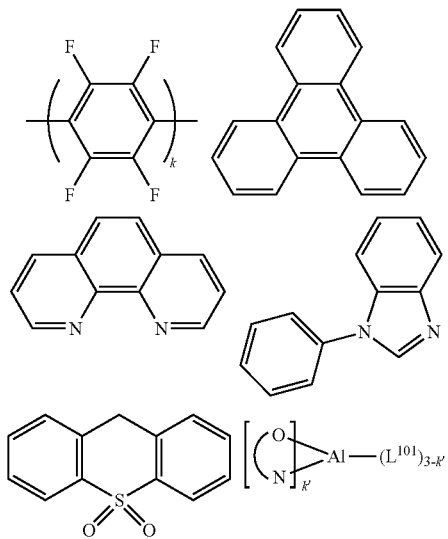

wherein k is an integer from 1 to 20; $L^{101}$ is an another ligand, k' is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

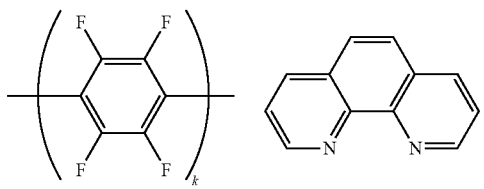

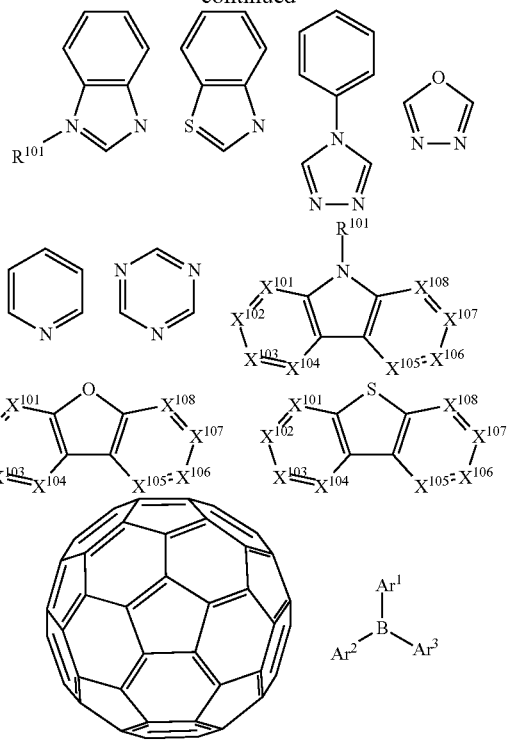

wherein $R^{101}$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. $Ar^1$ to $Ar^3$ has the similar definition as Ar's mentioned above. k is an integer from 1 to 20. $X^{101}$ to $X^{108}$ is selected from C (including CH) or N.

In another aspect, the metal complexes used in ETL contains, but not limit to the following general formula:

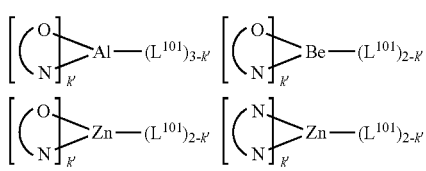

wherein (O—N) or (N—N) is a bidentate ligand, having metal coordinated to atoms O, N or N, N; $L^{101}$ is another ligand; k' is an integer value from 1 to the maximum number of ligands that may be attached to the metal.

In any above-mentioned compounds used in each layer of the OLED device, the hydrogen atoms can be partially or fully deuterated. Thus, any specifically listed substituent, such as, without limitation, methyl, phenyl, pyridyl, etc. encompasses undeuterated, partially deuterated, and fully deuterated versions thereof. Similarly, classes of substituents such as, without limitation, alkyl, aryl, cycloalkyl, heteroaryl, etc. also encompass undeuterated, partially deuterated, and fully deuterated versions thereof.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table A below. Table A lists non-limiting classes of materials, non-limiting examples of compounds for each class, and references that disclose the materials.

TABLE A

| MATERIAL | EXAMPLES OF MATERIAL | PUBLICATIONS |
| --- | --- | --- |
| Hole injection materials | | |
| Phthalocyanine and porphyrin compounds | | Appl. Phys. Lett. 69, 2160 (1996) |
| Starburst triarylamines | | J. Lumin. 72-74, 985 (1997) |
| $CF_x$ Fluorohydrocarbon polymer | $-[CH_xF_y]_n-$ | Appl. Phys. Lett. 78, 673 (2001) |
| Conducting polymers (e.g., PEDOT:PSS, polyaniline, polythiophene) | | Synth. Met. 87, 171 (1997) WO2007002683 |
| Phosphonic acid and silane SAMs | | US20030162053 |

TABLE A-continued
| MATERIAL | EXAMPLES OF MATERIAL | PUBLICATIONS |
|---|---|---|
| Triarylamine or polythiophene polymers with conductivity dopants | 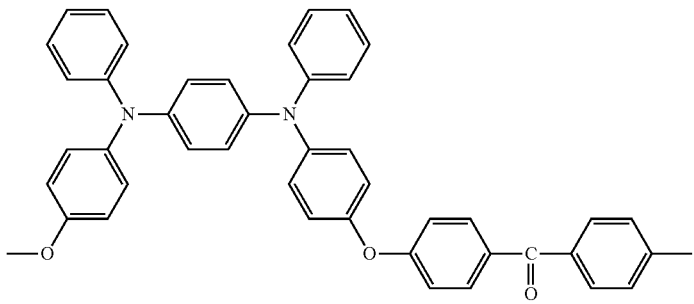 and 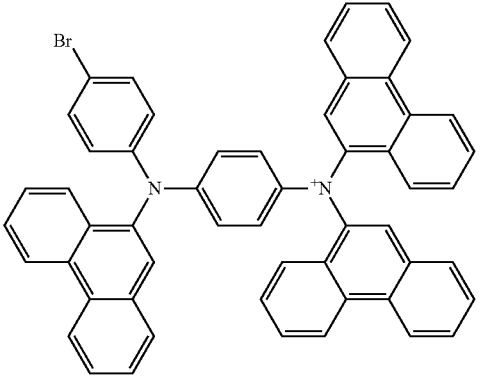 [SMILES: Brc1ccc(N(c2ccc([NH+](c3cc4ccccc4c4ccccc34)c3cc4ccccc4c4ccccc34)cc2)c2cc3ccccc3c3ccccc23)cc1] 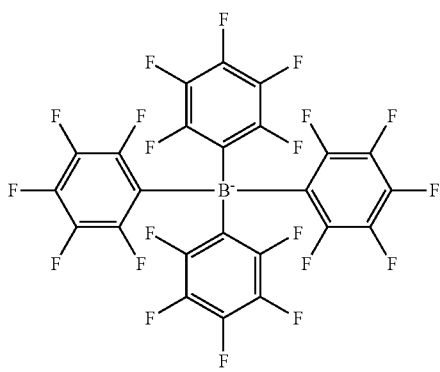 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F] | EP1725079A1 |
| Organic compounds with conductive inorganic compounds, such as molybdenum and tungsten oxides | 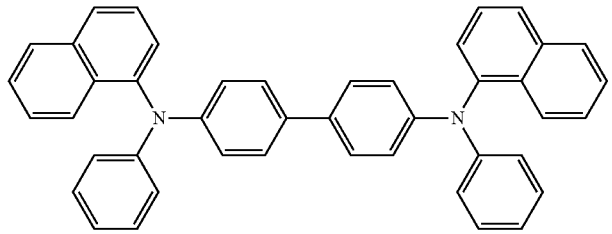 + MoO$_x$ | US20050123751 SID Symposium Digest, 37, 923 (2006) WO2009018009 |
| n-type semiconducting organic complexes | 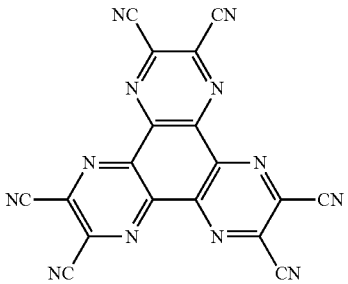 [SMILES: N#Cc1nc2c3nc(C#N)c(C#N)nc3c3nc(C#N)c(C#N)nc3c2nc1C#N] | US20020158242 |

TABLE A-continued

| MATERIAL | EXAMPLES OF MATERIAL | PUBLICATIONS |
| --- | --- | --- |
| Metal organometallic complexes | | US20060240279 |
| Cross-linkable compounds | | US20080220265 |
| Polythiophene based polymers and copolymers | | WO 2011075644<br>EP2350216 |

Hole transporting materials

| | | |
| --- | --- | --- |
| Triarylamines (e.g., TPD, α-NPD) | | Appl. Phys. Lett. 51, 913 (1987) |

| MATERIAL | EXAMPLES OF MATERIAL | PUBLICATIONS |
|---|---|---|
| | 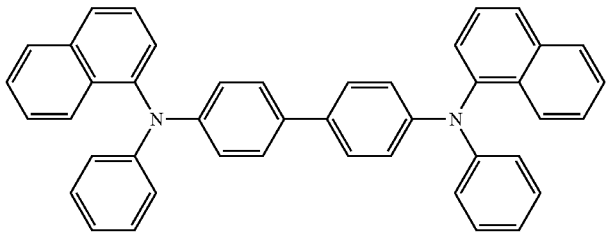 [SMILES: c1ccc(N(c2ccc(-c3ccc(N(c4ccccc4)c4cccc5ccccc45)cc3)cc2)c2cccc3ccccc23)cc1] | U.S. Pat. No. 5,061,569 |
| | 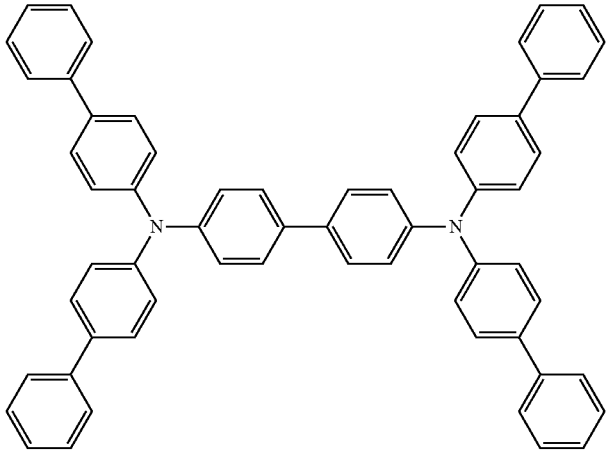 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | EP650955 |
| | 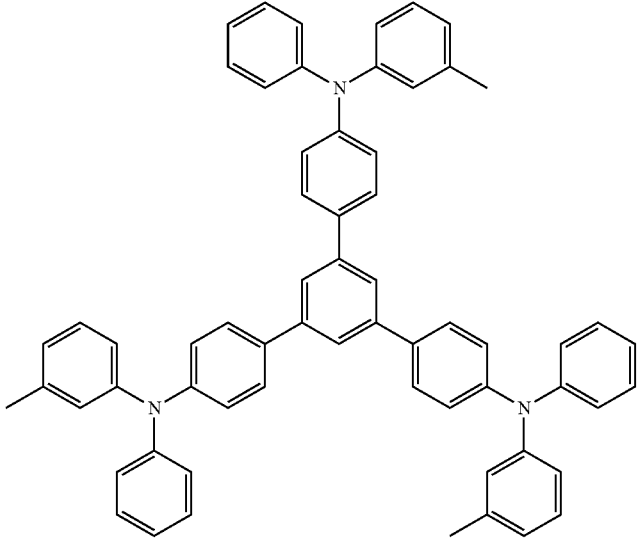 [SMILES: Cc1cccc(N(c2ccccc2)c2ccc(-c3cc(-c4ccc(N(c5ccccc5)c5cccc(C)c5)cc4)cc(-c4ccc(N(c5ccccc5)c5cccc(C)c5)cc4)c3)cc2)c1] | J. Mater. Chem. 3, 319 (1993) |

TABLE A-continued

| MATERIAL | EXAMPLES OF MATERIAL | PUBLICATIONS |
|---|---|---|
| | | Appl. Phys. Lett. 90, 183503 (2007) |
| | | Appl. Phys. Lett. 90, 183503 (2007) |
| Triarylamine on spirofluorene core | | Synth. Met. 91, 209 (1997) |
| Arylamine carbazole compounds | | Adv. Mater. 6, 677 (1994), US20080124572 |

TABLE A-continued
| MATERIAL | EXAMPLES OF MATERIAL | PUBLICATIONS |
|---|---|---|
| Triarylamine with (di)benzothiophene/ (di)benzofuran | 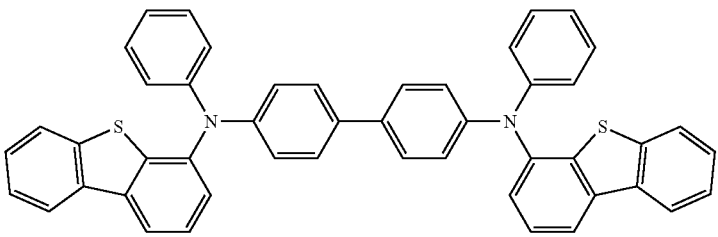 [SMILES: c1ccc(N(c2ccc(-c3ccc(N(c4ccccc4)c4cccc5c4sc4ccccc45)cc3)cc2)c2cccc3c2sc2ccccc23)cc1] | US20070278938, US20080106190 US20110163302 |
| Indolocarbazoles | 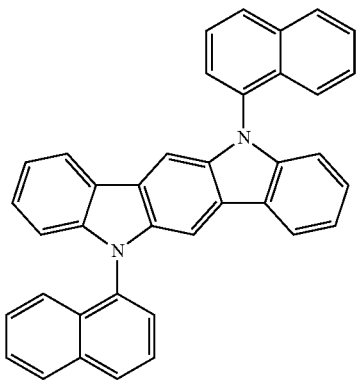 [SMILES: c1ccc2c(-n3c4ccccc4c4cc5c(cc43)c3ccccc3n5-c3cccc4ccccc34)cccc2c1] | Synth. Met. 111, 421 (2000) |
| Isoindole compounds | 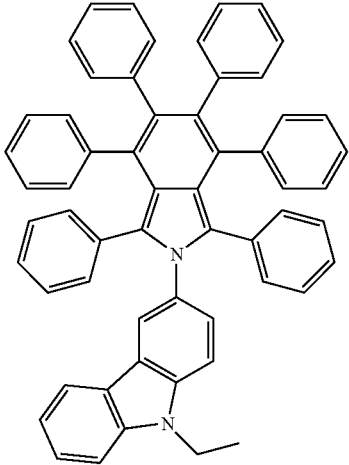 [SMILES: CCn1c2ccccc2c2cc(-n3c(-c4ccccc4)c4c(-c5ccccc5)c(-c5ccccc5)c(-c5ccccc5)c(-c5ccccc5)c4c3-c3ccccc3)ccc21] | Chem. Mater. 15, 3148 (2003) |
| Metal carbene complexes | 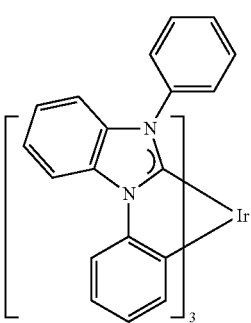 | US20080018221 |

TABLE A-continued

| MATERIAL | EXAMPLES OF MATERIAL | PUBLICATIONS |
|---|---|---|
| | Phosphorescent OLED host materials Red hosts | |
| Arylcarbazoles | | Appl. Phys. Lett. 78, 1622 (2001) |
| Metal 8-hydroxyquinolates (e.g., Alq$_3$, BAlq) | | Nature 395, 151 (1998) |
| | | US20060202194 |
| | | WO2005014551 |
| | | WO2006072002 |
| Metal phenoxybenzothiazole compounds | | Appl. Phys. Lett. 90, 123509 (2007) |
| Conjugated oligomers and polymers (e.g., polyfluorene) | | Org. Electron. 1, 15 (2000) |

TABLE A-continued
| MATERIAL | EXAMPLES OF MATERIAL | PUBLICATIONS |
|---|---|---|
| Aromatic fused rings | 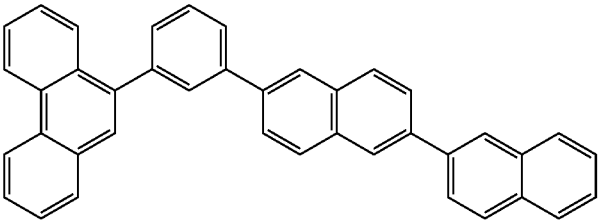 [SMILES: c1cc(-c2ccc3cc(-c4ccc5ccccc5c4)ccc3c2)cc(-c2cc3ccccc3c3ccccc23)c1] | WO2009066779, WO2009066778, WO2009063833, US20090045731, US20090045730, WO2009008311, US20090008605, US20090009065 |
| Zinc complexes | 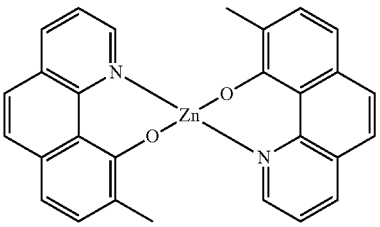 | WO2010056066 |
| Chrysene based compounds | 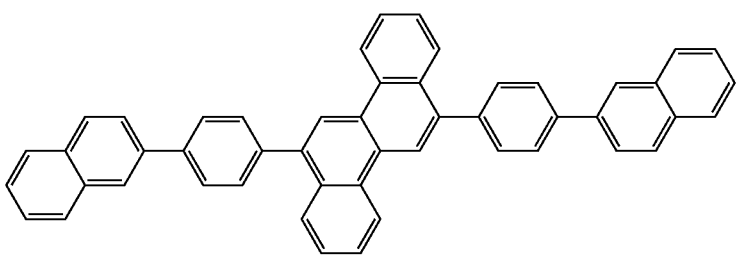 [SMILES: c1ccc2cc(-c3ccc(-c4cc5c6ccccc6c(-c6ccc(-c7ccc8ccccc8c7)cc6)cc5c5ccccc45)cc3)ccc2c1] | WO2011086863 |
Green hosts
| | | |
|---|---|---|
| Arylcarbazoles | 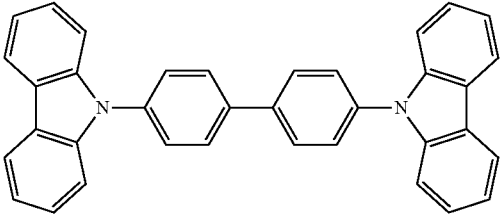 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |
| | 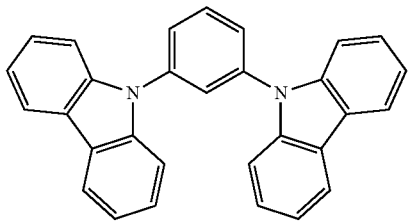 [SMILES: c1cc(-n2c3ccccc3c3ccccc32)cc(-n2c3ccccc3c3ccccc32)c1] | US20030175553 |
| | 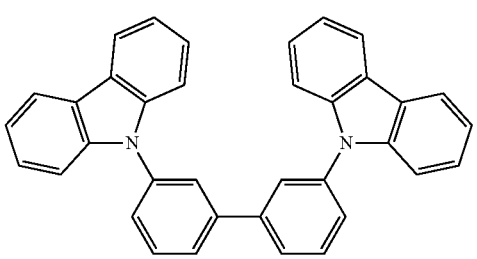 [SMILES: c1cc(-c2cccc(-n3c4ccccc4c4ccccc43)c2)cc(-n2c3ccccc3c3ccccc32)c1] | WO2001039234 |

TABLE A-continued

| MATERIAL | EXAMPLES OF MATERIAL | PUBLICATIONS |
| --- | --- | --- |
| Aryltriphenylene compounds | | US20060280965 |
| | | US20060280965 |
| | | WO2009021126 |
| Poly-fused heteroaryl compounds | | US20090309488<br>US20090302743<br>US20100012931 |
| Donor acceptor type molecules | | WO2008056746 |

TABLE A-continued
| MATERIAL | EXAMPLES OF MATERIAL | PUBLICATIONS |
|---|---|---|
| | 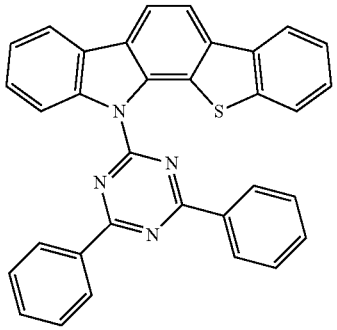 [SMILES: c1ccc(-c2nc(-c3ccccc3)nc(-n3c4ccccc4c4ccc5c6ccccc6sc5c43)n2)cc1] | WO2010107244 |
| Aza-carbazole/DBT/DBF | 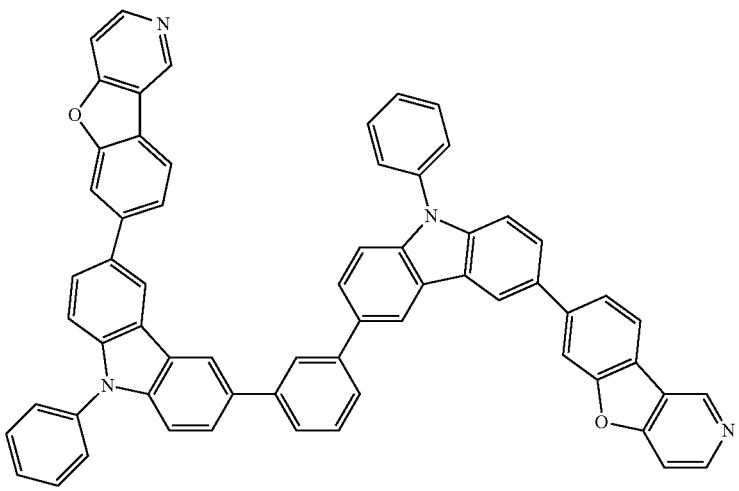 [SMILES: c1ccc(-n2c3ccc(-c4cccc(-c5ccc6c(c5)c5cc(-c7ccc8c(c7)oc7ccncc78)ccc5n6-c5ccccc5)c4)cc3c3cc(-c4ccc5c(c4)oc4ccncc45)ccc32)cc1] | JP2008074939 |
| | 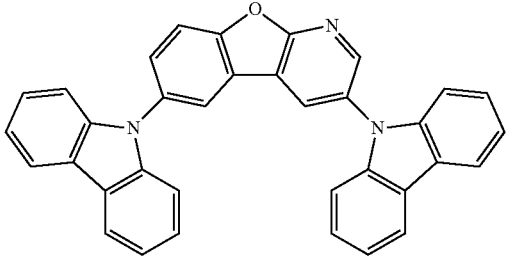 [SMILES: c1ccc2c(c1)c1ccccc1n2-c1ccc2oc3ncc(-n4c5ccccc5c5ccccc54)cc3c2c1] | US20100187984 |
| Polymers (e.g., PVK) | 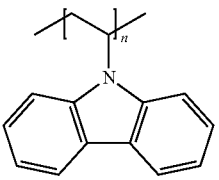 | Appl. Phys. Lett. 77, 2280 (2000) |
| Spirofluorene compounds | 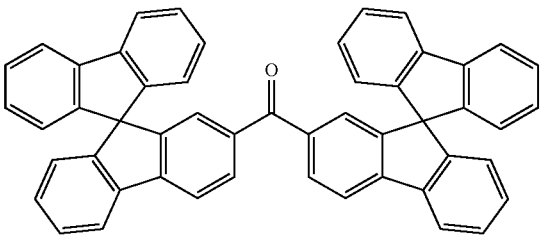 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2] | WO2004093207 |

TABLE A-continued

| MATERIAL | EXAMPLES OF MATERIAL | PUBLICATIONS |
| --- | --- | --- |
| Metal phenoxybenzooxazole compounds | | WO2005089025 |
| | | WO2006132173 |
| | | JP200511610 |
| Spirofluorene-carbazole compounds | | JP2007254297 |
| | | JP2007254297 |

TABLE A-continued

| MATERIAL | EXAMPLES OF MATERIAL | PUBLICATIONS |
| --- | --- | --- |
| Indolocarbazoles | | WO2007063796 |
| | | WO2007063754 |
| 5-member ring electron deficient heterocycles (e.g., triazole, oxadiazole) | | J. Appl. Phys. 90, 5048 (2001) |
| | | WO2004107822 |
| Tetraphenylene complexes | | US20050112407 |

TABLE A-continued

| MATERIAL | EXAMPLES OF MATERIAL | PUBLICATIONS |
| --- | --- | --- |
| Metal phenoxypyridine compounds | | WO2005030900 |
| Metal coordination complexes (e.g., Zn, Al with N^N ligands) | | US20040137268, US20040137267 |//
| Blue hosts | | |
| Arylcarbazoles | | Appl. Phys. Lett. 82, 2422 (2003) |
| | | US20070190359 |
| Dibenzothiophene/Dibenzofuran-carbazole compounds | | WO2006114966, US20090167162 |
| | | US20090167162 |

| MATERIAL | EXAMPLES OF MATERIAL | PUBLICATIONS |
|---|---|---|
| | 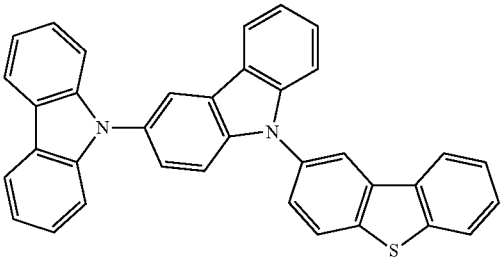 [SMILES: c1ccc2c(c1)sc1ccc(-n3c4ccccc4c4cc(-n5c6ccccc6c6ccccc65)ccc43)cc12] | WO2009086028 |
| | 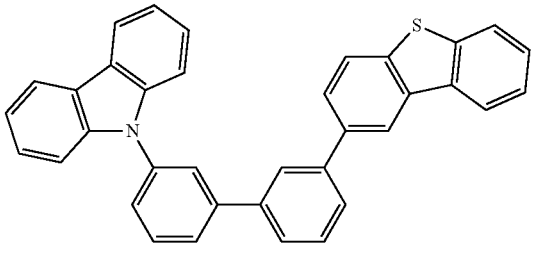 [SMILES: c1cc(-c2cccc(-n3c4ccccc4c4ccccc43)c2)cc(-c2ccc3sc4ccccc4c3c2)c1] | US20090030202, US20090017330 |
| | 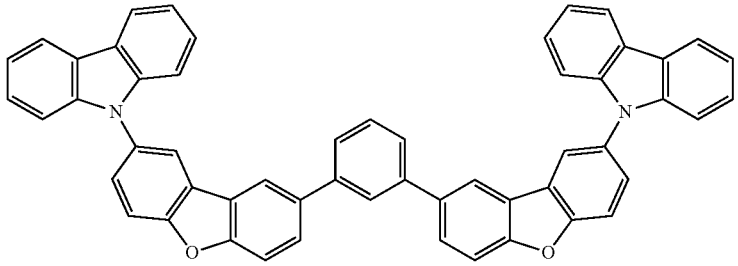 [SMILES: c1cc(-c2ccc3oc4ccc(-n5c6ccccc6c6ccccc65)cc4c3c2)cc(-c2ccc3oc4ccc(-n5c6ccccc6c6ccccc65)cc4c3c2)c1] | US20100084966 |
| Silicon aryl compounds | 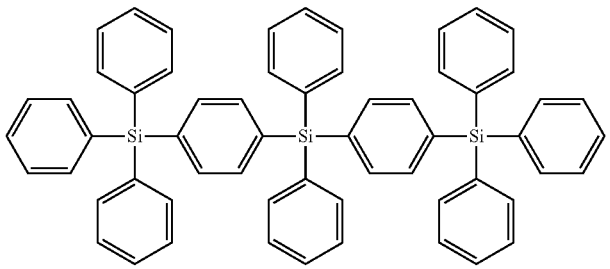 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 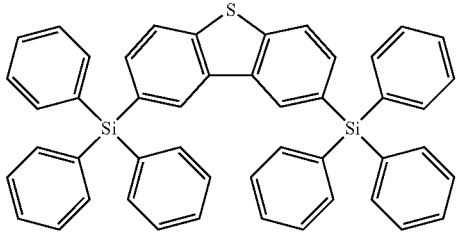 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |

TABLE A-continued

| MATERIAL | EXAMPLES OF MATERIAL | PUBLICATIONS |
| --- | --- | --- |
| Silicon/Germanium aryl compounds | | EP2034538A |
| Aryl benzoyl ester | | WO2006100298 |
| Carbazole linked by non-conjugated groups | | US20040115476 |
| Aza-carbazoles | | US20060121308 |
| High triplet metal organometallic complex | | U.S. Pat. No. 7,154,114 |

TABLE A-continued

| MATERIAL | EXAMPLES OF MATERIAL | PUBLICATIONS |
|---|---|---|
| | Phosphorescent dopants | |
| | Red dopants | |
| Heavy metal porphyrins (e.g., PtOEP) | | Nature 395, 151 (1998) |
| Iridium(III) organometallic complexes | | Appl. Phys. Lett. 78, 1622 (2001) |
| | | US20030072964 |
| | | US20030072964 |
| | | US20060202194 |

TABLE A-continued

| MATERIAL | EXAMPLES OF MATERIAL | PUBLICATIONS |
|---|---|---|
| | | US20060202194 |
| | | US20070087321 |
| | | US20080261076<br>US20100090591 |
| | | US20070087321 |
| | | Adv. Mater. 19, 739 (2007) |

TABLE A-continued

| MATERIAL | EXAMPLES OF MATERIAL | PUBLICATIONS |
|---|---|---|
| | | WO2009100991 |
| | | WO2008101842 |
| | | U.S. Pat. No. 7,232,618 |
| Platinum(II) organometallic complexes | | WO2003040257 |
| | | US20070103060 |

TABLE A-continued

| MATERIAL | EXAMPLES OF MATERIAL | PUBLICATIONS |
| --- | --- | --- |
| Osminum(III) complexes | [Os complex structure with F₃C-pyrazole-pyridine ligand and Os(PPhMe$_2$)$_2$] | Chem. Mater. 17, 3532 (2005) |
| Ruthenium(II) complexes | [Ru complex structure with tBu-pyrazole-isoquinoline ligand and Ru(PPhMe$_2$)$_2$] | Adv. Mater. 17, 1059 (2005) |
| Rhenium (I), (II), and (III) complexes | [Re complex with 8-hydroxyquinoline and (CO)$_4$] | US20050244673 |

Green dopants

| MATERIAL | EXAMPLES OF MATERIAL | PUBLICATIONS |
| --- | --- | --- |
| Iridium(III) organometallic complexes | [Ir(ppy)$_3$ structure] and its derivatives | Inorg. Chem. 40, 1704 (2001) |
|  | [Ir(ppy)$_2$(acac) structure] | US20020034656 |

| MATERIAL | EXAMPLES OF MATERIAL | PUBLICATIONS |
|---|---|---|
| | 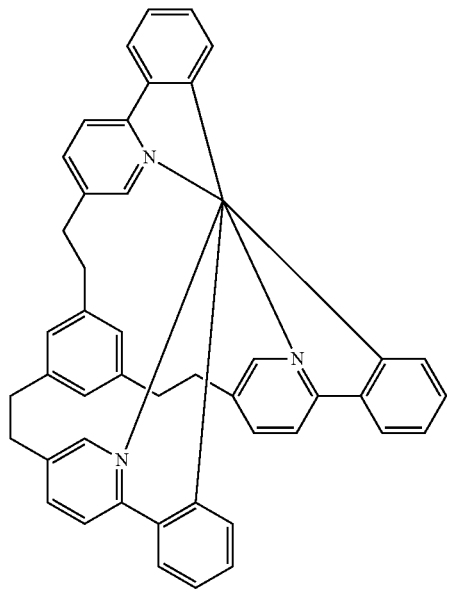 | U.S. Pat. No. 7,332,232 |
| | 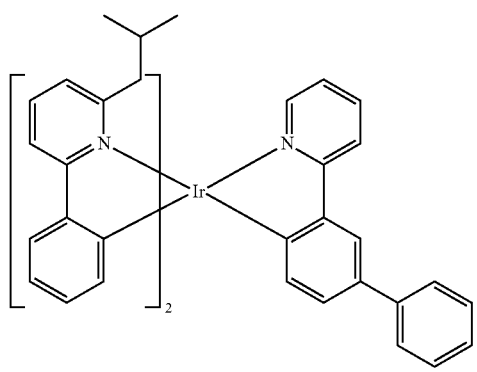 | US20090108737 |
| | 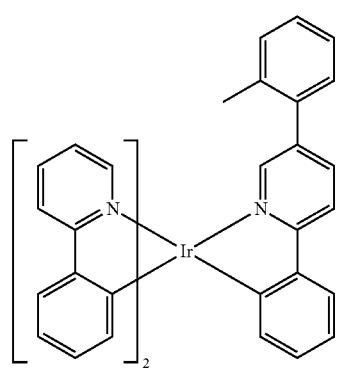 | WO2010028151 |

TABLE A-continued
| MATERIAL | EXAMPLES OF MATERIAL | PUBLICATIONS |
|---|---|---|
| | 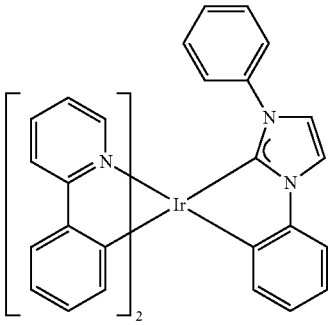 | EP1841834B |
| | 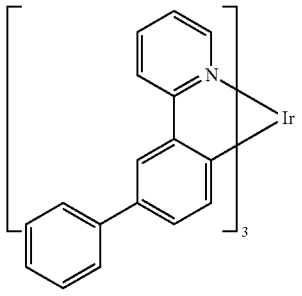 | US20060127696 |
| | 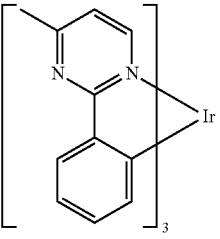 | US20090039776 |
| | 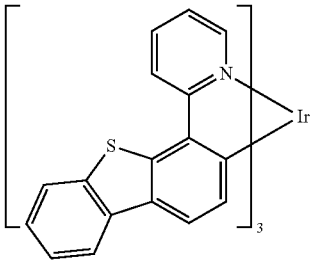 | U.S. Pat. No. 6,921,915 |
| | 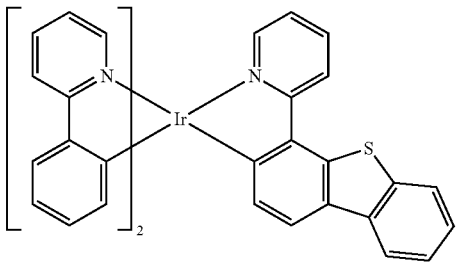 | US20100244004 |

TABLE A-continued
| MATERIAL | EXAMPLES OF MATERIAL | PUBLICATIONS |
|---|---|---|
| | 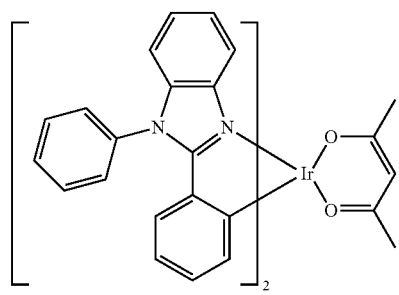 | U.S. Pat. No. 6,687,266 |
| | 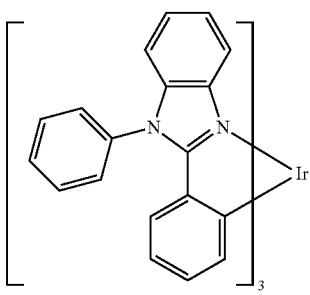 | Chem. Mater. 16, 2480 (2004) |
| | 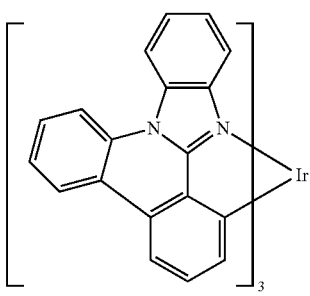 | US20070190359 |
| | 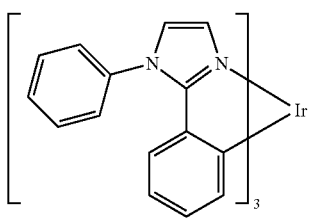 | US 20060008670 JP2007123392 |
| | 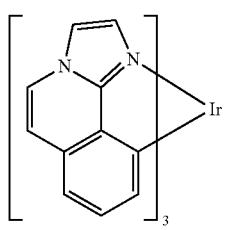 | WO2010086089, WO2011044988 |
| | 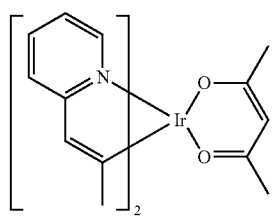 | Adv. Mater. 16, 2003 (2004) |

TABLE A-continued
| MATERIAL | EXAMPLES OF MATERIAL | PUBLICATIONS |
|---|---|---|
| | 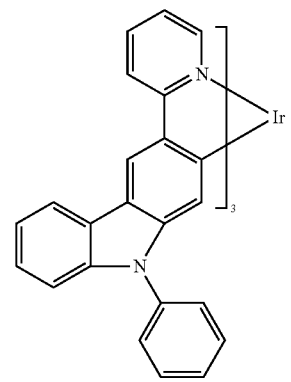 | Angew. Chem. Int. Ed. 2006, 45, 7800 |
| | 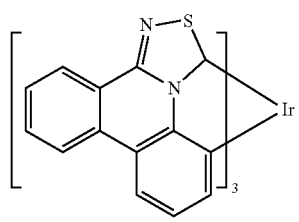 | WO2009050290 |
| | 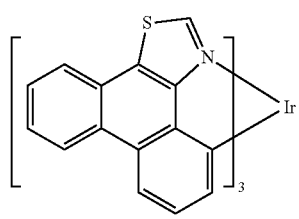 | US20090165846 |
| | 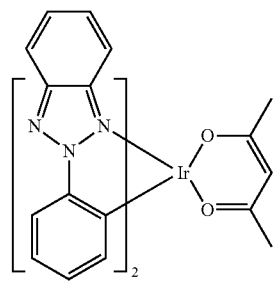 | US20080015355 |
| | 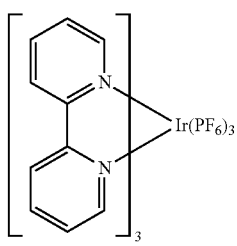 | US20010015432 |
| | 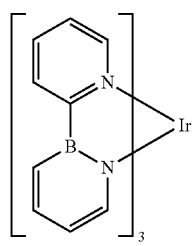 | US20100295032 |

TABLE A-continued

| MATERIAL | EXAMPLES OF MATERIAL | PUBLICATIONS |
| --- | --- | --- |
| Monomer for polymeric metal organometallic compounds | | U.S. Pat. No. 7,250,226, U.S. Pat. No. 7,396,598 |
| Pt(II) organometallic complexes, including polydentated ligands | | Appl. Phys. Lett. 86, 153505 (2005) |
| | | Appl. Phys. Lett. 86, 153505 (2005) |
| | | Chem. Lett. 34, 592 (2005) |
| | | WO2002015645 |

TABLE A-continued

| MATERIAL | EXAMPLES OF MATERIAL | PUBLICATIONS |
|---|---|---|
| | | US20060263635 |
| | | US20060182992<br>US20070103060 |
| Cu complexes | | WO2009000673 |
| | | US20070111026 |

TABLE A-continued

| MATERIAL | EXAMPLES OF MATERIAL | PUBLICATIONS |
|---|---|---|
| Gold complexes | | Chem. Commun. 2906 (2005) |
| Rhenium(III) complexes | | Inorg. Chem. 42, 1248 (2003) |
| Osmium(II) complexes | | U.S. Pat. No. 7,279,704 |
| Deuterated organometallic complexes | | US20030138657 |

TABLE A-continued
| MATERIAL | EXAMPLES OF MATERIAL | PUBLICATIONS |
|---|---|---|
| Organometallic complexes with two or more metal centers | 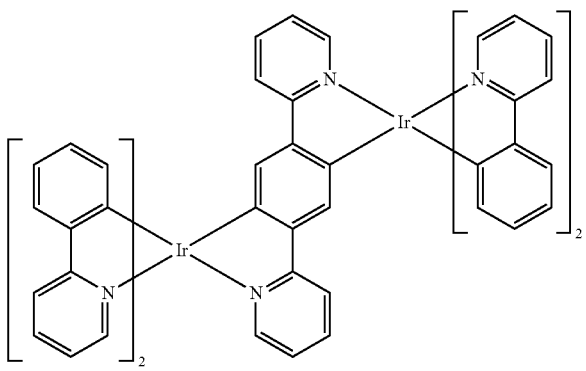 | US20030152802 |
| | 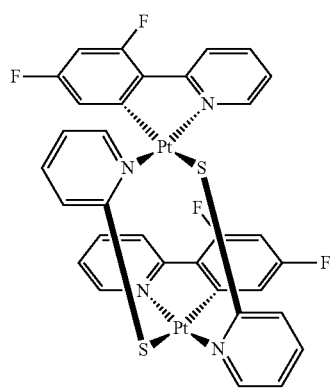 | U.S. Pat. No. 7,090,928 |
Blue dopants
| | | |
|---|---|---|
| Iridium(III) organometallic complexes | 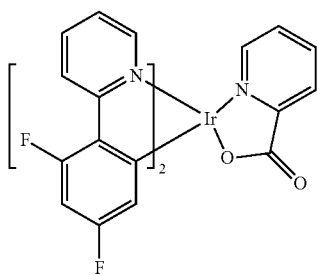 | WO2002002714 |
| | 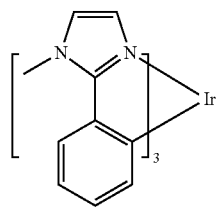 | WO2006009024 |
| | 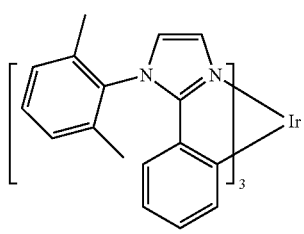 | US20060251923<br>US20110057559<br>US20110204333 |

TABLE A-continued

| MATERIAL | EXAMPLES OF MATERIAL | PUBLICATIONS |
|---|---|---|
| | | U.S. Pat. No. 7,393,599, WO2006056418, US20050260441, WO2005019373 |
| | | U.S. Pat. No. 7,534,505 |
| | | WO2011051404 |
| | | U.S. Pat. No. 7,445,855 |
| | | US20070190359, US20080297033 US20100148663 |

TABLE A-continued

| MATERIAL | EXAMPLES OF MATERIAL | PUBLICATIONS |
|---|---|---|
| | | U.S. Pat. No. 7,338,722 |
| | | US20020134984 |
| | | Angew. Chem. Int. Ed. 47, 4542 (2008) |
| | | Chem. Mater. 18, 5119 (2006) |
| | | Inorg. Chem. 46, 4308 (2007) |

TABLE A-continued
| MATERIAL | EXAMPLES OF MATERIAL | PUBLICATIONS |
|---|---|---|
| | 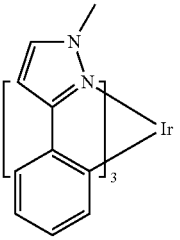 | WO2005123873 |
| | 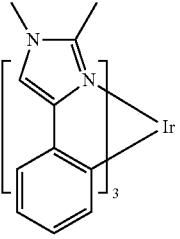 | WO2005123873 |
| | 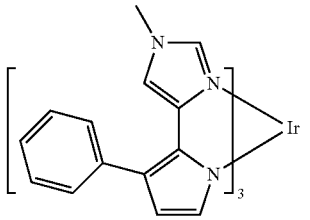 | WO2007004380 |
| | 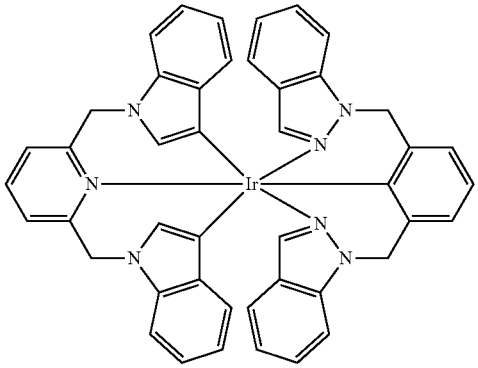 | WO2006082742 |
| Osmium(II) complexes | 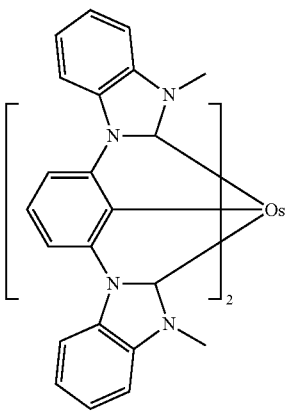 | U.S. Pat. No. 7,279,704 |

TABLE A-continued

| MATERIAL | EXAMPLES OF MATERIAL | PUBLICATIONS |
| --- | --- | --- |
| | (Os(PPh₃) pyrazolyl-pyridine complex structure) | Organometallics 23, 3745 (2004) |
| Gold complexes | Ph₂P-CH₂-PPh₂ bridged Au-Cl dimer | Appl. Phys. Lett. 74, 1361 (1999) |
| Platinum(II) complexes | (Pt complex with dimethylthiophene, pyrimidine, and tetrakis(pyrazolyl)borate) | WO2006098120, WO2006103874 |
| Pt tetradentate complexes with at least one metal-carbene bond | (Pt tetradentate carbene complex) | U.S. Pat. No. 7,655,323 |

Exciton/hole blocking layer materials

| MATERIAL | EXAMPLES OF MATERIAL | PUBLICATIONS |
| --- | --- | --- |
| Bathocuprine compounds (e.g., BCP, BPhen) | (BCP structure) | Appl. Phys. Lett. 75, 4 (1999) |
| | (BPhen structure) | Appl. Phys. Lett. 79, 449 (2001) |
| Metal 8-hydroxyquinolates (e.g., BAlq) | (BAlq structure) | Appl. Phys. Lett. 81, 162 (2002) |

TABLE A-continued

| MATERIAL | EXAMPLES OF MATERIAL | PUBLICATIONS |
|---|---|---|
| 5-member ring electron deficient heterocycles such as triazole, oxadiazole, imidazole, benzoimidazole | | Appl. Phys. Lett. 81, 162 (2002) |
| Triphenylene compounds | | US20050025993 |
| Fluorinated aromatic compounds | | Appl. Phys. Lett. 79, 156 (2001) |

TABLE A-continued

| MATERIAL | EXAMPLES OF MATERIAL | PUBLICATIONS |
|---|---|---|
| Phenothiazine-S-oxide | | WO2008132085 |
| Silylated five-membered nitrogen, oxygen, sulfur or phosphorus dibenzoheterocycles | | WO2010079051 |
| Aza-carbazoles | | US20060121308 |

Electron transporting materials

| | | |
|---|---|---|
| Anthracene-benzoimidazole compounds | | WO2003060956 |
| | | US20090179554 |

TABLE A-continued

| MATERIAL | EXAMPLES OF MATERIAL | PUBLICATIONS |
| --- | --- | --- |
| Aza triphenylene derivatives | | US20090115316 |
| Anthracene-benzothiazole compounds | | Appl. Phys. Lett. 89, 063504 (2006) |
| Metal 8-hydroxyquinolates (e.g., $Alq_3$, $Zrq_4$) | | Appl. Phys. Lett. 51, 913 (1987)<br>U.S. Pat. No. 7,230,107 |
| Metal hydroxybenzoquinolates | | Chem. Lett. 5, 905 (1993) |
| Bathocuprine compounds such as BCP, BPhen, etc | | Appl. Phys. Lett. 91, 263503 (2007) |
| | | Appl. Phys. Lett. 79, 449 (2001) |

| MATERIAL | EXAMPLES OF MATERIAL | PUBLICATIONS |
|---|---|---|
| 5-member ring electron deficient heterocycles (e.g., triazole, oxadiazole, imidazole, benzoimidazole) | 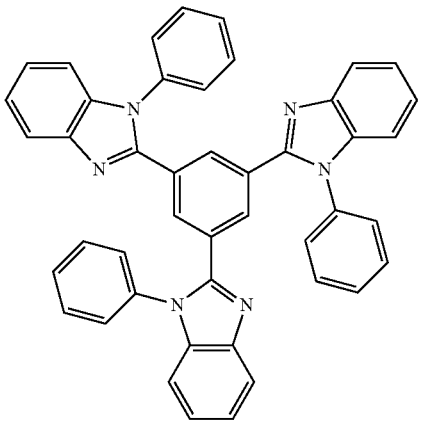 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 74, 865 (1999) |
| | 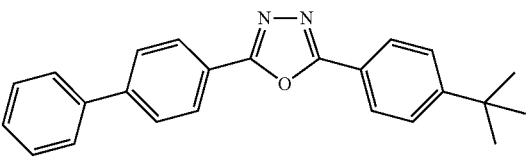 [SMILES: CC(C)(C)c1ccc(-c2nnc(-c3ccc(-c4ccccc4)cc3)o2)cc1] | Appl. Phys. Lett. 55, 1489 (1989) |
| | 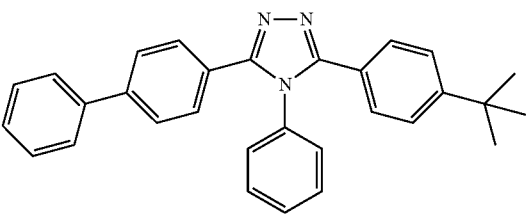 [SMILES: CC(C)(C)c1ccc(-c2nnc(-c3ccc(-c4ccccc4)cc3)n2-c2ccccc2)cc1] | Jpn. J. Apply. Phys. 32, L917 (1993) |
| Silole compounds | 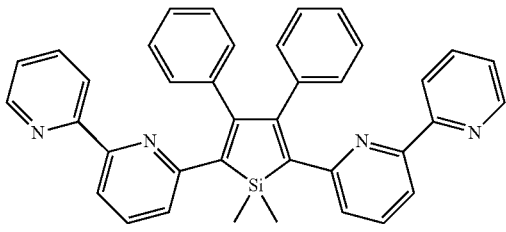 [SMILES: C[Si]1(C)C(c2cccc(-c3ccccn3)n2)=C(c2ccccc2)C(c2ccccc2)=C1c1cccc(-c2ccccn2)n1] | Org. Electron. 4, 113 (2003) |
| Arylborane compounds | 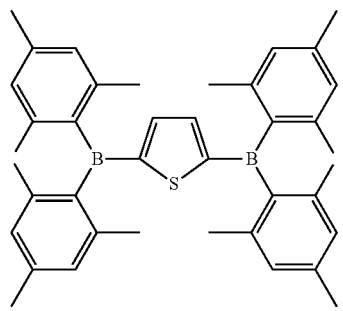 [SMILES: Cc1cc(C)c(B(c2ccc(B(c3c(C)cc(C)cc3C)c3c(C)cc(C)cc3C)s2)c2c(C)cc(C)cc2C)c(C)c1] | J. Am. Chem. Soc. 120, 9714 (1998) |
| Fluorinated aromatic compounds | 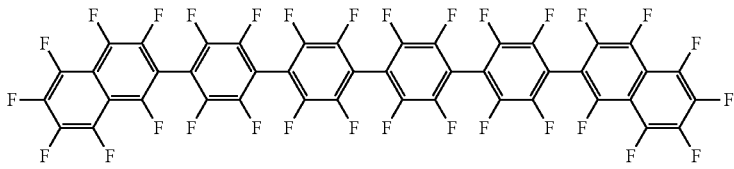 [SMILES: Fc1c(F)c(-c2c(F)c(F)c(-c3c(F)c(F)c4c(F)c(F)c(F)c(F)c4c3F)c(F)c2F)c(F)c(F)c1-c1c(F)c(F)c(-c2c(F)c(F)c(-c3c(F)c(F)c4c(F)c(F)c(F)c(F)c4c3F)c(F)c2F)c(F)c1F] | J. Am. Chem. Soc. 122, 1832 (2000) |

TABLE A-continued

| MATERIAL | EXAMPLES OF MATERIAL | PUBLICATIONS |
|---|---|---|
| Fullerene (e.g., C60) | 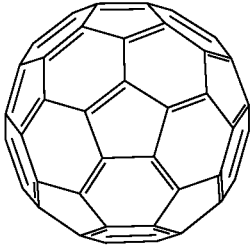 [SMILES: c1cc2c3ccc4c5ccc6c7ccc8c9ccc%10c1c1c2c2c3c4c3c5c6c4c7c8c5c9c%10c1c1c2c3c4c51] | US20090101870 |
| Triazine complexes | 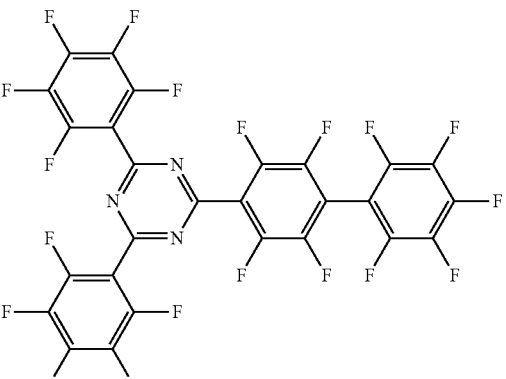 | US20040036077 |
| Zn (N^N) complexes | 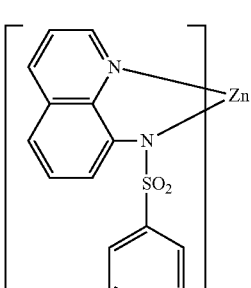 | U.S. Pat. No. 6,528,187 |

Experimental Data

The inventors have compared the performance of some examples of the inventive compound against prior art compounds. The compounds' sublimation temperature and color CIE values were compared and their respective values are summarized in Table 1 below. The sublimation temperature of Comparative example 2 compound is 281° C. In the inventive compounds Compound 9 and Compound 3, one of the deuterated di-substituted methyl groups on pyridine of Comparative example 2 compound is replaced by isopropyl-d7. The sublimation temperatures of Compound 9 and Compound 3 are significantly lower at 261° C. and 253° C., respectively, despite the fact that these compounds have higher molecular weight than Comparative example 2 compound. Lower sublimation temperatures advantageously allow for easier purification of the compounds of Formula I and allow the compounds of Formula I to have better thermal stability in manufacturing. In addition, the color CIE x coordinates of Compound 9 and Compound 3 are both less than Comparative example 1 and 2. Thus, they are more saturated green than Comparative example 1 and 2, which is a desired property, especially for display application. In 1931 CIE (Commission Internationale de l'Eclairage) Chromaticity Diagram the lower value for CIE x and higher value for CIE y represent higher green color saturation. These results were unexpected because in comparison between Comparative example 1 and Comparative example 2 complexes, the di-methyl substitution on pyridine of Comparative example 2 actually increased the sublimation temperature. Although Comparative example 1 has a lower sublimation temperature than the inventive compounds Compound 9 and Compound 3, the color CIE of Comparative example 1 is red shifted compared to the other compounds, which is not desired for this class of green phosphorescent emitters. Therefore, the inventive compounds result in more color saturation and lower sublimation temperature which are beneficial properties in manufacturing of PHOLED device.

TABLE 1

| Compound | Sublimation T (° C.) | 1931 CIE (x, y) |
|---|---|---|
| 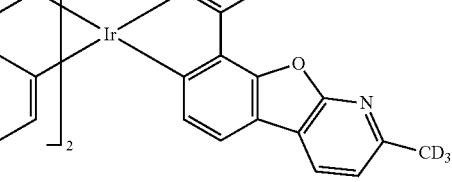  Comparative example 1 | 246 | 0.352, 0.622 |
| 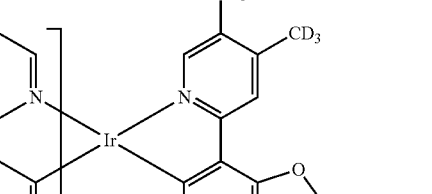  Comparative example 2 | 281 | 0.312, 0.638 |
| 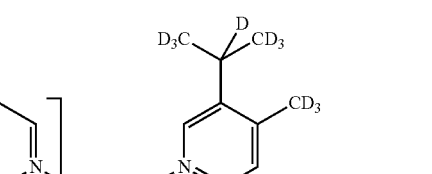  Compound 9 | 261 | 0.311, 0.639 |
| 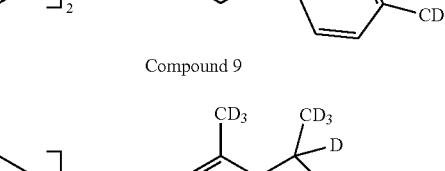  Compound 3 | 253 | 0.310, 0.640 |

Similar substitution effect was observed in the 2-phenylpyridine ligand in the claimed heteroleptic iridium complexes. In Table 2 below, the sublimation temperatures of Comparative examples 3, are fairly high around 270° C. In the inventive compound Compound 13, in which one of the methyl groups in the 2-phenylpyridine ligand is replaced with isopropyl, the observed sublimation temperature is significantly lower at 235° C., despite the fact that Compound 13 have higher molecular weight than Comparative example 3 compound.

TABLE 2

| Compounds | Sublimation T (° C.) |
|---|---|
| 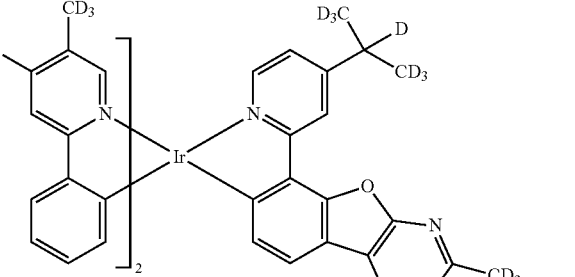<br>Comparative example 3 | 268 |
| 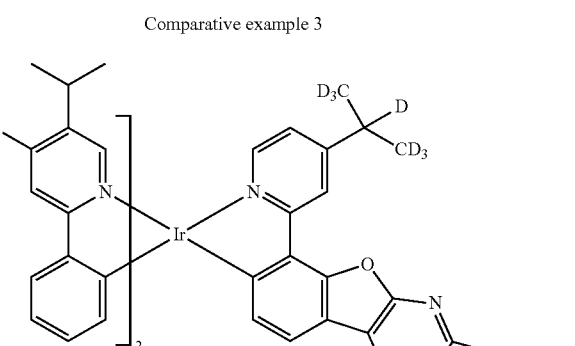<br>Compound 13 | 235 |

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

What is claimed is:

1. A compound having the formula $Ir(L_A)_n(L_B)_{3-n}$, wherein the compound has a structure according to Formula V:

Formula V

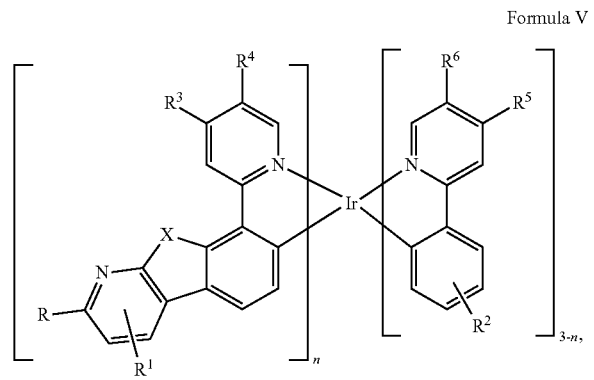

wherein X is O, S, or Se;
wherein $R^1$ represents mono-, di- substitution, or no substitution;
wherein $R^2$ represents mono-, di-, tri-, tetra-substitution, or no substitution;
wherein any adjacent substitutions in R, $R^1$, $R^2$, $R^3$, $R^4$, $R^5$, and $R^6$ are optionally linked together to form a ring;
wherein R is selected from the group consisting of alkyl, cycloalkyl, its partially or fully deuterated variants thereof, and combinations thereof;
wherein $R^1$ and $R^2$ are each independently hydrogen or a substitution selected from the group consisting of halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, combinations thereof, and partially or fully deuterated variations of any of the foregoing;
wherein $R^3$, $R^4$, $R^5$, and $R^6$ are each independently selected from the group consisting of hydrogen, deuterium, alkyl, cycloalkyl, and combinations thereof;
wherein n is an integer from 1 to 3; and
wherein the total number of carbons in at least one of the pairs $R^3$ and $R^4$, and $R^5$ and $R^6$ is at least four.

2. The compound of claim 1, wherein n is 1.
3. The compound of claim 1, wherein X is O.
4. The compound of claim 1, wherein $R^1$ and $R^2$ are each independently selected from the group consisting of hydrogen, deuterium, alkyl, cycloalkyl, and combinations thereof.
5. The compound of claim 1, wherein at least one of the following conditions (1) and (2) is true:

(1) $R^3$ and $R^4$ are each independently selected from the group consisting of alkyl, cycloalkyl, partially or fully deuterated variants thereof, and combinations thereof; and total number carbons in $R^3$ and $R^4$ combined is at least four; and (2) $R^5$ and $R^6$ are each independently selected from the group consisting of alkyl, cycloalkyl, partially or fully deuterated variants thereof, and combinations thereof; and total number of carbons in $R^5$ and $R^6$ combined is at least four.

6. The compound of claim 1, wherein $R^1$ is selected from hydrogen or a substitution selected from the group consisting of alkyl, cycloalkyl, partially and fully deuterated variant thereof, and combinations thereof.

7. The compound of claim 1, wherein $L_A$ is selected from the group consisting of:

$L_{A2}$

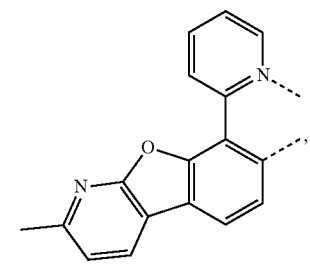

$L_{A3}$

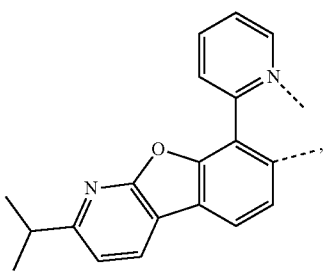

$L_{A4}$

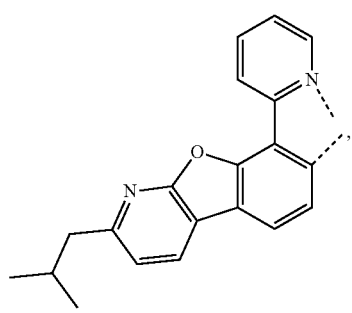

$L_{A5}$

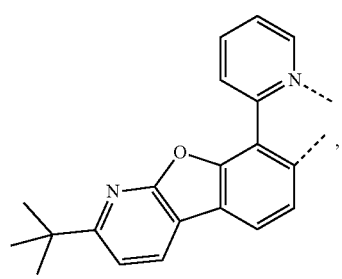

-continued $L_{A6}$

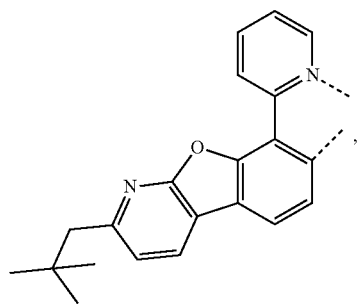

$L_{A7}$

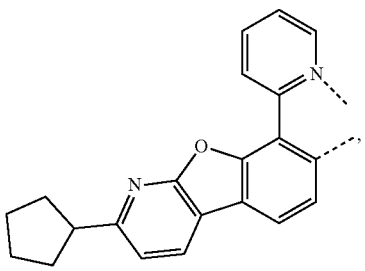

$L_{A8}$

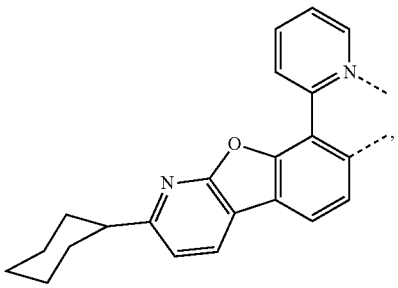

$L_{A9}$

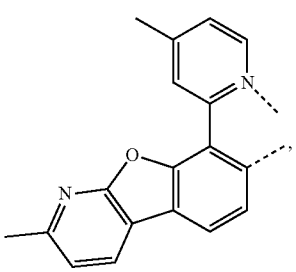

$L_{A10}$

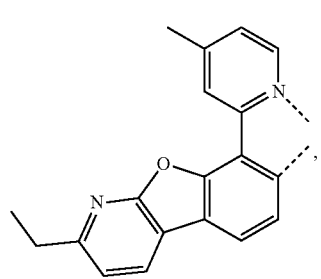

L_{A11} 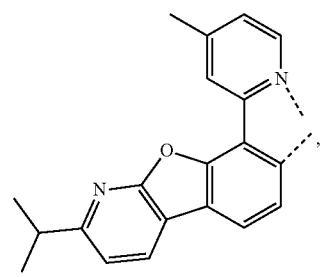
L_{A12} 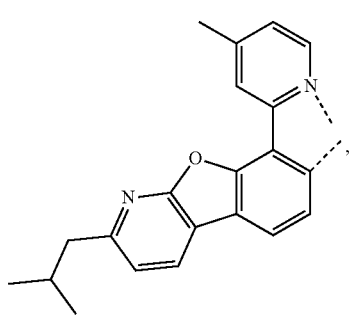
L_{A13} 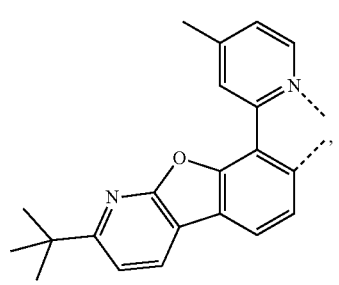
L_{A14} 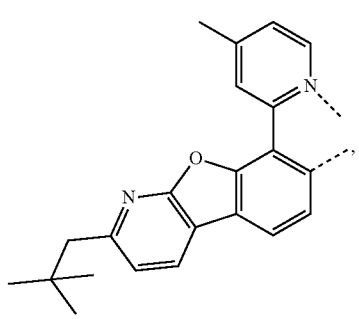
L_{A15} 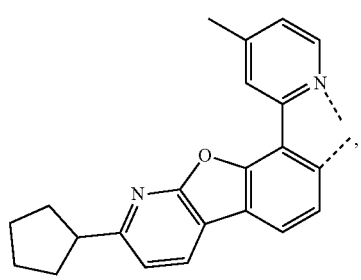
L_{A16} 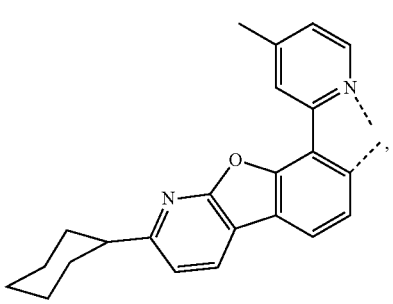
L_{A17} 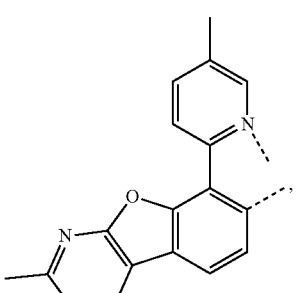
L_{A18} 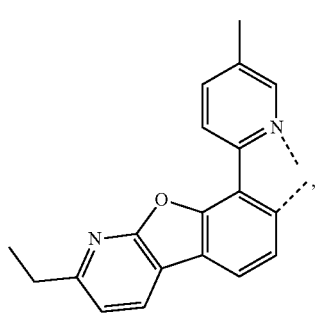
L_{A19} 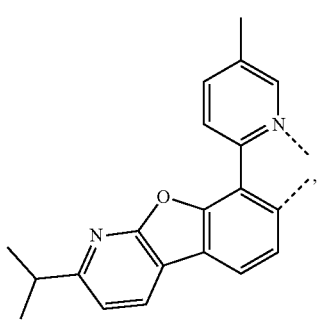
L_{A20} 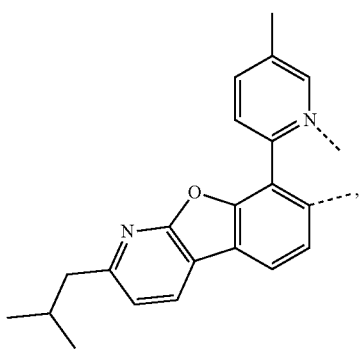

L<sub>A21</sub>
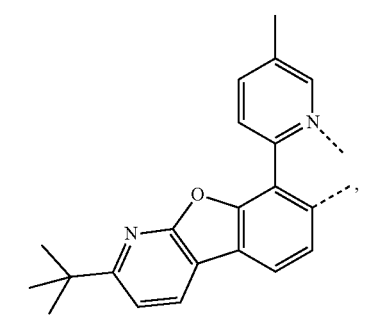
L<sub>A22</sub>
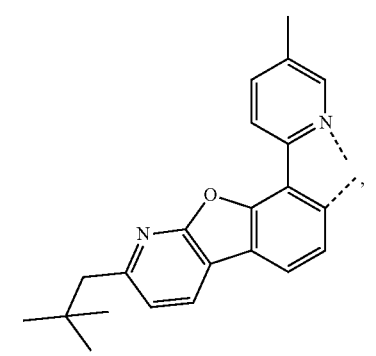
L<sub>A23</sub>
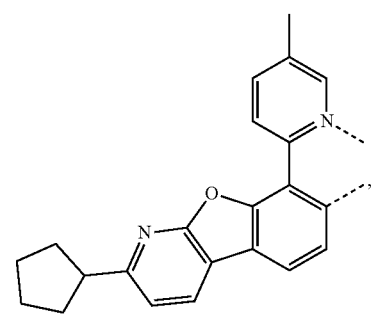
L<sub>A24</sub>
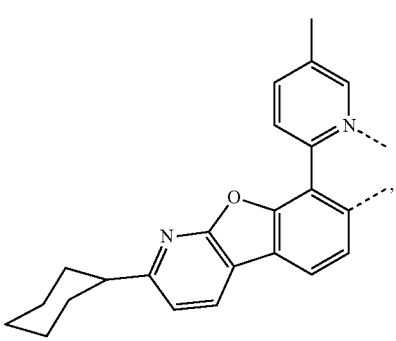
L<sub>A25</sub>
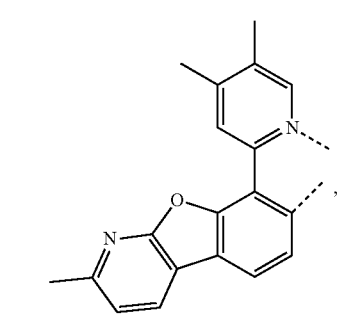
L<sub>A26</sub>
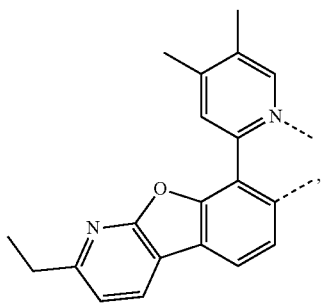
L<sub>A27</sub>
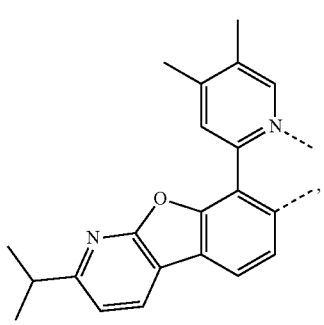
L<sub>A28</sub>
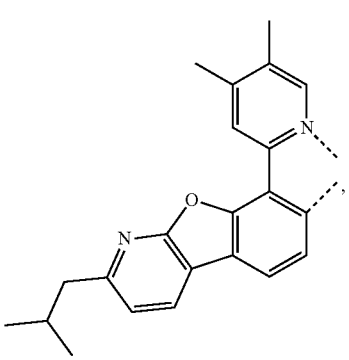
L<sub>A29</sub>
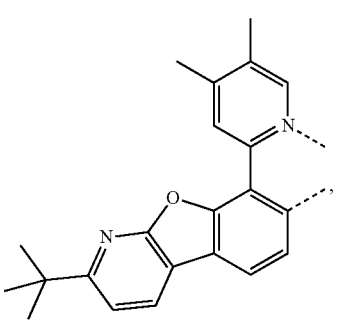
L<sub>A30</sub>
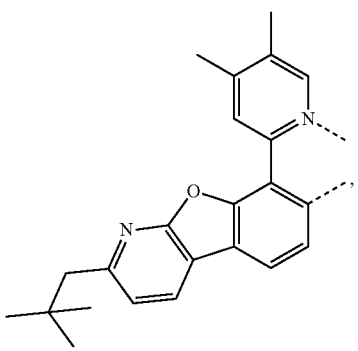

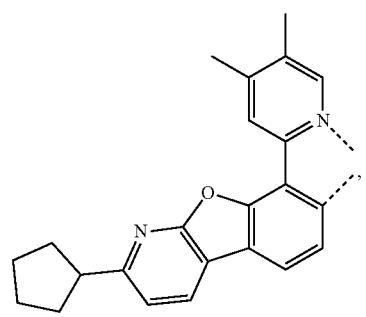 L_{A31}
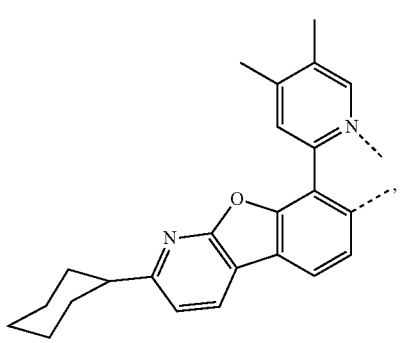 L_{A32}
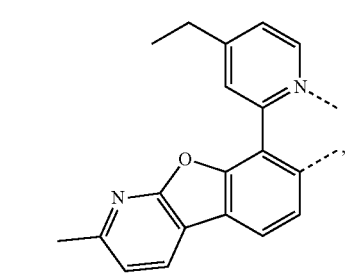 L_{A33}
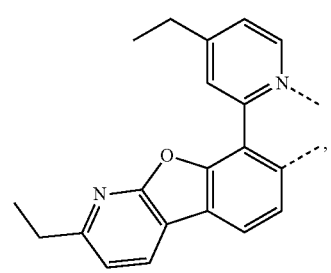 L_{A34}
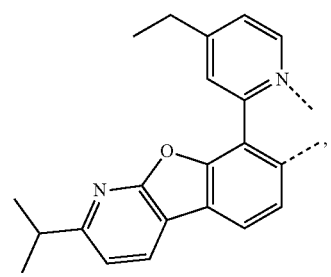 L_{A35}
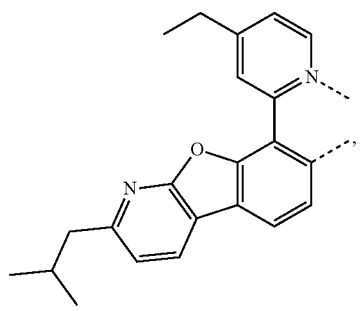 L_{A36}
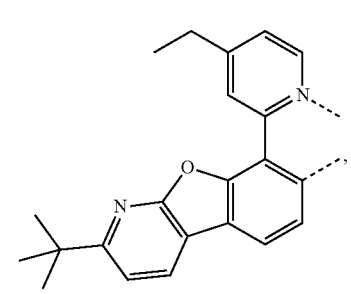 L_{A37}
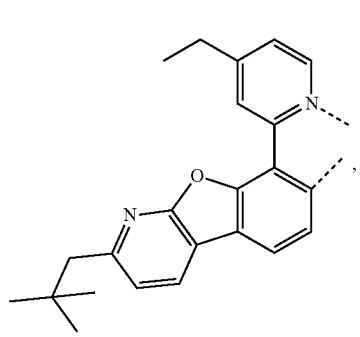 L_{A38}
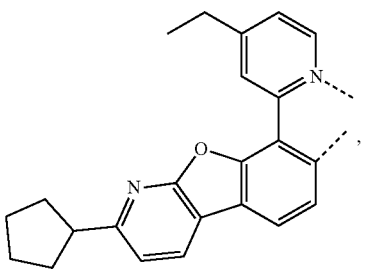 L_{A39}
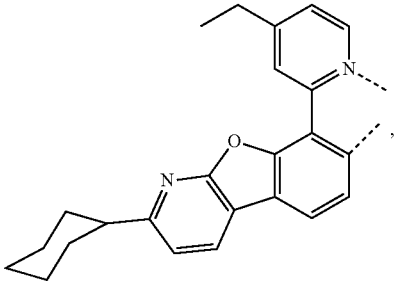 L_{A40}

L<sub>A41</sub> 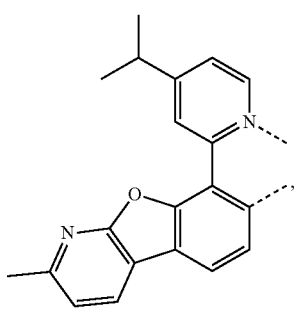
L<sub>A42</sub>
L<sub>A43</sub>
L<sub>A44</sub>
L<sub>A45</sub>
L<sub>A46</sub> 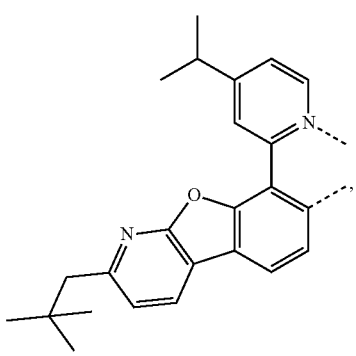
L<sub>A47</sub> 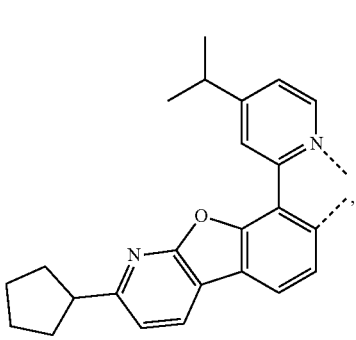
L<sub>A48</sub> 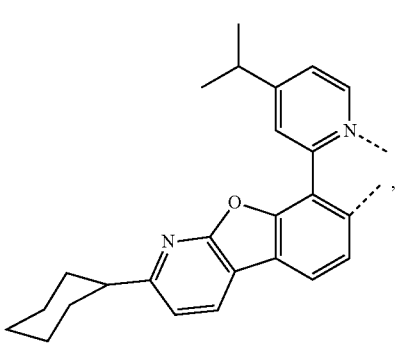
L<sub>A49</sub> 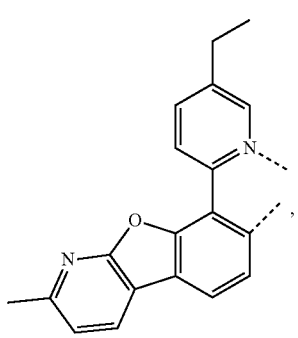

L<sub>A50</sub> 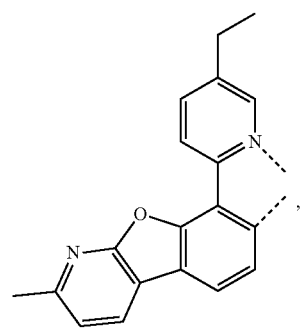
L<sub>A51</sub> 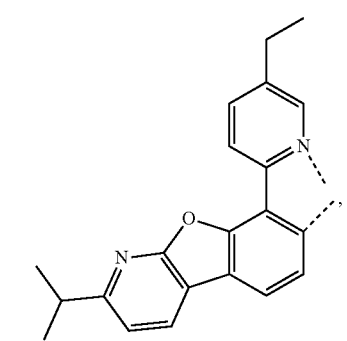
L<sub>A52</sub> 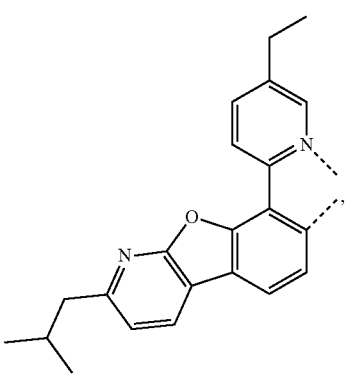
L<sub>A53</sub> 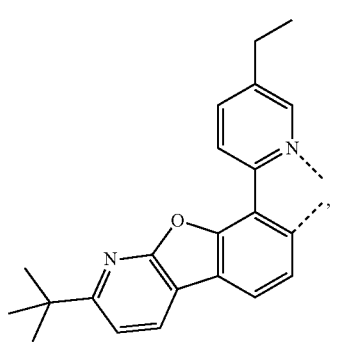
L<sub>A54</sub> 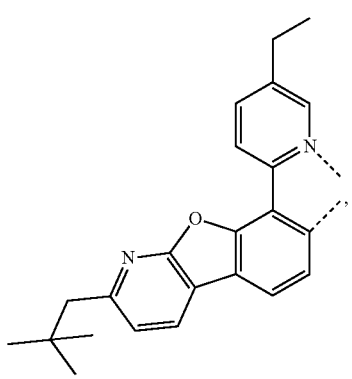
L<sub>A55</sub> 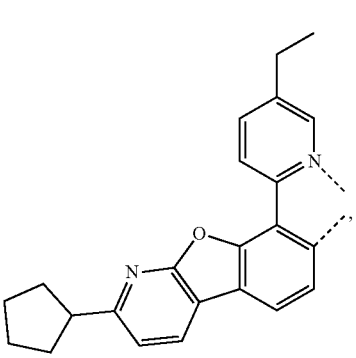
L<sub>A56</sub> 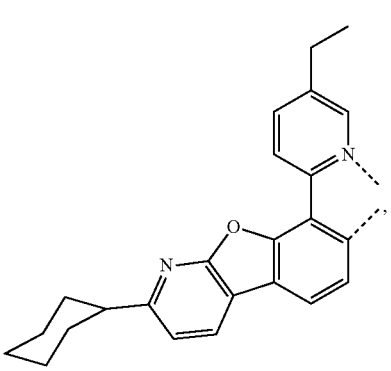
L<sub>A57</sub> 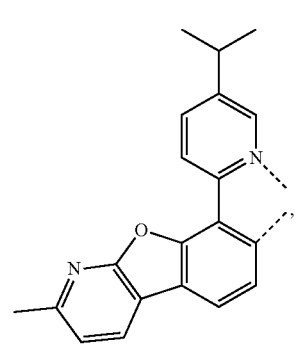

-continued
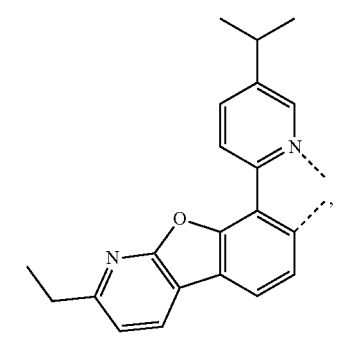
L_{A58}
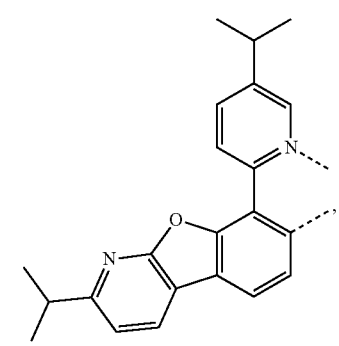
L_{A59}
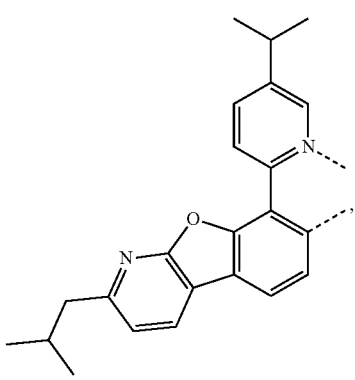
L_{A60}
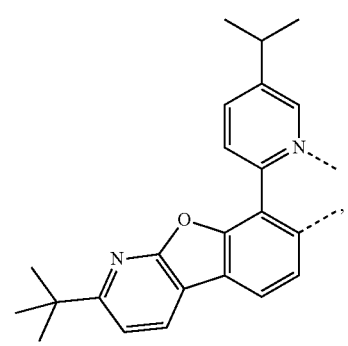
L_{A61}
-continued
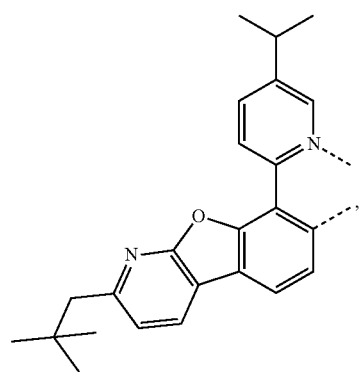
L_{A62}
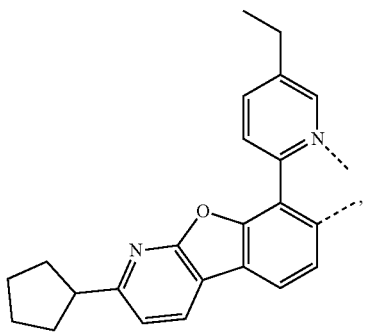
L_{A63}
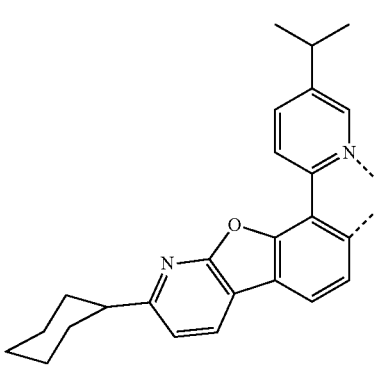
L_{A64}
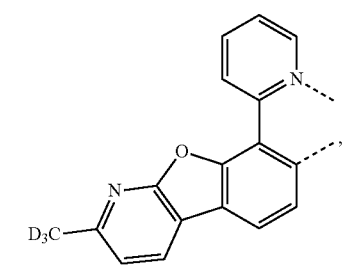
L_{A65}
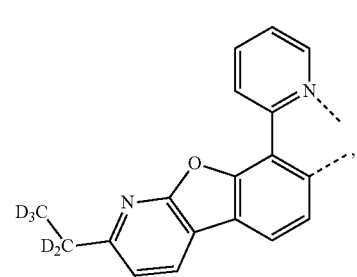
L_{A66}

L<sub>A67</sub>
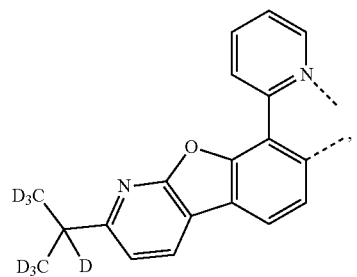
L<sub>A68</sub>
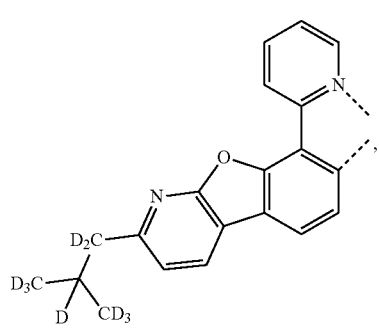
L<sub>A69</sub>
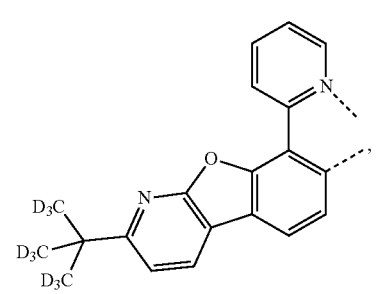
L<sub>A70</sub>
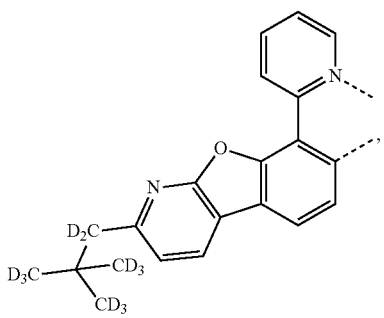
L<sub>A71</sub>
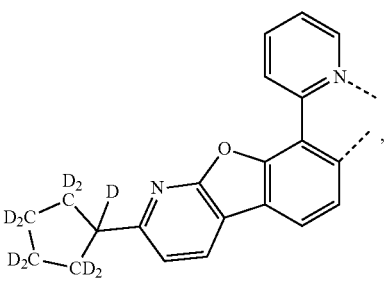
L<sub>A72</sub>
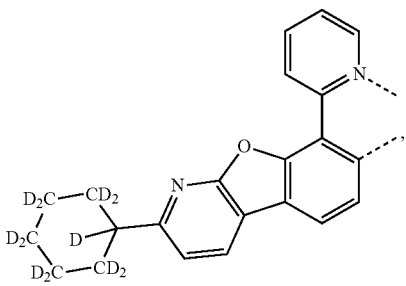
L<sub>A73</sub>
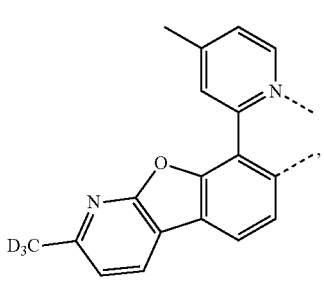
L<sub>A74</sub>
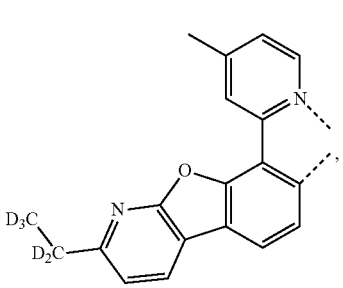
L<sub>A75</sub>
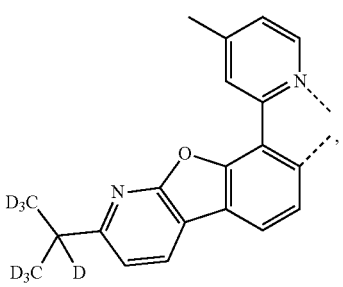
L<sub>A76</sub>
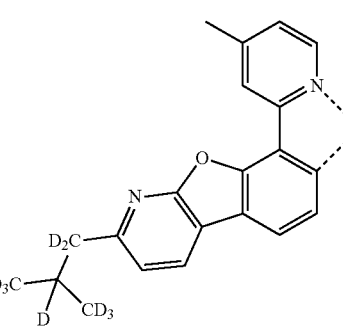

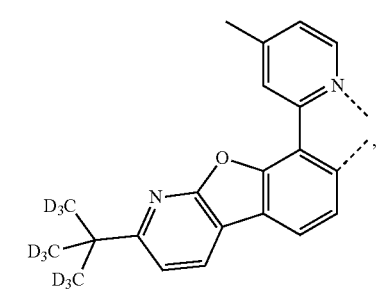
L_A77
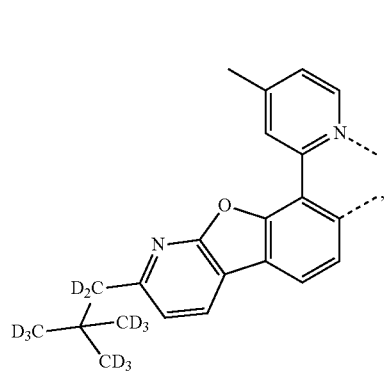
L_A78
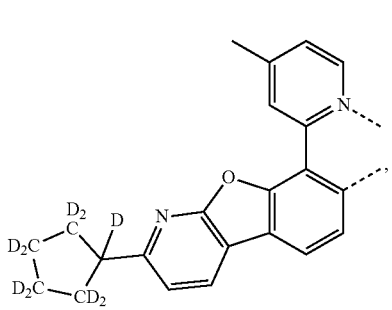
L_A79
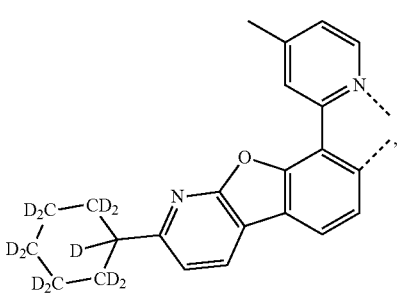
L_A80
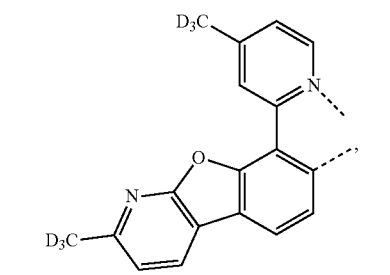
L_A81
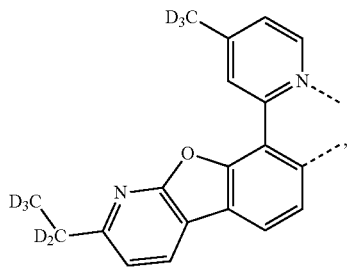
L_A82
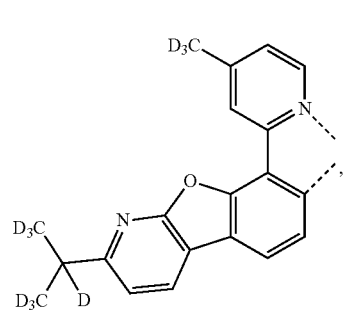
L_A83
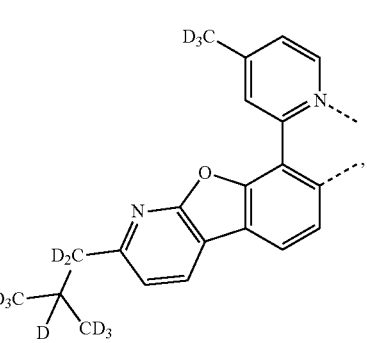
L_A84
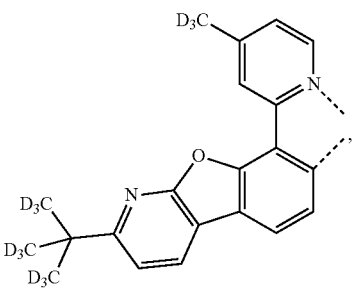
L_A85
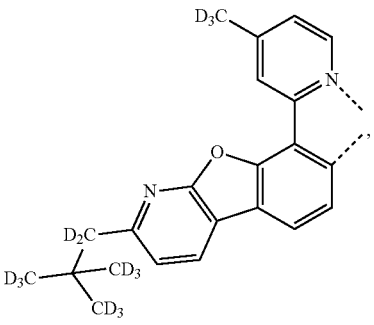
L_A86

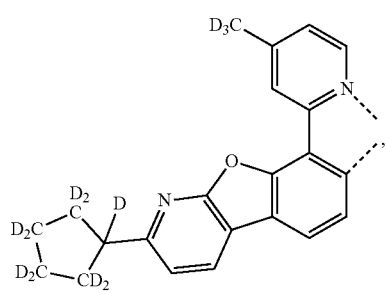 L_{A87}
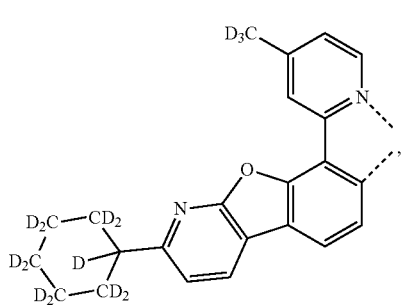 L_{A88}
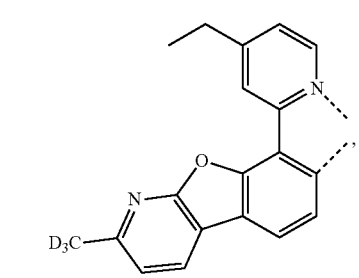 L_{A89}
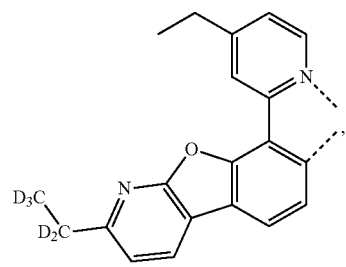 L_{A90}
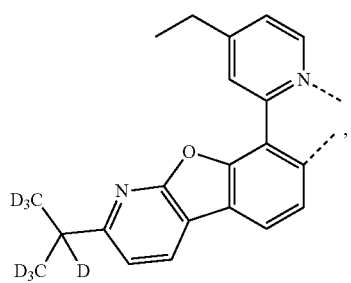 L_{A91}
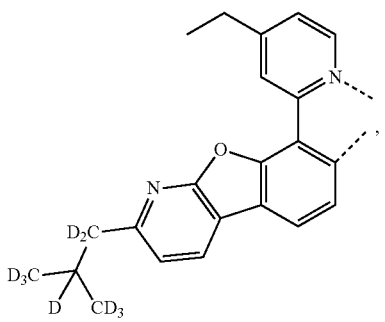 L_{A92}
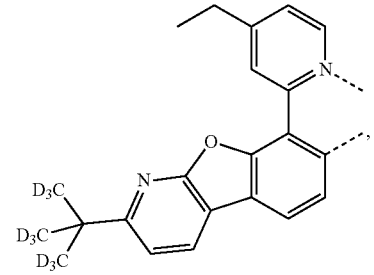 L_{A93}
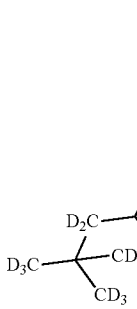 L_{A94}
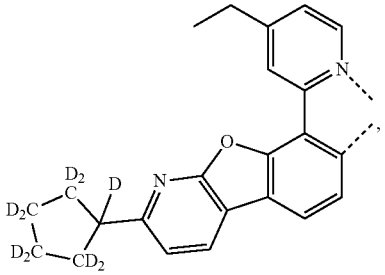 L_{A95}
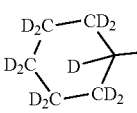 L_{A96}

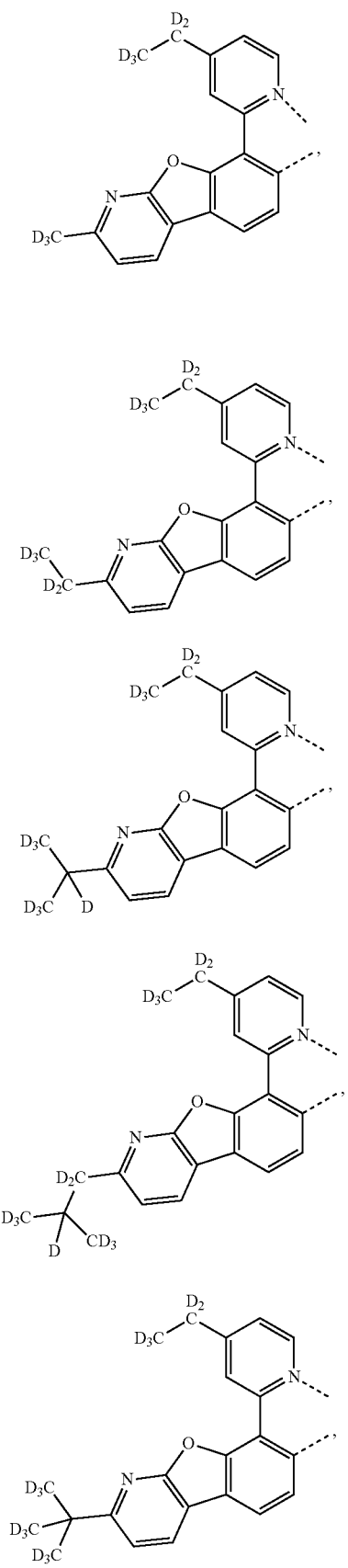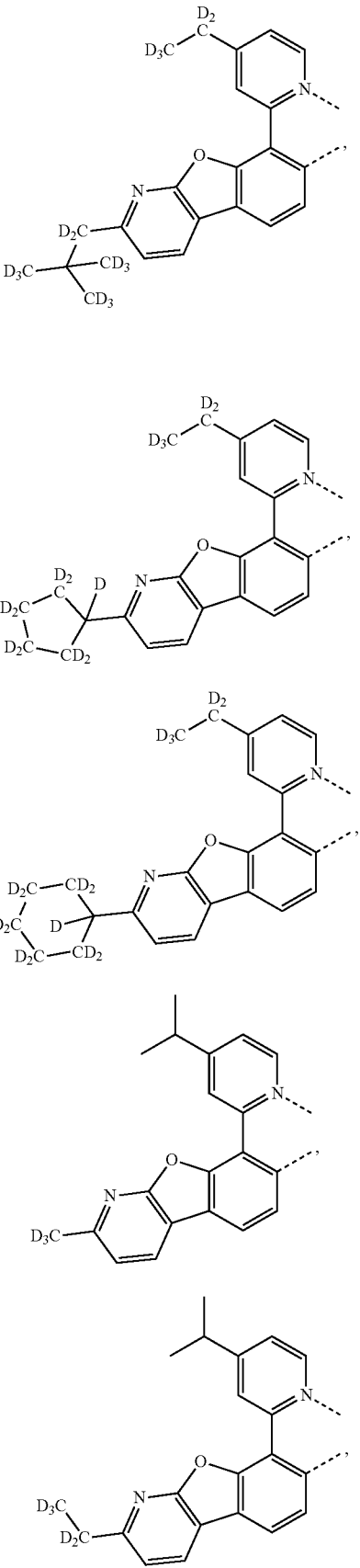

L<sub>A107</sub>
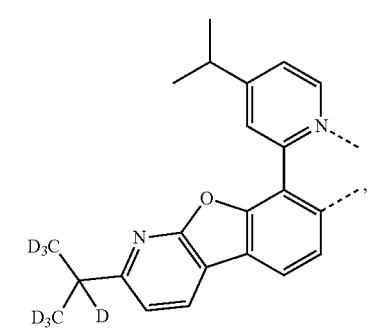
L<sub>A108</sub>
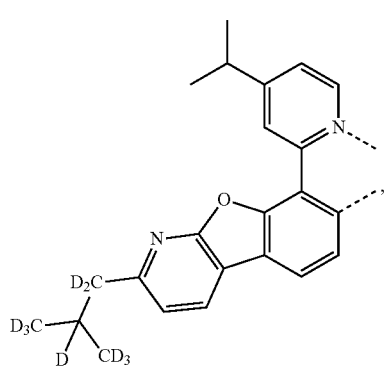
L<sub>A109</sub>
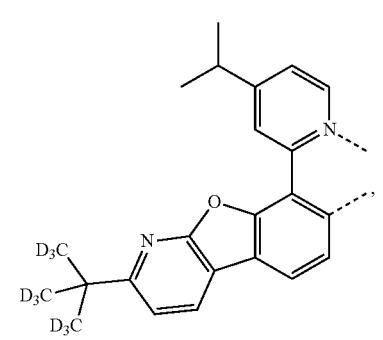
L<sub>A110</sub>
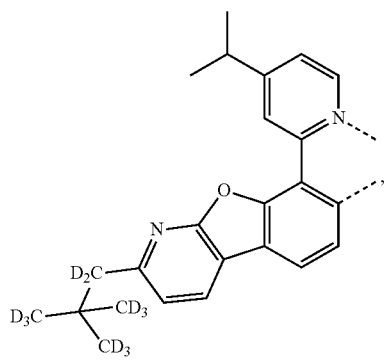
L<sub>A111</sub>
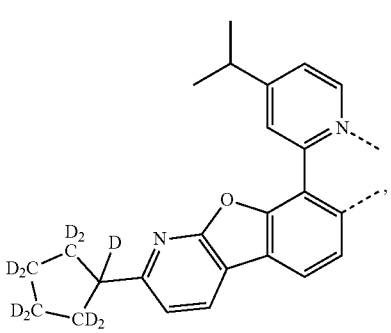
L<sub>A112</sub>
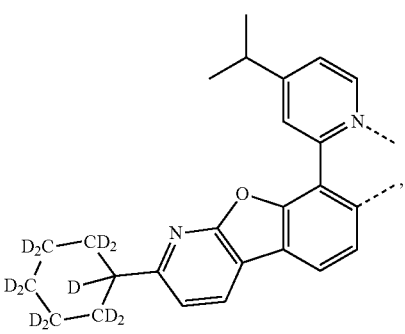
L<sub>A113</sub>
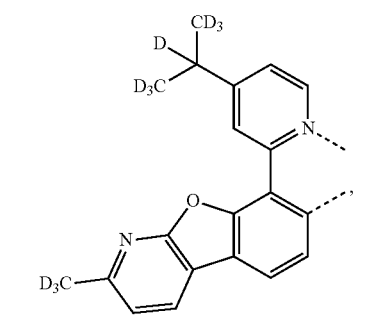
L<sub>A114</sub>
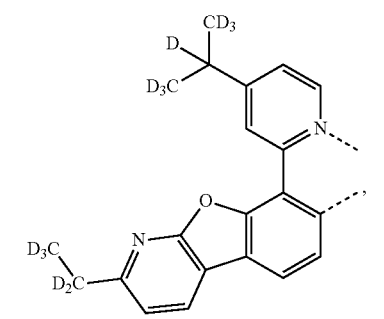
L<sub>A115</sub>
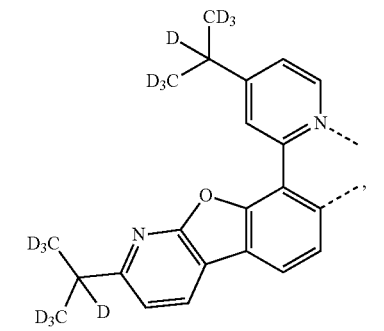

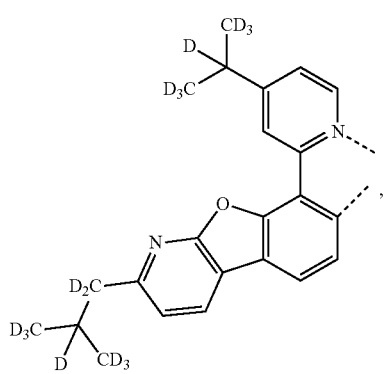
L<sub>A116</sub>
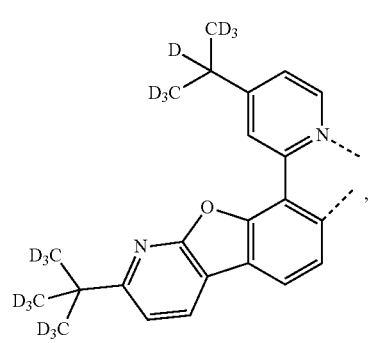
L<sub>A117</sub>
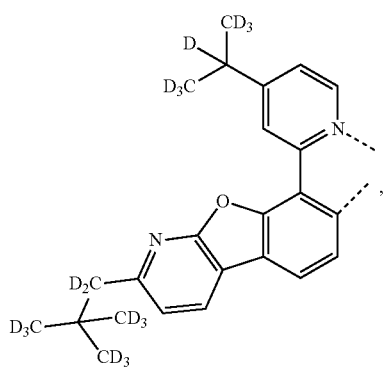
L<sub>A118</sub>
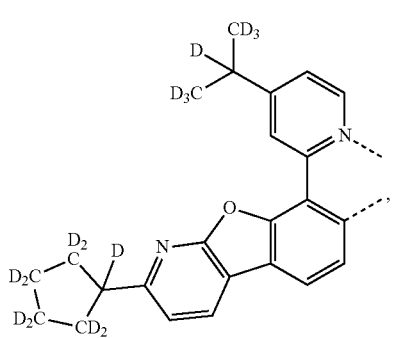
L<sub>A119</sub>
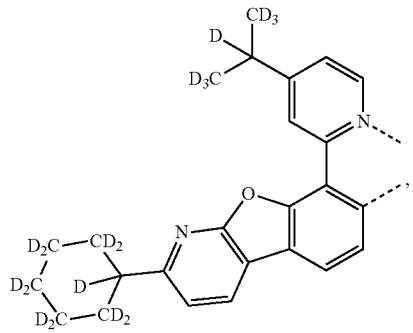
L<sub>A120</sub>
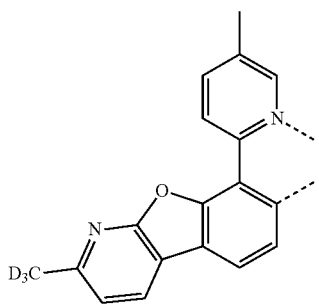
L<sub>A121</sub>
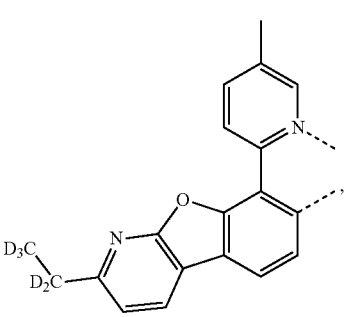
L<sub>A122</sub>
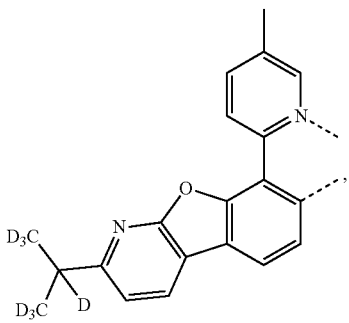
L<sub>A123</sub>
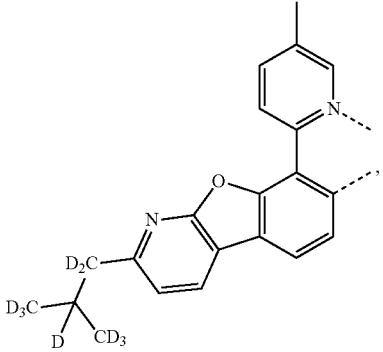
L<sub>A124</sub>

317
-continued
L_A125
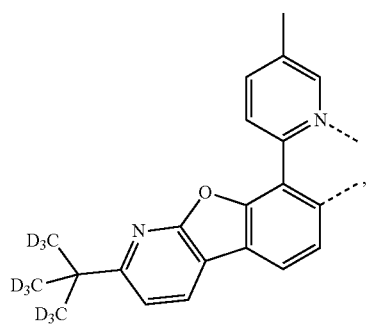
L_A126
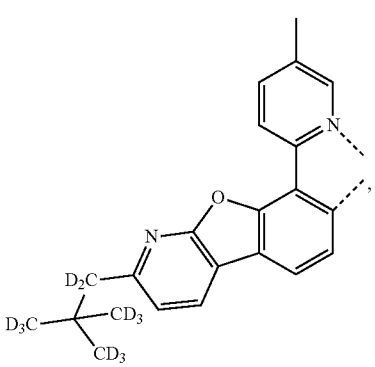
L_A127
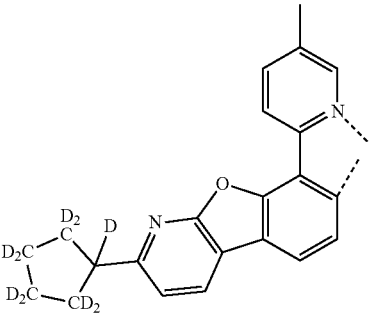
L_A128
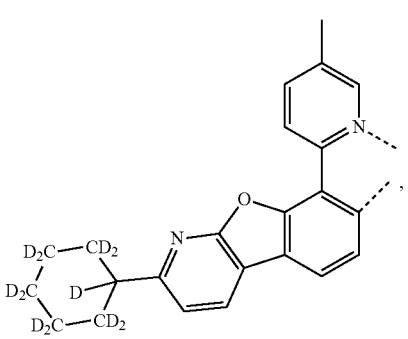
318
-continued
L_A129
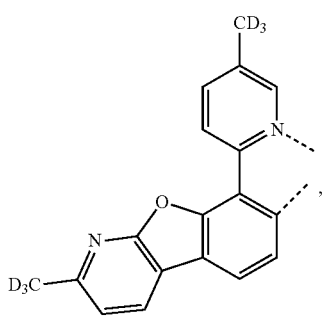
L_A130
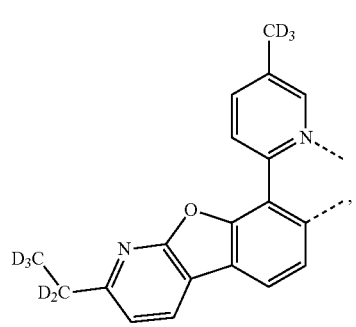
L_A131
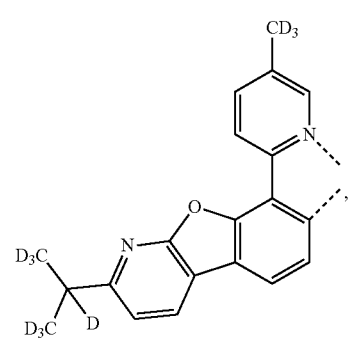
L_A132
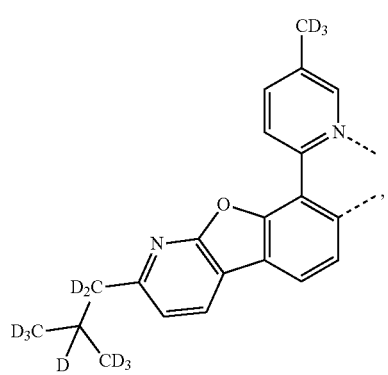

L<sub>A133</sub>
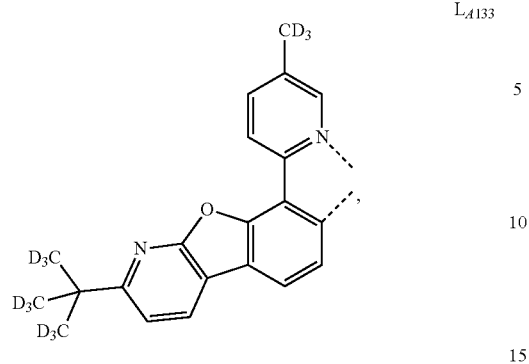
L<sub>A137</sub>
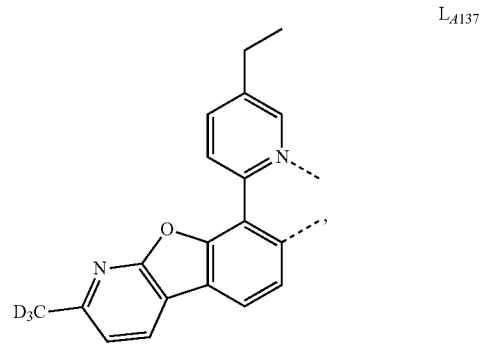
L<sub>A134</sub>
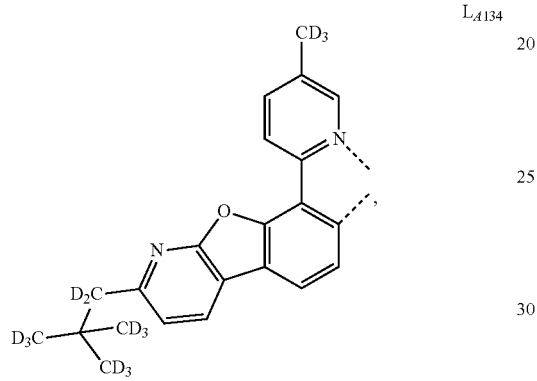
L<sub>A138</sub>
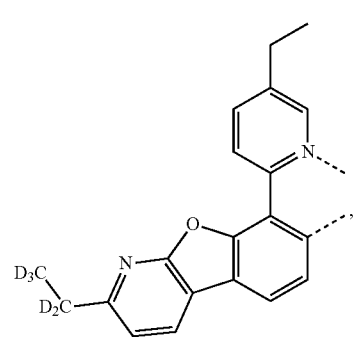
L<sub>A135</sub>
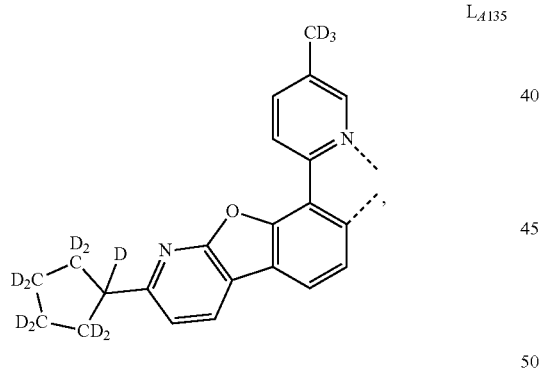
L<sub>A139</sub>
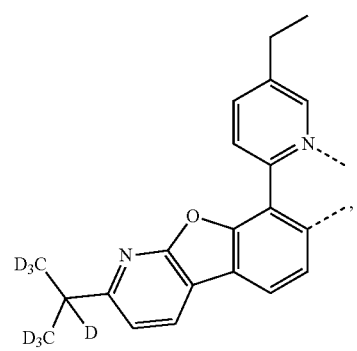
L<sub>A136</sub>
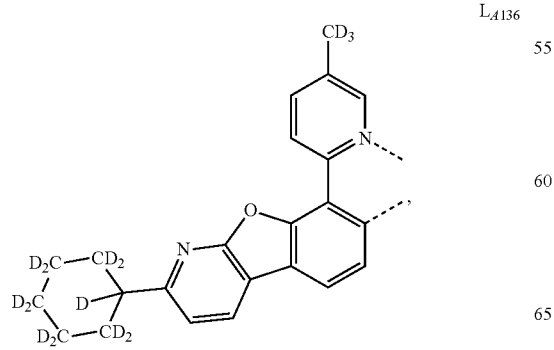
L<sub>A140</sub>
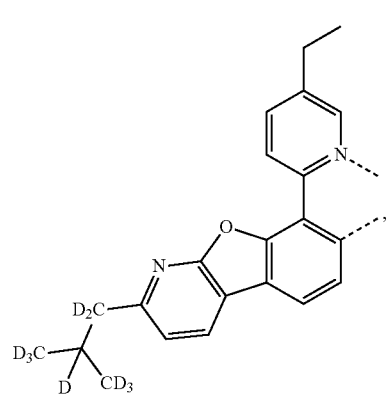

321
-continued
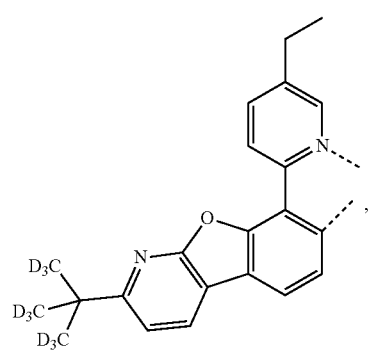
L_{A141}
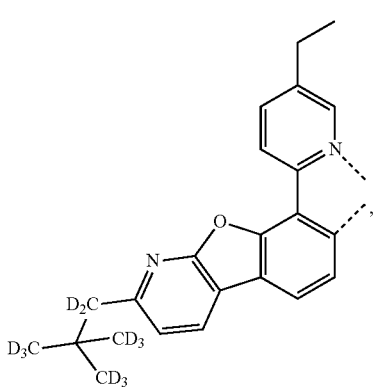
L_{A142}
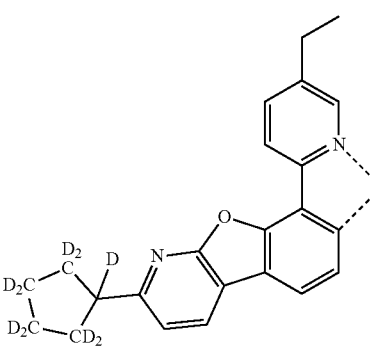
L_{A143}
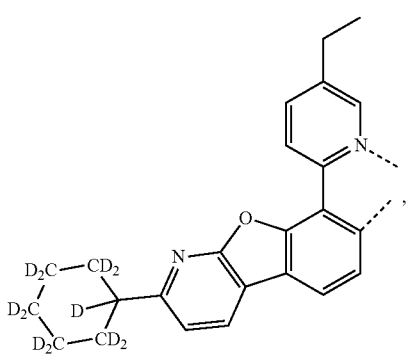
L_{A144}
322
-continued
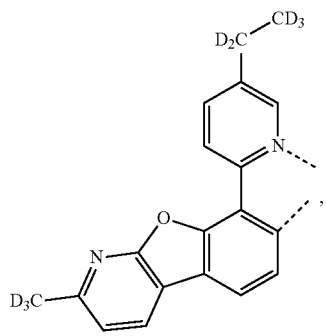
L_{A145}
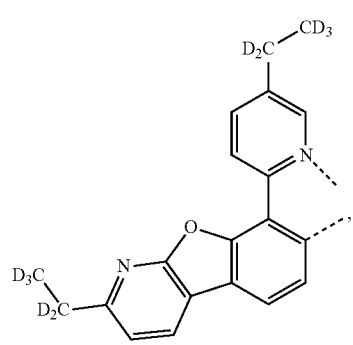
L_{A146}
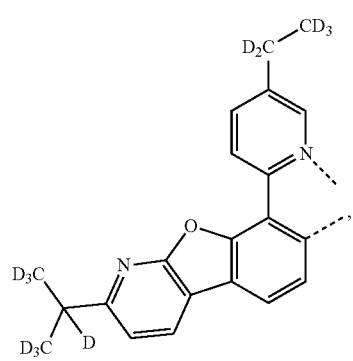
L_{A147}
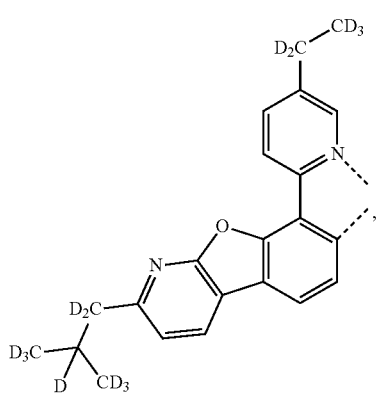
L_{A148}

L<sub>A149</sub>
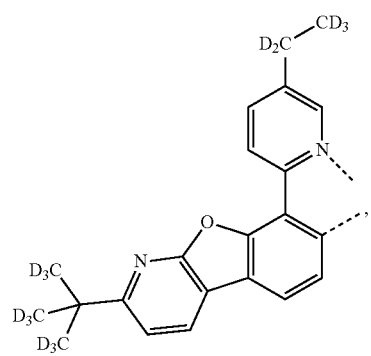
L<sub>A150</sub>
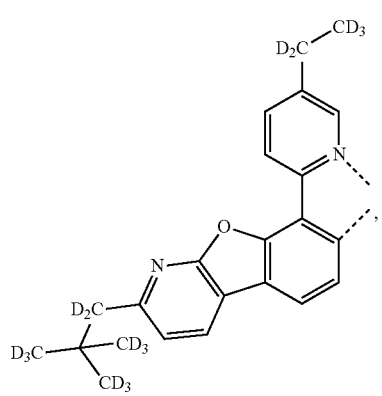
L<sub>A151</sub>
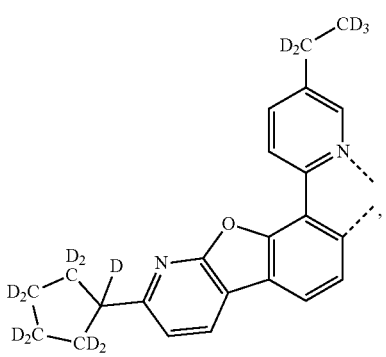
L<sub>A152</sub>
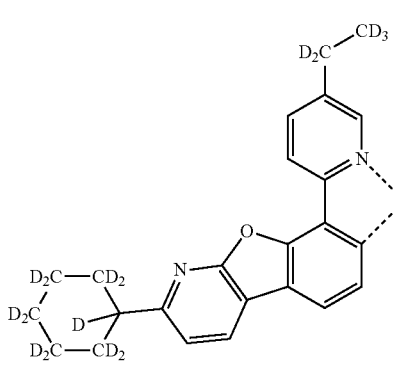
L<sub>A153</sub>
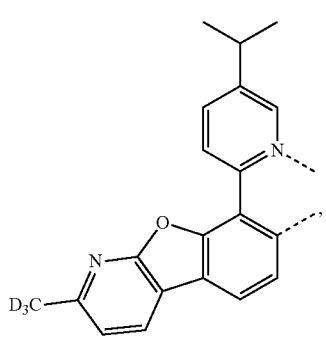
L<sub>A154</sub>
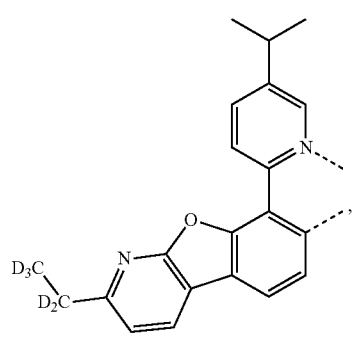
L<sub>A155</sub>
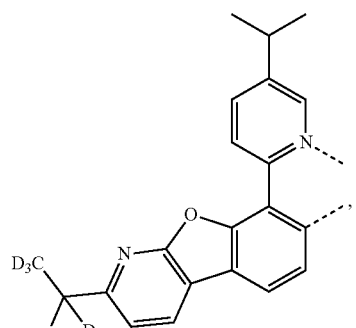
L<sub>A156</sub>
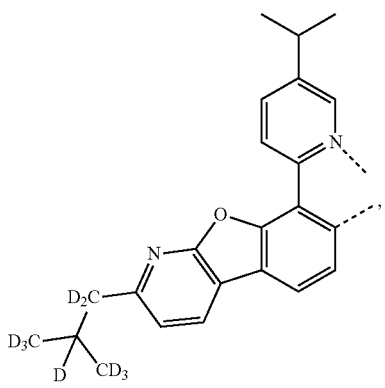

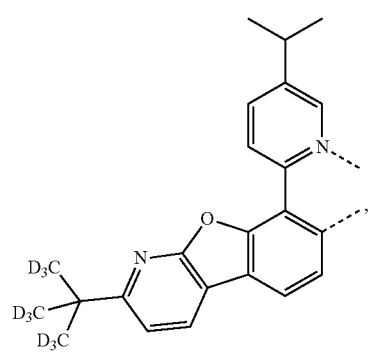 L_{A157}
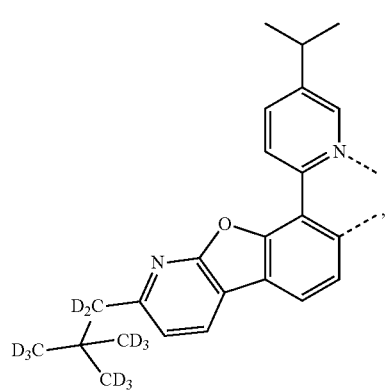 L_{A158}
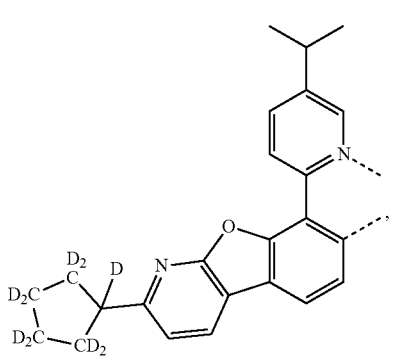 L_{A159}
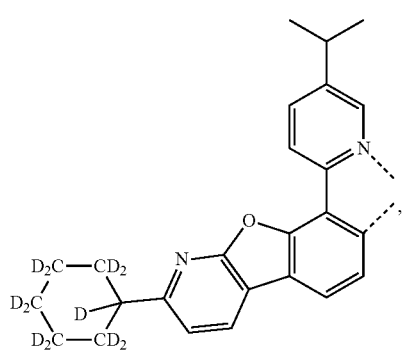 L_{A160}
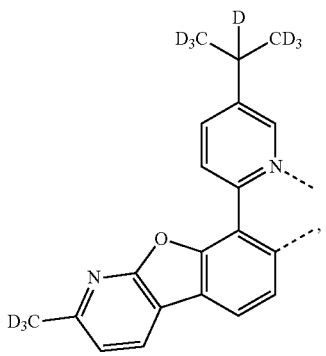 L_{A161}
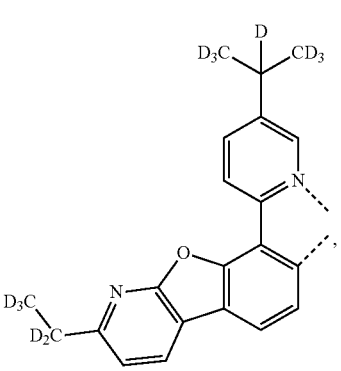 L_{A162}
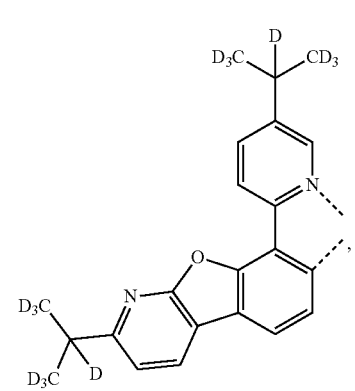 L_{A163}
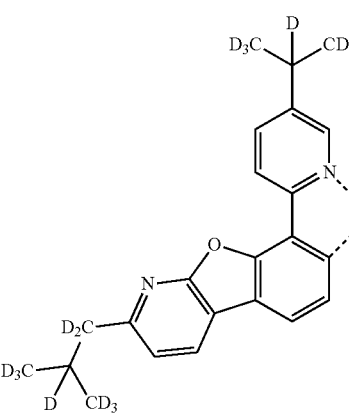 L_{A164}

L_{A165}
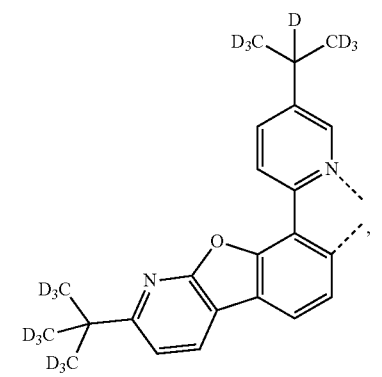
L_{A166}
L_{A167}
L_{A168}
L_{A169}
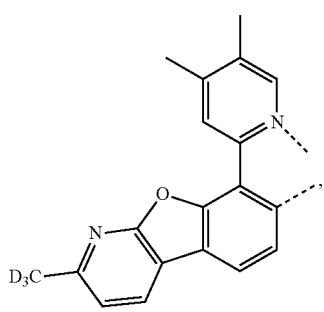
L_{A170}
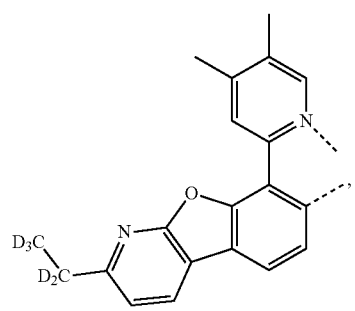
L_{A171}
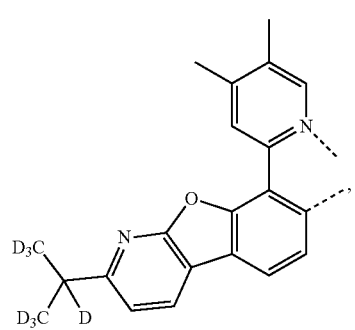
L_{A172}
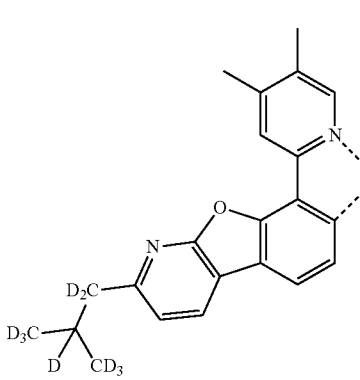
L_{A173}
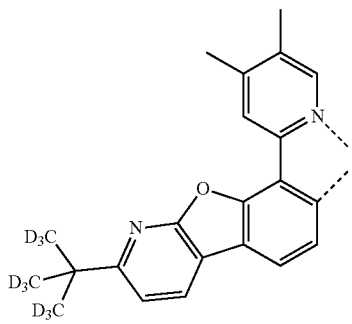

L_{A174}
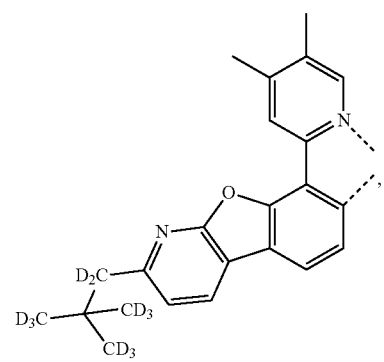
L_{A175}
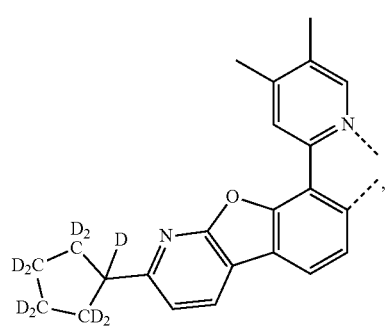
L_{A176}
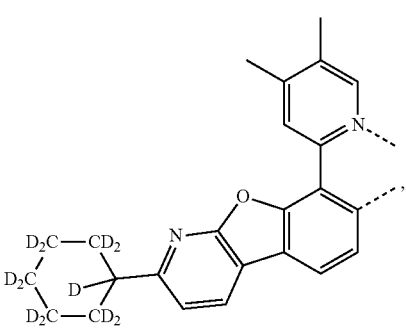
L_{A177}
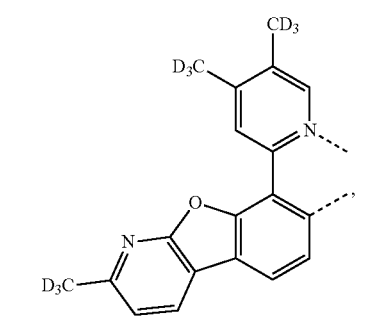
L_{A178}
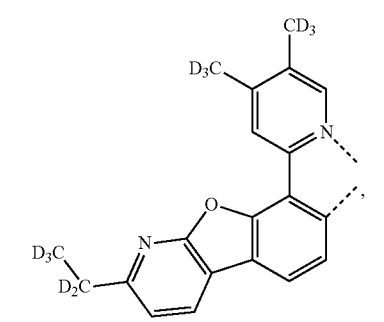
L_{A179}
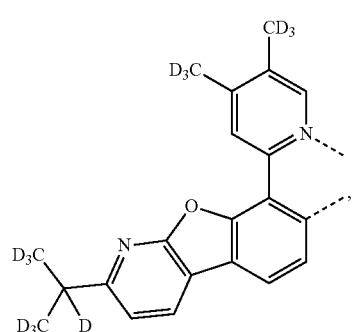
L_{A180}
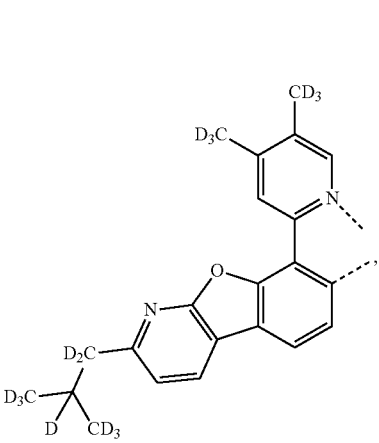
L_{A181}
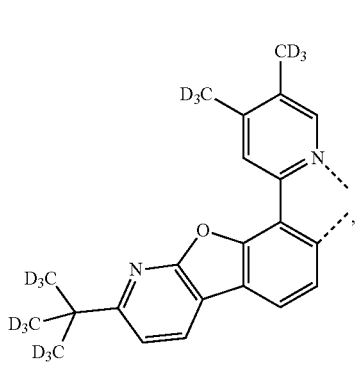
L_{A182}
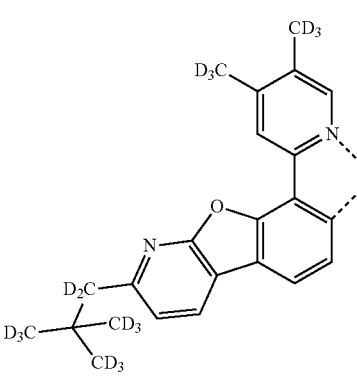

-continued
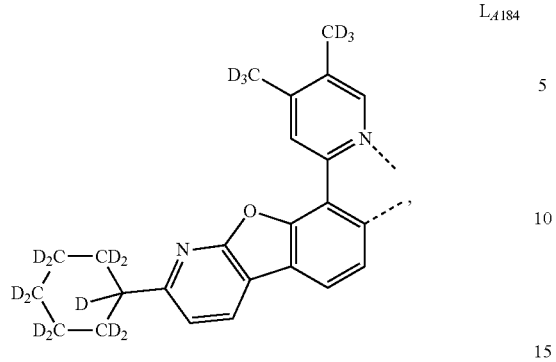 L<sub>A184</sub>
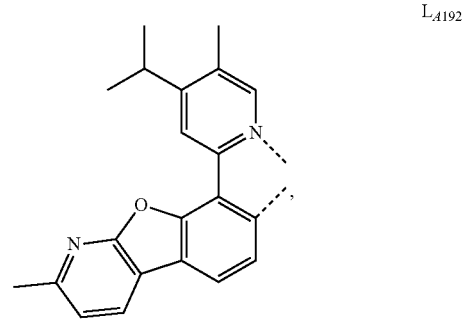 L<sub>A192</sub>
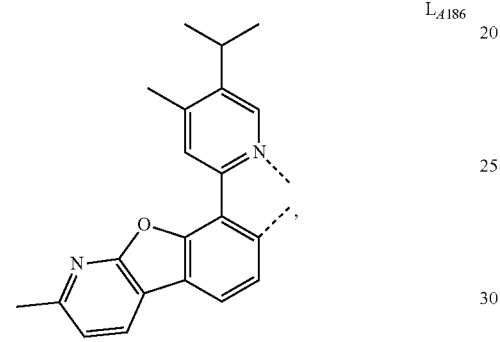 L<sub>A186</sub>
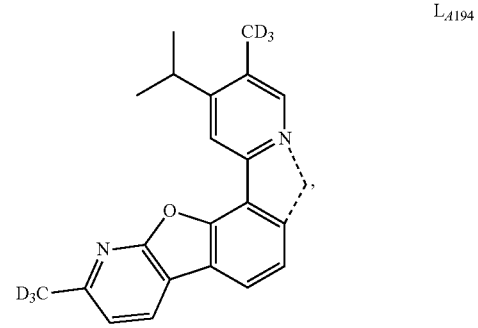 L<sub>A194</sub>
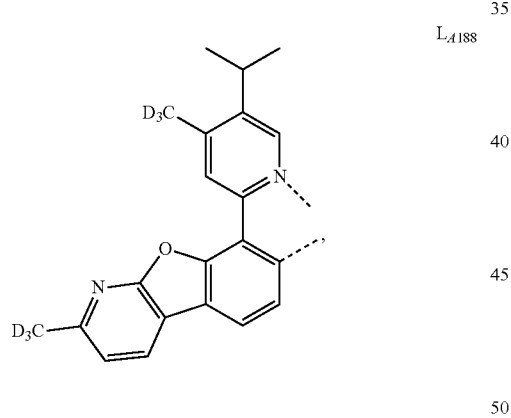 L<sub>A188</sub>
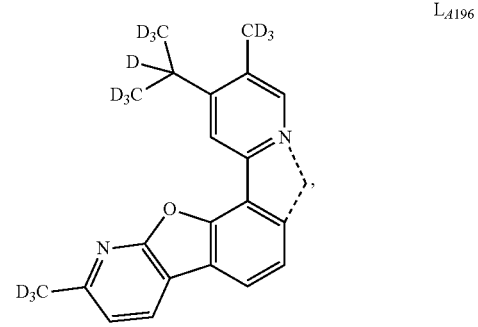 L<sub>A196</sub>
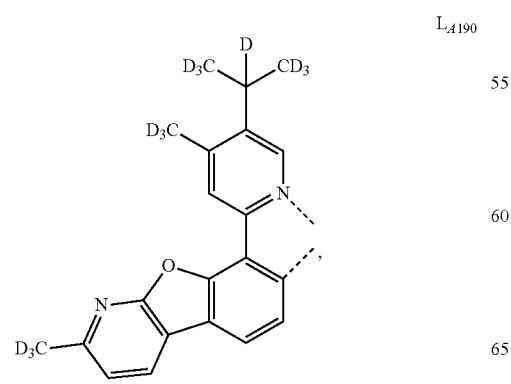 L<sub>A190</sub>
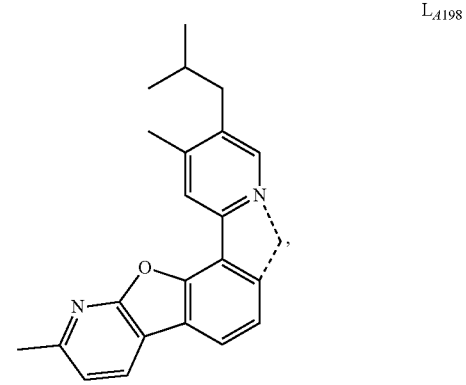 L<sub>A198</sub>

L_{A200}
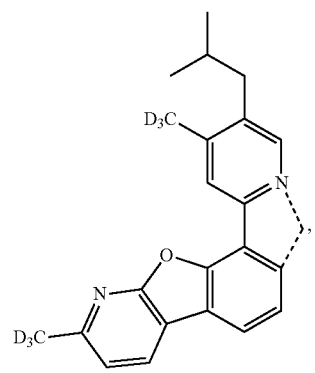
L_{A202}
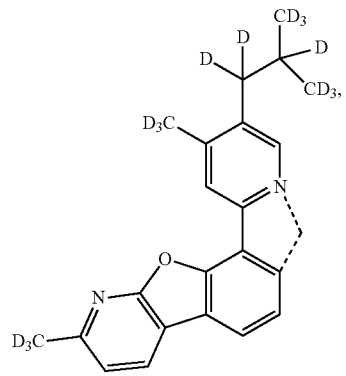
L_{A203}
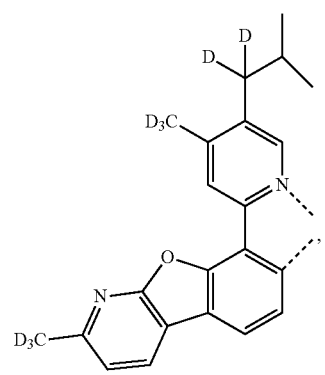
L_{A205}
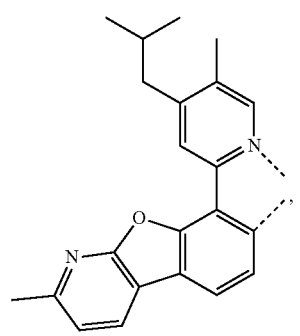
L_{A207}
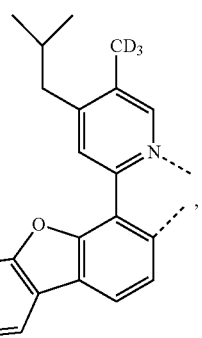
L_{A208}
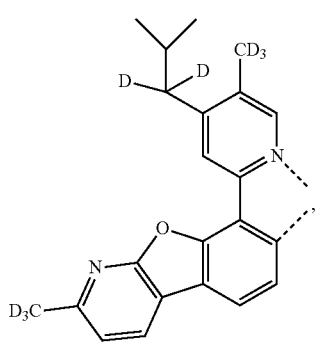
L_{A210}
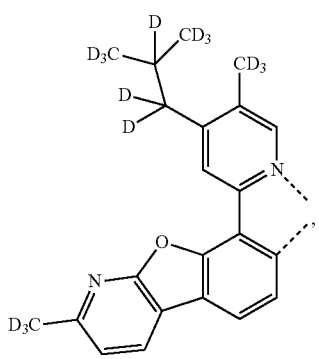
L_{A212}
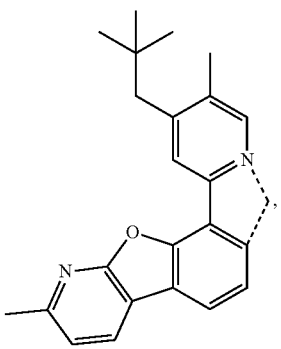

L<sub>A214</sub>
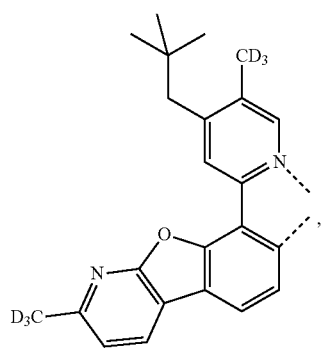
L<sub>A216</sub>
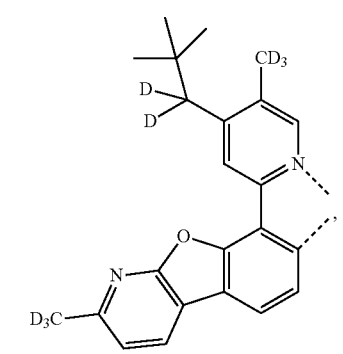
L<sub>A217</sub>
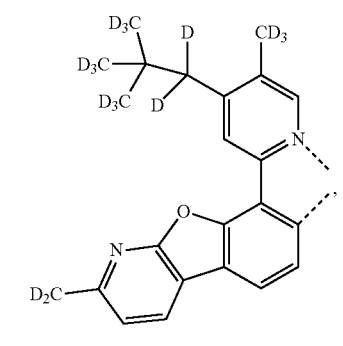
L<sub>A219</sub>
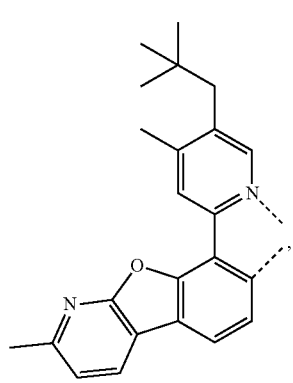
L<sub>A221</sub>
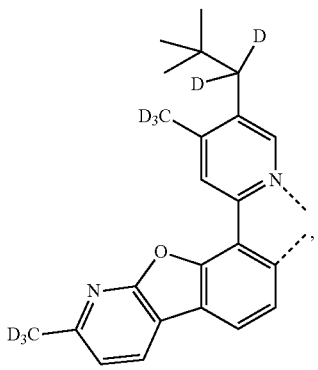
L<sub>A223</sub>
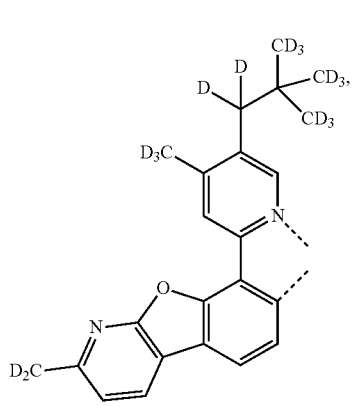
L<sub>A225</sub>
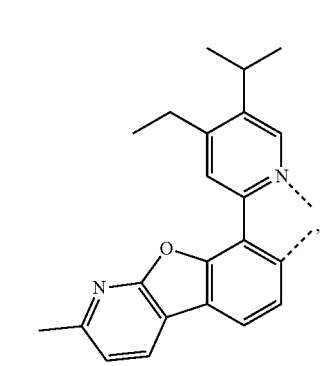
L<sub>A227</sub>
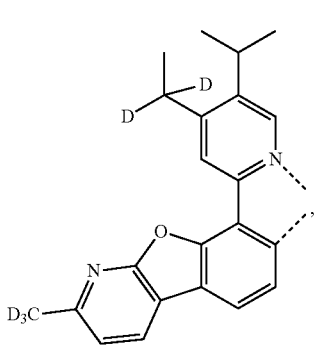

L_{A228}
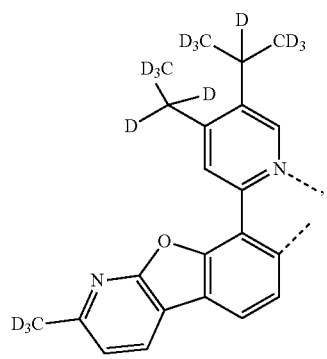
L_{A234}
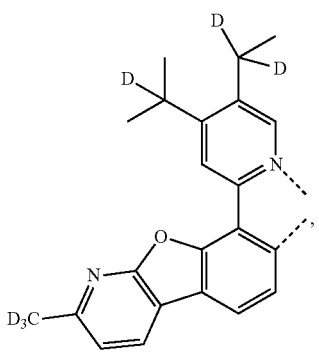
L_{A229}
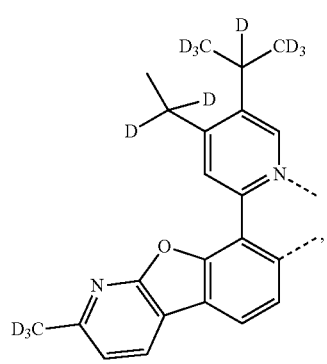
L_{A235}
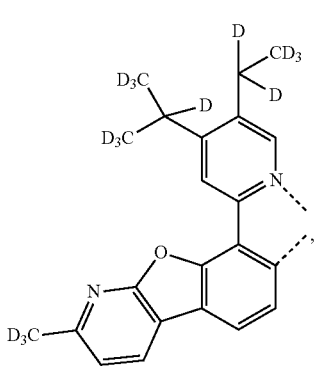
L_{A231}
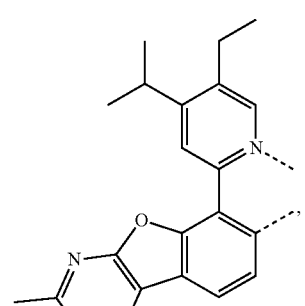
L_{A236}
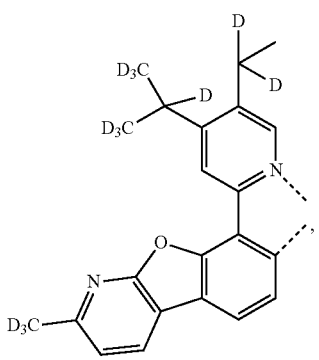
L_{A233}
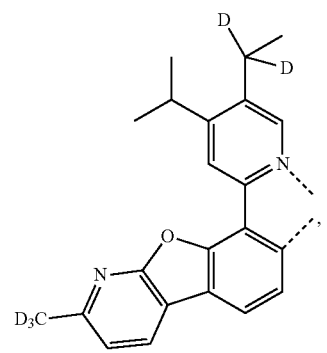
L_{A238}
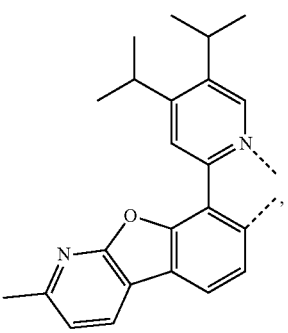

L<sub>A239</sub>
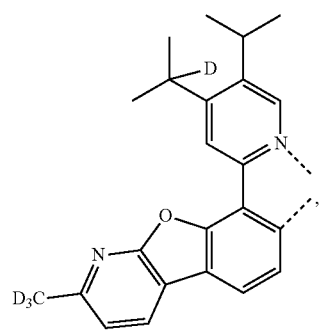
L<sub>A241</sub>
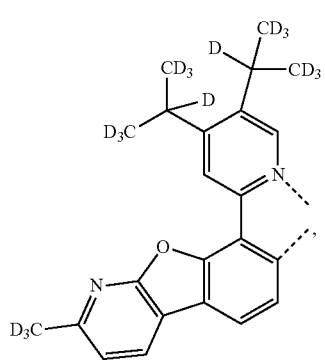
L<sub>A243</sub>
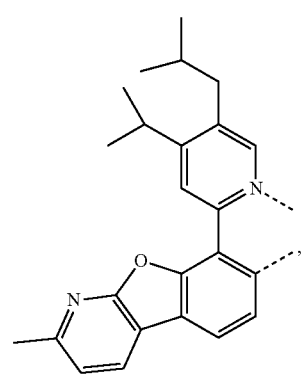
L<sub>A245</sub>
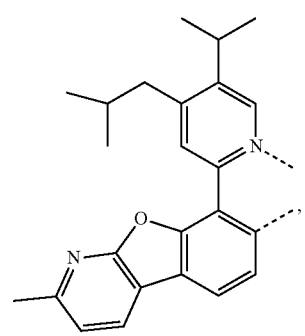
L<sub>A247</sub>
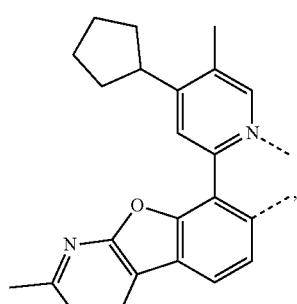
L<sub>A249</sub>
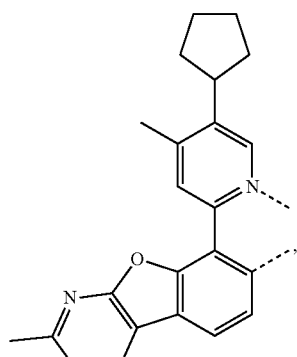
L<sub>A250</sub>
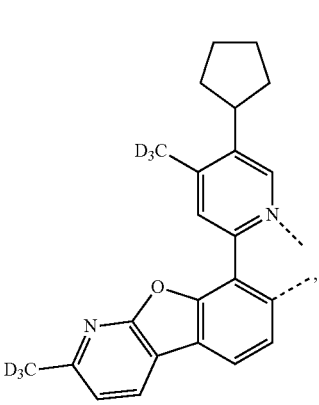
L<sub>A251</sub>
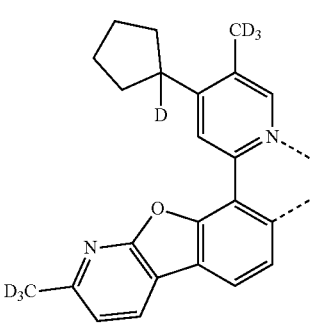

L_{A253}
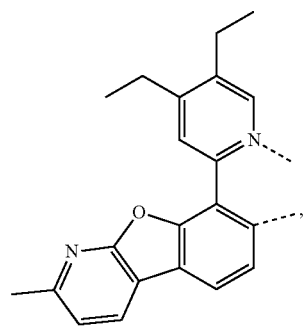
L_{A254}
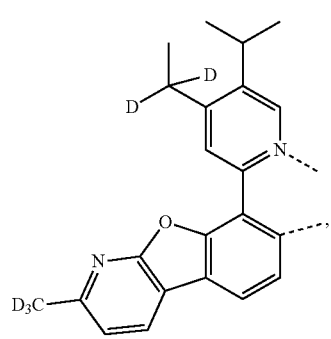
L_{A255}
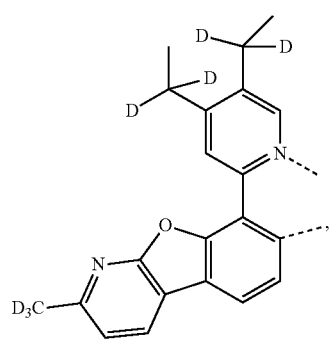
L_{A256}
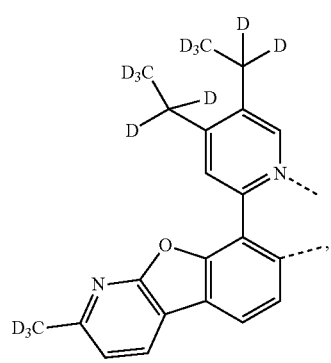
L_{A257}
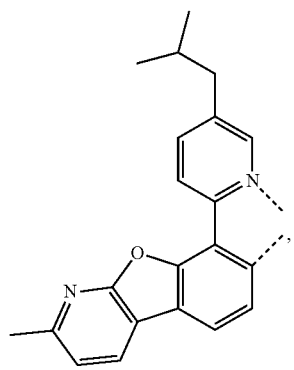
L_{A258}
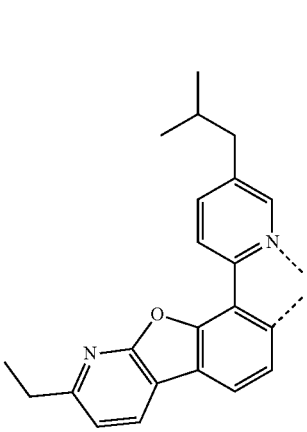
L_{A259}
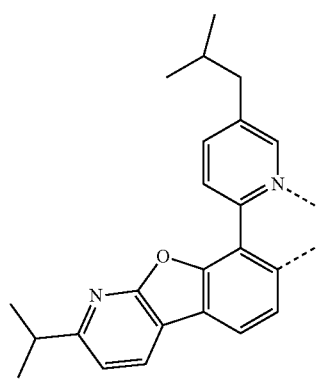
L_{A260}
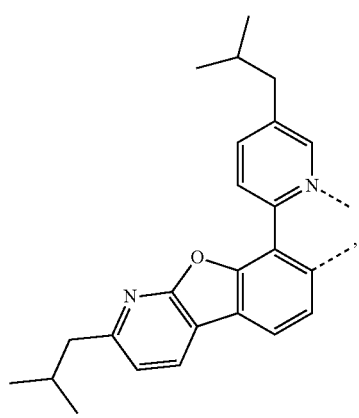

L<sub>A261</sub>
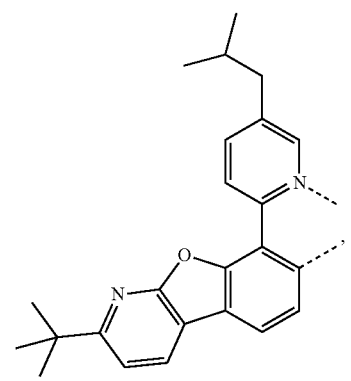
L<sub>A262</sub>
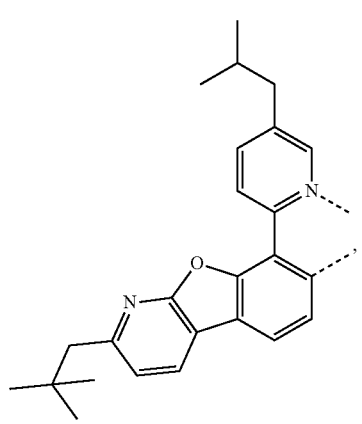
L<sub>A263</sub>
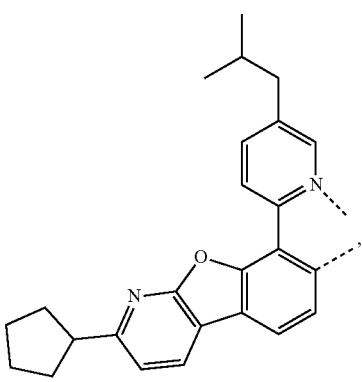
L<sub>A264</sub>
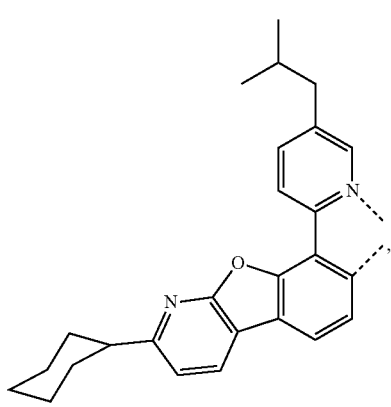
L<sub>A265</sub>
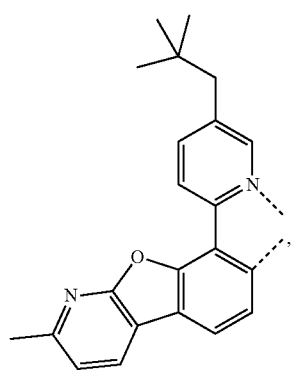
L<sub>A266</sub>
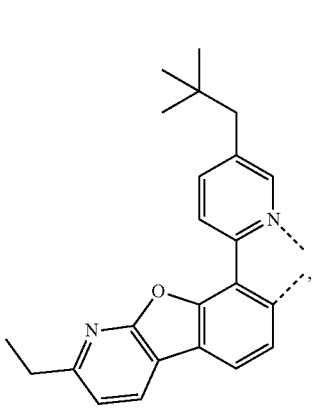
L<sub>A267</sub>
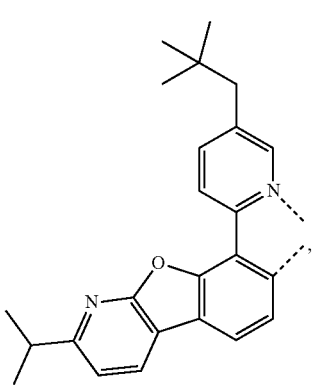
L<sub>A268</sub>
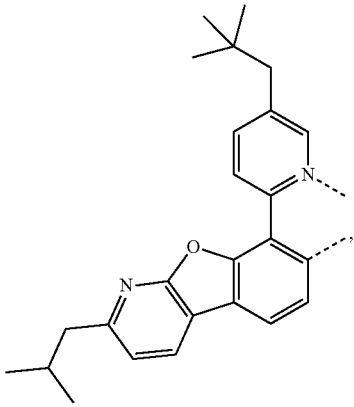

L<sub>A269</sub>
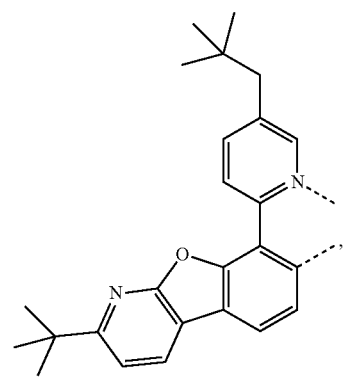
L<sub>A270</sub>
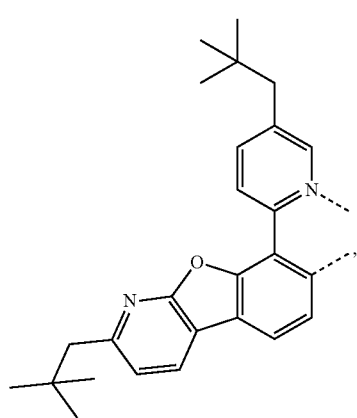
L<sub>A271</sub>
L<sub>A273</sub>
L<sub>A274</sub>
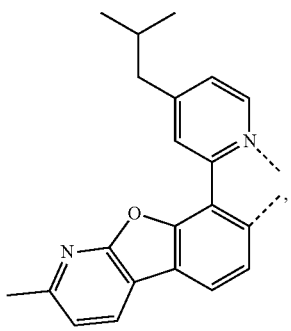
L<sub>A275</sub>
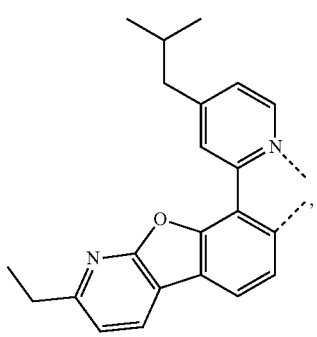
L<sub>A276</sub>
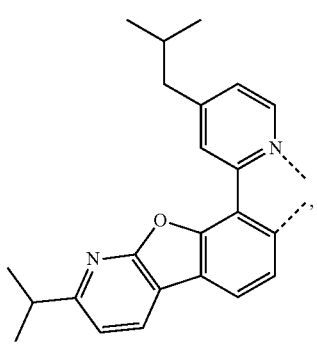
L<sub>A277</sub>
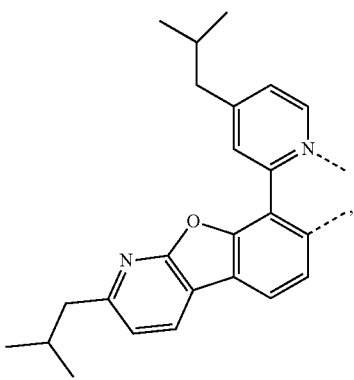

| | |
|---|---|
| L_{A278} 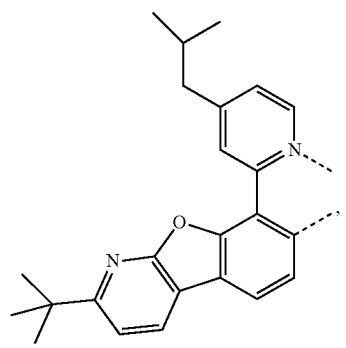 | L_{A282} 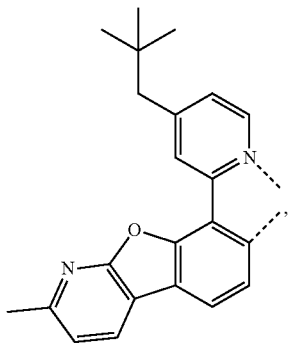 |
| L_{A279} 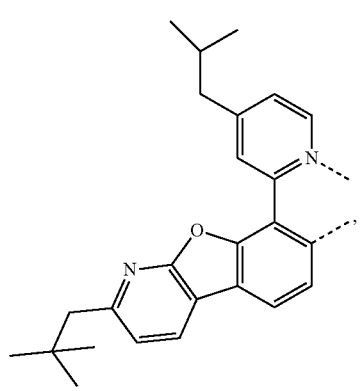 | L_{A283} 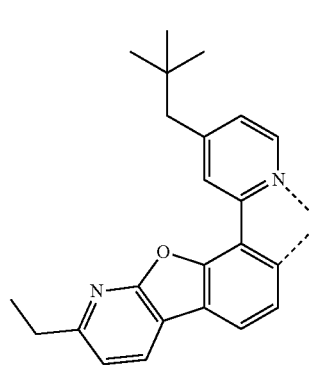 |
| L_{A280} 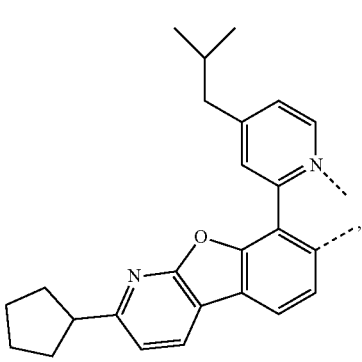 | L_{A284} 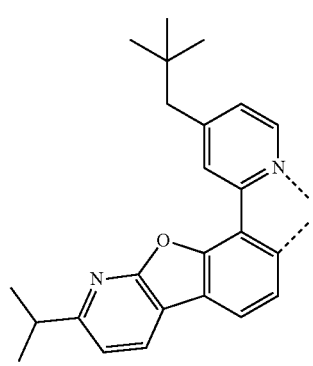 |
| L_{A281} 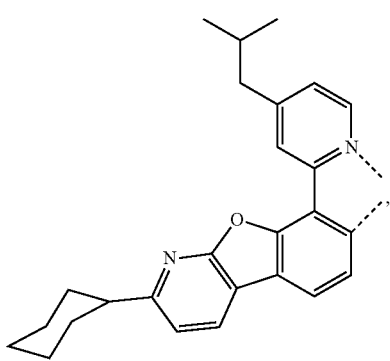 | L_{A285} 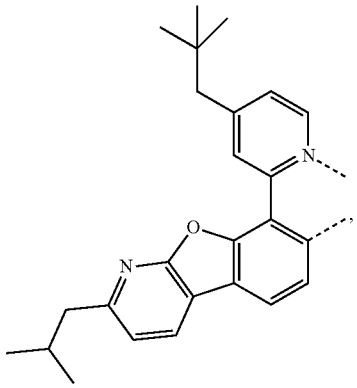 |

-continued
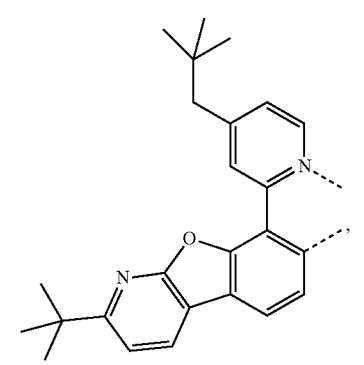
L<sub>A286</sub>
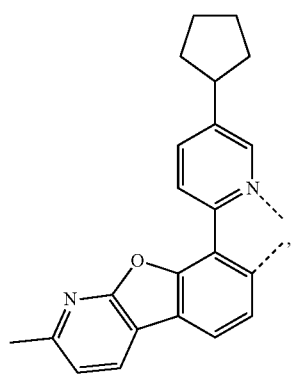
L<sub>A290</sub>
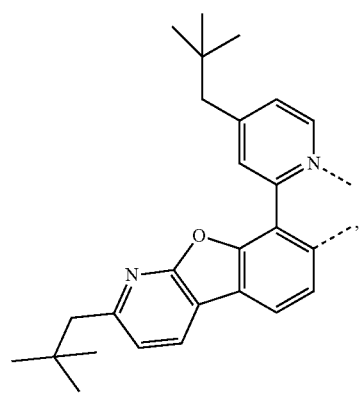
L<sub>A287</sub>
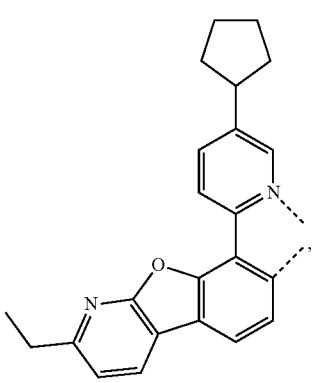
L<sub>A291</sub>
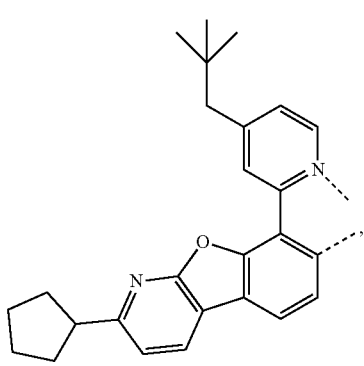
L<sub>A288</sub>
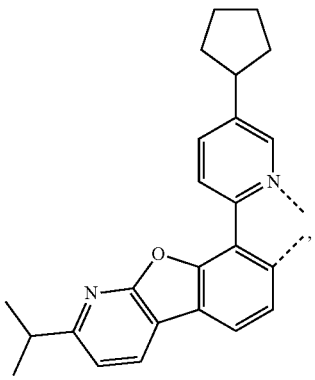
L<sub>A292</sub>
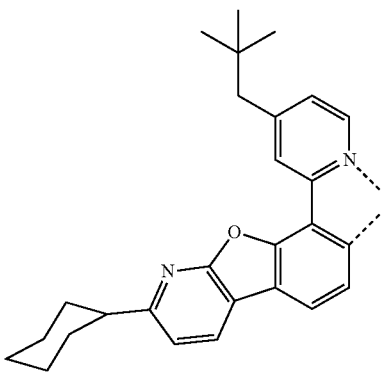
L<sub>A289</sub>
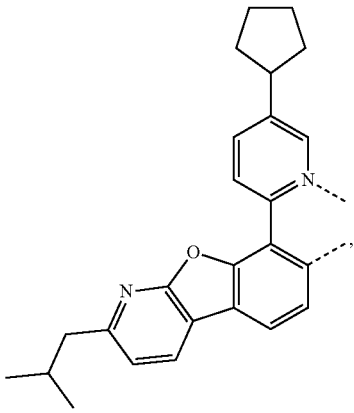
L<sub>A293</sub>

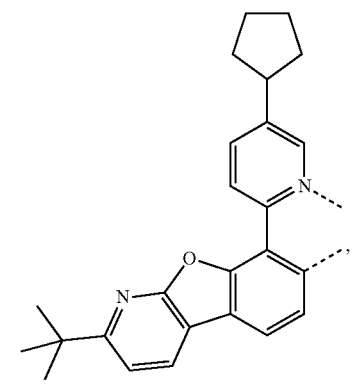
L<sub>A294</sub>
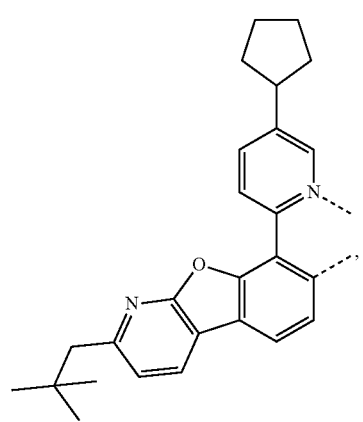
L<sub>A295</sub>
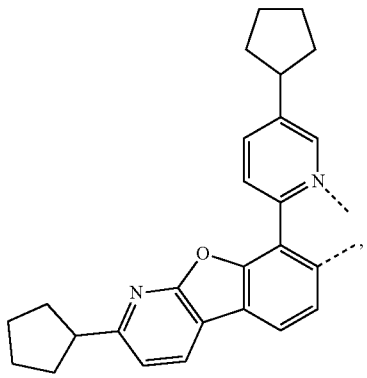
L<sub>A296</sub>
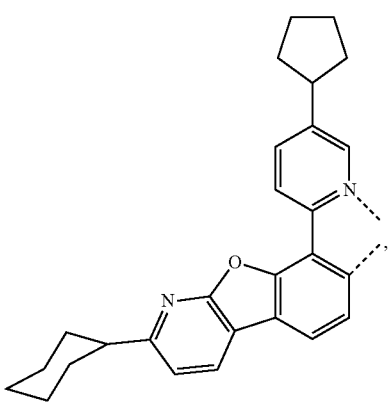
L<sub>A297</sub>
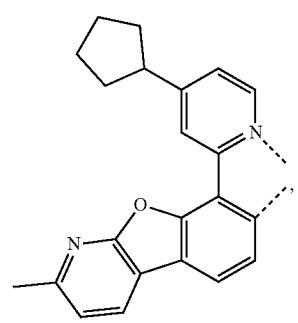
L<sub>A298</sub>
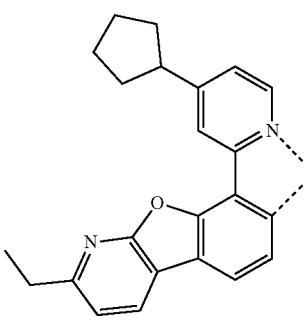
L<sub>A299</sub>
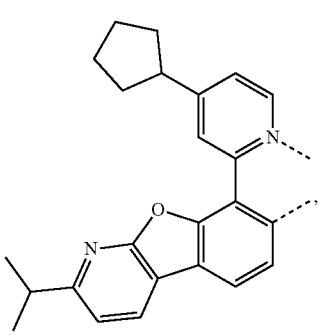
L<sub>A300</sub>
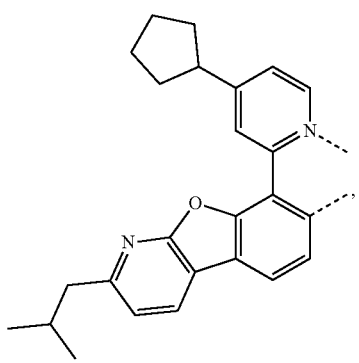
L<sub>A301</sub>

L_{A302} 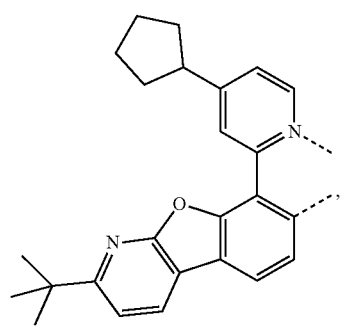
L_{A303} 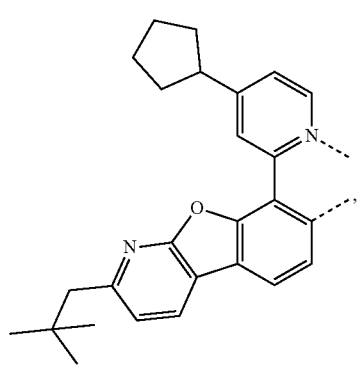
L_{A304} 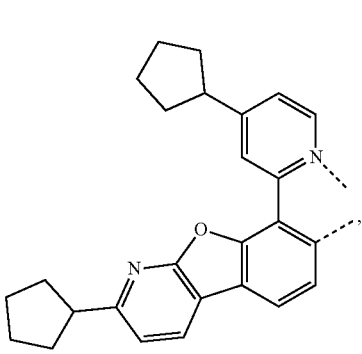
L_{A305} 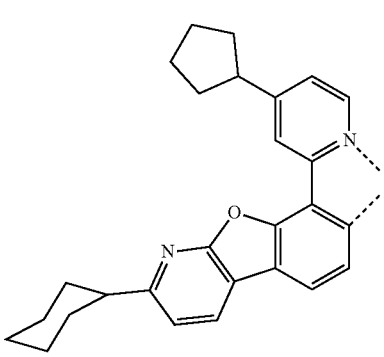
L_{A306} 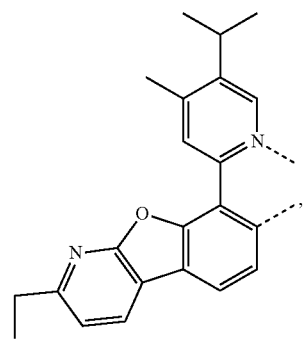
L_{A307} 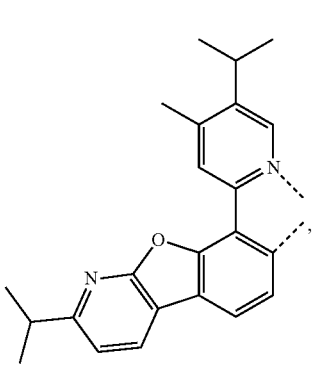
L_{A308} 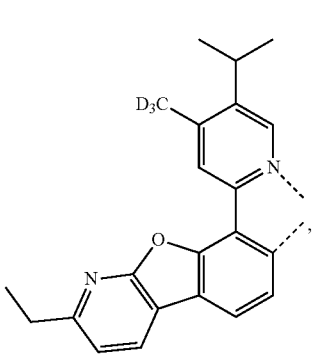
L_{A309} 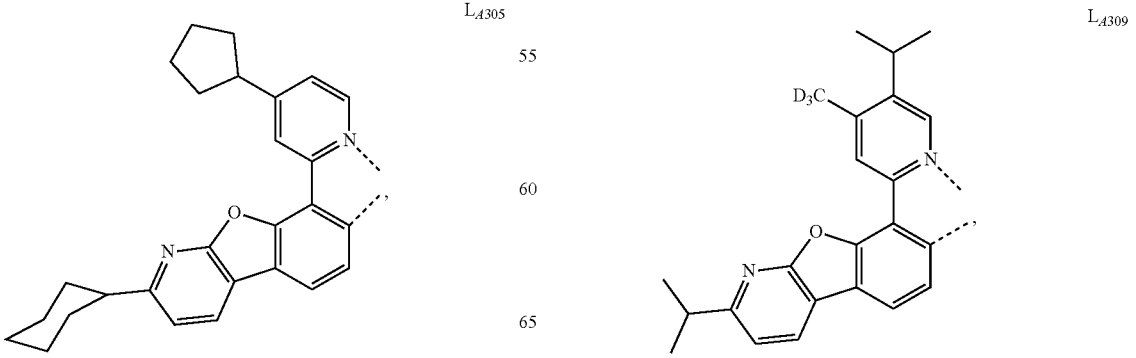

L_A310 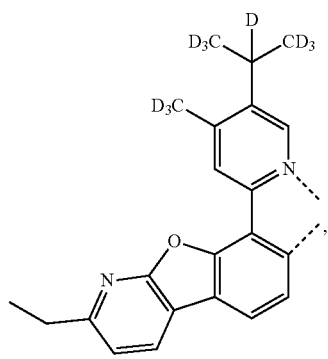
L_A311 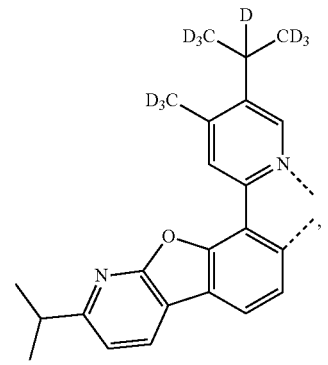
L_A312 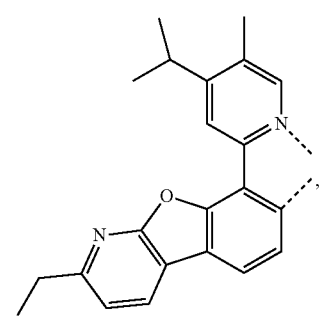
L_A313 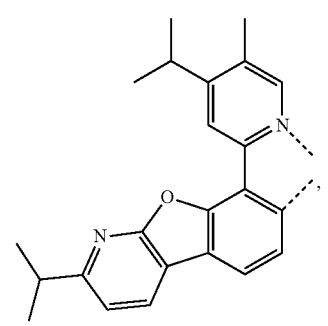
L_A314 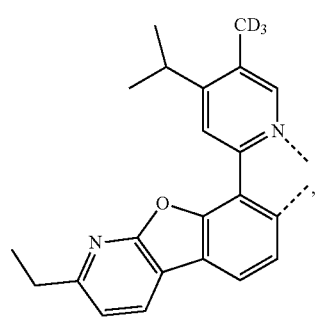
L_A315 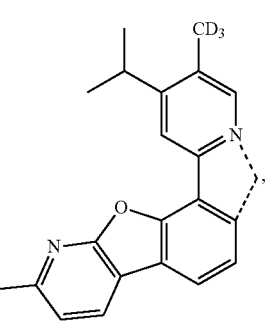
L_A316 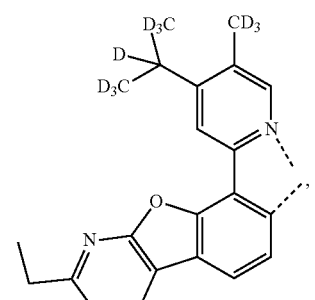
L_A317 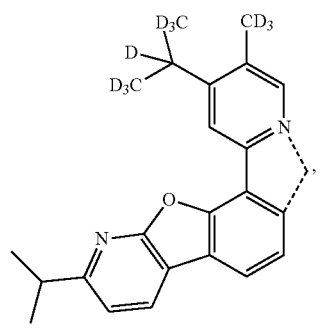

| | |
|---|---|
| L$_{A318}$ 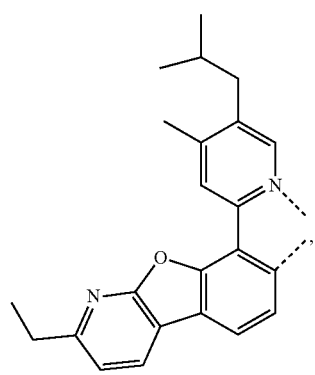 | L$_{A322}$ 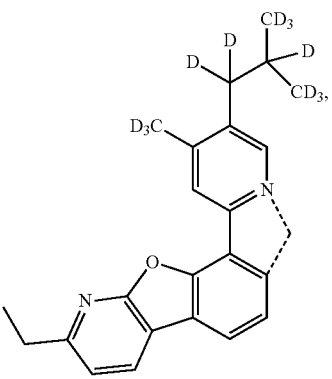 |
| L$_{A319}$ 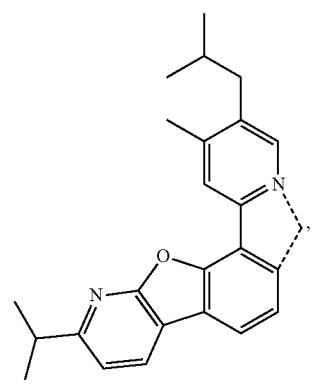 | L$_{A323}$ 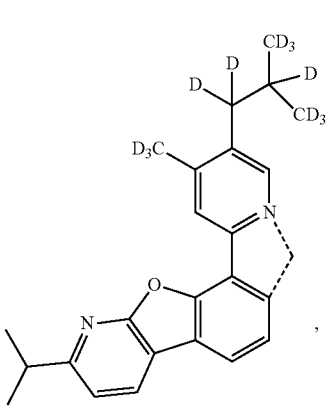 |
| L$_{A320}$ 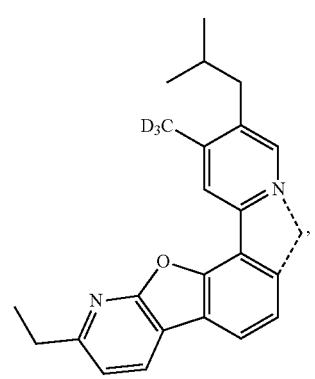 | L$_{A324}$ 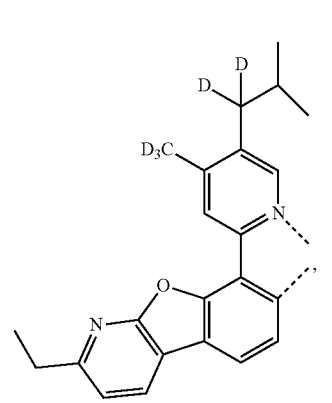 |
| L$_{A321}$ 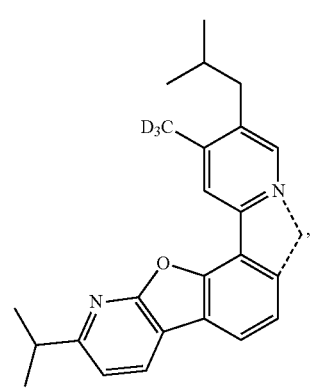 | L$_{A325}$ 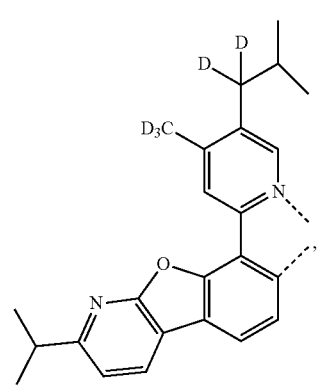 |

L_{A326} 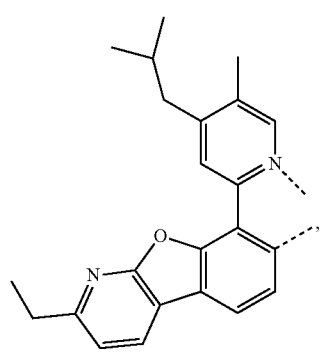
L_{A327} 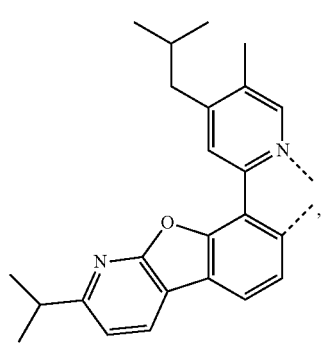
L_{A328} 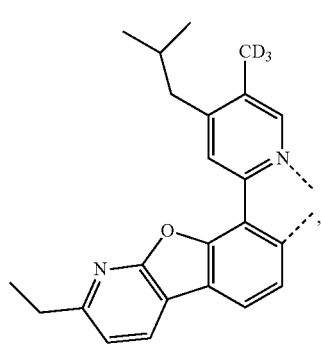
L_{A329} 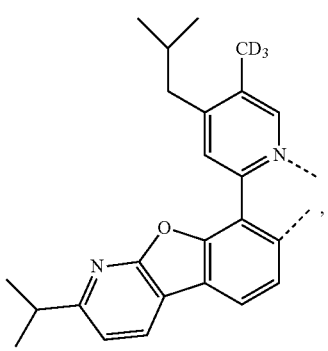
L_{A330} 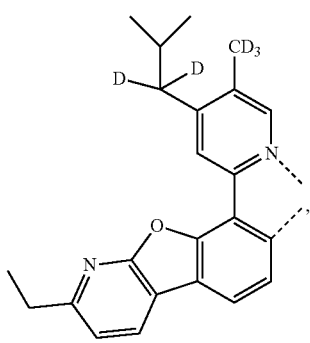
L_{A331} 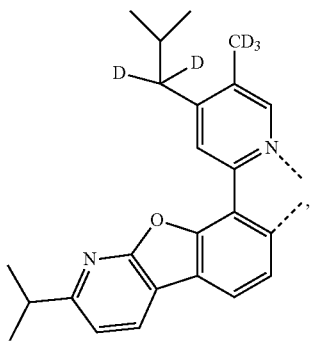
L_{A332} 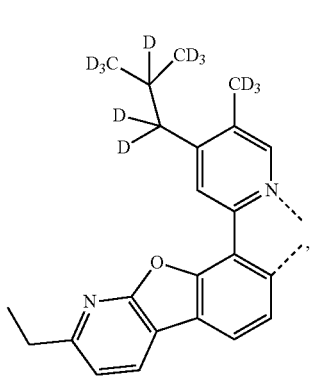
L_{A333} 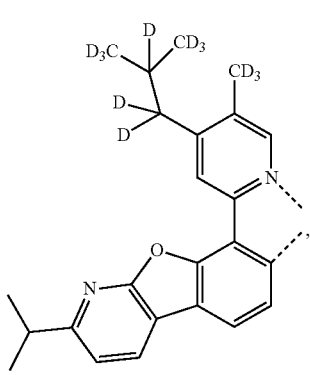

L<sub>A334</sub>
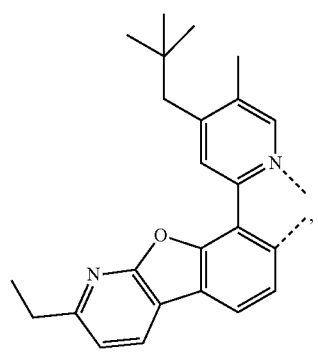
L<sub>A335</sub>
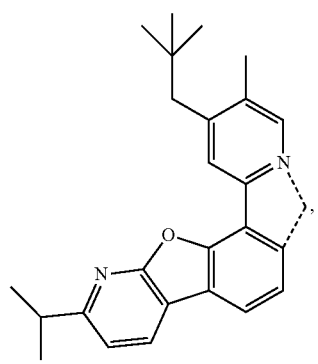
L<sub>A336</sub>
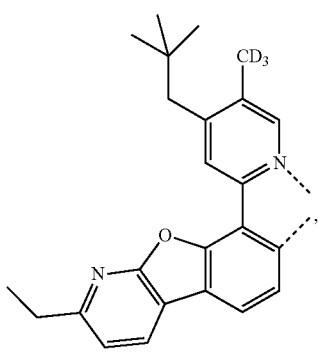
L<sub>A337</sub>
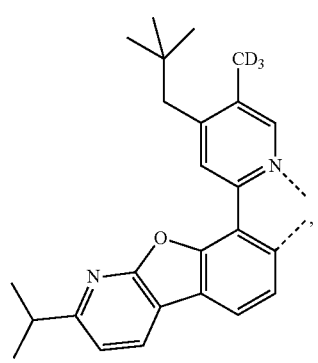
L<sub>A338</sub>
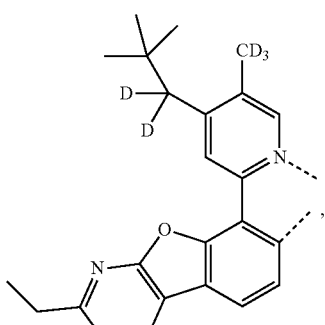
L<sub>A339</sub>
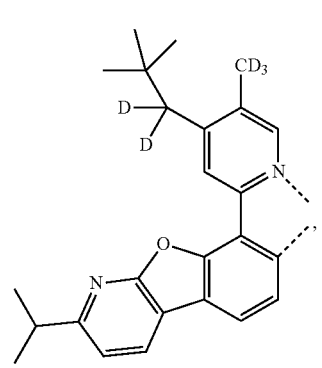
L<sub>A340</sub>
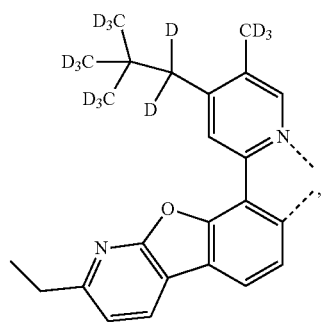
L<sub>A341</sub>
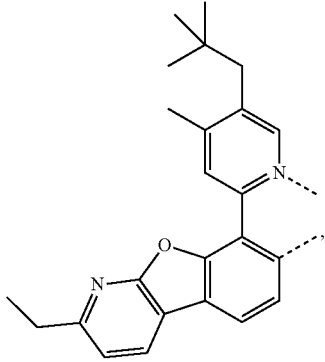

L_A342
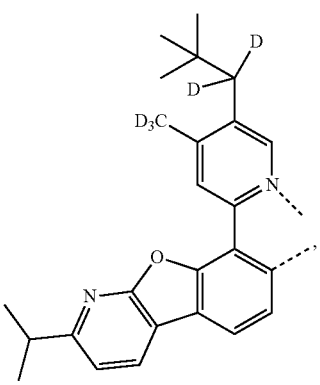
L_A343
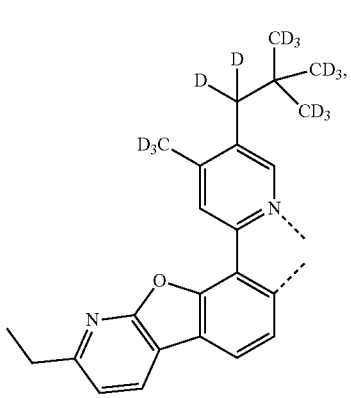
L_A344
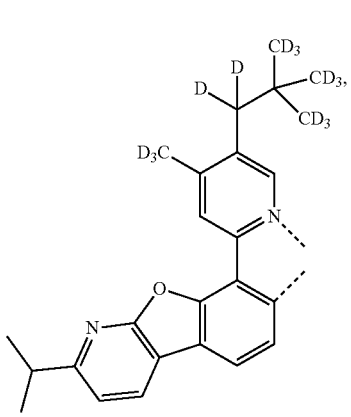
L_A345
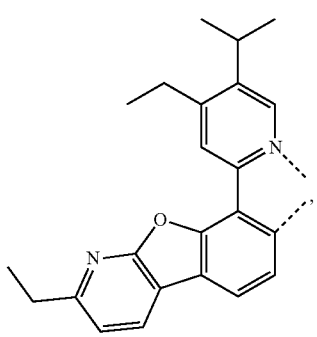
L_A346
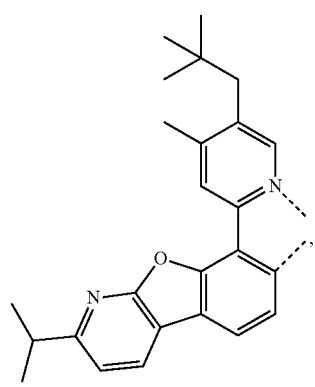
L_A347
L_A348
L_A349

-continued
L_{A350}
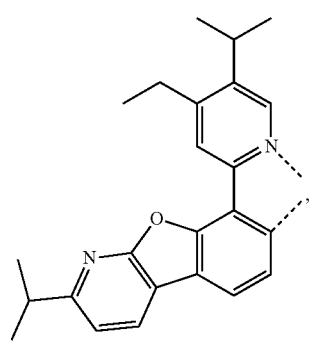
L_{A351}
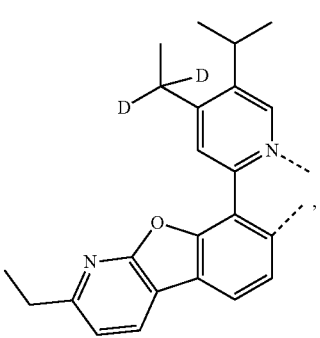
L_{A352}
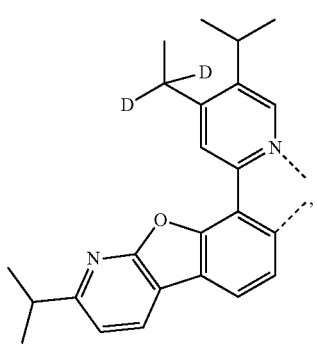
L_{A353}
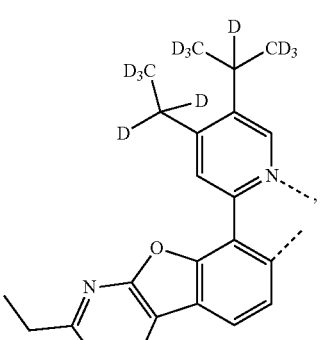
-continued
L_{A354}
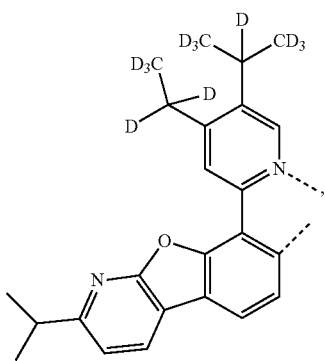
L_{A355}
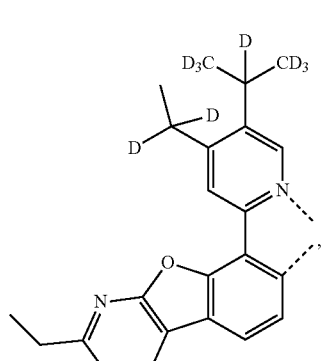
L_{A356}
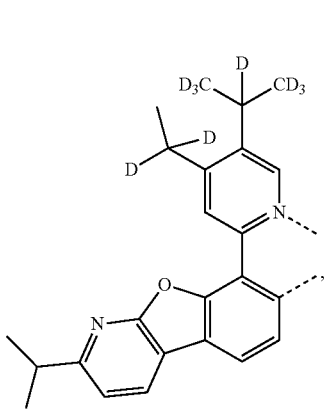
L_{A357}
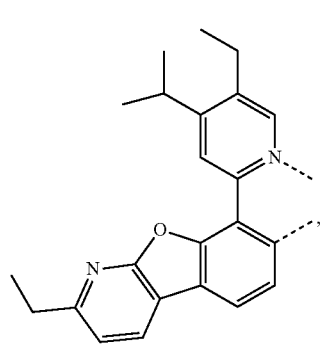

L<sub>A358</sub> 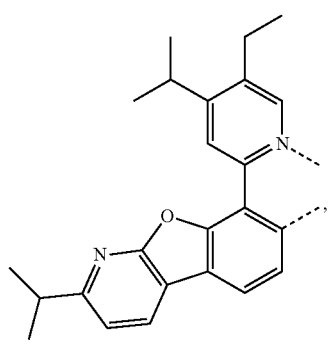
L<sub>A359</sub> 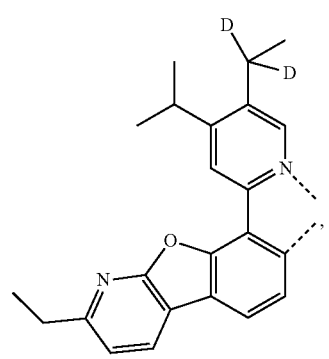
L<sub>A360</sub> 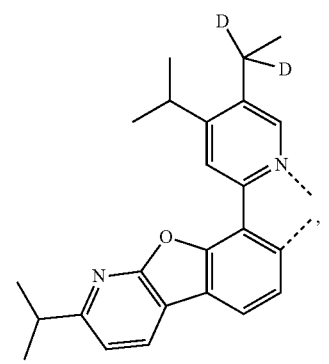
L<sub>A361</sub> 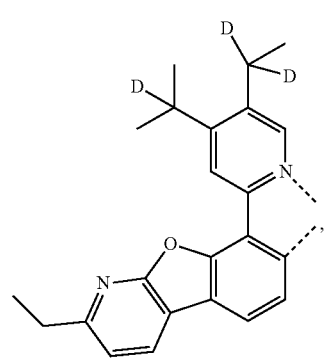
L<sub>A362</sub> 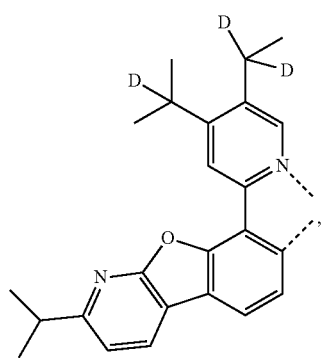
L<sub>A363</sub> 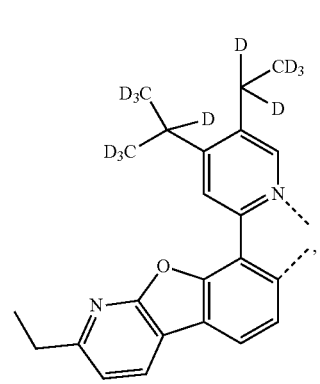
L<sub>A364</sub> 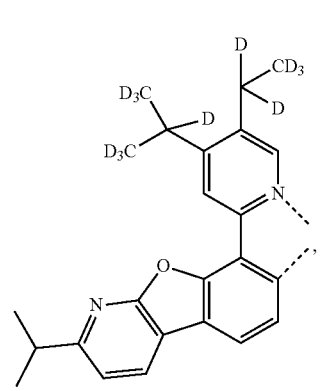
L<sub>A365</sub> 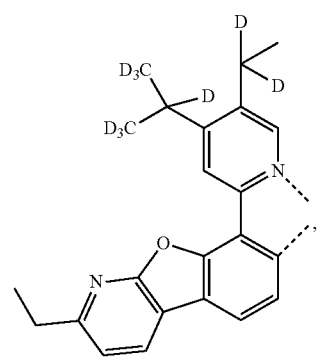

-continued
L_{A366}
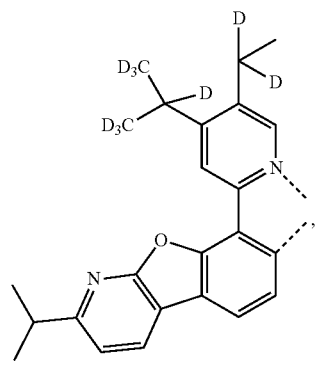
L_{A367}
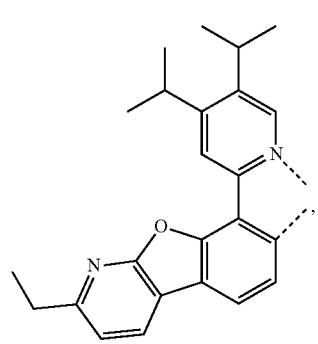
L_{A368}
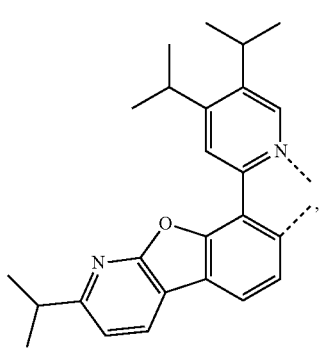
L_{A369}
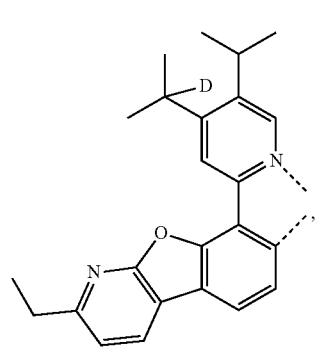
L_{A370}
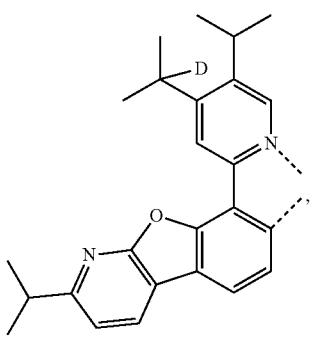
L_{A371}
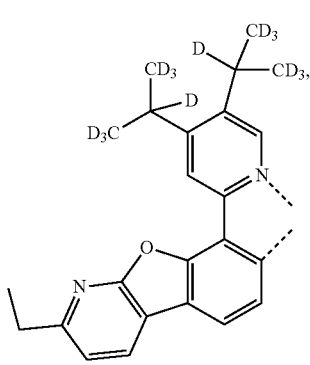
L_{A372}
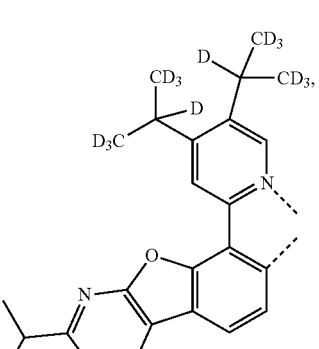
L_{A373}
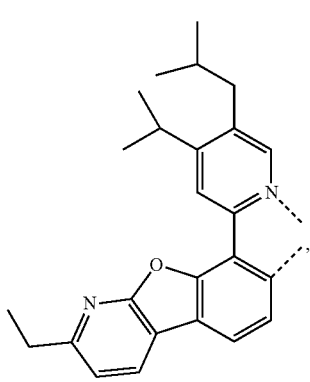

L_{A374}
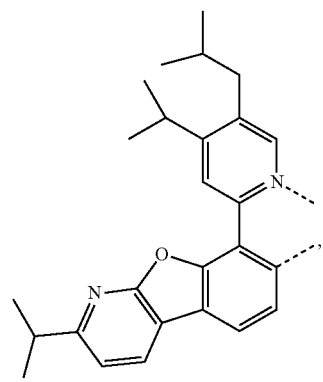
L_{A375}
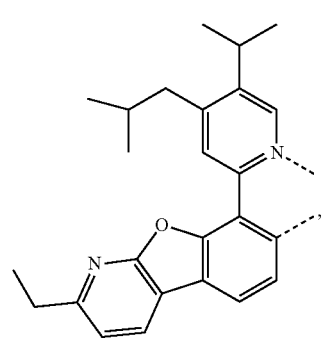
L_{A376}
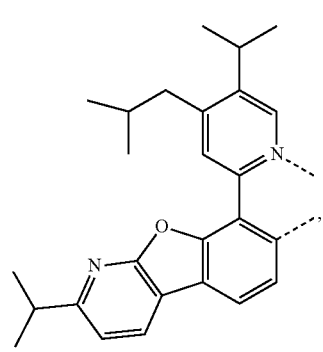
L_{A377}
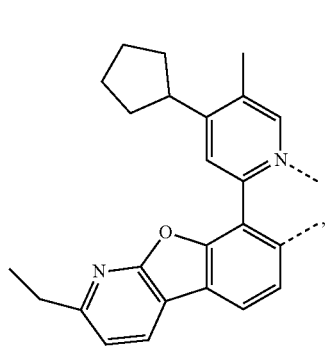
L_{A378}
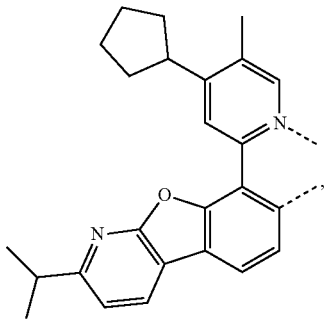
L_{A379}
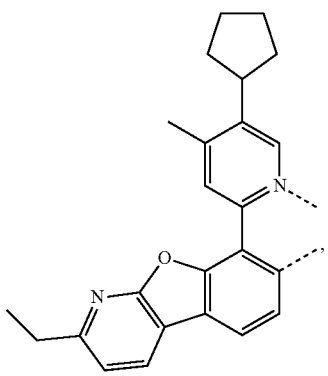
L_{A380}
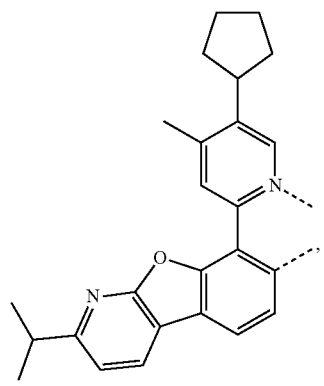
L_{A381}
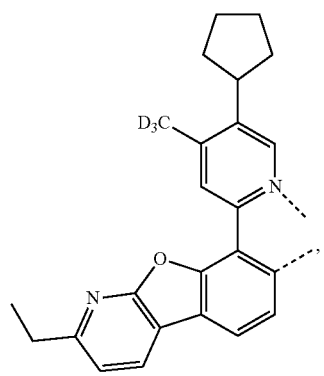

L_{A382}
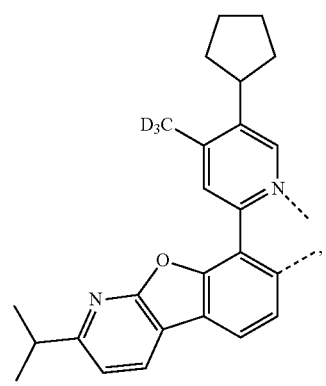
L_{A383}
L_{A384}
L_{A385}
L_{A386}
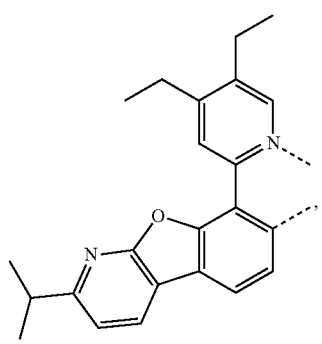
L_{A387}
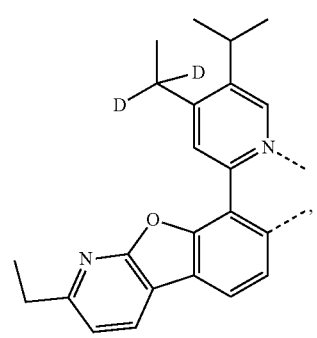
L_{A388}
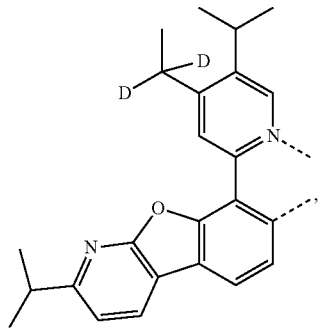
L_{A389}
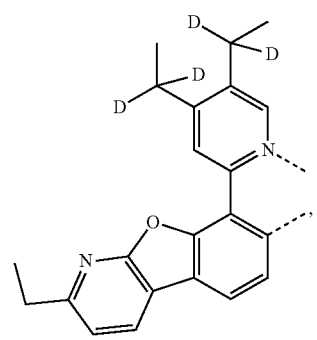

L<sub>A390</sub> 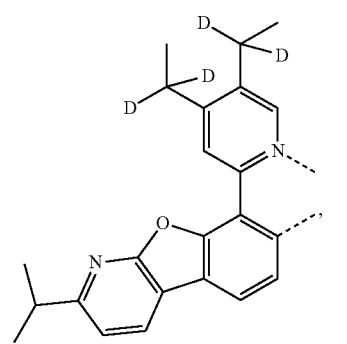
L<sub>A391</sub> 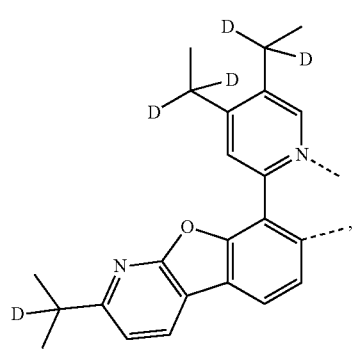
L<sub>A392</sub> 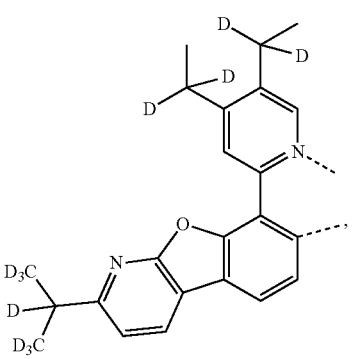
L<sub>A393</sub> 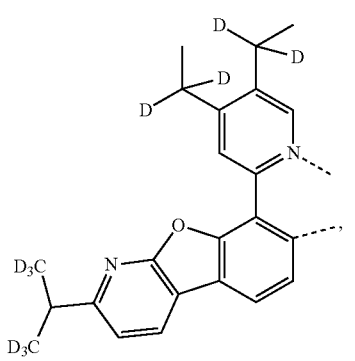
L<sub>A394</sub> 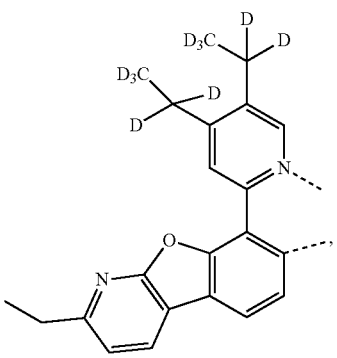
L<sub>A395</sub> 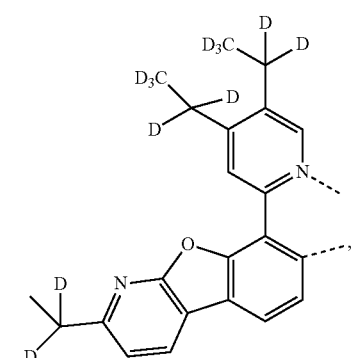
L<sub>A396</sub> 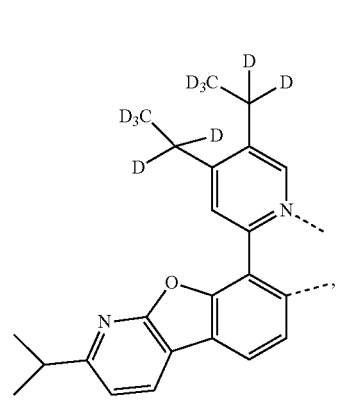
L<sub>A397</sub> 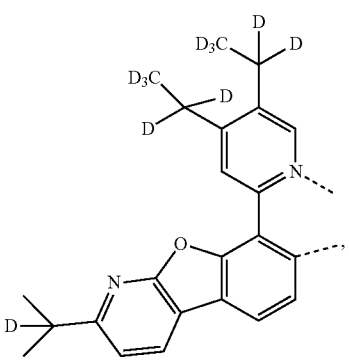

L_{A398}
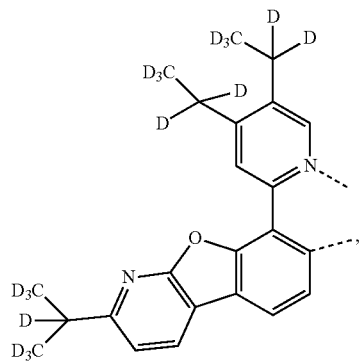
L_{A399}
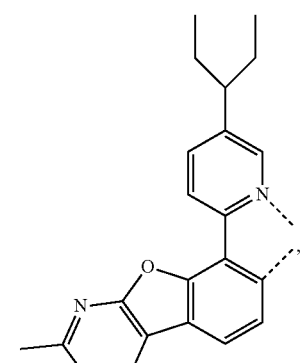
L_{A400}
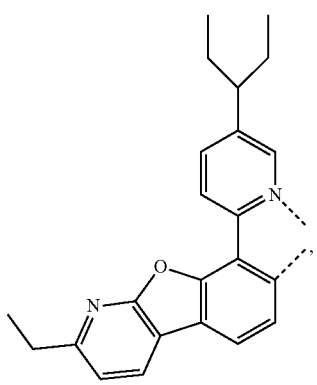
L_{A401}
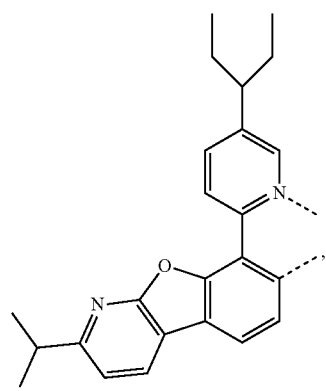
L_{A402}
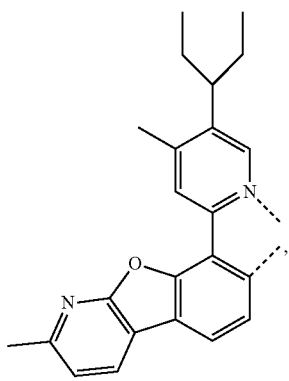
L_{A403}
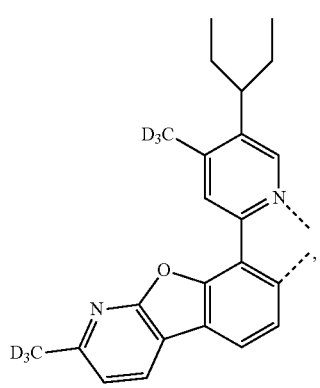
L_{A404}
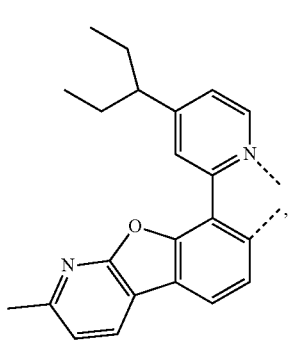
L_{A405}
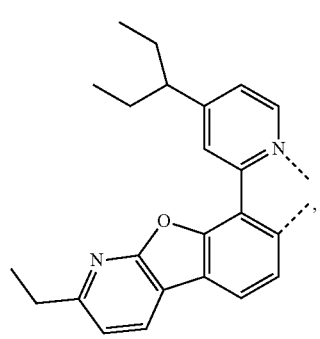

L_{A406}
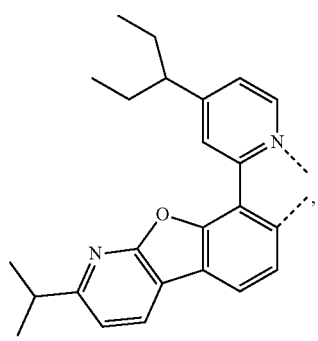
L_{A407}
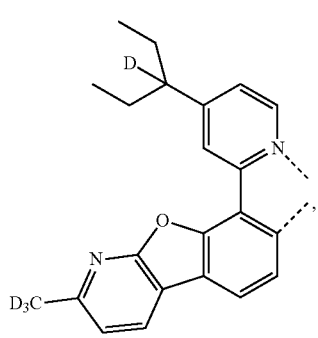
L_{A408}
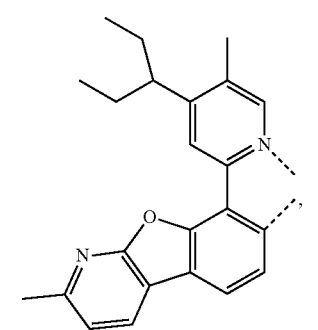
L_{A409}
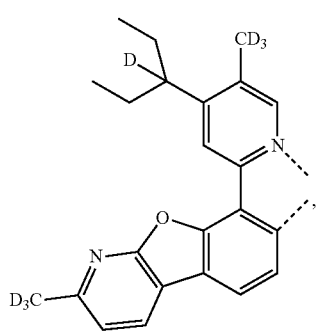
L_{A410}
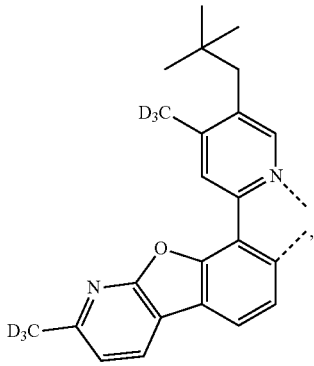
L_{A411}
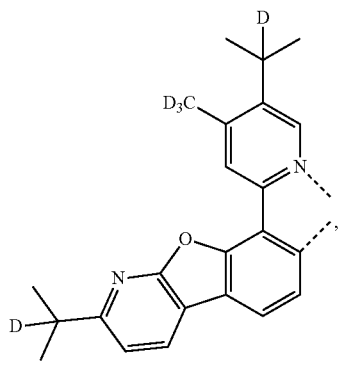
L_{A412}
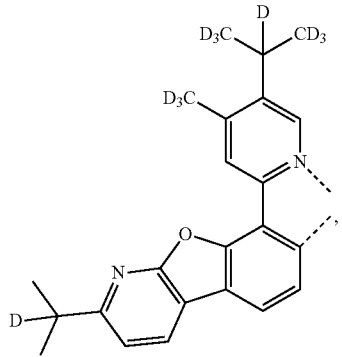
L_{A413}
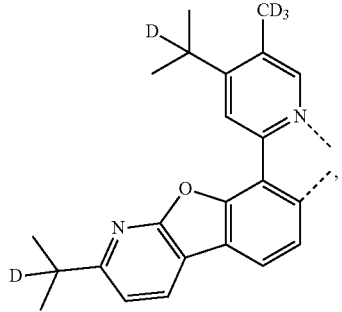

381
-continued
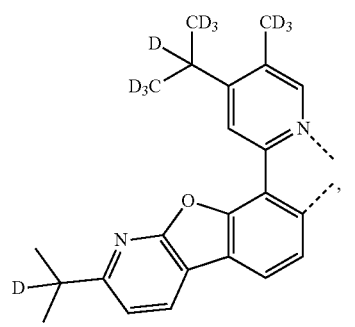
L_{A415}
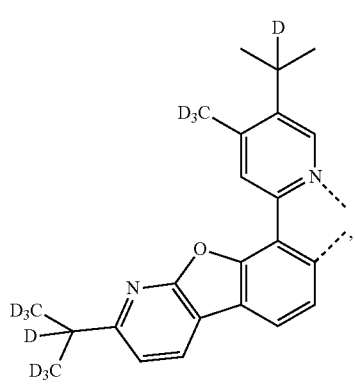
L_{A416}
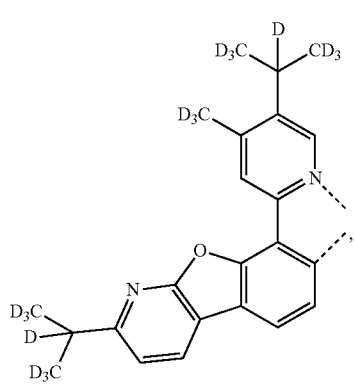
L_{A417}
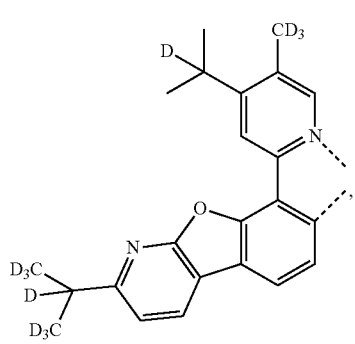
382
-continued
L_{A414}
L_{A418}
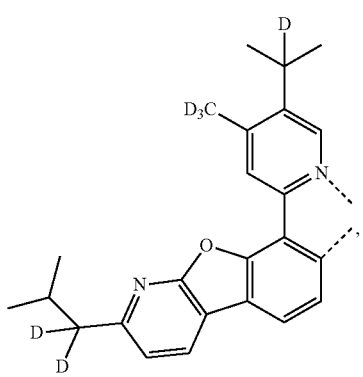
L_{A419}
L_{A420}
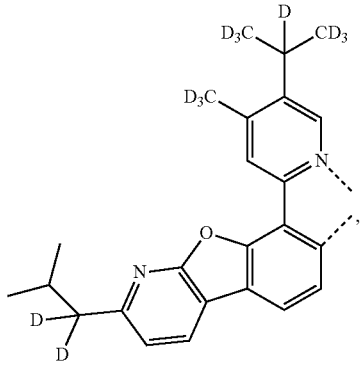
L_{A421}
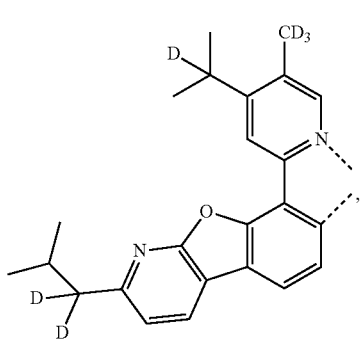

-continued
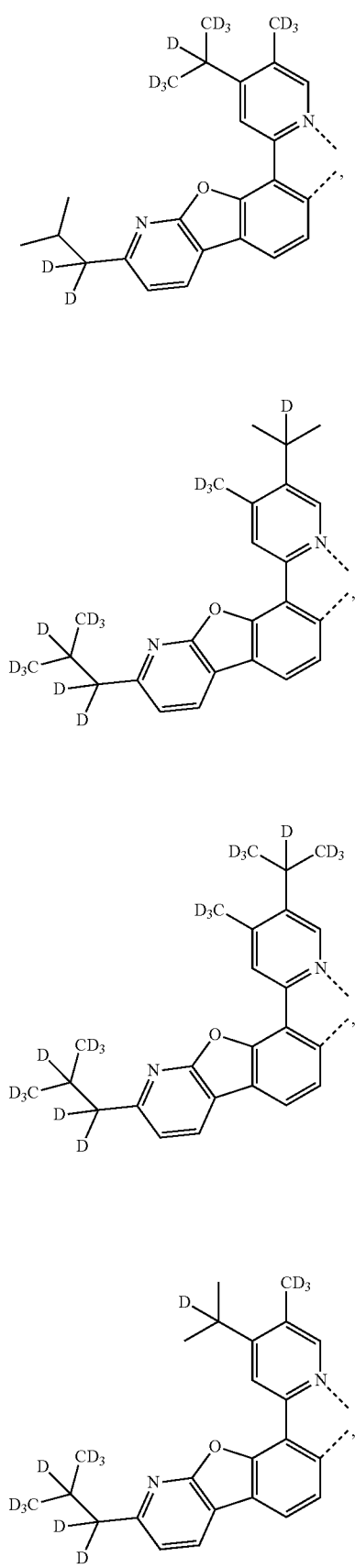
L_{A422}
L_{A423}
L_{A424}
L_{A425}
-continued
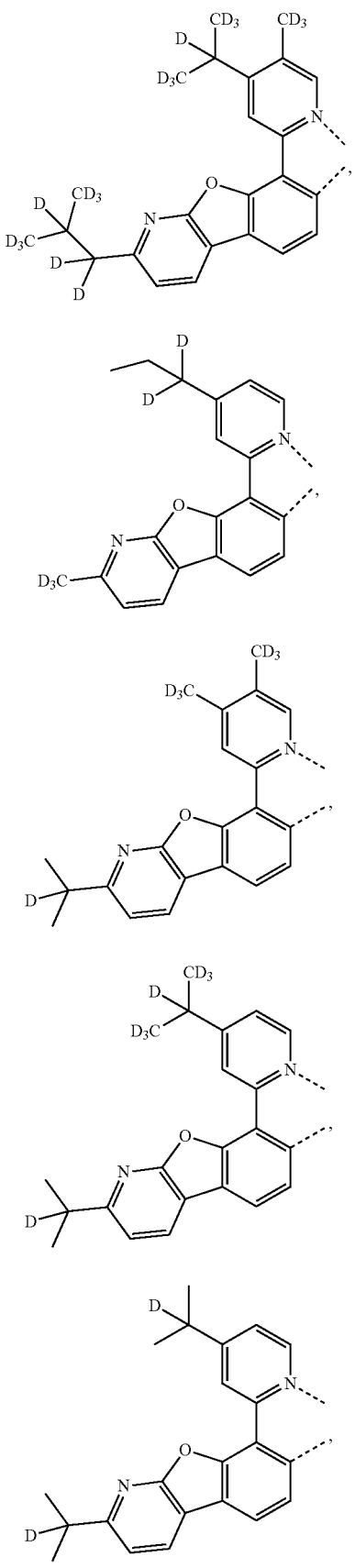
L_{A426}
L_{A427}
L_{A428}
L_{A430}
L_{A431}

L<sub>A434</sub>
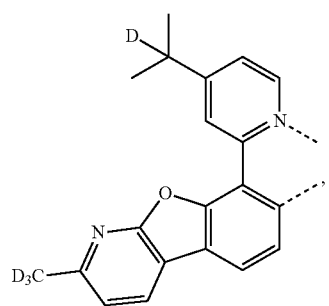
L<sub>A436</sub>
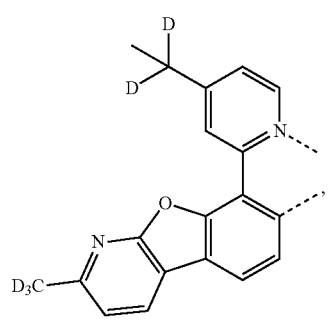
L<sub>A437</sub>
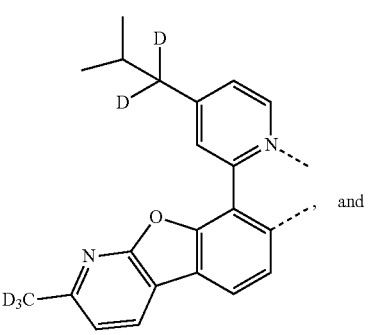, and
L<sub>A440</sub>
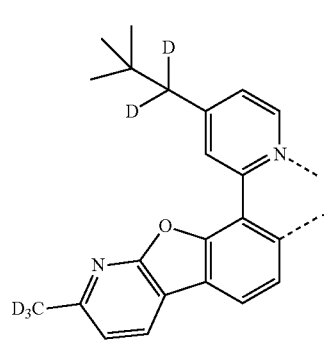
8. the compound of claim 1, wherein L<sub>B</sub> is selected from the group consisting of:
L<sub>B1</sub>
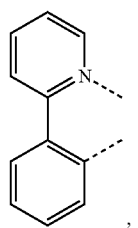,
L<sub>B2</sub>
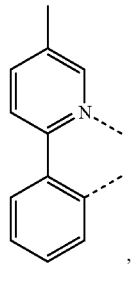,
L<sub>B3</sub>
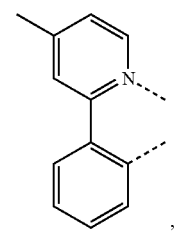,
L<sub>B5</sub>
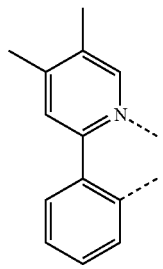,
L<sub>B9</sub>
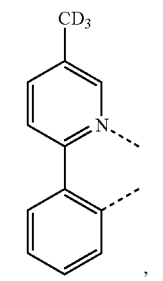,
L<sub>B10</sub>
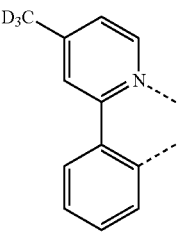,

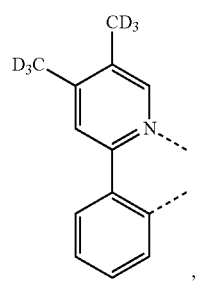 $L_{B12}$
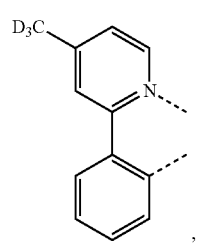 $L_{B10}$
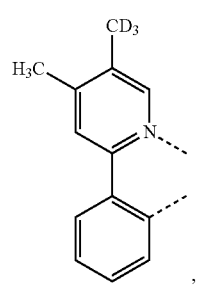 $L_{B16}$
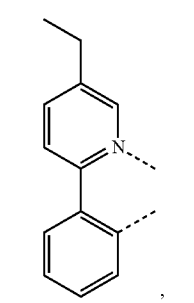 $L_{B17}$
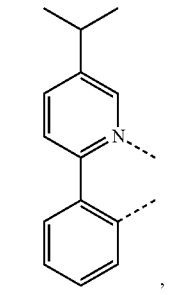 $L_{B18}$
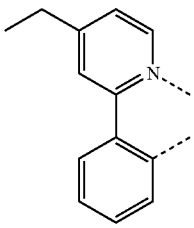 $L_{B19}$
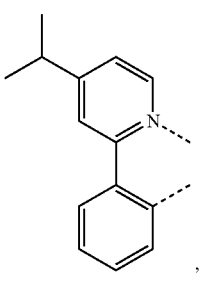 $L_{B20}$
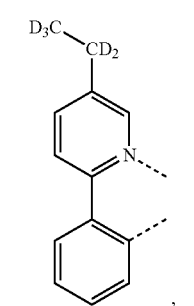 $L_{B23}$
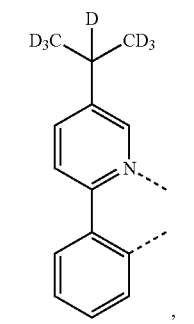 $L_{B24}$
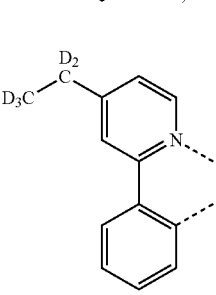 $L_{B25}$

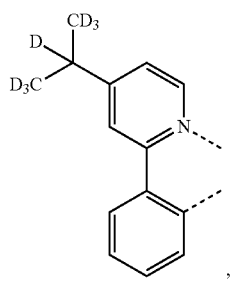 L_{B26}
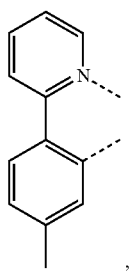 L_{B30}
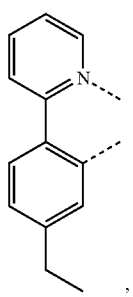 L_{B31}
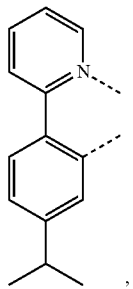 L_{B32}
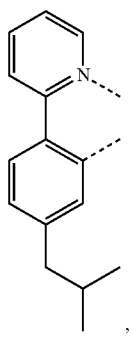 L_{B33}
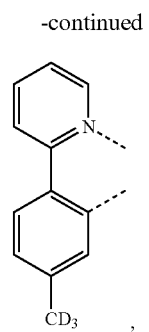 L_{B34}
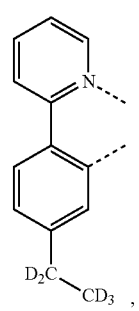 L_{B35}
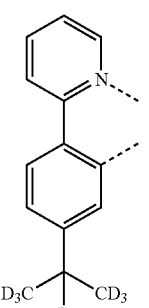 L_{B36}
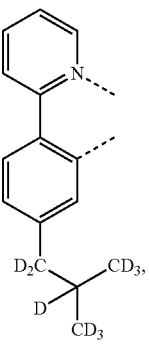 L_{B37}
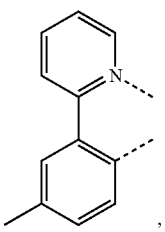 L_{B38}

391
-continued
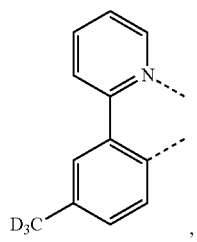
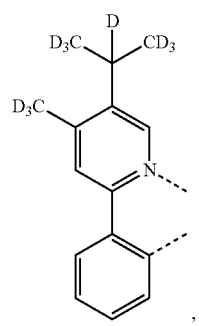
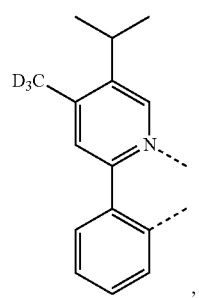
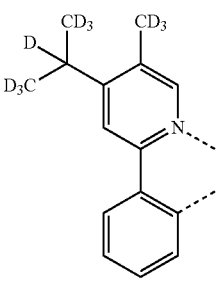
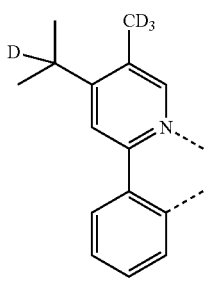
392
-continued
L_{B39}
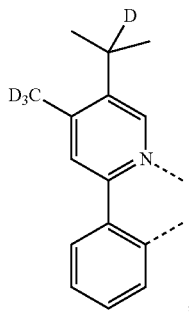 L_{B44}
L_{B40}
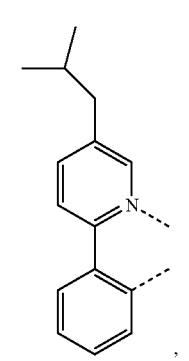 L_{B45}
L_{B41}
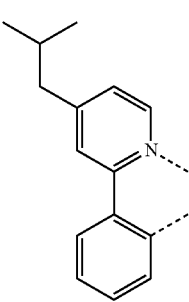 L_{B46}
L_{B42}
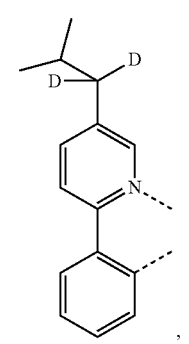 L_{B47}
L_{B43}
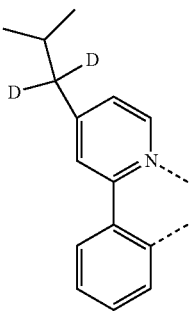 L_{B48}

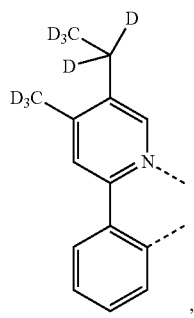 $L_{B49}$
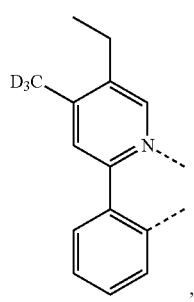 $L_{B50}$
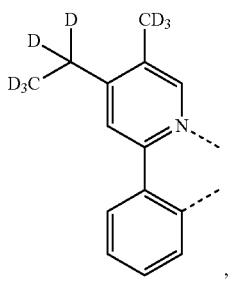 $L_{B51}$
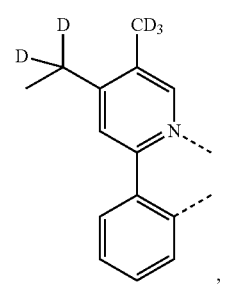 $L_{B52}$
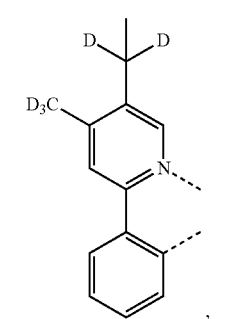 $L_{B53}$
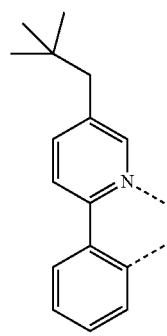 $L_{B54}$
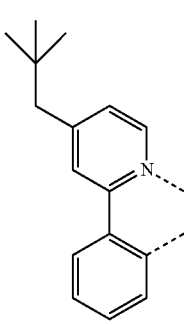 $L_{B55}$
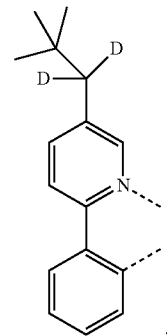 $L_{B56}$
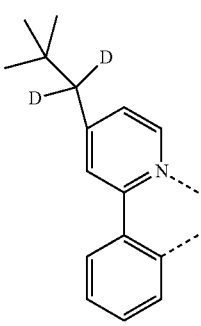 $L_{B57}$
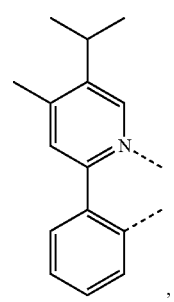 $L_{B58}$

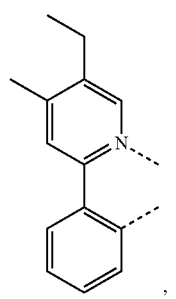, L_{B59}
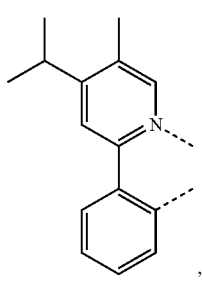, L_{B60}
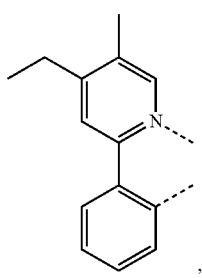, L_{B61}
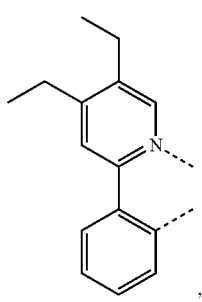, L_{B62}
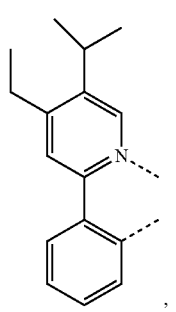, L_{B63}
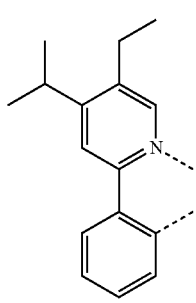, L_{B64}
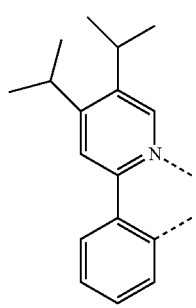, L_{B65}
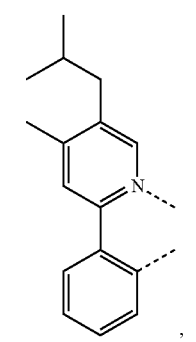, L_{B66}
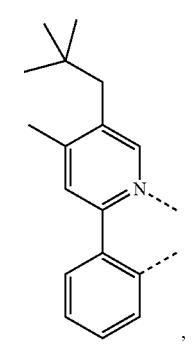, L_{B67}
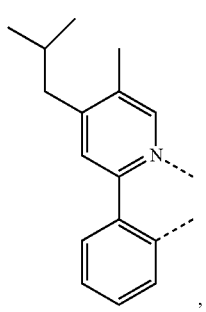, L_{B68}

397
-continued
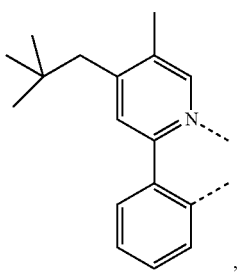
$L_{B69}$
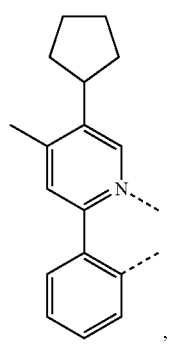
$L_{B70}$
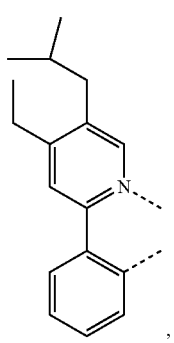
$L_{B71}$
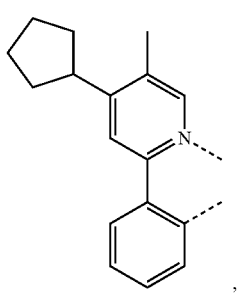
$L_{B72}$
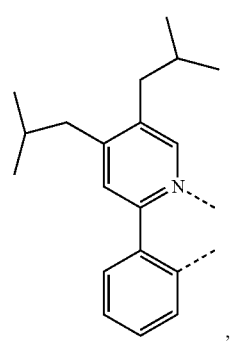
$L_{B73}$
398
-continued
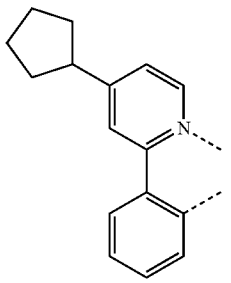
$L_{B74}$
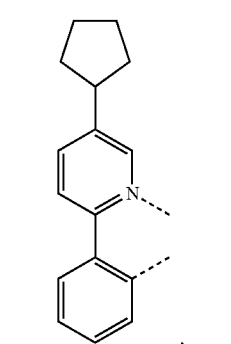
$L_{B75}$
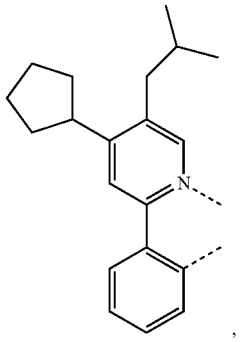
$L_{B76}$
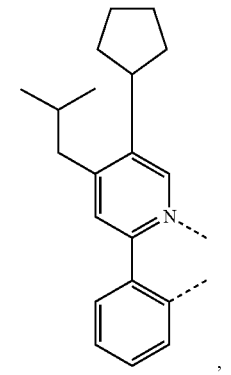
$L_{B77}$

| | | |
|---|---|---|
| L_{B78} | 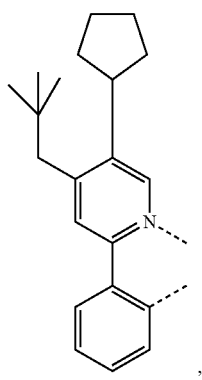 | 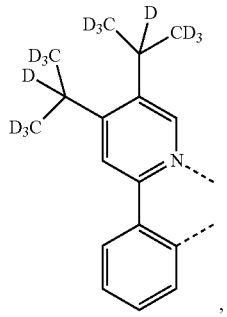 | L_{B88}
| L_{B79} | 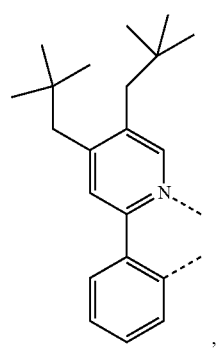 | 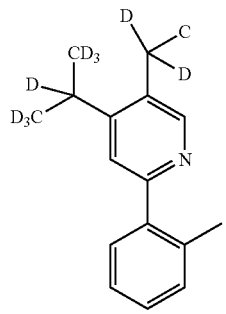 | L_{B89}
| L_{B80} | 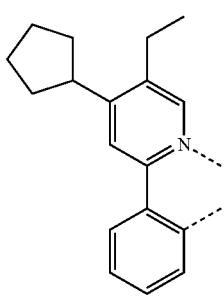 | 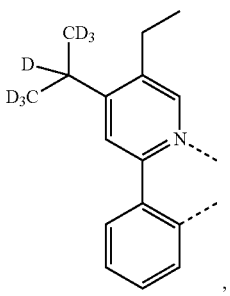 | L_{B90}
| L_{B81} | 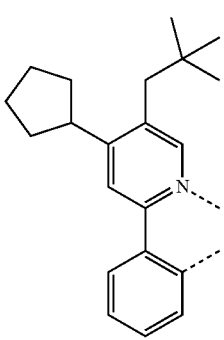 | 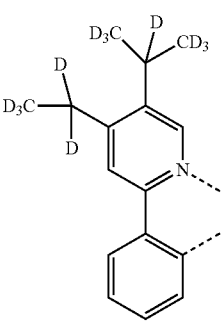 | L_{B91}
| | | 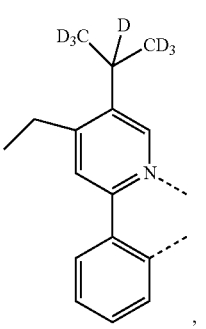 | L_{B92}

-continued
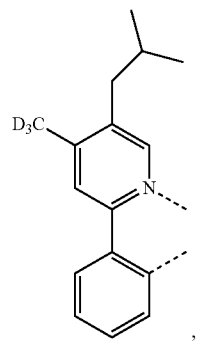 L_{B94}
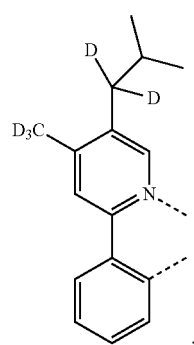 L_{B95}
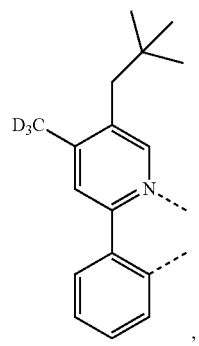 L_{B96}
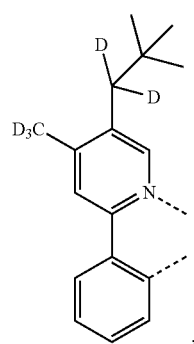 L_{B97}
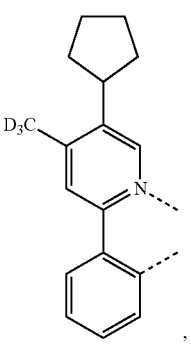 L_{B98}
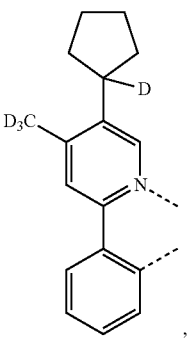 L_{B99}
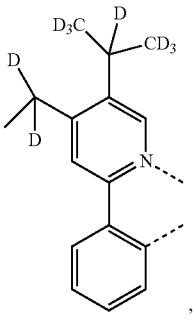 L_{B100}
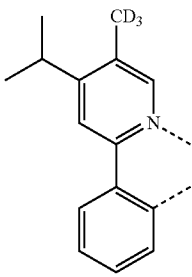 L_{B101}
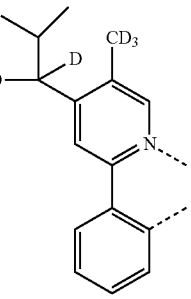 L_{B102}

403 -continued

L_{B103}

L_{B104}

L_{B105}

L_{B106}

L_{B107}

404 -continued

L_{B108}

L_{B109}

L_{B110}

L_{B111}

L_{B112}

L_{B114}
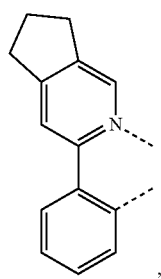
L_{B116}
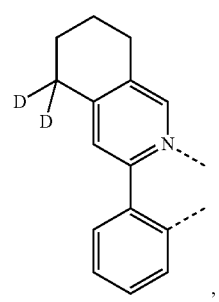
L_{B118}
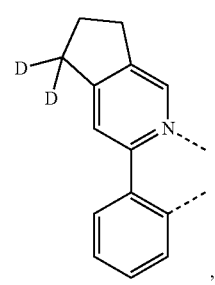
L_{B120}
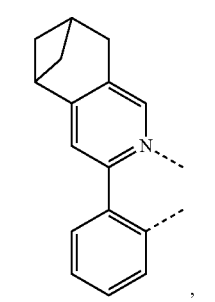
L_{B121}
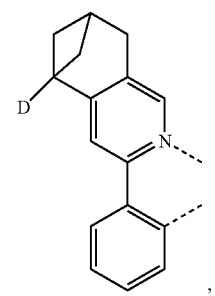
L_{B122}
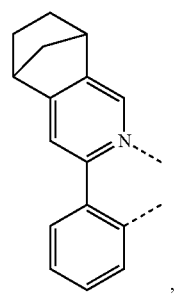
L_{B123}
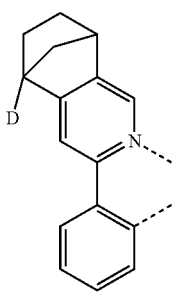
L_{B124}
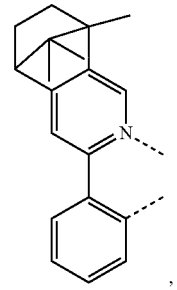
L_{B125}
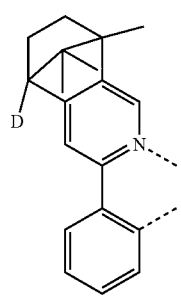
L_{B126}
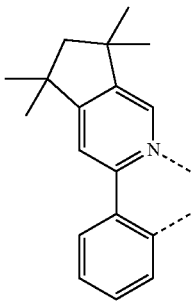

| | | | |
|---|---|---|---|
| L$_{B132}$ | 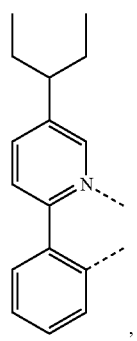 | L$_{B135}$ | 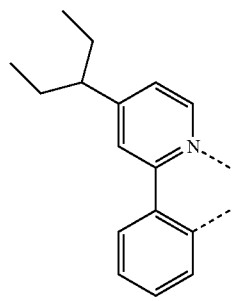 |
| L$_{B132}$ | 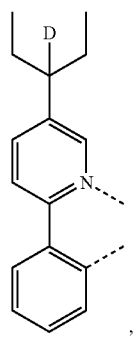 | L$_{B136}$ | 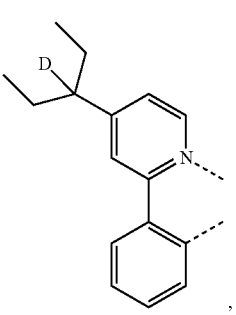 |
| L$_{B133}$ | 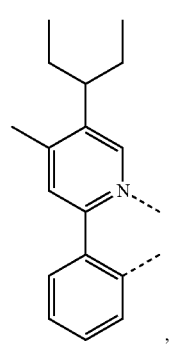 | L$_{B137}$ | 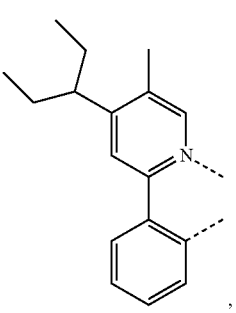 |
| L$_{B134}$ | 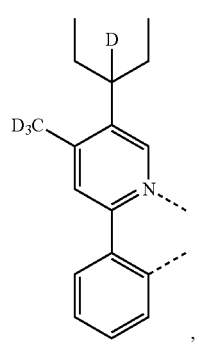 | L$_{B138}$ | 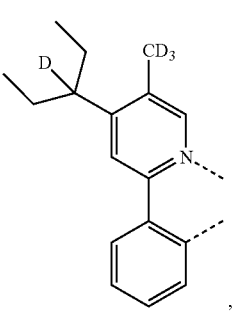 |
| | | L$_{B139}$ | 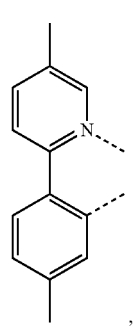 |

-continued
L<sub>B140</sub>
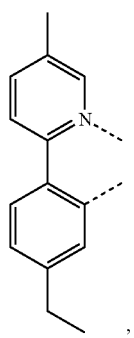
L<sub>B141</sub>
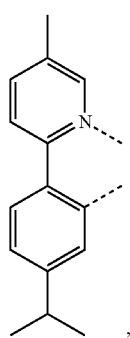
L<sub>B142</sub>
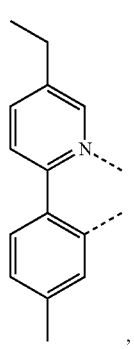
L<sub>B143</sub>
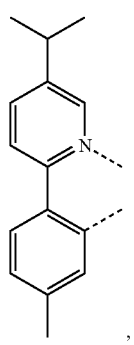
-continued
L<sub>B144</sub>
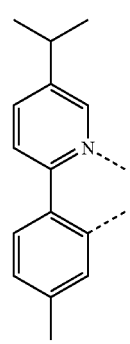
L<sub>B145</sub>
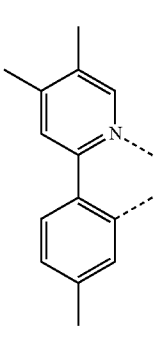
L<sub>B146</sub>
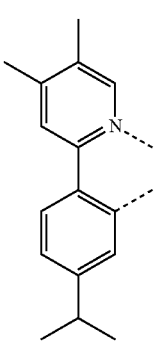
L<sub>B147</sub>
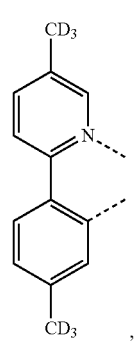

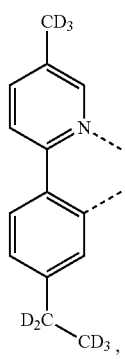 L_{B148}
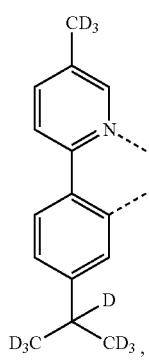 L_{B149}
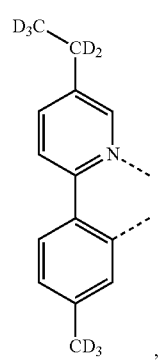 L_{B150}
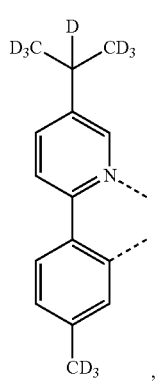 L_{B151}
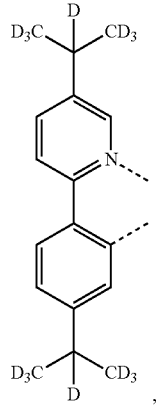 L_{B152}
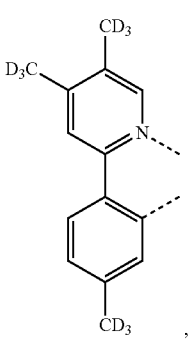 L_{B153}
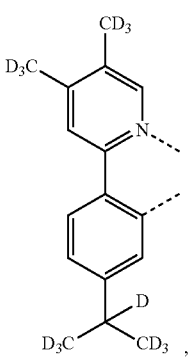 L_{B154}
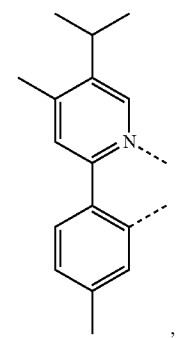 L_{B155}

$L_{B156}$
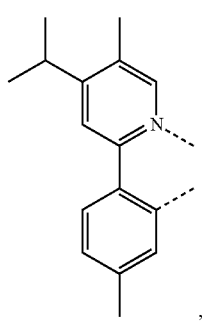
$L_{B157}$
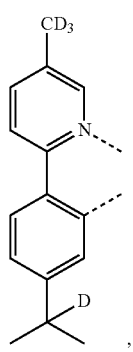
$L_{B158}$
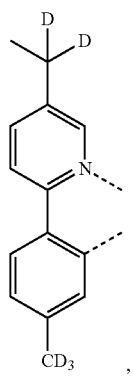
$L_{B159}$
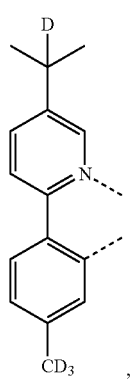
$L_{B160}$
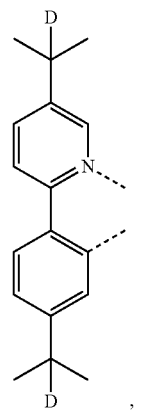
$L_{B161}$
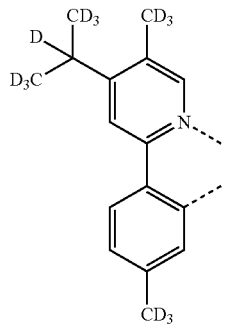
, and
$L_{B162}$
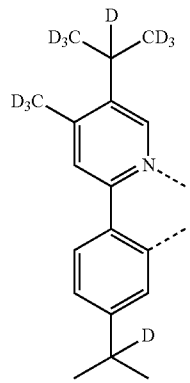
.
9. The compound of claim 1, wherein the compound is selected from the group consisting of:
Compound 3
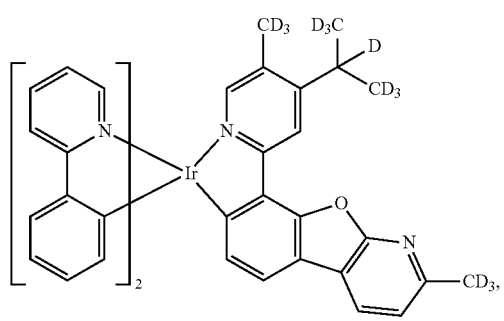

Compound 5
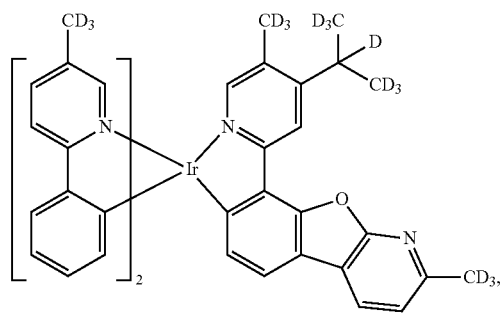
Compound 6
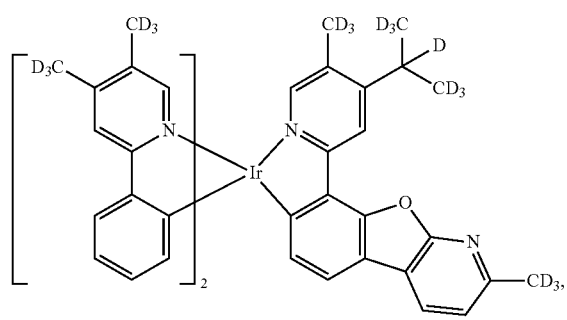
Compound 9
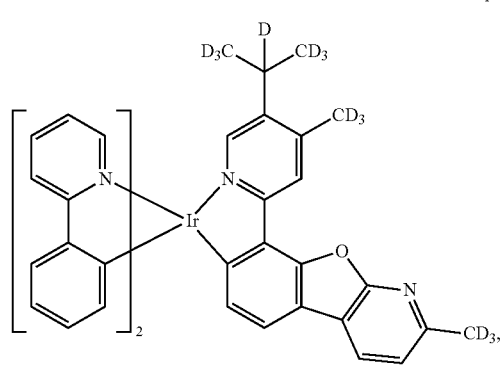
Compound 10
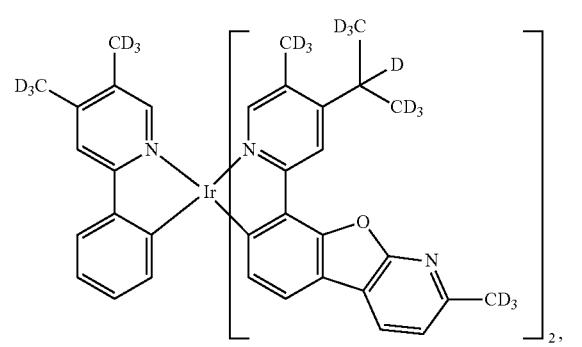
Compound 11
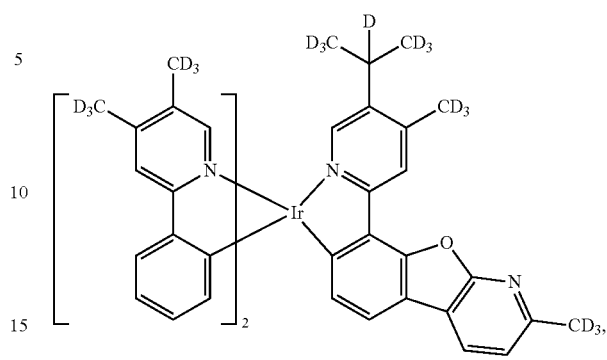
Compound 12
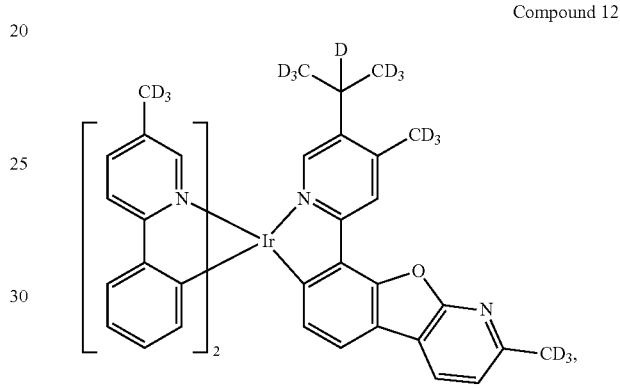
Compound 13
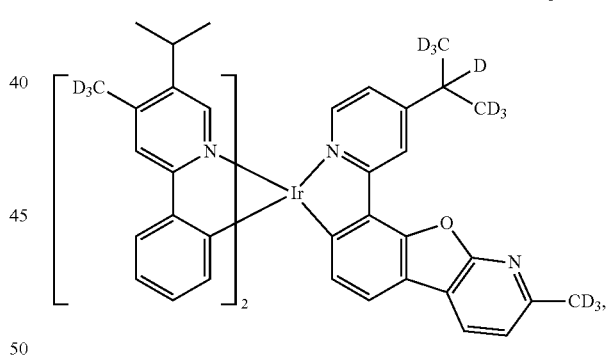
Compound 14
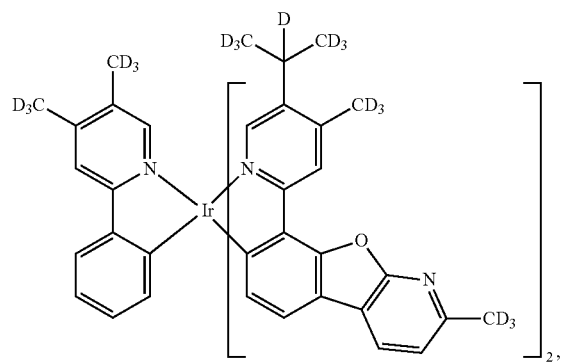

Compound 16
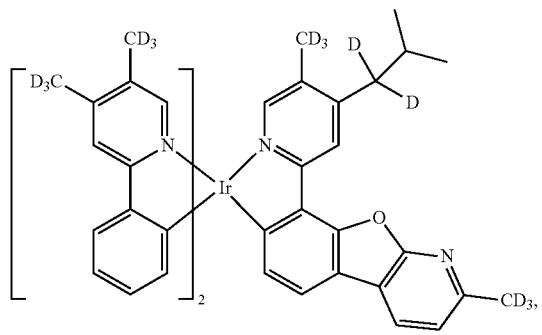
Compound 20
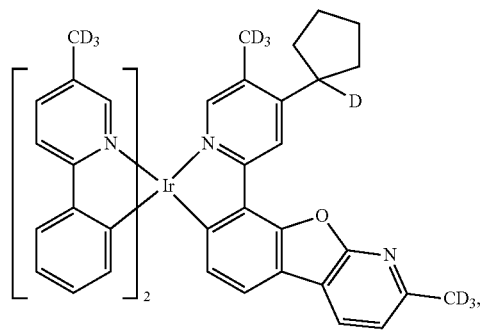
Compound 17
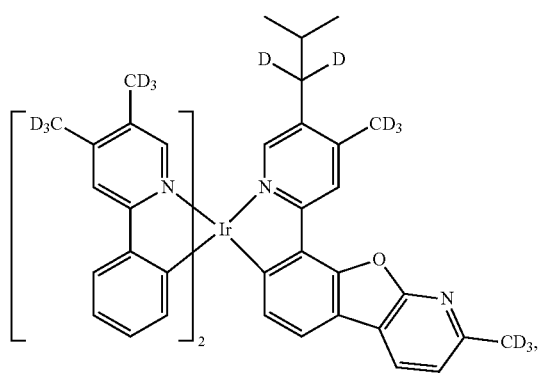
Compound 21
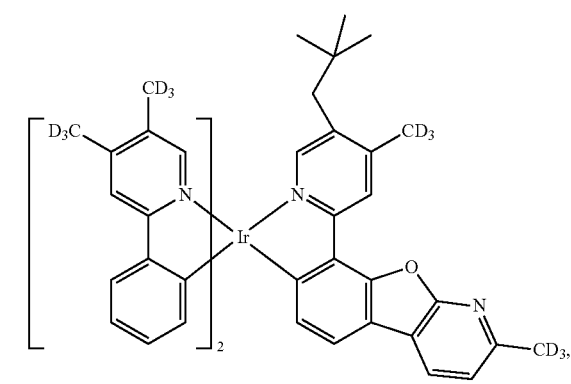
Compound 18
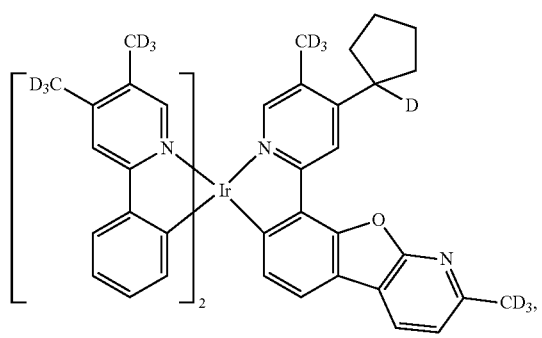
Compound 22
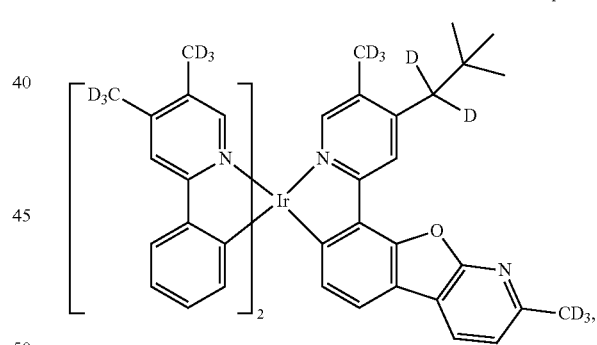
Compound 19
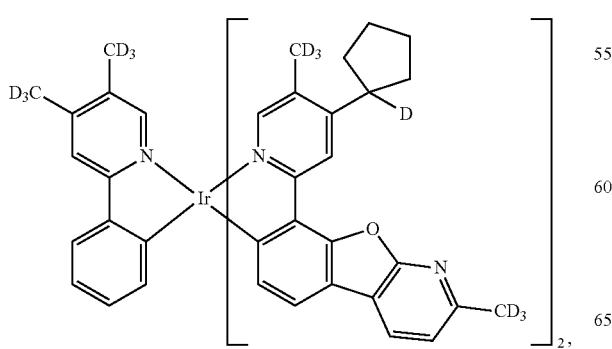
Compound 23
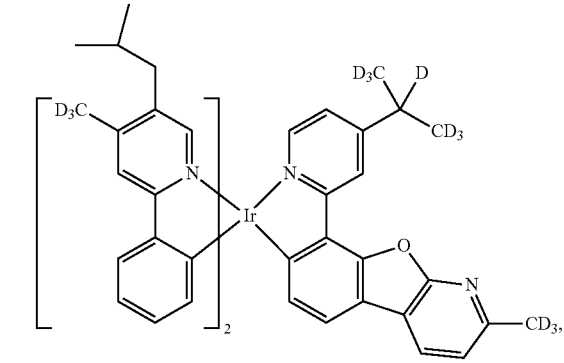

-continued
Compound 24
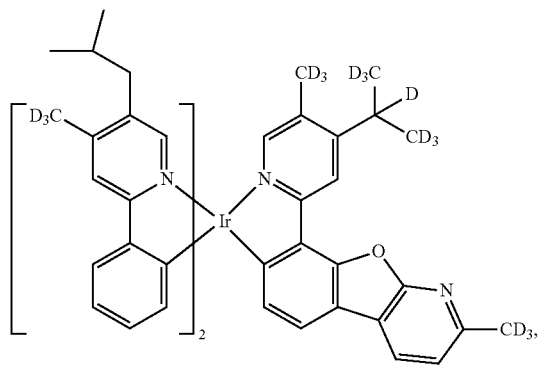
Compound 25
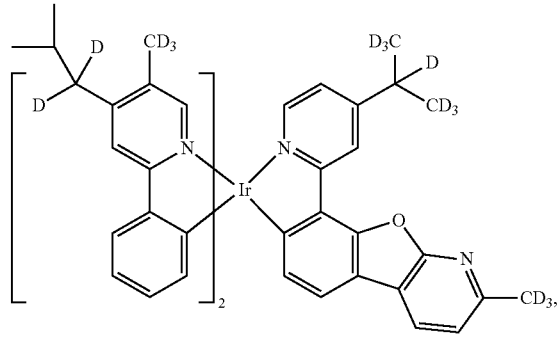
Compound 26
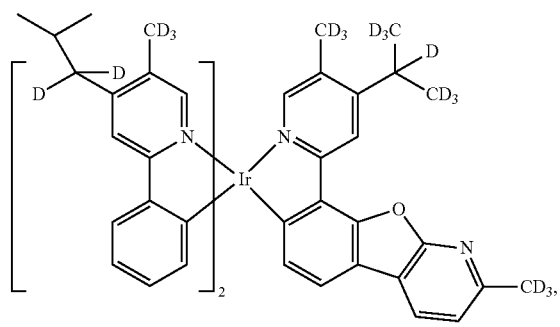
Compound 27
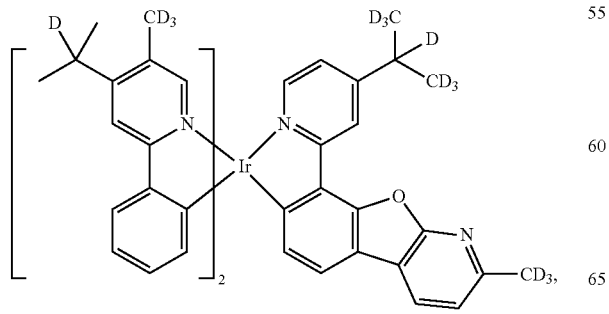
-continued
Compound 28
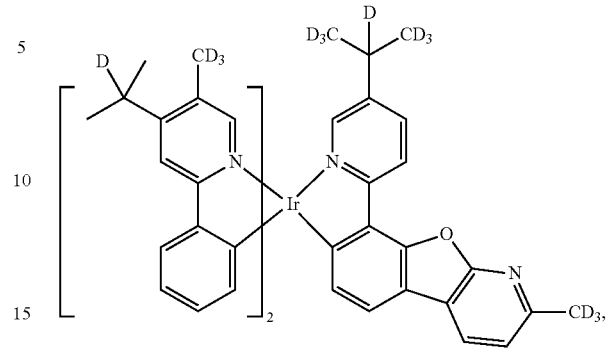
Compound 29
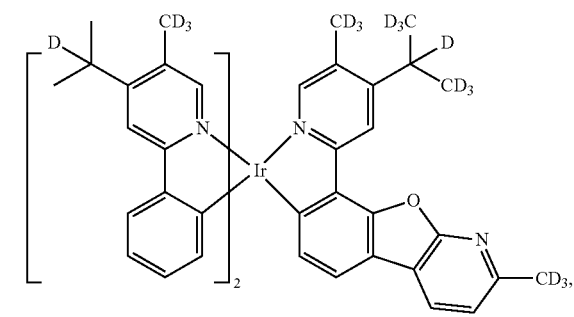
Compound 30
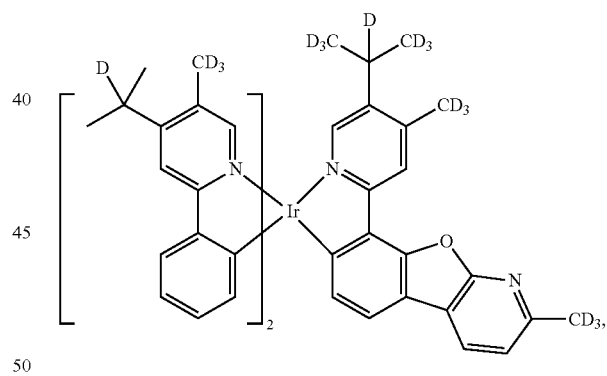
Compound 31
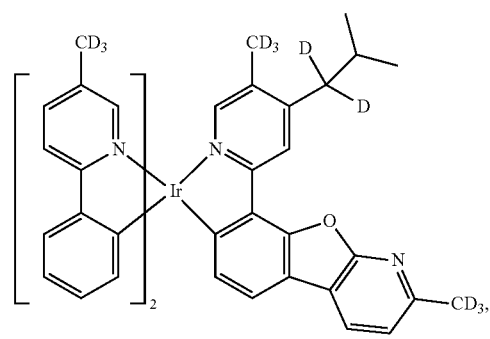

-continued
Compound 32
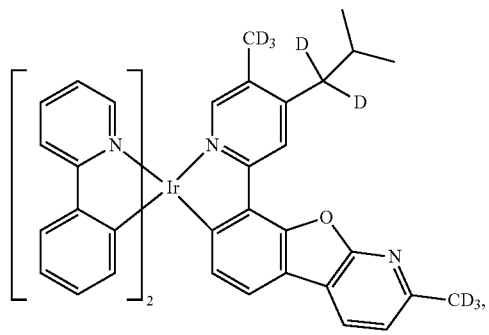
Compound 33
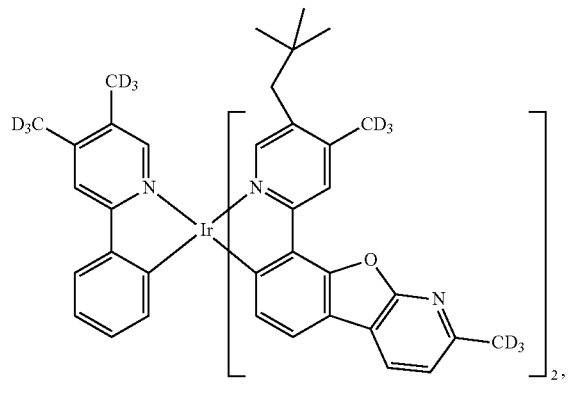
Compound 34
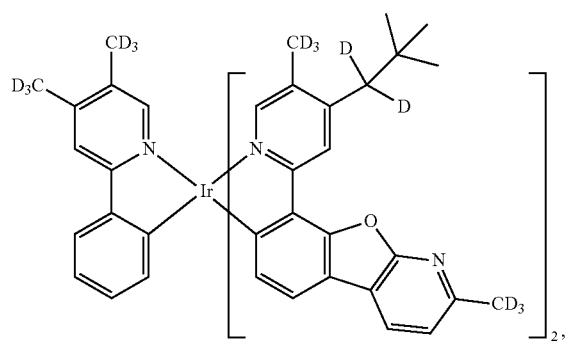
Compound 35
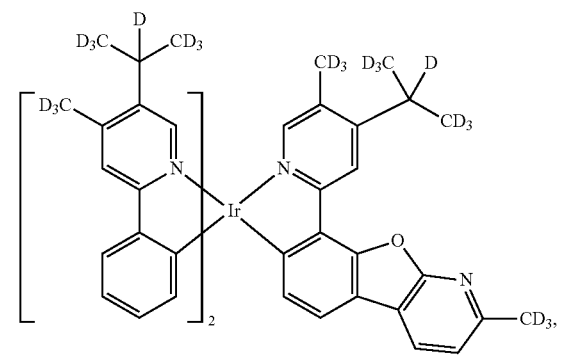
-continued
Compound 36
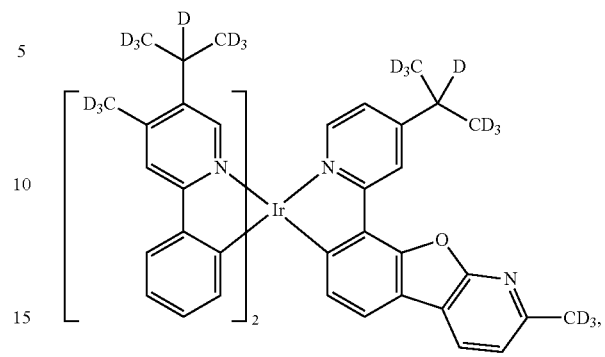
Compound 37
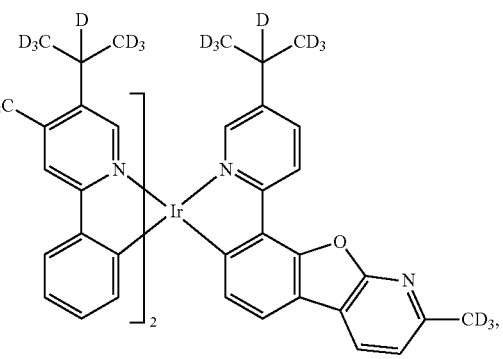
Compound 38
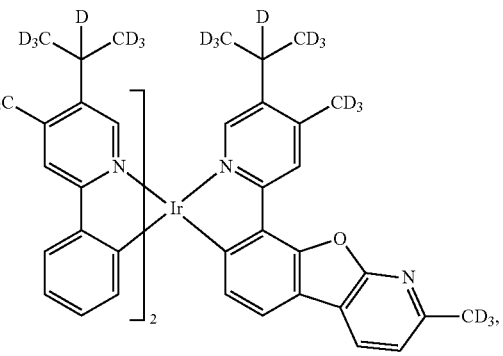
Compound 39
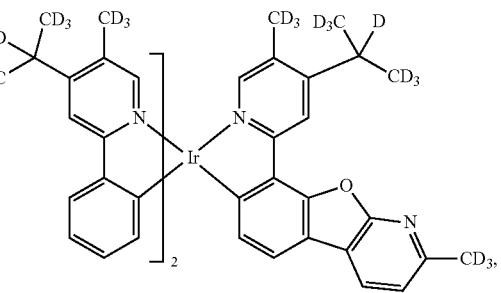

Compound 40
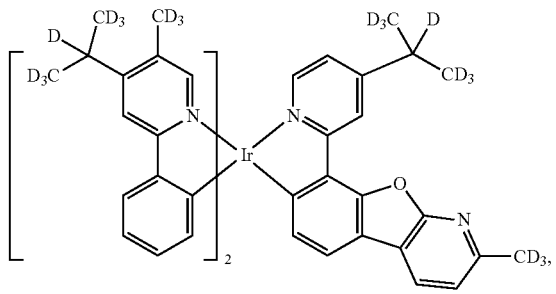
Compound 46
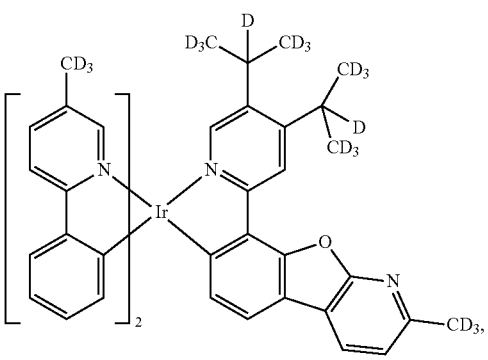
Compound 41
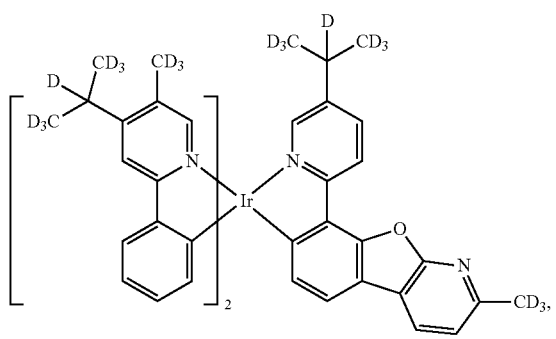
Compound 48
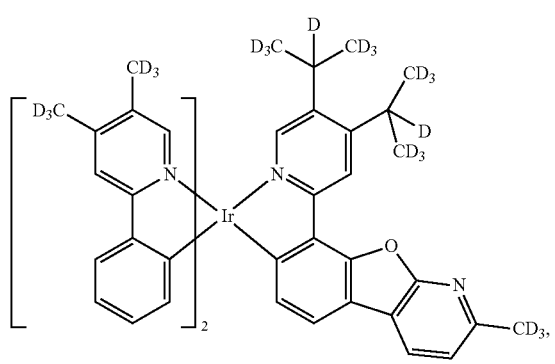
Compound 42
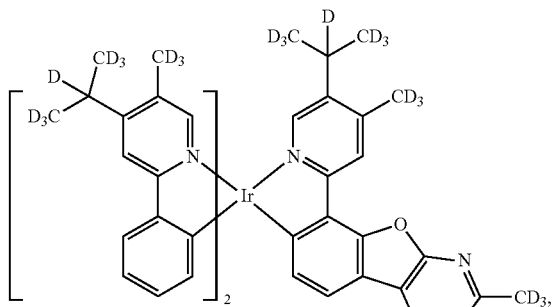
Compound 50
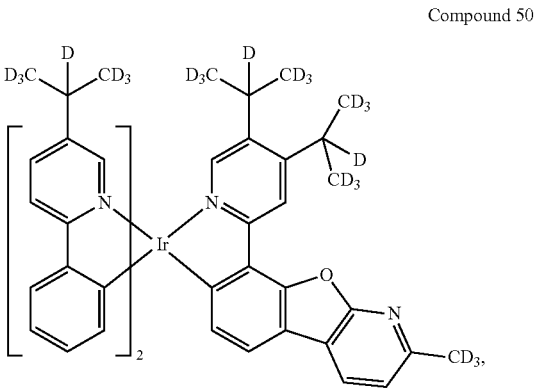
Compound 44
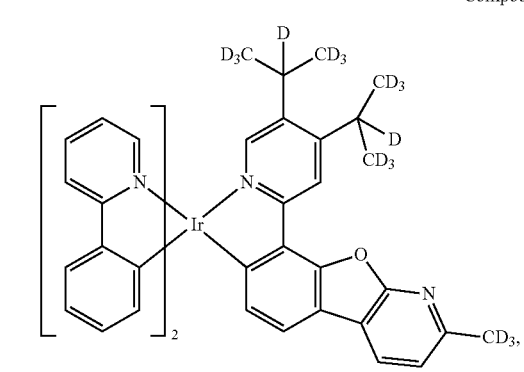
Compound 51
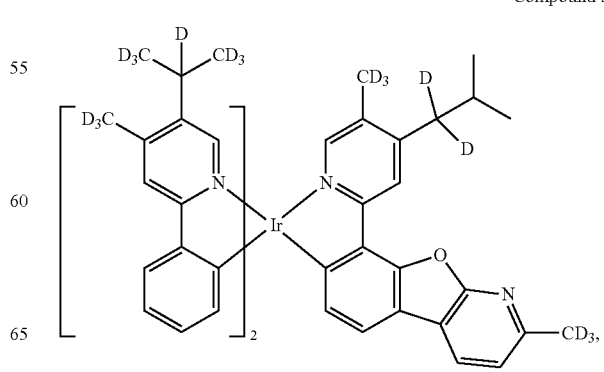

Compound 52
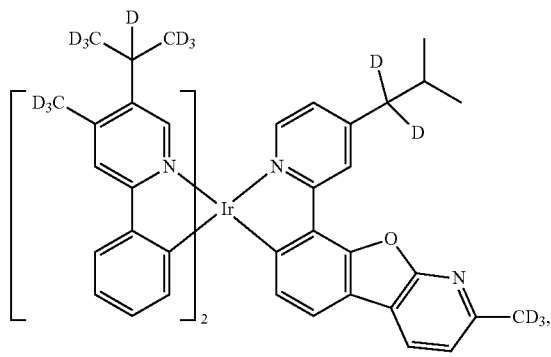
Compound 56
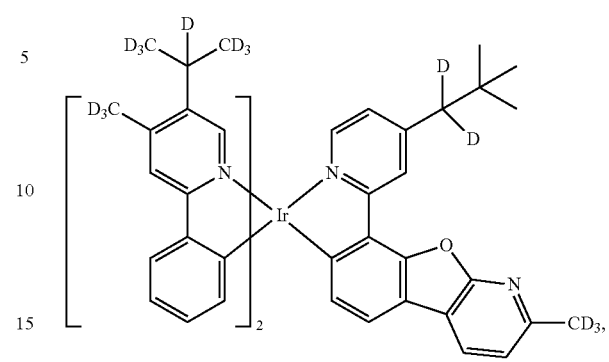
Compound 53
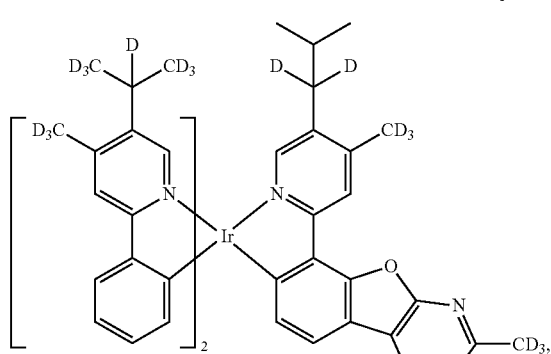
Compound 57
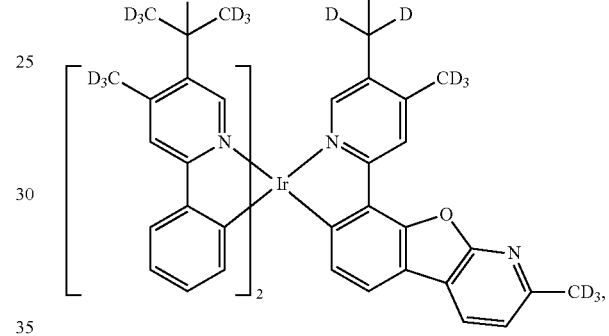
Compound 54
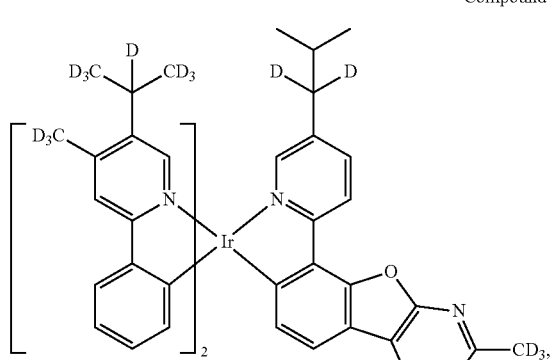
Compound 58
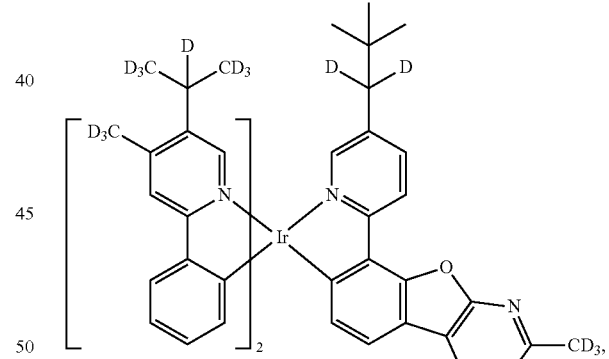
Compound 55
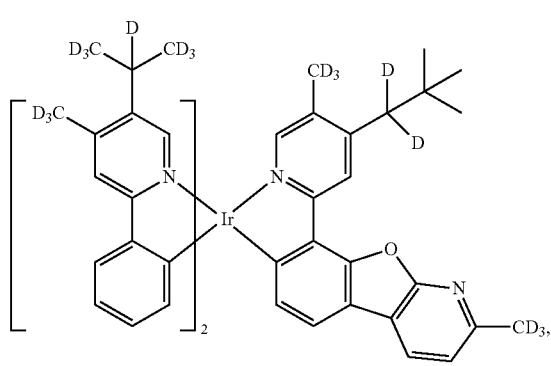
Compound 59
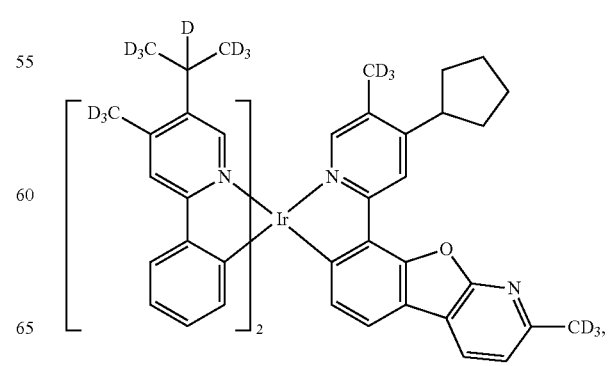

Compound 60
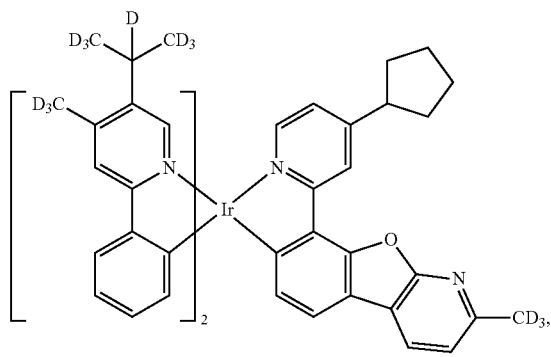
Compound 64
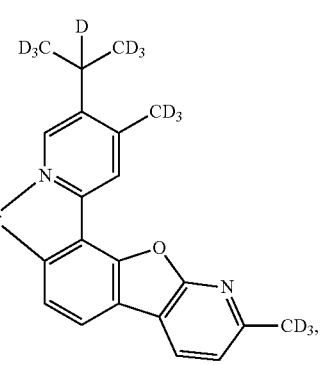
Compound 61
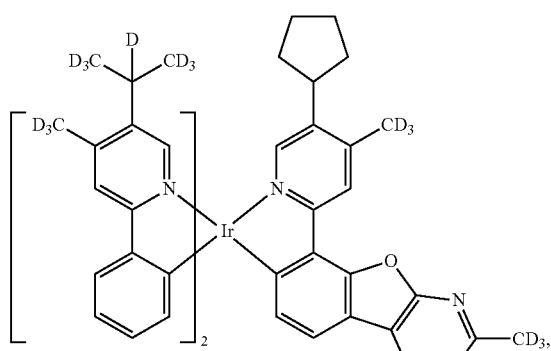
Compound 65
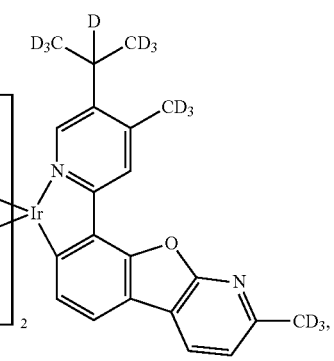
Compound 62
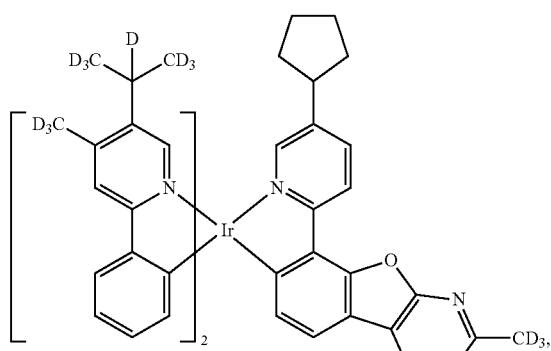
Compound 66
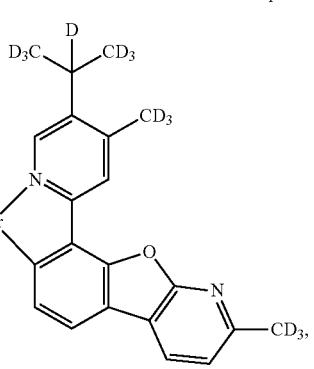
Compound 63
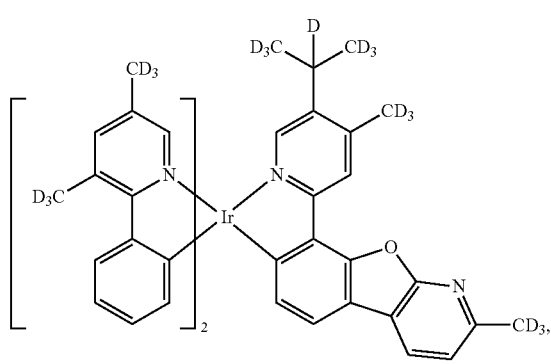
Compound 67
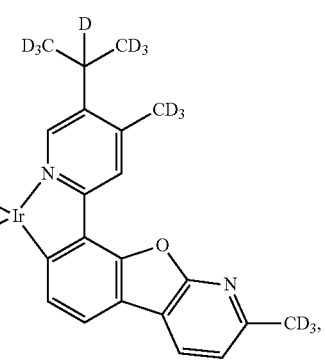

Compound 68
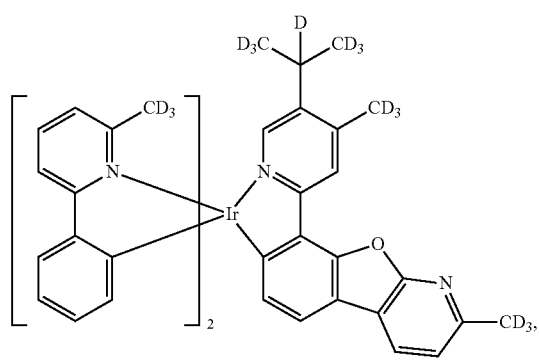
Compound 72
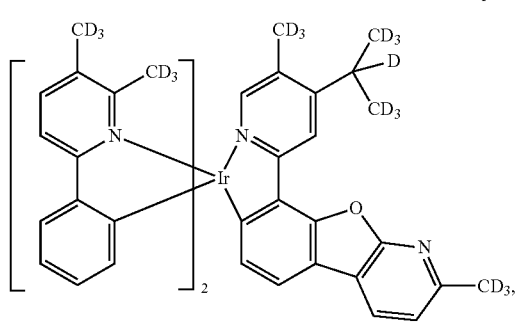
Compound 69
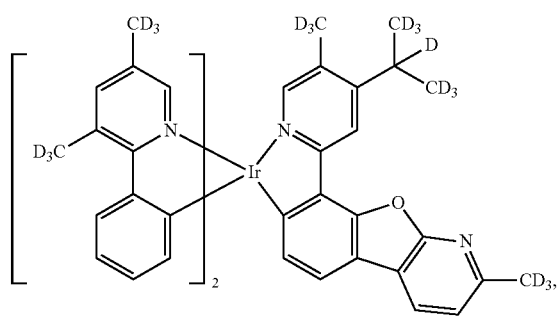
Compound 73
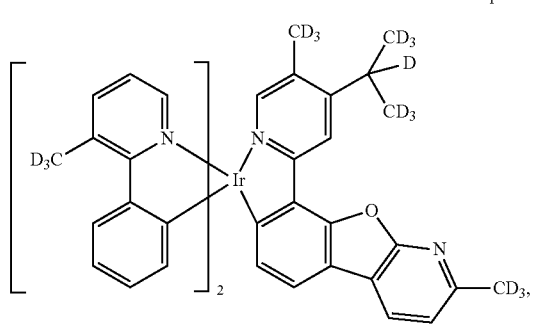
Compound 70
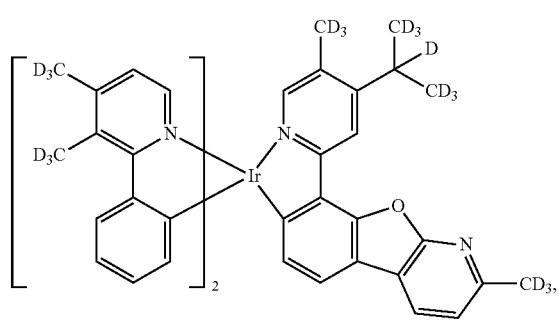
Compound 74
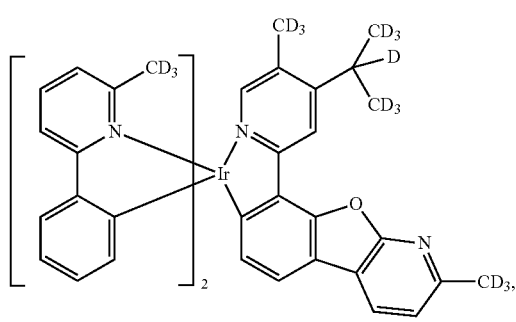
Compound 71
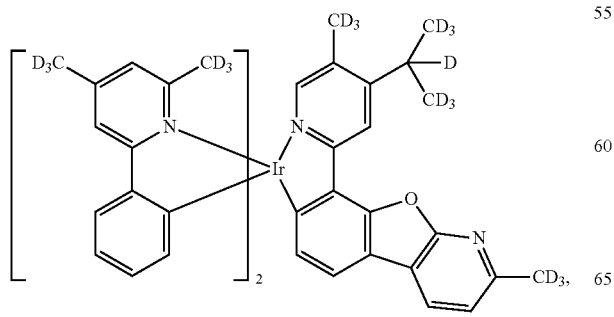
Compound 75
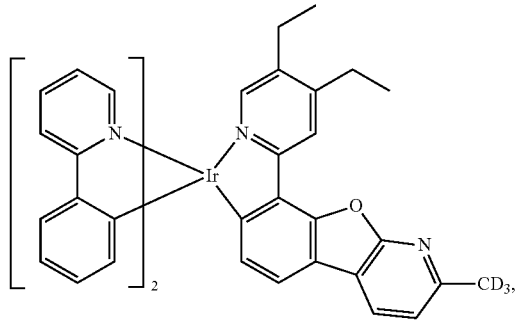

Compound 76
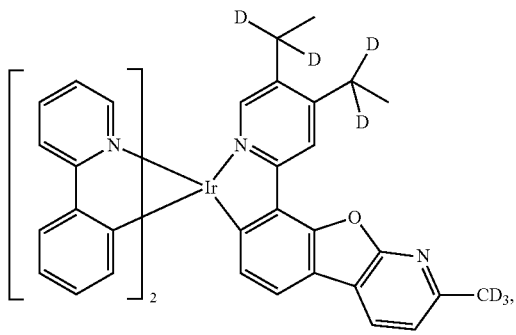
Compound 83
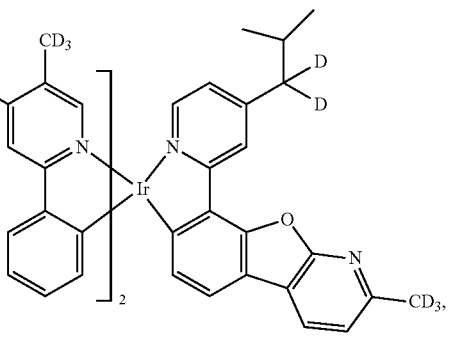
Compound 77
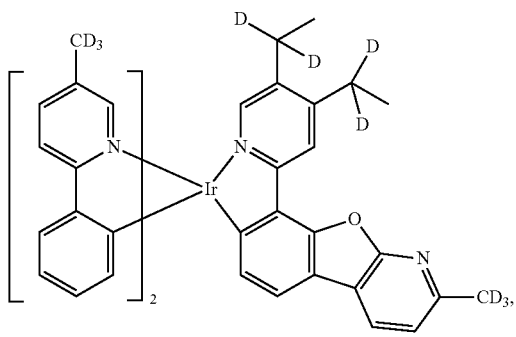
Compound 85
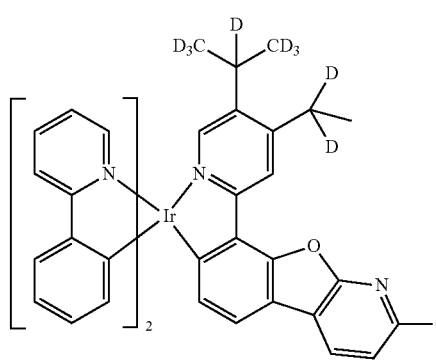
Compound 78
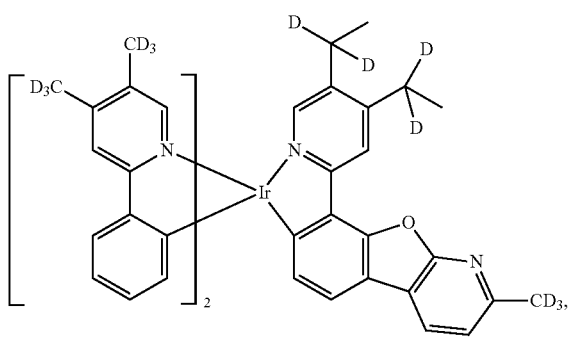
Compound 86
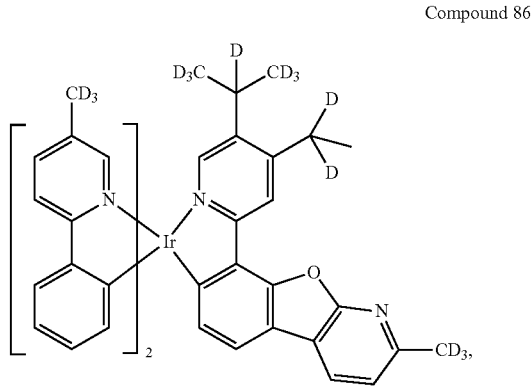
Compound 81
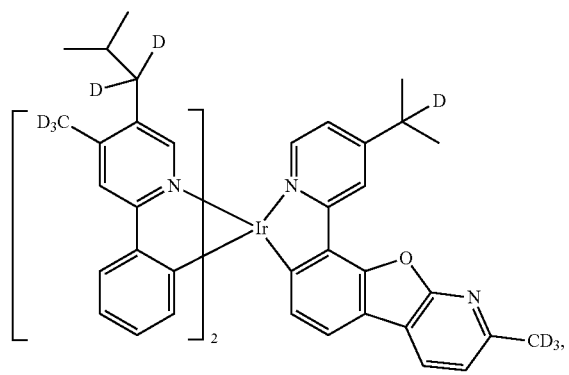
Compound 87
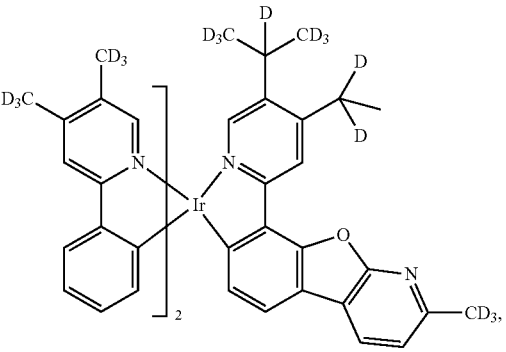

Compound 88
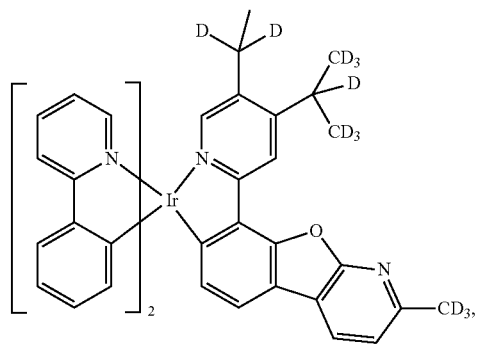
Compound 92
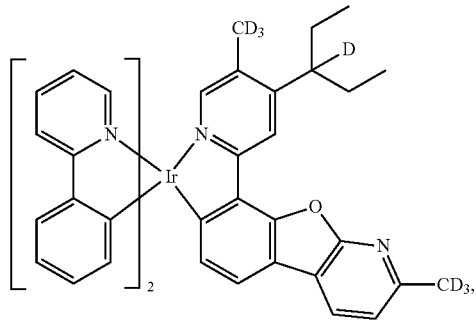
Compound 89
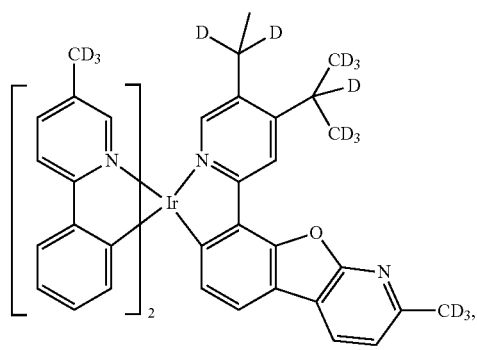
Compound 93
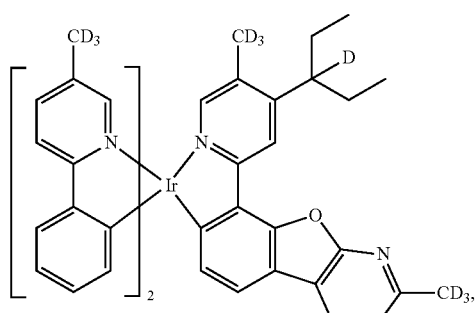
Compound 90
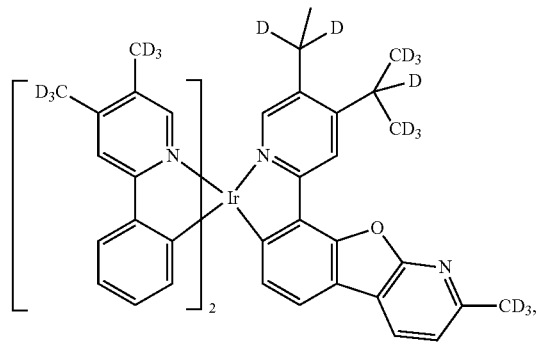
Compound 94
Compound 91
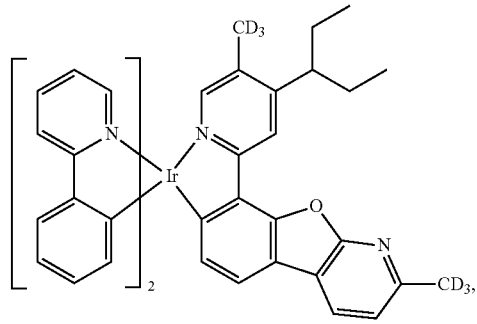
Compound 95
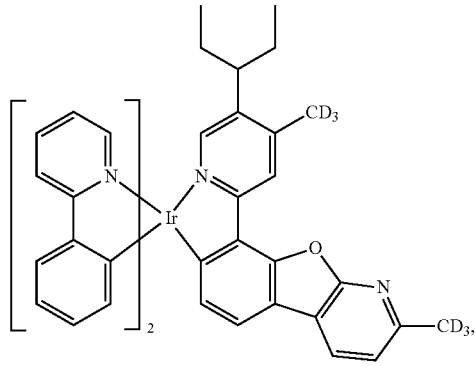

Compound 96
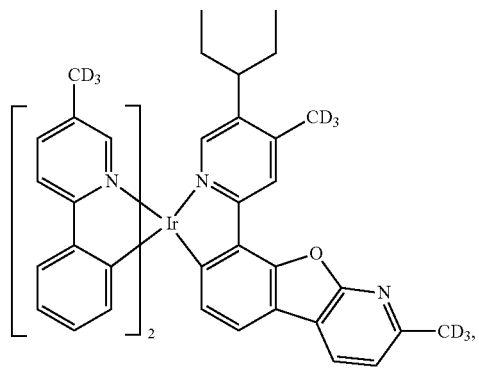
Compound 97
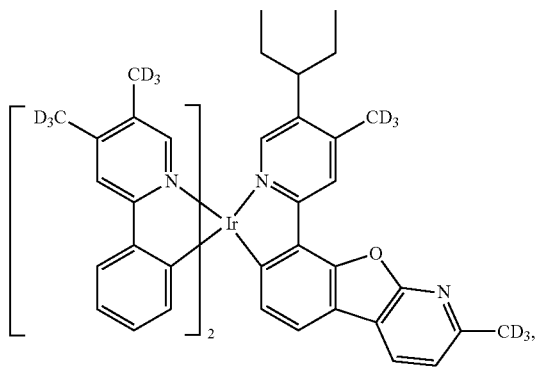
Compound 98
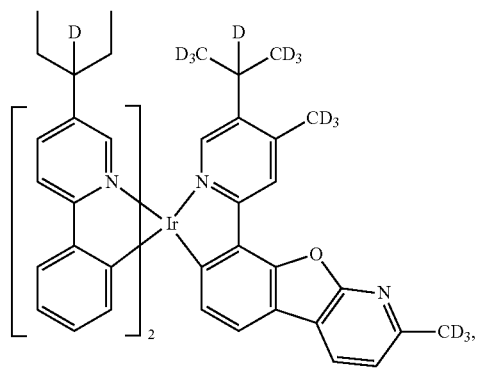
Compound 99
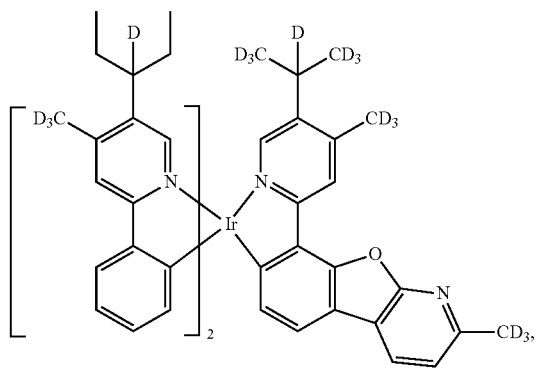
Compound 100
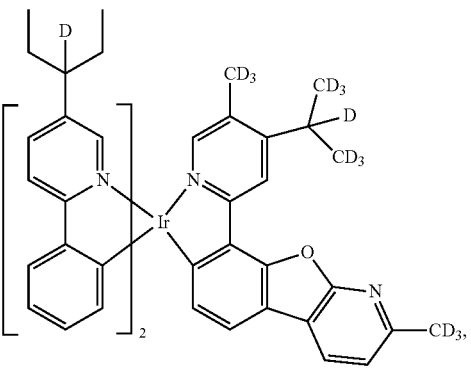
Compound 101
Compound 102
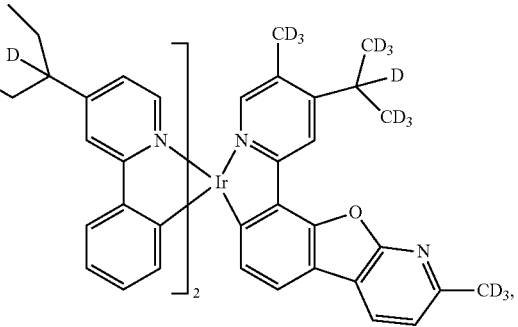
Compound 103
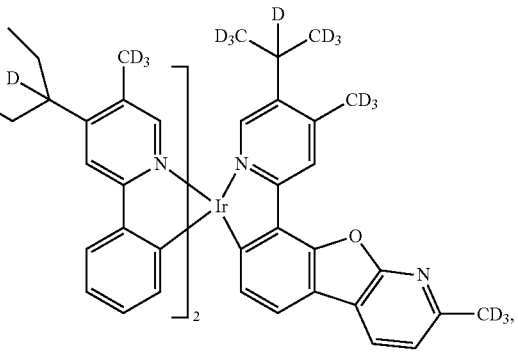

Compound 104
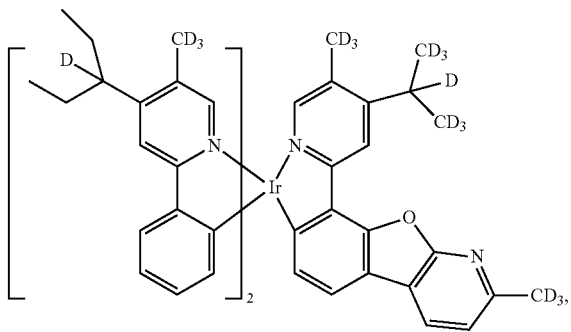
Compound 105
Compound 106
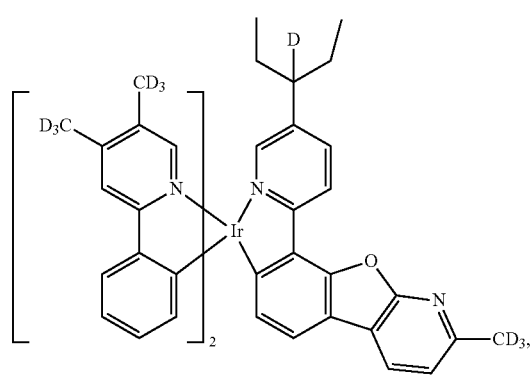
Compound 107
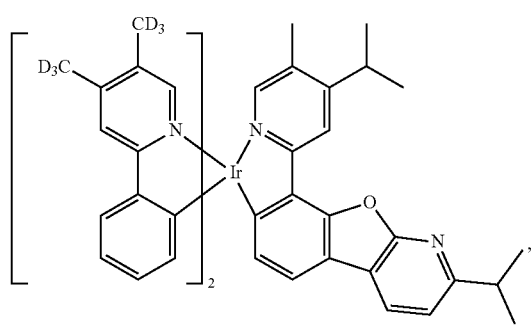
Compound 108
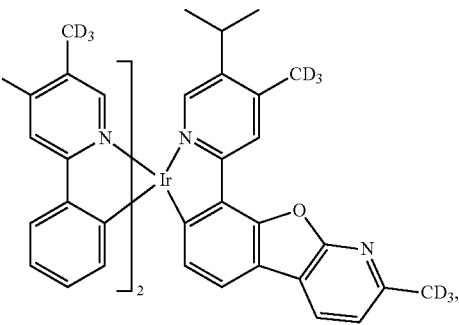
Compound 109
Compound 110
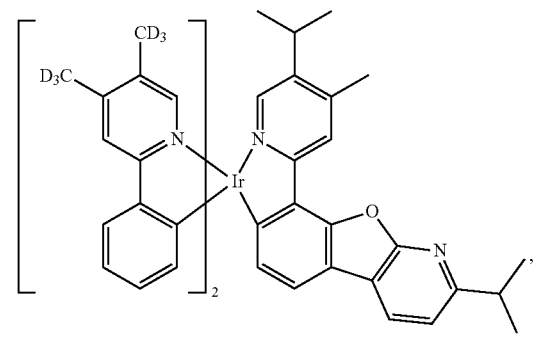
Compound 111

Compound 112
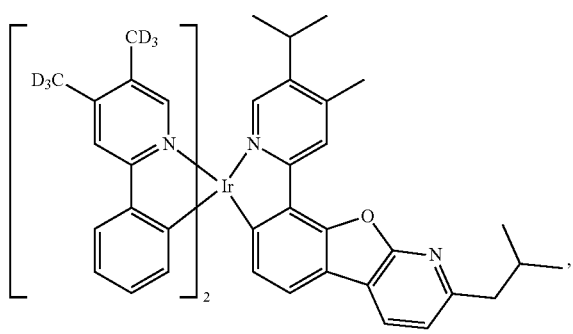
Compound 116
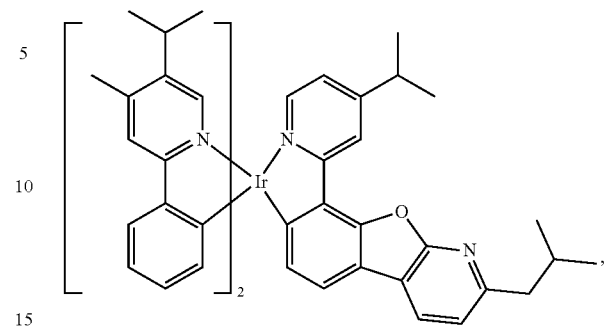
Compound 113
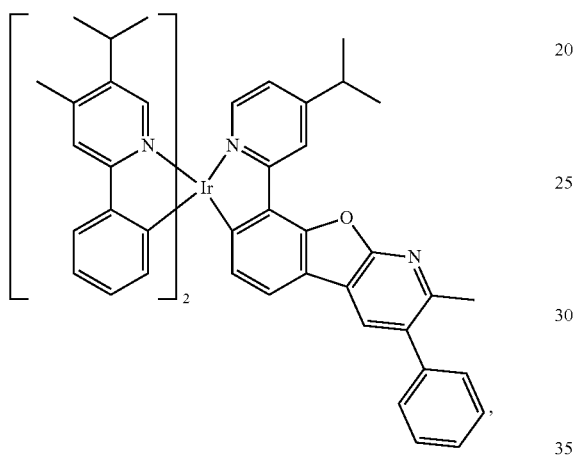
Compound 117
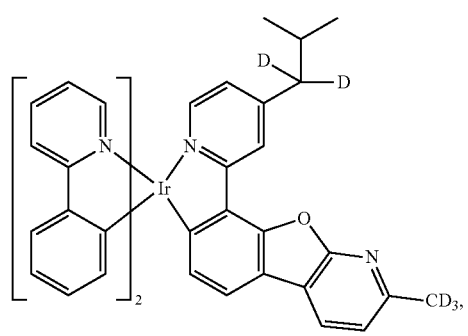
Compound 114
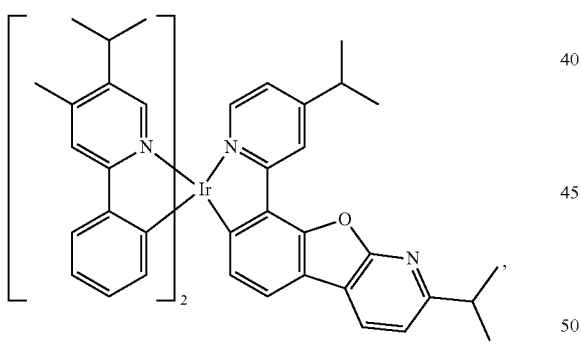
Compound 118
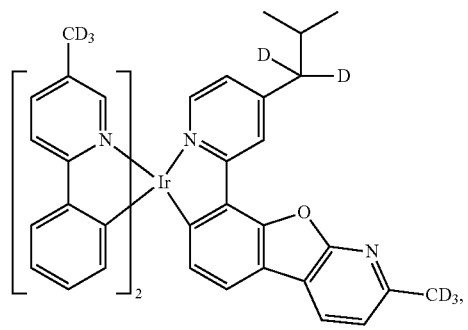
Compound 115
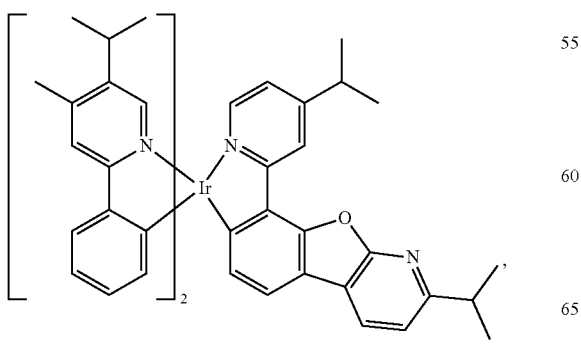
Compound 119
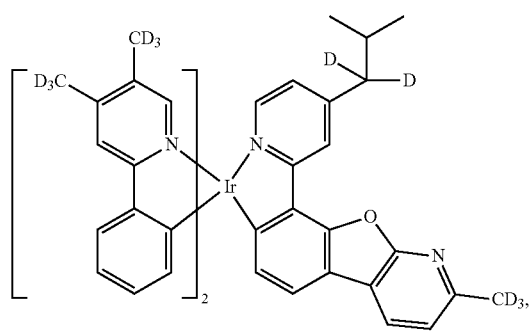

-continued

Compound 120

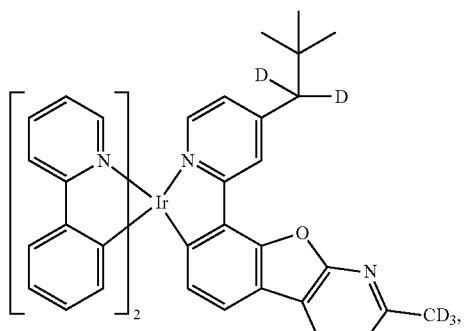

Compound 121

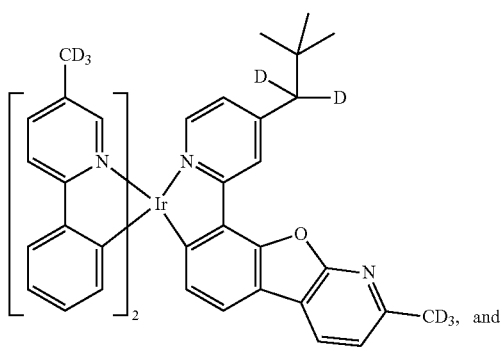

Compound 122

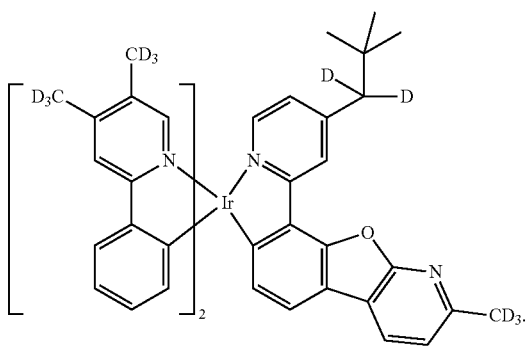

10. A formulation comprising a compound having a structure according to Formula V:

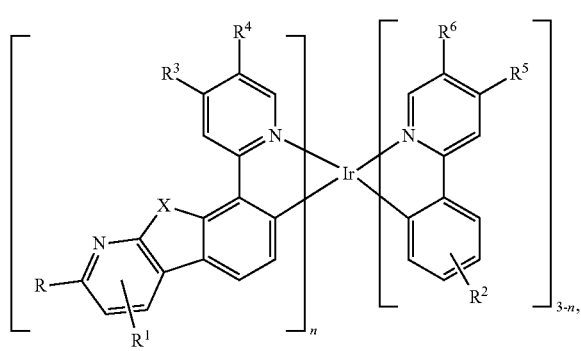

wherein X is O, S, or Se;
wherein $R^1$ represents mono-, di- substitution, or no substitution;
wherein $R^2$ represents mono-, di-, tri-, tetra-substitution, or no substitution;
wherein any adjacent substitutions in R, $R^1$, $R^2$, $R^3$, $R^4$, $R^5$, and $R^6$ are optionally linked together to form a ring;
wherein R is selected from the group consisting of alkyl, cycloalkyl, its partially or fully deuterated variants thereof, and combinations thereof;
wherein $R^1$ and $R^2$ are each independently hydrogen or a substitution selected from the group consisting of halide, alkyl, cycloalkyl, heteroalkyl, arylalkyl, alkoxy, aryloxy, amino, sily, alkenyl, cycloalkenyl, heteroalkenyl, alkynyl, aryl, heteroaryl, acyl, carbonyl, carboxylic, acids, ester, nitrile, isonitrile, sulfanyl, sulfinyl, sulfonyl, phosphino, combinations thereof, and partially or fully deuterated variations of any of the foregoing;
wherein $R^3$, $R^4$, $R^5$, and $R^6$ are each independently selected from the group consisting of hydrogen, deuterium, alkyl, cycloalkyl, and combinations thereof;
wherein n is an integer from 1 to 3; and
wherein the total number of carbons in at least one of the pairs $R^3$ and $R^4$, and $R^5$ and $R^6$ is at least four.

11. A first device comprising a first organic light emitting device, the first organic light emitting device comprising:
an anode;
a cathode; and
an organic layer, disposed between the anode and the cathode, the organic layer comprising a compound having a structure according to Formula V:

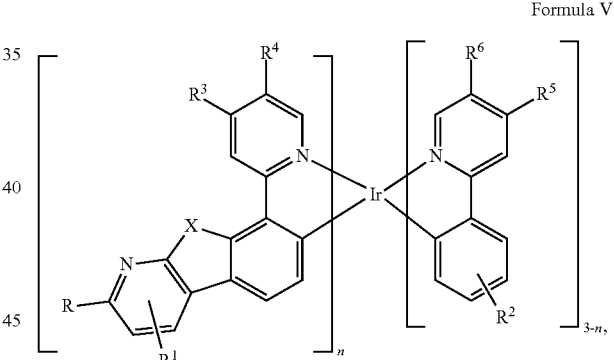

wherein X is O, S, or Se;
wherein $R^1$ represents mono-, di- substitution, or no substitution;
wherein $R^2$ represents mono-, di-, tri-, tetra-substitution, or no substitution;
wherein any adjacent substitutions in R, $R^1$, $R^2$, $R^3$, $R^4$, $R^5$, and $R^6$ are optionally linked together to form a ring;
wherein R is selected from the group consisting of alkyl, cycloalkyl, its partially or fully deuterated variants thereof, and combinations thereof;
wherein $R^1$ and $R^2$ are each independently hydrogen or a substitution selected from the group consisting of halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic, acids, ester, nitrile, isonitrile, sulfanyl, sulfinyl, sulfonyl, phosphino, combinations thereof, and partially or fully deuterated variations of any of the foregoing;

wherein R³, R⁴, R⁵, and R⁶ are each independently selected from the group consisting of hydrogen, deuterium, alkyl, cycloalkyl, and combinations thereof;

wherein n is an integer from 1 to 3; and wherein the total number of carbons in at least one of the pairs R³ and R⁴, and R⁵ and R⁶ is at least four.

12. The first device of claim 11, wherein the first device is selected from the group consisting of a consumer product, an electronic component module, an organic light-emitting device, and a lighting panel.

13. The first device of claim 11, wherein the organic layer is an emissive layer and the compound is an emissive dopant or a non-emissive dopant.

14. The first device of claim 11, wherein the organic layer further comprises a host, wherein the host comprises a triphenylene containing benzo-fused thiophene or benzo-fused furan;

wherein any substituent in the host is an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, CH=CH—$C_nH_{2n+1}$, C≡C—$C_nH_{2n+1}$, $Ar_1$, $Ar_1$-$Ar_2$, and $C_nH_{2n}$-$Ar_1$;

wherein n is from 1 to 10; and wherein $Ar_1$ and $Ar_2$ are independently selected from the group consisting of benzene, biphenyl, naphthalene, triphenylene, carbazole, and heteroaromatic analogs thereof.

15. The first device of claim 11, wherein the organic layer further comprises a host, wherein the host comprises at least one chemical group selected from the group consisting of triphenylene, carbazole, dibenzothiophene, dibenzofuran, dibenzoselenophene, azatriphenylene, azacarbazole, aza-dibenzothiophene, aza-dibenzofuran, and aza-dibenzoselenophene.

16. The first device of claim 11, wherein the organic layer further comprises a host, wherein the host is selected from the group consisting of:

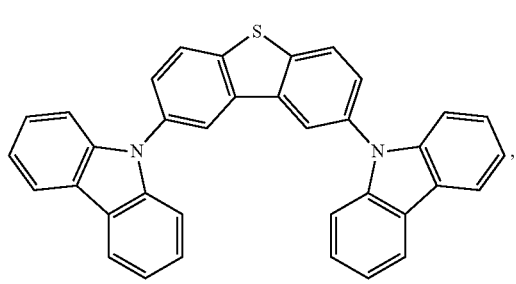

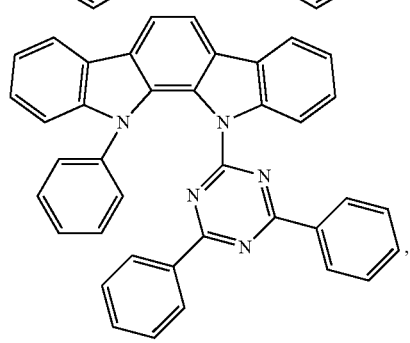

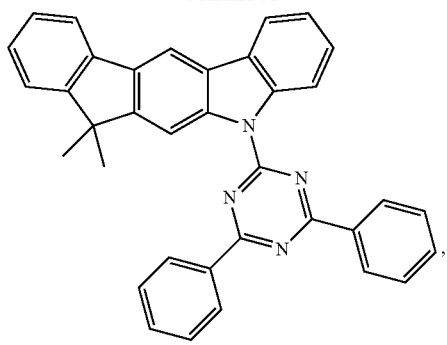

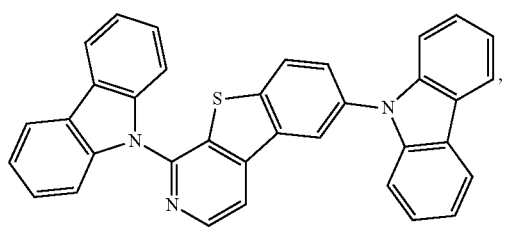

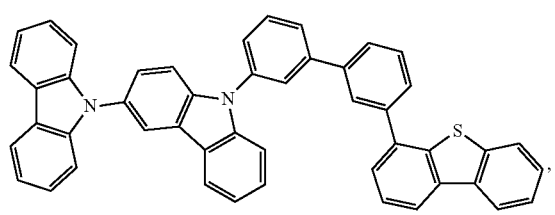

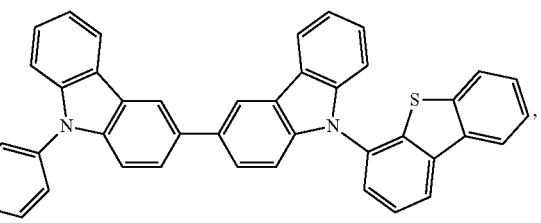

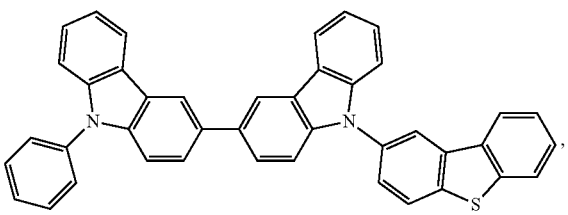

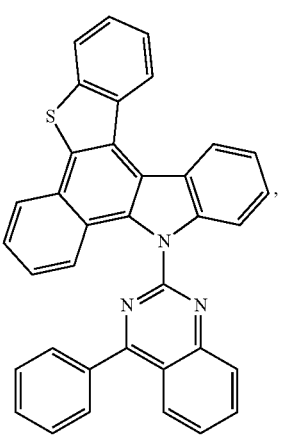

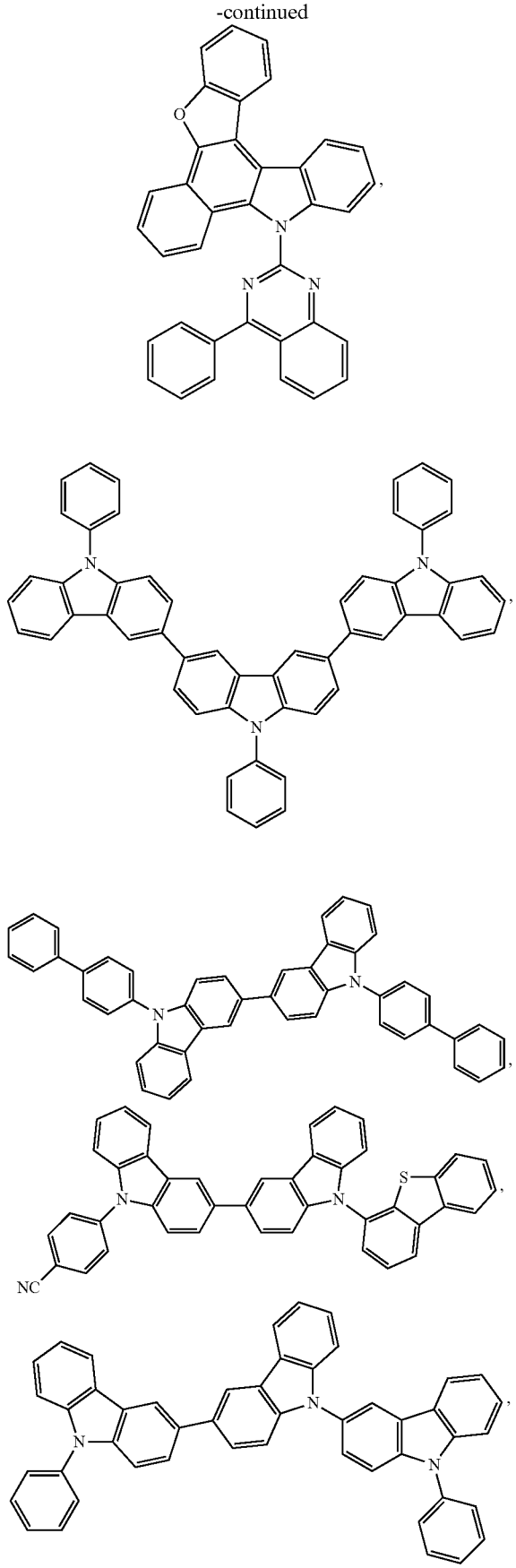
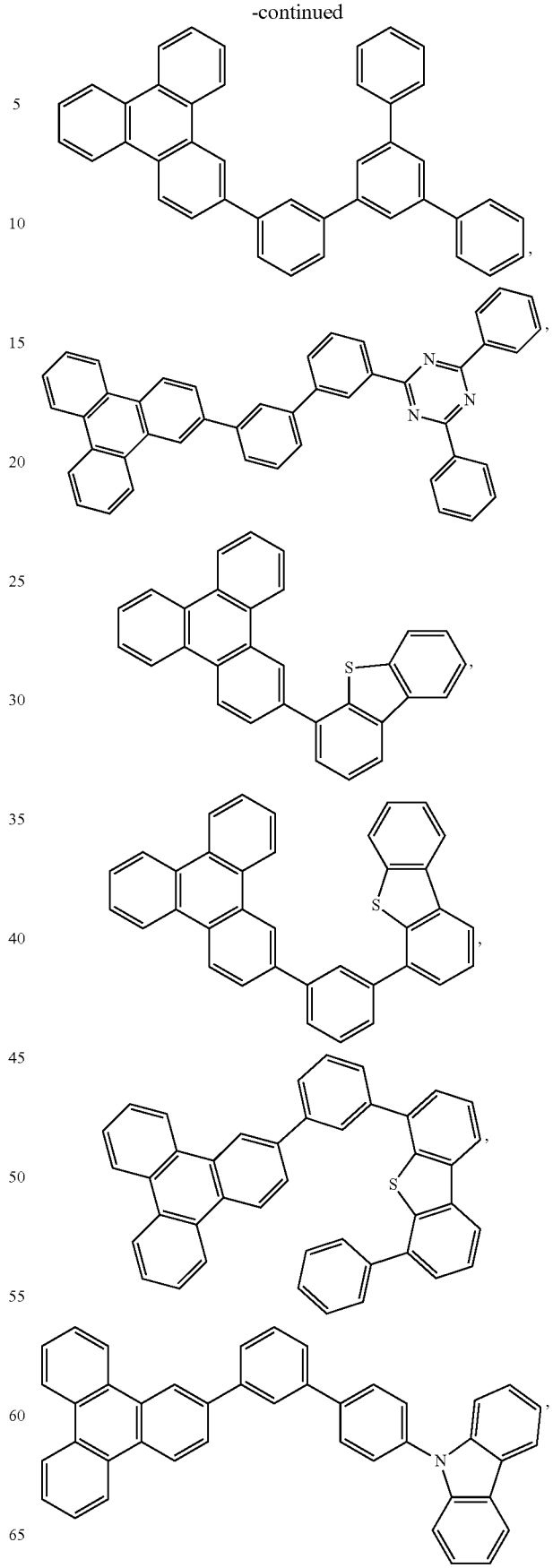

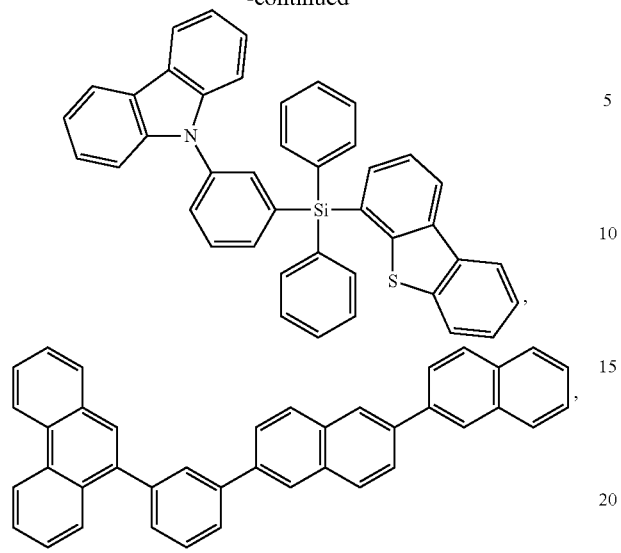
and combinations thereof.